US012599073B2

(12) United States Patent
Lv et al.

(10) Patent No.: US 12,599,073 B2
(45) Date of Patent: Apr. 14, 2026

(54) WHEAT CENH3 ALLELES

(71) Applicant: Syngenta Crop Protection AG, Basel (CH)

(72) Inventors: Jian Lv, Beijing (CN); Kun Yu, Beijing (CN); Juan Wei, Beijing (CN); Chunxia Liu, Beijing (CN); Hongju Zhou, Beijing (CN); Timothy Kelliher, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 38 days.

(21) Appl. No.: 18/426,902

(22) Filed: Jan. 30, 2024

(65) Prior Publication Data
US 2024/0334892 A1    Oct. 10, 2024

Related U.S. Application Data

(62) Division of application No. 17/286,950, filed as application No. PCT/CN2019/110404 on Oct. 10, 2019, now Pat. No. 12,016,286.

(30) Foreign Application Priority Data

Oct. 12, 2018    (CN) .......................... 201980063899.2

(51) Int. Cl.
A01H 6/46 (2018.01)

(52) U.S. Cl.
CPC .................................. A01H 6/4678 (2018.05)

(58) Field of Classification Search
None
See application file for complete search history.

(56) References Cited

FOREIGN PATENT DOCUMENTS

| | | | | |
|---|---|---|---|---|
| RU | 2551781 C2 | 5/2015 | | |
| WO | 2009068313 A2 | 6/2009 | | |
| WO | WO-2016138021 A1 * | 9/2016 | ............... | A01H 1/08 |
| WO | 2017058022 A1 | 4/2017 | | |

OTHER PUBLICATIONS

Yuan, Jing, et al. "Characterization of two CENH 3 genes and their roles in wheat evolution." New Phytologist 206.2 (2015): 839-851. (Year: 2015).*
International Search Report dated Jan. 16, 2020, mailed in International Application No. PCT/CN2019/110404.
Duan Minxiao et al. Progress of CENHJ-mediated Haploid Induction Technology Molecular Plant Breeding 25, Aug. 2017(Aug. 25, 2017) No. 10 VaLIS ISSN: 1672-416X sec pp. 4127-4131.
Ravi, Met al. Haploid plants produced by centromere-mediated genome elimination Nature 25 Mar. 2010 (Mar. 25, 2010) No. 7288 vol. 464 ISSN:0028-0836 see pp. 615-618.

Ceccherini, Isabella, et al., Strategies for the Identification of Intron-Exon Boundaries and Point Mutations: The Example of the RET Proto-Oncogene, ETHODS: A Companion to Methods in Enzymology 9, 98-105 (1996) Article No. 0013.
Muiruri, Kariuki S., et al., "Expressed Centromere Specific Histone 3 (CENH3) Variants in Cultivated Triploid and Wild Diploid Bananas (*Musa* spp.)", Front. Plant Sci., Jun. 29, 2017 Sec. Plant Biotechnology vol. 8—2017 [https://doi.org/10.3389/fpls.2017. 01034.
Xue, Chenxiao, et al., Manipulating mRNA splicing by base editing in plants, Sci China Life Sci 61, https://doi.org/10.1007/s11427- 018-9392-7, received Sep. 14, 2018; accepted Sep. 20, 2018; published online Sep. 27, 2018.
Brown, John W.S., et al., "*Aradidopsis* intron mutations and pre- mRNA splicing", The Plant Journal, 1996, 10(5), pp. 771-780.
Oneil, J. Patrick, et al., "Mutations that alter RNA splicing of the human HPRT gene: & review of the spectrum" Mutation Research 411, 1998, pp. 179-214.
Li, Chaokun, et al. "CRISPR/Cas9-mediated editing of GABRR2 gene in RGC-5 cells induces random exon deletion, exon splicing and new exon recruitment", Biochemical Engineering Journal (2018), https://doi.org/10.1016/j.bej.2018.08.005.
Mou, Haiwei, et al. "CRISPR/Cas9-mediated genome editing induces exon skipping by alternative splicing or exon deletion", Mou et al. Genome Biology (2017) 18:108 DOI 10.1186/s13059-017-1237-8.
Sharpe, Joshua J., et al., "Unexpected consequences: exon skipping caused by CRISPR-generated mutations", Sharpe and Cooper Genome Biology (2017) 18:109 DOI 10.1186/s13059-017-1240-0.
Gapinske, Michael, et al., "CRISPR-SKIP: programmable gene splicing with single base editors", Genome Biology (2018) 19:107 https://doi.org/10.1186/s13059-018-1482-5.
Eckardt, Nancy A., "The Plant Cell Reviews Alternative Splicing", The Plant Cell, vol. 25: 3639, Oct. 2013, www.plantcell.org.
Staiger, Dorothee, et al., et al., "Alternative Splicing at the Inter- section of Biological Timing, Development, and Stress Responses", The Plant Cell, vol. 25: 3640-3656, Oct. 2013, www.plantcell.org.
Reddy, Anireddy S., et al., "Complexity of the Alternative Splicing Landscape in Plants", The Plant Cell, vol. 25: 3657-3683, Oct. 2013, www.plantcell.org.
E.V. Evtushenko et al., "Conserved Molecular Structure of the Centromeric Histone CENH3 in Secale and its Phylogenetic Rela- tionships", www.nature.com/scientificreports, May 31, 2017, pp. 1-10.
Pauwels, Laurens et al.: "A Dual sgRNA Approach for Functional Genomics in *Arabidopsis thaliana*", G3 GENESIGENOMESIGENETICS, vol. 8, No. 8, Jun. 8, 2018 (Jun. 8, 2018), pp. 2603-2615, XP055922111, DOI: 10.1534/g3.118. 200046 Retrieved from the Internet: URL:http://academic.oup.com/ g3journal/article-pdf/8/8/2603/37126009/g3journal2603.pdf.

(Continued)

*Primary Examiner* — Weihua Fan
(74) *Attorney, Agent, or Firm* — Amanda Bublitz

(57) ABSTRACT

The present invention relates to wheat plants comprising a mutation causing an alteration of the amino acid sequence in centromere histone H3 (CENH3), which have the biological activity of a haploid inducer. Further, the present invention provides methods of generating the wheat plants of the present invention and haploid and doubled haploid wheat plants obtainable by crossing the wheat plants of the present invention with wildtype wheat plants.

3 Claims, 1 Drawing Sheet

Specification includes a Sequence Listing.

(56)  References Cited

OTHER PUBLICATIONS

Extended ESR for EP19870975.0, mailed on Jun. 2, 2022.
Tarantul V. Z. Tolkovyj biotehnologiceskij slovar' russko-anglijskij
(Explanatory Russian-English Dictionary of Biotechnology). Lan-
guages of Slavic Cultures Publishing House, Moscow, 2009, pp.
583, 584.

* cited by examiner

WHEAT CENH3 ALLELES

RELATED APPLICATION INFORMATION

This application is a divisional of, and claims the benefit thereof, U.S. patent application Ser. No. 17/286,950, filed Apr. 20, 2021, which is a § 371 of International Application No. PCT/CN2019/110404, filed Oct. 10, 2019, which claims priority to CN application No. 201980063899.2, filed Oct. 12, 2018, the contents of which are incorporated herein by reference.

FIELD OF THE INVENTION

The disclosure relates to the field of agriculture. In particular, the disclosure relates to CenH3 proteins and polynucleotides encoding them, methods for the production of haploid as well as subsequent doubled haploid plants, and plants and seeds derived thereof, particularly in wheat species.

SEQUENCE LISTING

This application is accompanied by a sequence listing entitled 81696WOPCT_ST25.txt, created Sep. 30, 2019, which is approximately 112 kilobytes in size. This sequence listing is incorporated herein by reference in its entirety. This sequence listing is submitted herewith via EFS-Web, and is in compliance with 37 C.F.R. § 1.824(a)(2)-(6) and (b).

BACKGROUND

A high degree of heterozygosity in breeding material can make plant breeding and selection for beneficial traits a very time consuming process. Extensive population screening, even with the latest molecular breeding tools, is both laborious and costly. The creation of haploid plants followed by chemical or spontaneous genome doubling has proven to be an efficient way to solve the problem of high heterozygosity and accelerate the breeding process. Such technology is also referred to as doubled haploid production system. The use of the doubled haploid production system has allowed breeders to achieve homozygosity at all loci in a single generation via whole-genome duplication. This effectively obviates the need for selfing or backcrossing, where normally at least 7 generations of selfing or backcrossing would be needed to reduce the heterozygosity to an acceptable level.

Haploid plants can be generated according to different methodologies. For instance, haploid plants can be produced in some crops by using a method referred to as microspore culture. However, this method is costly, time-consuming, and does not work in all crops. In some crop species, (doubled) haploid plants can be obtained by parthenogenesis of the egg cell or by elimination of one of the parental genomes. However, such methods are not optimal as they only work in few selected crop species and yield rather low rates of (doubled) haploid plants.

WO2011/044132 discloses a method for producing haploid plants consisting of inactivating or altering or knocking out the centromere-specific H3 (CenH3) protein in a plant. In a first step, the method consists of eliminating or knocking down the endogenous CenH3 gene in plant. In a second step, an expression cassette encoding a mutated or altered CenH3 protein is introduced in the plant. The mutated or altered CenH3 protein is generated by fusing an, optionally GFP-tagged, H3.3 N-terminal domain to the endogenous CenH3 histone-fold domain. Such methodology is also known as "GFP-tailswap" or "tailswap" (also reviewed in Britt and Kuppu, Front Plant Sci. 2016; 7: 357). The crossing of the plant harboring such tailswap with a wildtype plant (i.e., having functional endogenous CenH3 protein without a tailswap), causes uniparental genome elimination, which in turn results in the production of a haploid plant. Some haploid induction, though less frequent, was also found with N-terminal addition of GFP to endogenous CenH3 (no tailswap). However, this methodology is not ideal as it laborious, time-consuming and requires generating a transgenic plant.

WO2014/110274 describes a method for producing haploid plants consisting of crossing a first plant expressing an endogenous CenH3 gene to a second plant referred to as a haploid inducer plant having a genome from at least two species, wherein a majority of the genome is from a first species and the genome comprises a heterologous genomic region from a second species, wherein the heterologous genomic region encodes a CenH3 polypeptide different from the CenH3 of the first species (also described in Maheshwari et al, PLoS Genet. 2015 Jan. 26; 11(1):e1004970)). However, this methodology is not optimal as it suffers from the same pitfall as above—it is laborious, time-consuming and requires generating a transgenic plant. Further, the method is associated with low yield of haploid plants.

Other methods consist of introducing one or more point mutations leading to single amino acid change in the C-terminal histone fold domain of CenH3 protein or CenH3 gene coding the CenH3 protein. Examples of such mutations in the C-terminal histone fold domain of the CenH3 protein were reported in Karimi-Ashtiyani et al (2015) Proc Natl Acad Sci USA. 2015 Sep. 8; 112(36):11211-16; Kuppu, et al. (2015) PLoS Genet. 2015 Sep. 9; 11(9):e1005494. However, the success of such methods is mitigated as some, as not all of these mutations were found to be sufficient to induce uniparental genome elimination after crossing with a wildtype plant to produce a haploid plant.

Wheat (*Triticum aestivum*) is a particularly complex organism for editing or mutating its genes, as it is a hexaploid organism. Evolved over thousands of years and several cross-breedings with ancestor wheat species, *Triticum aestivum* comprises three genomes: A (possibly from *T. monoccum* or Einkorn wheat), B (possibly from *T. searsii*), and D (possibly from *T. tauschii*). Each genome has 7 chromosomes. *Triticum aestivum* has two copies of each genome, i.e., AA BB DD; thus it has 42 chromosomes total (6 complete genomes each with 7 chromosomes). See generally *The Evolution of Wheat* at www.cerealsdb.uk.net/cerealgenomics/WheatBP/Documents/DOC_Evolution.php, last accessed 10 Jul. 2019. Furthermore, an edit or mutation in one copy of one gene may not present observable effects in *Triticum aestivum*, as the additional 5 copies likely would compensate for the mutant copy. In order to truly observe a knockout mutation's effect, one would have to mutate all 6 copies.

Therefore, it remains elusive which mutation(s) or modification(s) in the CenH3 protein or CenH3 gene coding for the CenH3 protein are capable or sufficient to induce uniparental genome elimination to produce haploid plants. Thus, there remains a need in the art for alternative or improved methods that allow efficient generation of haploid plants (e.g. less labor-intensive, less-time consuming, less expensive, and/or do not necessarily require making a transgenic plant), which can subsequently be doubled to produce doubled haploid plants. With doubled haploid production systems, homozygosity may be achieved in one generation.

SUMMARY

To meet this need, one embodiment of the invention is a wheat plant comprising at least an A genome, a B genome, and a D genome, wherein the B genome comprises a knock-out mutation in a CENH3 gene, and optionally wherein the D genome comprises a knock-out mutation in a CENH3 gene, and further wherein the A genome comprises a mutated CENH3 gene comprising at least one knock-down mutation at a 5' splice site of an intron. In one aspect, the knock-down mutation is a restored frame shift mutation or a large deletion mutation. In another embodiment, the wheat plant is homozygous for a knock-out mutation in a CENH3 gene in the B genome. In an alternate embodiment, the wheat plant is biallelic for a knock-out mutation in a CENH3 gene in the B genome. In another embodiment, the wheat plant is homozygous for a knock-out mutation in a CENH3 gene in the D genome. In an alternate embodiment, the wheat plant is biallelic for a knock-out mutation in a CENH3 gene in the D genome. In yet another embodiment, the wheat plant is homozygous, biallelic, or a combination thereof for a knock-out mutation in a CENH3 gene in the B genome and the D genome. In another embodiment, the wheat plant is homozygous for the restored frame shift CENH3 mutation; or it is heterozygous for the restored frame shift CENH3 mutation; or it is biallelic for the restored frame shift CENH3 mutation.

Another aspect of the invention is a method of generating a haploid-inducing wheat plant, the method comprising: (a) obtaining at least a wheat plant cell comprising at least three genomes; (b) mutating two of the three genomes to obtain homozygous knock-out mutations in a CENH3 gene; (c) mutating the third genome to obtain a homozygous knock-down mutation in a CENH3 gene; and (d) generating a wheat plant therefrom comprising homozygous knock-out mutations in a CENH3 gene of two of the three genomes and further comprising a homozygous knock-down mutation in a CENH3 gene of the third genome; whereby the wheat plant generated from step (d) produces haploid progeny when crossed with a wildtype wheat plant. In one embodiment, the three genomes comprise an A genome, a B genome, and a D genome. In another, the knock-out mutations in a CENH3 gene occur in the B and D genomes. In yet another, the knock-down mutation in a CENH3 gene occurs in the A genome. In one aspect, the knock-down mutations in a CENH3 gene in the A genome are restored frame shift mutations. In another aspect, the restored frame shift mutations are selected from the group consisting of SEQ ID NO:

56, a nucleic acid sequence 70% identical to SEQ ID NO: 56, SEQ ID NO: 63, a nucleic acid sequence 70% identical to SEQ ID NO: 63, SEQ ID NO: 69, and a nucleic acid sequence 70% identical to SEQ ID NO: 69.

Another aspect of the invention is a wheat plant comprising a mutated CENH3 gene comprising at least one deletion mutation in the N-terminal domain resulting in a frame shift, a restored frame shift, or a large deletion. Yet another aspect is a wheat plant comprising a mutated CENH3 gene comprising at least one insertion mutation in the N-terminal domain resulting in a frame shift, a restored frame shift, or a large deletion.

Another aspect of the invention is a method of generating an engineered restored frame shift in a gene of a cell, comprising: (a) contacting the genome with a site-directed nuclease ("SDN") and at least two guide nucleic acids, wherein the at least two guide nucleic acids target at least two target sequences within the gene; (b) permitting the SDN to cut the gene at the at least two target sequences, thereby losing an intervening sequence between the at least two target sequences; and allowing endogenous DNA repairs to occur; whereby the endogenous DNA repairs results in a gene having an engineered restored frame shift. In one embodiment, the lost intervening sequence of step (b) comprises (N) base pairs, where (N) is a multiple of 3.

Yet another aspect of the invention is a method of generating a haploid wheat plant, comprising: (a) obtaining a wheat plant; (b) crossing the wheat plant to the wheat plant comprising a mutated CENH3 gene; and (c) selecting a progeny generated from the crossing step; wherein the progeny is a haploid wheat plant. In one embodiment, the wheat plant of step (a) is the paternal parent. In another embodiment, the wheat plant of step (a) is the maternal parent. In another embodiment, the method comprises a further step of converting the progeny wheat plant into a doubled haploid wheat plant.

It is another aspect of the invention to provide a wheat plant comprising a mutated CENH3 allele comprising a nucleic acid sequence at least 70% identical to a sequence selected from the group consisting of SEQ ID NO: 53-73, wherein the mutation is an restored frame shift mutation, and wherein the wheat plant generates haploid progeny when crossed with a wildtype diploid wheat plant. In one embodiment, the wheat plant comprises at least one copy of the mutated CENH3 allele; in another embodiment, the wheat plant comprises at least two copies of the mutated CENH3 allele; in yet another embodiment, the wheat plant comprises at least three copies of the mutated CENH3 allele. In one embodiment, the mutated CENH3 allele comprises a nucleic acid sequence 80, 90, 95, or 100% identical to SEQ ID NO: 53-73.

TABLE 1

| | BRIEF DESCRIPTION OF THE SEQUENCES IN THE SEQUENCE LISTING | | |
|---|---|---|---|
| SEQ ID NO: | Pimer ID (or Probe ID) | Location or function | Brief Description |
| 1 | S2-α1A | 5' UTR of TaCenH3α-A | TaCenH3α-A genomic sequence cloning in |
| 2 | As-α1A/B/D | Exon 5 of TaCenH3α-A/B/D | Fielder |
| 3 | S-α1A/B/D | Exon 5 of TaCenH3α-A/B/D | |
| 4 | As-α1A | Exon 7 of TaCenH3α-A | |
| 5 | S-α1B | 5' UTR of TaCenH3α-B | TaCenH3α-B genomic sequence cloning in |
| 6 | As-α1A/B | Exon 5 of TaCenHBα-A/B | Fielder |
| 7 | S-α1A/B/D | Exon 5 of TaCenH3α-A/B/D | |
| 8 | As-α1B/D | Exon 7 of TaCenH3α-B/D | |
| 9 | S2-α1D | 5' UTR of TaCenH3α-D | TaCenH3α-D genomic sequence cloning in |
| 10 | As-α1A/B/D | Exon 5 of TaCenH3α-A/B/D | Fielder |
| 11 | S-α1A/B/D | Exon 5 of TaCenH3α-A/B/D | |

TABLE 1-continued

BRIEF DESCRIPTION OF THE SEQUENCES IN THE SEQUENCE LISTING

| SEQ ID NO: | Pimer ID (or Probe ID) | Location or function | Brief Description |
|---|---|---|---|
| 12 | As-α1B/D | Exon 7 of TaCenH3α-B/D | |
| 13 | qRT(A)-S | Sense primer | TaCenH3α-A expression |
| 14 | qRT(A)-As | Antisense primer | |
| 15 | qRT(A)-probe | Probe | |
| 16 | qRT(B)-S | Sense primer | TaCenH3α-B expression |
| 17 | qRT(B)-As | Antisense primer | |
| 18 | qRT(B)-probe | Probe | |
| 19 | qRT(B)-S | Sense primer | TaCenH3α-D expression |
| 20 | qRT(B)-As | Antisense primer | |
| 21 | qRT(B)-probe | Probe | |
| 22 | TQ1115-S | Sense primer | Control assay for the qRT-PCR, targeting ADP-ribosylation factor |
| 23 | TQ1115-As | Antisense primer | |
| 24 | TQ1115-probe | Probe | |
| 25 | gRNA1 | sgRNA targeting exon2-intron2 junction | |
| 26 | gRNA2 | sgRNA targeting intron3-exon4 junction | TaCenH3α sgRNAs |
| 27 | gRNA3 | sgRNA targeting exon1 | |
| 28 | gRNA4 | sgRNA targeting intron2-exon3 junction | |
| 29 | KW2917R | Antisense primer | |
| 30 | KW2917F1 | Sense primer | KASP assay - 2917 |
| 31 | KW2917F2 | Sense primer | |
| 32 | KWI1728R | Antisense primer | |
| 33 | KW11728F1 | Sense primer | KASP assay - 11728 |
| 34 | KW11728F2 | Sense primer | |
| 35 | KW11091R | Antisense primer | |
| 36 | KW11091F1 | Sense primer | KASP assay - 11091 |
| 37 | KW11091F2 | Sense primer | |
| 38 | KW11511R | Antisense primer | |
| 39 | KW11511F1 | Sense primer | RASP assay - 11511 |
| 40 | KW11511F2 | Sense primer | |
| 41 | KW11129R | Antisense primer | |
| 42 | KW11129F1 | Sense primer | KASP assay - 11129 |
| 43 | KW11129F2 | Sense primer | |
| 44 | e35S -S | Sense primer | |
| 45 | e35S -As | Antisense primer | Transgenic copy number check |
| 46 | e35S-probe | Probe | |
| 47 | PMI - S | Sense primer | |
| 48 | PMI - As | Antisense primer | Transgenic copy number check |
| 49 | PMI - probe | Probe | |
| 50 | FA | Sense primer | TaCENH3α-A edit sequencing primers |
| 51 | R3 | Antisense primer | |
| 52 | M13R | Antisense primer | Clone sequence primer |
| 53 | M13F | Sense primer | |
| 54 | F1 | Sense primer | TaCENH3α RT-PCR primer |
| 55 | R1 | Antisense primer | |
| 56 | A* genomic sequence in A004A | gRNA1, ins A; gRNA2, ins A | Genomic sequence in TaCENH3α-A |
| 57 | A* CDS sequence in A004A | Restored frame shift in N terminal | Restored frame shift in N terminal in TaCENH3α-A |
| 58 | a CDS sequence in A004A | Premature stop | Loss of function in TaCENH3α-A |
| 59 | A* protein sequence in A004A | Restored frame shift in N terminal | Restored frame shift in N terminal in TaCENH3α-A |
| 60 | a protein sequence in A004A | Premature stop | Loss of function in TaCENH3α-A |
| 61 | B genomic sequence in A004A | gRNA1, WT; gRNA2, WT | WT TaCENH3α-B |
| 62 | d genomic sequence in A004A | gRNA1, WT; gRNA2, ˆA | Loss of function in TaCENH3α-D |
| 63 | A* genome sequence in C003A | gRNA1, ΔG; gRNA2 ˆA | Transgenic copy number check |
| 64 | A* CDS sequence in C003A | gRNA1, ΔG; gRNA2, ˆA | Restored frame shift in N terminal in TaCENH3α-A |
| 65 | A* protein sequence in C003A | gRNA1, ΔG; gRNA2, ˆA | Restored frame shift in N terminal in TaCENH3α-A |
| 66 | b genomic sequence in C003A | gRNA1, WT; gRNA2, ˆA | Loss of function in TaCSENH3α-B |
| 67 | b protein sequence in C003A | gRNA1, WT; gRNA2, ˆA | Loss of function in TaCENH3α-B |
| 68 | d genomic sequence in C003A | gRNA1, WT; gRNA2, ˆA | Loss of function in TaCENH3α-D |
| 69 | A* genomic sequence in A073A | gRNA3, ˆA; gRNA4, ΔG | Restored frame- shift in N terminal in TaCENH3α-A |
| 70 | A* CDS sequence in A073A | gRNA3, ˆA; gRNA4, ΔG | Restored frame shift in N terminal in TaCENH3α-A |
| 71 | A* protein sequence in A073A | gRKA3, ˆA; gRNA4, ΔG | Restored frame shift in N terminal in TaCENH3α-A |

TABLE 1-continued

BRIEF DESCRIPTION OF THE SEQUENCES IN THE SEQUENCE LISTING

| SEQ ID NO: | Pimer ID (or Probe ID) | Location or function | Brief Description |
|---|---|---|---|
| 72 | b genomic sequence in A073A | gRNA3, WT; gRNA4, ^A | Loss of function in TaCENH3α-B |
| 73 | d genomic sequence in A073A | gRNA3, ΔGTC; gRNA4, ^A | Loss of function in TaCENH3α-D |
| 74 | | | Construct 24195 |
| 75 | | | Construct 24194 |
| 76 | | | Amino acid sequence lost in RES |
| 77 | | | Amino acid sequence added in RES |
| 78 | | | Amino acid sequence added in RES |
| 79 | SQ-1 primer | | |

BRIEF DESCRIPTION OF THE FIGURES

FIG. 1 shows the TaCenH3α gene structure and relative gRNA locations. Exons are numbered and represented by thick bars. Introns are represented by thin lines. Length of both is represented by width.

DEFINITIONS

This invention is not limited to the particular methodology, protocols, cell lines, plant species or genera, constructs, and reagents described herein. The terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon."

The term "biallelic" refers to a gene pair that is neither homozygous (AA or aa) nor heterozygous (Aa). Rather, both genes in the pair have been edited but not identically. For example, the CenH3 gene pair on the A chromosome in this invention may comprise one RFS mutation in one allele resulting in a knock-down of the gene upon expression, while the other allele comprises a knock-out mutation. This may be indicated symbolically as "A*a" and is indicative of a biallelic mutation.

The term "specific DNA sequence" indicates a polynucleotide sequence having a nucleotide sequence homology of more than 80%, preferably more than 85%, more preferably more than 90%, even more preferably more than 95%, still more preferably more than 97%, most preferably more than 99% with another named sequence.

"cDNA" refers to a single-stranded or a double-stranded DNA that is complementary to and derived from mRNA. The term "centromere-specific variant of histone H3 protein" ("CenH3 protein" or simply "CENH3"), as used herein, refers to a protein that is a member of the kinetochore complex. CenH3 protein is also known as CENP-A protein. The kinetochore complex is located on chromatids where the spindle fibers attach during cell division to pull sister chromatids apart. CenH3 proteins belong to a well-characterized class of proteins that are variants of H3 histone proteins. These proteins are essential for proper formation and function of the kinetochore, and help the kinetochore associate with DNA. Cells that are deficient in CenH3 fail to localize kinetochore proteins on chromatids and show strong chromosome segregation defects (i.e., all chromosomes from the plant expressing the deficient CenH3 protein are eliminated or lost, leading to a change in the ploidy of somatic cells (e.g., reduction in the number of chromosome set such as diploid to haploid)). Therefore, CenH3 proteins have been subject to intensive research for their potential use in doubled haploid production system. CenH3 proteins are characterized by a variable tail domain (also referred to as "N-terminal domain" or "N-terminal tail domain") and a conserved histone fold domain (also referred to as "C-terminal domain") made up of three alpha-helical regions connected by loop sections. The CenH3 histone fold domain is relatively well conserved between CenH3 proteins from different species. The histone fold domain is located at the carboxyl terminus of an endogenous CenH3 protein. In contrast to the histone-fold domain, the N-terminal tail domain of CenH3 is highly variable even between closely related species.

"CenH3-encoding polynucleotide having one or more active mutations" refers to a non-endogenous or endogenous mutated CenH3-encoding polynucleotide that encodes a CenH3 protein having one or more active mutations, which when present in a plant in the absence of its endogenous CenH3-encoding polynucleotide and/or endogenous CenH3 protein, allows the plant to be viable, and allows generation of haploid progeny, or progeny with aberrant ploidy, when the plant is crossed with a wild-type plant. The plant comprising a CenH3-encoding polynucleotide having one or more active mutations may be referred to as a "modified plant." The percentage of haploid progeny or progeny with aberrant ploidy that is generated upon crossing with a wild-type plant can, for instance, be at least 0.1, 0.5, 1, 5, 10, 20 percent or more. A mutation that causes a transition from the endogenous CenH3-encoding polynucleotide to a CenH3-encoding polynucleotide having one or more active mutations is herein referred to as an active mutation. An active mutation in a CenH3 protein context may result, among other things, in reduced centromere loading, a less functional CenH3 protein and/or a reduced functionality in the separation of chromosomes during cell division. One or more active mutations may be introduced into the CenH3-encoding polynucleotide by any of several methods well-known to the skilled person, for example, by random mutagenesis, such as induced by treatment of seeds or plant cells with chemicals or radiation, targeted mutagenesis, the application of endonucleases, by generation of partial or complete protein domain deletions, or by fusion with heterologous sequences.

A plant may be made to lack the endogenous CenH3-encoding polynucleotide by knocking out or inactivating the endogenous CenH3-encoding polynucleotide. Alternatively, the endogenous CenH3-encoding polynucleotide may be modified to encode an inactive or non-functional CenH3 protein.

The modified plant comprising the CenH3-encoding polynucleotide having one or more active mutations as taught herein may be crossed to a wild-type plant either as a pollen parent or as an ovule parent. In an embodiment, a CenH3 protein having one or more active mutations may comprise 1, 2, 3, 4, 5, 6, 7, 8, 9, 10, 12, 15, 20 or more amino acid changes relative to the endogenous CenH3 protein. In an embodiment, a CenH3-encoding polynucleotide having one or more active mutations has 70, 75, 80, 85, 90, 95, 96, 97, 98, 99, 99.5 percent sequence identity to the endogenous CenH3-encoding polynucleotide, preferably over the full length. The skilled person would readily be able to ascertain whether or not a modified plant as taught herein comprises one or more active mutations. For example, the skilled person may make use of predictive tools such as SIFT (Kumar P, Henikoff S, Ng P C. (2009) Predicting the effects of coding non-synonymous variants on protein function using the SIFT algorithm. Nat Protoc; 4(7): 1073-81. doi: 10.1038/nprot.2009.86) to propose such active mutation. The one or more active mutations may then be made in a plant, and expression of endogenous CenH3 protein in the plant should be knocked out. The plant may be considered to comprise one or more active mutations when the percentage of haploid progeny or progeny with aberrant ploidy that is generated upon crossing with a wild-type plant is at least 0.1, 0.5, 1, 5, 10, 20 percent or more.

Crossing a plant that lacks an endogenous CenH3-encoding polynucleotide, or that lacks expression of endogenous CenH3 protein, and that expresses a CenH3 protein having one or more active mutations either as a pollen or as an ovule parent with a wildtype plant (i.e., it expresses an endogenous CenH3 protein) results in progeny that is haploid or shows aberrant ploidy. Such a plant comprises only chromosomes of the parent that expresses the endogenous CenH3 protein, and no chromosomes of the plant expressing the CenH3 protein having one or more active mutation.

The term "aberrant ploidy" as used herein refers to a situation where a cell comprises an aberrant or abnormal number of sets of chromosomes. For instance, a cell having one or three sets of chromosomes per cell when the usual number is two is a cell having aberrant ploidy. In the present invention, the active mutant CenH3 proteins and methods using them, can be used to generate mutant plants having aberrant ploidy, e.g., to generate haploid plants while the non-mutant plant is diploid. The haploid plants can be used to accelerate breeding programs to create homozygous lines and obviate the need for inbreeding.

The term "chimeric construct", "chimeric gene", "chimeric polynucleotide" or chimeric nucleic acid" (and similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains (1) polynucleotides (e.g., DNA), including regulatory and coding polynucleotides that are not found together in nature (i.e., at least one of polynucleotides is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In a preferred aspect of the present invention the chimeric construct, chimeric gene, chimeric polynucleotide or chimeric nucleic acid comprises an expression cassette comprising a polynucleotides of the present invention under the control of regulatory polynucleotides, particularly under the control of regulatory polynucleotides functional in plants.

The term "chromosome" is used herein as recognized in the art as meaning the self-replicating genetic structure in the cellular nucleus containing the cellular DNA and bearing the linear array of genes.

A "coding polynucleotide" is a polynucleotide that is transcribed into RNA, such as mRNA, rRNA, tRNA, snRNA, sense RNA or antisense RNA. Preferably the RNA is then translated in an organism to produce a protein. It may constitute an "uninterrupted coding polynucleotide", i.e., lacking an intron, such as in a cDNA, or it may include one or more introns bounded by appropriate splice junctions. An "intron" is a poly(ribo)nucleotide which is contained in the primary transcript but which is removed through cleavage and religation of the RNA within the cell to create the mature mRNA that can be translated into a protein.

The term "doubled haploid plant" as used herein refers to a genotype formed when haploid cells undergo chromosome doubling. Artificial production of doubled haploids is important in plant breeding. Doubled haploids can be produced in vivo or in vitro. Haploid embryos are produced in vivo by parthenogenesis, pseudogamy, or chromosome elimination. A wide variety of in vitro methods are known for generating doubled haploid organisms from haploid organisms. A non-limiting example of a method for generating doubled haploid in vitro consist of treating somatic haploid cells, haploid embryos, haploid seeds, or haploid plants produced from haploid seeds with a chromosome doubling agent such as colchicine. In the present invention, homozygous double haploid plants can be regenerated from haploid cells by contacting the haploid cells with chromosome doubling agents, such as colchicine, anti-microtubule herbicides, or nitrous oxide to create homozygous doubled haploid cells. Methods of chromosome doubling are disclosed in, for example, U.S. Pat. Nos. 5,770,788; 7,135,615, and US Patent Publication Nos. 2004/0210959 and 2005/0289673; Antoine-Michard, S. et al., Plant Cell, Tissue Organ Cult., Cordrecht, the Netherlands, Kluwer Academic Publishers 48(3):203-207 (1997); Kato, A., Maize Genetics Coopera- tion Newsletter 1997, 36-37; and Wan, Y. et al., Trends Genetics 77: 889-892 (1989). Wan, Y. et al., Trends Genetics 81: 205-21 1 (1991), the disclosures of which are incorpo- rated herein by reference. Double haploid plants can be further crossed to other plants to generate F1, F2, or sub- sequent generations of plants with desired traits. Conven- tional inbreeding procedures take seven generations to achieve approximately complete homozygosity, whereas doubled haploidy achieves it in one generation.

The term "E0" refers to the edited plant in the first instance. That is, a plant cell which is edited by, e.g., CRISPR, and then allowed to mature into a plant has become the E0 plant. An E1 plant is the edit-comprising progeny (usually but not necessarily self-fertilized) of the E0. Likewise, an E2 plant is the edit-comprising progeny (usually but not necessarily self-fertilized) of the E1 plant. An E3, E4, E5, etc., plant is likewise generationally removed from the E0 plant.

The terms "gene editing," "editing," "genome editing," "GE," and the like refer to site-specific mutations made at a target sequence. This may also be referred to as "targeted mutagenesis." As used herein, the term "targeted mutagen- esis" or "mutagenesis strategy" refers to any method of mutagenesis that results in the intentional mutagenesis of a chosen gene. Targeted mutagenesis includes the methods CRISPR, TILLING, TALEN, and other methods not yet discovered but which may be used to achieve the same outcome. Mutagenesis may be performed in accordance with any of the techniques known in the art, such as, and not limited to, synthesizing an oligonucleotide having one or more mutations within the sequence of a particular regula- tory sequence. In particular, site-specific mutagenesis is a technique useful in the preparation of promoter mutants, through specific mutagenesis of the underlying DNA. RNA- guided endonucleases ("RGEN," e.g., CRISPR/Cas9) may also be used. The technique further provides a ready ability to prepare and test sequence variants, for example, incor- porating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleo- tides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered. See generally, U.S. Pat. No. 10,285,348, incorporated by refer- ence herein in its entirety.

The terms "edited N-terminal tail" or "edited N-terminal domain" are used interchangeably here throughout.

The term "endogenous" as used in the context of the present invention in combination with protein or gene means that said protein or gene originates from the plant in which it is still contained. Often an endogenous gene will be present in its normal genetic context in the plant. In another context, the term "endogenous" can refer to normal func- tions of a cell. For example and not by way of limitation, "endogenous DNA repair" refers to a cell's normal DNA repair mechanisms, enzymes, and processes.

The term "expression" when used with reference to a polynucleotide, such as a gene, ORF or portion thereof, or a transgene in plants, refers to the process of converting genetic information encoded in a gene into RNA (e.g., mRNA, rRNA, tRNA, or snRNA) through "transcription" of the gene (i.e., via the enzymatic action of an RNA poly- merase), and into protein where applicable (e.g. if a gene encodes a protein), through "translation" of mRNA.

Gene expression can be regulated at many stages in the process. For example, in the case of antisense or dsRNA constructs, respectively, expression may refer to the tran- scription of the antisense RNA only or the dsRNA only. In embodiments, "expression" refers to the transcription and stable accumulation of sense (mRNA) or functional RNA. "Expression" may also refer to the production of protein.

The terms "homology", "sequence similarity" or "sequence identity" of nucleotide or amino acid sequences mean a degree of identity or similarity of two or more sequences and may be determined conventionally by using known software or computer programs such as the Best-Fit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2:482-489 (1981), to find the best segment of identity or similarity between two sequences. Sequence comparison between two or more polynucleotides or poly- peptides is generally performed by comparing portions of the two sequences over a comparison window to identify and compare local regions of sequence similarity. The comparison window is generally from about 20 to 200 contiguous nucleotides. Gap performs global alignments: all of one sequence with all of another similar sequence using the method of Needleman and Wunsch, J. Mol. Biol. 48:443- 453 (1970). When using a sequence alignment program such as BestFit to determine the degree of DNA sequence homol- ogy, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blo- sum80, may be selected to optimize identity, similarity or homology scores.

The term "locus" refers to a position (e.g., of a gene, a genetic marker, or the like) on a chromosome of a given species.

The term "primer", as used herein, refers to an oligo- nucleotide which is capable of annealing to the amplification target allowing a DNA polymerase to attach, thereby serving as a point of initiation of DNA synthesis when placed under conditions in which synthesis of primer extension product is induced, e.g., in the presence of nucleotides and an agent for polymerization such as DNA polymerase and at a suitable temperature and pH. The (amplification) primer is prefer- ably single stranded for maximum efficiency in amplifica- tion. Preferably, the primer is an oligodeoxyribonucleotide. The primer is generally sufficiently long to prime the syn- thesis of extension products in the presence of the agent for polymerization. The exact lengths of the primers will depend on many factors, including temperature and composition (A/T and G/C content) of primer. A pair of bi-directional primers consists of one forward and one reverse primer as commonly used in the art of DNA amplification such as in PCR amplification. It will be understood that "primer," as used herein, may refer to more than one primer, particularly in the case where there is some ambiguity in the information regarding the terminal sequence(s) of the target region to be amplified. Hence, a "primer" includes a collection of primer oligonucleotides containing sequences representing the possible variations in the sequence or includes nucleotides which allow a typical base pairing. The oligonucleotide primers may be prepared by any suitable method. Methods for preparing oligonucleotides of specific sequence are known in the art, and include, for example, cloning and restriction of appropriate sequences, and direct chemical synthesis. Chemical synthesis methods may include, for example, the phospho di or tri-ester method, the diethylphosphoramidate method and the solid support method disclosed in, for example, U.S. Pat. No. 4,458,066. The primers may be labeled, if desired, by incorporating means detectable by, for instance, spectroscopic, fluorescence, photochemical, biochemical, immunochemical, or chemical means. Template-dependent extension of the oligonucleotide primer(s) is catalyzed by a polymerizing agent in the presence of adequate amounts of the four deoxyribonucleotide triphosphates (dATP, dGTP, dCTP and dTTP, i.e. dNTPs) or analogues, in a reaction medium which is comprised of the appropriate salts, metal cations, and pH buffering system. Suitable polymerizing agents are enzymes known to catalyze primer- and template-dependent DNA synthesis. Known DNA polymerases include, for example, *E. coli* DNA polymerase I or its Klenow fragment, T4 DNA polymerase, and Taq DNA polymerase. The reaction conditions for catalyzing DNA synthesis with these DNA polymerases are known in the art. The products of the synthesis are duplex molecules consisting of the template strands and the primer extension strands, which include the target sequence. These products, in turn, serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount may vary, and is determined by the function which the product polynucleotide is to serve. The PCR method is well described in handbooks and known to the skilled person. After amplification by PCR, the target polynucleotides may be detected by hybridization with a probe polynucleotide which forms a stable hybrid with that of the target sequence under low, moderate or even highly stringent hybridization and wash conditions. If it is expected that the probes will be essentially completely complementary (i.e., about 99% or greater) to the target sequence, highly stringent conditions may be used. If some mismatching is expected, for example if variant strains are expected with the result that the probe will not be completely complementary, the stringency of hybridization may be lessened. However, conditions are typically chosen which rule out nonspecific/adventitious binding. Conditions, which affect hybridization, and which select against nonspecific binding are known in the art, and are described in, for example, Sambrook and Russell, 2001. Generally, lower salt concentration and higher temperature increase the stringency of hybridization conditions. "PCR primer" is preferably understood within the scope of the present invention to refer to relatively short fragments of single-stranded DNA used in the PCR amplification of specific regions of DNA.

The terms "protein," "peptide" and "polypeptide" are used interchangeably herein.

The term "promoter" refers to a polynucleotide, usually upstream (5') of its coding polynucleotide, which controls the expression of the coding polynucleotide by providing the recognition for RNA polymerase and other factors required for proper transcription.

The term "site-directed nuclease" refers to any enzyme guided by a nucleotide sequence to a target sequence within a strand of DNA. The site-directed nuclease is preferably CRISPR-based, but could also be a meganuclease, a transcription-activator like effector nuclease (TALEN), or a zinc finger nuclease. Site-directed nuclease(s) may be referred to by the acronym "SDN." SDNs include but are not limited to meganucleases (MNs), zinc-finger nucleases (ZFNs), transcription-activator like effector nucleases (TALENs), Cas9 nuclease, Cpf1 (Cas12a) nuclease, dCas9-FokI, dCpf1-FokI, chimeric Cas9-cytidine deaminase, chimeric Cas9-adenine deaminase, chimeric FEN1-FokI, and Mega-TALs, a nickase Cas9 (nCas9), chimeric dCas9 non-FokI nuclease and dCpf1 non-FokI nuclease; and further wherein the guide nucleic acid is a guide RNA.

The terms "stringent conditions" or "stringent hybridization conditions" include reference to conditions under which a polynucleotide will hybridize to its target sequence to a detectably greater degree than other sequences (e.g., at least 2-fold over background). Stringent conditions are sequence-dependent and will be different in different circumstances. By controlling the stringency of the hybridization and/or washing conditions, target polynucleotides can be identified which are 100% complementary to the probe (homologous probing). Alternatively, stringency conditions can be adjusted to allow some mismatching in sequences so that lower degrees of similarity are detected (heterologous probing). Typically, stringent conditions will be those in which the salt concentration is less than approximately 1.5 M Na ion, typically about 0.01 to 1.0 M Na ion (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions also may be achieved with the addition of destabilizing agents such as formamide. Exemplary low stringency conditions include hybridization with a buffer solution of 30 to 35% formamide, 1 M NaCl, 1% SDS (w/v; sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the Tm can be approximated from the equation of Meinkoth and Wahl (Anal. Biochem., 138:267-284, 1984): Tm=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen, Laboratory Techniques in Biochemistry and Molecular Biology Hybridization with Nucleic Acid Probes, Part I, Chapter 2 "Overview of principles of hybridization and the strategy of nucleic acid probe assays", Elsevier, N.Y. (1993); and Current Protocols in Molecular Biology, Chapter 2, Ausubel, et al., eds., Greene Publishing and Wiley-Interscience, New York (1995). Methods of stringent hybridization are known in the art which conditions can be calculated by means known in the art. This is disclosed in Sambrook et al., Molecular Cloning: A Laboratory Manual, 2nd Ed., Cold Spring Harbor Laboratory Press, 1989, Cold Spring Harbor, N.Y. and Current Protocols in Molecular Biology, Ausebel et al, eds., John Wiley and Sons, Inc., 2000. Methods of determining percent sequence identity are known in the art, an example of which is the GCG computer sequence analysis software (GCG, Inc, Madison Wis.).

As used herein, the term "restored frame shift" ("RFS") refers to a mutation or series of mutations in a gene which, individually or in combination, interrupts the coding sequence of a gene yet does not alter the frame of the coding sequence. This may also be referred to as "restoring frame synchronization." For example, a DNA coding sequence comprises a series of codons. Each codon comprises three nucleotides, and each codon-when transcribed into RNA-codes for one amino acid upon translation. An insertion/deletion mutation ("indel") of one or two nucleotides into the coding sequence will cause a shift in the coding frame (a "frame shift"). However, insertions or deletions, whether individually or in combination, which occur cumulatively as a multiple of three will restore the codons to its original frame, even if the coding sequence itself is altered. See, e.g., B. N. Ames and H. J. Whitfield, Jr., *Frameshift Mutagenesis in Salmonella*, COLD SPRING HARB. SYMP. QUANT. BIOL. 31:221-225 (1966). For example, and within the scope of this definition, a sequence comprising at least two indel mutation deletions—whether consecutive or not—and in which the indel mutations cause the reading frame to be restored to its original frame is a sequence comprising a restored frameshift mutation. The term "engineered restored frame shift" may also be used to describe a RFS mutation which has been created by genome editing or genome modification.

As used herein, the term "large deletion" ("LD") refers to a mutation which causes the loss of several consecutive nucleotides. In particular, a large deletion refers to the loss of 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100 or more nucleotides. In some embodiments, the sequence lost in an LD will be a multiple of 3 (i.e., 3, 6, 9, 12, 15, 18, 21, 24, 27, 30, etc.) In other embodiments, an LD mutation may also occur in conjunction with an indel mutation elsewhere in the same sequence, thereby causing a restored frame shift mutation.

In the context of the present invention, the use of the term "wildtype" or "wildtype plant" refers to a plant which does not carry a mutant CenH3 protein or gene (i.e., does not comprise one or more active mutations taught here) and which endogenously expresses or produces functional CenH3 genes and proteins.

DETAILED DESCRIPTION

Here, we induced alternative splicing in wheat (*Triticum aestivum*) by applying CRISPR-Cas9 to edit cis-splicing sequences including 5' and 3' splice sites. We chose wheat as the target model organism because wheat is hexaploid, which gives wheat functional genomic redundancy. As a target gene, we chose the centromeric protein-encoding gene CENTROMERIC HISTONE 3 ("CenH3") because modifications in this gene should produce plants with value for crop breeding. CenH3 is responsible for the faithful segregation of chromosomes during cell division. Unlike H3 and other conventional histones, CENH3 has a long, hypervariable N-terminal tail. See J. Monen, et al. *Separase Cleaves the N-Tail of the CENP-A Related Protein CPAR-1 at the Meiosis I Metaphase-Anaphase Transition in C. elegans*, PLoS ONE 10:e0125382 (2015). Directed or natural modification of the tail triggers compensatory changes in the kinetochore, which may enable CENH3 to drive speciation through impairing meiosis or inhibiting zygotic chromosome segregation. See I. Lermontova, et al., *Knockdown of CENH3 in Arabidopsis reduces mitotic divisions and causes sterility by disturbed meiotic chromosome segregation*, PLANT J 68:40-50 (2011) and M. Ravi and R. Bondada, *Genome Elimination by Tailswap CenH3: In Vivo Haploid Production in Arabidopsis thaliana*, METHODS MOL BIOL 1469:77-99 (2016). Swapping the N-terminal tail with an H3 tail led to haploid induction in *Arabidopsis* (M. Ravi and S. Chan, *Haploid plants produced by centromere-mediated genome elimination*, NATURE 464:615-618 (2010)) and maize (T. Kelliher, et al., *Maternal Haploids are Preferentially Induced by CENH3-tailswap Transgenic Complementation in Maize*, FRONT. PLANT SCI., doi.org/10.3389/fpls.2016.00414 31(7):414 (2016). Haploid induction is an aberrant reproductive process that leads to ploidy reduction from one generation to the next. Haploids can be doubled to produce inbred lines, saving six generations of self-pollination normally required to generate new pure-bred stocks. Delivering the tail-swap approach to crops requires multiple generations to assemble the native allele knockout and stable insertion of transgenes. We were able to induce AS by directly editing N-terminal sequences in wheat CenH3. These novel CenH3 sequences were studied to determine whether and in what combination mutant CENH3 proteins might cause haploid induction in wheat. Under the circumstances we describe, it does.

Therefore, one embodiment of the invention is a wheat plant comprising at least an A genome, a B genome, and a D genome, wherein the B genome comprises a knock-out mutation in a CENH3 gene, and optionally wherein the D genome comprises a knock-out mutation in a CENH3 gene, and further wherein the A genome comprises a mutated CENH3 gene comprising at least one knock-down mutation at a 5' splice site of an intron. In one aspect, the knock-down mutation is a restored frame shift mutation or a large deletion mutation. In another embodiment, the wheat plant is homozygous for a knock-out mutation in a CENH3 gene in the B genome. In an alternate embodiment, the wheat plant is biallelic for a knock-out mutation in a CENH3 gene in the B genome. In another embodiment, the wheat plant is homozygous for a knock-out mutation in a CENH3 gene in the D genome. In an alternate embodiment, the wheat plant is biallelic for a knock-out mutation in a CENH3 gene in the D genome. In yet another embodiment, the wheat plant is homozygous, biallelic, or a combination thereof for a knock-out mutation in a CENH3 gene in the B genome and the D genome. In another embodiment, the wheat plant is homozygous for the restored frame shift CENH3 mutation; or it is heterozygous for the restored frame shift CENH3 mutation; or it is biallelic for the restored frame shift CENH3 mutation.

Another aspect of the invention is a method of generating a haploid-inducing wheat plant, the method comprising: (a) obtaining at least a wheat plant cell comprising at least three genomes; (b) mutating two of the three genomes to obtain homozygous knock-out mutations in a CENH3 gene; (c) mutating the third genome to obtain a homozygous knock-down mutation in a CENH3 gene; and (d) generating a wheat plant therefrom comprising homozygous knock-out mutations in a CENH3 gene of two of the three genomes and further comprising a homozygous knock-down mutation in a CENH3 gene of the third genome; whereby the wheat plant generated from step (d) produces haploid progeny when crossed with a wildtype wheat plant. In one embodiment, the three genomes comprise an A genome, a B genome, and a D genome. In another, the knock-out mutations in a CENH3 gene occur in the B and D genomes. In yet another, the knock-down mutation in a CENH3 gene occurs in the A genome. In one aspect, the knock-down mutations in a CENH3 gene in the A genome are restored frame shift mutations. In another aspect, the restored frame shift mutations are selected from the group consisting of SEQ ID NO: 56, a nucleic acid sequence 70% identical to SEQ ID NO: 56, SEQ ID NO: 63, a nucleic acid sequence 70% identical to SEQ ID NO: 63, SEQ ID NO: 69, and a nucleic acid sequence 70% identical to SEQ ID NO: 69.

Another aspect of the invention is a wheat plant comprising a mutated CENH3 gene comprising at least one deletion mutation in the N-terminal domain resulting in a frame shift, a restored frame shift, or a large deletion. Yet another aspect is a wheat plant comprising a mutated CENH3 gene comprising at least one insertion mutation in the N-terminal domain resulting in a frame shift, a restored frame shift, or a large deletion.

Another aspect of the invention is a method of generating an engineered restored frame shift in a gene of a cell, comprising: (a) contacting the genome with a site-directed nuclease ("SDN") and at least two guide nucleic acids, wherein the at least two guide nucleic acids target at least two target sequences within the gene; (b) permitting the SDN to cut the gene at the at least two target sequences, thereby losing an intervening sequence between the at least two target sequences; and allowing endogenous DNA repairs to occur; whereby the endogenous DNA repairs results in a gene having an engineered restored frame shift. In one embodiment, the lost intervening sequence of step (b) comprises (N) base pairs, where (N) is a multiple of 3.

Yet another aspect of the invention is a method of generating a haploid wheat plant, comprising: (a) obtaining a wheat plant; (b) crossing the wheat plant to the wheat plant comprising a mutated CENH3 gene; and (c) selecting a progeny generated from the crossing step; wherein the progeny is a haploid wheat plant. In one embodiment, the wheat plant of step (a) is the paternal parent. In another embodiment, the wheat plant of step (a) is the maternal parent. In another embodiment, the method comprises a further step of converting the progeny wheat plant into a doubled haploid wheat plant.

It is another aspect of the invention to provide a wheat plant comprising a mutated CENH3 allele comprising a nucleic acid sequence at least 70% identical to a sequence selected from the group consisting of SEQ ID NO: 56-73, wherein the mutation is an restored frame shift mutation, and wherein the wheat plant generates haploid progeny when crossed with a wildtype diploid wheat plant. In one embodiment, the wheat plant comprises at least one copy of the mutated CENH3 allele; in another embodiment, the wheat plant comprises at least two copies of the mutated CENH3 allele; in yet another embodiment, the wheat plant comprises at least three copies of the mutated CENH3 allele. In one embodiment, the mutated CENH3 allele comprises a nucleic acid sequence 80, 90, 95, or 100% identical to SEQ ID NO: 56-73.

EXAMPLES

Example 1: The Theory Behind Using Two N-Terminal Guide RNAs

CENH3-tailswap transgenes, when expressed heterologously in a line where the native CENH3 genes are knocked out, leads to haploid induction. See, e.g., U.S. Patent Application Publication No. 2019/0136250, incorporated herein by reference. This is called the tailswap approach. Importantly, there are no wildtype alleles in tailswap haploid inducer lines. The transgenes are inferred to have partial function and are capable of generating centromeres that are stable enough to get a normally-developing plant when homozygous. However, when the tailswap transgenes are heterologous with wildtype CENH3 in a cell, the tailswap transgenes are unstable and lead to successful haploid induction during outcross. It is critical in these designs of tailswap plants that the native CENH3 genes are knocked out and that the tailswap transgenes have significant alterations of the N-terminal domain combined with only minor, or preferably zero, alterations to the C-terminal domain. Haploid induction will not occur even if the mutant CENH3 genes encode CENH3 proteins that retain normal or near-normal functionality.

In order to achieve haploid induction in wheat, we directly edited the six CENH3α genes to knock out several copies and create modifications to the N-terminal domain (leaving the C-terminal domain intact) in still other copies. Based on our experiments measuring the gene expression of the A, B, & D genomes's CENH3α genes, we particularly focused on creating N-terminal modifications in the A genome, and knockouts in the B and D genome. If our edits were successful, we would leave zero copies of CENH3α normal (intact): All genes would be edited, but the outcomes of the editing would differ. Importantly, our editing design did not include any CENH3 transgenes-we simply wanted to create the partial function, N-terminal modified version of the A genome CENH3α through direct editing.

Typically, large alterations to regions encoding proteins can be achieved through CRISPR SDN II genome editing (also called allele replacement ("AR") or homologous recombination ("HR")), but the efficiency of that technology is extremely low in plants and only rarely achieved in wheat. Therefore, we designed an editing strategy using two guide RNAs ("gRNAs") that had the potential to modify CENH3α to create a partial loss of function allele that had a large alteration (a change of more than 5 amino acids) of the N-terminal domain and a native (unaltered) sequence for the C-terminal domain. This would require specific cuts at both guide RNA sites. We knew that the selected guide RNAs would also edit the B and D genome's copies of CENH3α, and this was intentional. In fact, due to the unpredictability of each specific editing outcome for two guide RNAs, we expected that most edited alleles would be full loss of function alleles (in A, B and D genome copies), due to frame-shifts in the coding sequence that resulted in premature stop codons that truncated the CENH3α protein product and thus were complete knockouts of the native gene. However we also knew that if all copies of the CENH3α gene were knocked out, the plants would die because partial function of CENH3α is required for plant development. If the same guides that created a modified, haploid inducer allele in the A genome could simultaneously (in the same plants) knock out the B and D genome's alleles, it would help us: The result would be a perfectly conceived haploid inducer line. Thus our aim was to use two gRNAs to mimic the tailswap transgenic system by direct editing, but our key inventive step was instead of doing any allele replacement or CENH3α transgene, we generated novel, modified variants through small indels created by the nuclease cutting at the two guide RNAs in the N-terminal domain.

However, not every pair of guides possible had the potential to combine to create an altered N-terminal domain paired with a functional C-terminal domain: Not every pair of guides could produce those "edited N-terminal tail" altered copies with partial functions and haploid induction potential. Many of the guides, after checking what the edits would lead to in terms of the amino acid sequence, would lead to premature stop codons. In other words, we realized that we had to specifically select guide RNAs that we predicted could generate a combination of edits at the target sites that would generate amino acid sequences in the mature CENH3α protein product that contained dramatic alterations to the N-terminal domain, but left the C-terminal domain unaffected. In particular, we planned to screen plants and identify those that contained such productive, N-terminal modified alleles for the A genome's copies of CENH3α, and which also had knock out alleles for the B and D genome's copies of CENH3α. Knowing that site-directed nuclease-mediated editing does not always occur right away during transformation, we reasoned that in the E0 generation, we may generate knockout (full loss of function) alleles for some of the copies and also some partial loss of function (haploid inducer) alleles for still other copies of the CENH3α gene, and that these materials may be able to generate haploids by self-pollination—assuming the male and female gametes (sperm and egg cells) have different edits or different combinations of alleles and thus potentially different centromeres. In other words, we thought we may find some haploids in the E1 generation plants. We hoped to let those observations guide us towards selecting certain E1 plants to genotype (i.e., genotype diploid siblings from populations that gave rise to some haploids upon self-pollination) and identify the E1 plants that had the partial loss of function alleles in a homozygous state. If we could do that then we would use those particular plants to test the haploid induction rate via outcrossing. In summary, we thought that once we created stably-mutated lines we would be able to test whether they were really haploid inducers, but we knew that we could not do that in the first generation because the editing may not be 'complete' by that point in time—and that we needed to test and retest haploid induction in diverse genotypes in the E1 and E2 generations.

There were many guide RNAs that we could choose from that had appropriate PAM sites, but only a select couple of pairs that could create our desired haploid inducer alleles. Regarding the desired alleles, one way that a pair of guide RNAs could generate such alleles would be for the editing of the first gRNA target site to generate a frameshift which is then restored by a compensatory mutation at the second target site that puts the transcript back into the correct (native) frame. This would result in an altered N-terminal domain amino acid sequence for the intervening string of amino acids between the two guide RNA target sites, and would restore a "native" sequence for the C-terminal domain. Such alleles we decided to call restored frame-shift ("RFS") alleles. Alternatively, simultaneous or near-simultaneous cutting at both guide RNA target sites could result in a deletion of the intervening nucleic acid sequence. In many cases that deletion would produce a frameshift in the downstream sequence, but in some cases such a deletion could happen to leave the 3' sequence of the transcript in the normal frame, such that a significant part of the N-terminal domain amino acid sequence is absent from the resulting protein product, but again the C-terminal domain is left intact. We decided to call these large deletion ("LD") alleles. Finally, in some cases, we designed the gRNAs to target the splice site junctions, and edits at these target sites may generate alternative splicing patterns (for instance, it could lead to intron retention or exon skipping). These alternatively spliced ("AS") alleles in most cases would lead to premature stop codons and genetic knock outs, but we also found one guide RNA that, if the right edits and the right splicing happened, would not lead to any premature stop codons in frame. Instead it could result in a large insertion in the mature transcript, resulting in a significant alteration in the N-terminal domain by inserting a long stretch of amino acids, but then a specific edit at the second target site could put the sequence back into frame for the C-terminal domain. In other words, with smart design of the gRNAs, splice site mutation may be predicted to generate mature mRNA transcript variants that alter the amino acid code of the N-terminal domain but restore the normal frame and sequence of the C-terminal domain.

In the following examples, we describe in detail the specific guide RNAs and edits we recovered, and the combinations of edits in specific plants. We show in detail how we generated haploid inducer lines in wheat by direct-editing the native CENH3 genes using two guide RNAs targeted to the hypervariable N-terminal domain. As designed, the plants having mutations at both target sites in some cases produced protein products that contained significant alterations to the N-terminal domain amino acid sequence, without affecting the C-terminal domain amino acid sequence. We selected and maintained edited lines that had these type of edited N-terminal tail altered alleles CENH3 alleles and made sure that the other copies of the CenH3 genes (from the A, B, and D genome) were knocked out by mutations produced by those same guide RNAs. We recovered and tested haploid induction in lines that had the desired mutations, including the combination of A genome RFS alleles with B and D genome knockouts. These same lines, with the right combination of edits that we had predicted to generate haploids, indeed led to haploid induction.

Example 2: Determining the gRNA Sequences to Edit the Fielder Genome's CENH3α Genes There are two CenH3 genes in hexaploid wheat, TaCen3α and TaCenH3β. The A, B, and D genomes's copies of both genes were cloned in the wheat variety "Fielder" with primers designed against genome sequence of the variety "Chinese Spring_v2". The sequences are given (SEQ ID NOs: 1-12). Previous studies have shown that viral-induced gene silencing ("VIGS") of TaCenH3α led to dwarfism and reduced root prolificacy, whereas silencing of TaCenH3β reduced seed set (Yuan et al., New Phytol. 206(2):839-51. 2015). As is the case for most wheat genes, the specific expression patterns and functions of each of the A, B, and D genomes's homologues are not well studied. For genome editing, we opted to modify TaCenH3α in the Fielder spring wheat variety, reasoning that mutations in this gene should not have as much of an impact on seed setting as mutations in TaCenH3β. Homologue-specific Taqman qPCR assays were used to query the expression level of TaCENH3α-A, -B, and -D (SEQ ID NOs: 13-21), in reproductive tissues (pollen, ovary, and anther) as well as juvenile leaf tissue. TaCenH3α-A and -B were expressed at high levels in anthers, pollen and ovaries while the TaCenH3α-D expression transcript was nearly absent (Table 2). In leaf, TaCenH3α-A was the predominant transcript, which may indicate that loss of function of this gene contributes to the dwarf phenotype after TaCenH3α silencing.

TABLE 2

Relative expression of TaCenH3α-A, TaCenH3α-B, and TaCenH3α-D.

| Tissue | Relative expression (Mean ± SD) | | |
| --- | --- | --- | --- |
| | TaCenH3α-A | TaCenH3α-B | TaCenH3α-D |
| Leaf | 1.88 ± 0.36 | 0.00 ± 0.00 | 0.01 ± 0.00 |
| Anther | 44.08 ± 19.62 | 46.66 ± 18.83 | 0.47 ± 0.12 |
| Pollen | 43.62 ± 23.69 | 54.21 ± 17.28 | 4.03 ± 1.38 |
| Ovary | 22.39 ± 11.50 | 15.54 ± 2.73 | 0.19 ± 0.05 |

The guide RNAs were picked using NGG PAM sites and by our predictions of the types of amino acid sequences that would result in the CENH3 protein product if certain edits were made at those target sites. Importantly, most of the guide RNAs that we considered would not able to generate combinations of edits that produced RFS or AS alleles. We focused on selecting the few pairs of gRNAs that could conceivable do so. Guide RNA1 (ACGTCGGCGACACCGGTGCG; SEQ ID NO: 25) (underlined is the approximate site of double stranded break cut induced by the CRISPR-Cas9 complex) is located at the exon 2-intron 2 junction region. This gRNA1 was driven by the TaU6 promoter. Guide RNA2 (CTTGTGG-GAGCAGGGGCAAC; SEQ ID NO: 26) targets just after the intron 3-exon 4 junction, driven by TaU6. Guide RNA2 will not edit the 3' splice acceptor site of intron 3 in most cases. The choice to use two guide RNAs was made so that we could produce significant alterations, e.g., RFS, LDs, or AS alleles, in the N-terminal domain while still leaving the C-terminal domain in frame. For instance, in some plants and edited alleles, both gRNAs will cut at the same time, resulting in a deletion of the intervening sequence. In some cases, the resulting repair will produce a frameshift which will knockout the protein. In other cases, it will produce a shortened LD transcript that lacks intron 2, all of exon 3, and a portion of exon 4, removing approximately the amino acid sequence RAGRAAAPGGAQGA (SEQ ID NO: 76) from the protein product, constituting a significant alteration of the N-terminal domain.

Alternatively, a non-simultaneous cut at both sites could generate a frameshift at gRNA1 (for instance, any indel that hits the coding sequence and is not a multiple of 3) which is restored at the gRNA2 site by a complimentary indel, thus putting the coding sequence back in its normal frame. For example, a 1 nucleotide ("nt") deletion at gRNA1 and a 1 nt insertion at gRNA2 would restore the coding frame, leading to an RFS allele. This allele would likely not be a loss of function, assuming there are no stop codons generated in the intervening frameshifted sequence. From our evaluation of the potential changes, we could see that at least one combination of edits would generate an RFS between gRNA1 and gRNA2 that did not have any stop codon in the intervening sequence. Thus, we could predict which pairs of small indels at gRNA1 and gRNA2 would combine to give us a functional RFS allele.

The two guide RNAs could generate alternatively spliced ("AS") alleles that also have the capacity to act as RFS or large insertion alleles. Guide RNA1 will cut between the GT (SEQ ID NO: 25; underlined above). That is the 5' splice donor site at the end of exon 2. AS alleles could be generated if the GT is modified such that intron 2 is not correctly spliced, leading to the retention of intron 2 in the coding sequence. Upon translation, the ribosome would read through this intron and generate a novel insertion of 44-47 amino acids, depending on the nature of the indels at gRNA1 and gRNA2. This novel insertion can be predicted by reading the new coding frame after factoring in the indels and the translation of the new mature mRNA. For instance, if gRNA1 and gRNA2 generate insertions of a single A nucleotide at both sites of TaCENH3α-A, the transcript may be alternatively spliced leading to an insertion of the amino acid sequence "VARDLPGSLPFRFVLFSVFWSDLLVTC-STECRGEPGGRRPQGGLKGQ" (SEQ ID NO: 77) with removal of the WT sequence "RRAGRAAAPGGAQGA" (SEQ ID NO: 76) from exon 3 before the normal sequence is restored by the gRNA mutation. Likewise, a different mutation at gRNA1 (for example, the deletion of GTG) combined with gRNA2 (deletion of a C) can similarly be predicted to cause alternative splicing to generate a novel insertion of "GTFPGRFLFVSSCFLFFGLTCSSPVRR-NAEASRAGGGPRGGSRG" (SEQ ID NO: 78) with the removal of the native sequence "RAGRAAAPGGAQGA" (SEQ ID NO: 76). We can also predict that other mutation combinations at gRNA1 and gRNA2 would generate frameshifts that are not put back into frame, leading to loss of function alleles. Similarly, alternative spliced alleles induced at other sites in the N-terminal region of CenH3 would not be able to generate modified mRNA sequences with a C-terminal domain restored to the normal amino acid sequence, because there would be stop codons generated in the introns retained, or after skipping one or more exons. Therefore, the gRNAs can be selected specifically for their capacity to generate large changes in the N-terminal domain while leaving the C-terminal domain intact and translated normally.

Example 3: Construct Design and Plant Transformation

After cloning the specific sequences of TaCENH3α-A, -B, and -D in the Fielder variety with primers designed against genome sequence of Chinese Spring, we selected the gRNAs according to PAM sites. gRNA1

(ACGTCGGCGACACCGGTGCG; SEQ ID NO: 25) locates in exon 2-intron 2 junction region (FIG. 1). gRNA2 (CTTGTGGGAGCAGGGGCAAC; SEQ ID NO: 26) targets just after the intron 3-exon 4 junction. SpCas9 gene was wheat codon-optimized with two NLSs at both ends and driven by sugarcane Ubi promoter with two enhancers. The gRNA cassettes including the wheat U6 promoter and gRNA scaffolds was synthesized by GenScript (www.genscript-.com) and cloned into a binary vector, Construct 24194 (SEQ ID NO: 74).

Fielder was used for transformation, a spring wheat inbred. Immature embryos about 2.0-2.5 mm in diameter were harvested, sterilized with 70% ethanol for 1 min and 1% sodium hypochlorite for 10 min. After sterilization, immature embryos were isolated by scalpel and spatula into a small tube and centrifuged at 20,000×g at 4° C. for 10 min in inoculation medium. The isolated embryos were infected with *Agrobacterium* for 5 min, then transferred to co-cultivation medium at 23° C. in the dark for 2 days. The embryo axis was excised from the immature embryos before transferring to resting medium, cultured at 25° C. in the dark for 5 days, then transferred to selection medium containing mannose 15 g/L. See Y. Ishida, et al., Wheat (*Triticum aestivum* L.) *Transformation Using Immature Embryos*, METHODS IN MOLECULAR BIOLOGY 1223: 189-198 (2015). After 4 weeks, the vigorously grown calli were transferred to regeneration media to generate green plants. Surviving plants went through Taqman check, which analyzed the presence or absence of DNA segments from the transgenic DNA insertion; of these, only plants positive for 35S and PMI Taqman assays were sent to the greenhouse.

Example 4: Sequencing E0 Edited Plants

Genomic DNA was isolated from juvenile leaves of Tagman positive E0 plants. Sequencing was performed with high fidelity DNA polymerase, namely KOD-Plus-Neo (source: TOYOBO Life Science). TaCenH3α-A allele specific primers were used (FA, SEQ ID NO: 50; R3, SEQ ID NO: 51). PCR was performed as follows: 95° C. 5 min; 35 cycles of 95° C. 30 sec, 65° C. 30 sec, 68° C. 1 min; 68° C. 10 min. PCR reaction mixture comprises 11.5 μl distilled water, 2.5 μl 10×PCR buffer for KOD-Plus-Neo, 1 μl 2 mM dNTPs, 1 μl 25 mM MgSO₄, 1 μl KOD-Plus-Neo DNA polymerase, 1 μl forward primer FA (10 μM), 1 μl reverse primer R3 (10 μM), and 1 μl genomic DNA. PCR products were sequenced directly via SQ-1 primer (SEQ ID NO: 79) or cloned into pEASY-Blunt Zero cloning vector (Transgen Biotech). M13R (SEQ ID NO: 52) and M13F (SEQ ID NO: 53) were used for colony sequencing.

Example 5: Wheat Event A004A

The wheat event A004A exhibited haploid induction. The event number A004A is one of hundreds of transgenic plants that were produced via transformation of construct 24194. Tagman assay followed by direct sequencing indicated that the genotype for the TaCENH3α genes were AA*BBdd at E0 seedling stage. Here, a capital letter indicates a wild-type TaCENH3α allele without editing, a lower-case letter indicates a loss-of-function of allele, and a capital letter with an asterisk (*) indicates a restored frame shift (RFS), large deletion (LD) or alternatively spliced (AS) allele, which means a putative haploid inducer allele. The A004A plant A* allele contains an adenine insertion at the target site for gRNA 1, and another adenine insertion at the target site of gRNA2 (SEQ ID NO:56). The adenine insertion at gRNA1 is actually in the intron, 3 bp downstream from the end of Exon 2, and right after the 5' splice junction. It does not itself disrupt the coding sequence, but it may alter the splicing pattern in some instances. The adenine insertion at gRNA2 is in Exon 3, and shifts the frame of the coding sequence. Prediction of the splicing pattern induced by the insertion of an Adenine at the gRNA1 target site indicates that this may be an AS allele that exhibits intron retention (IR) of intron number 2, because having an extra adenine after the 5' splice donor site can alter the initiation of intron removal, triggering alternative splicing. Alternative splicing in this case would to an insertion of many amino acids leading into exon 3. If there were alternative splicing, analysis of the outcome indicates that the sequences in exon 3 would be out of frame until the gRNA2 edit, which is another insertion of an adenine, restores the normal frame and amino acid code for the C-terminal domain.

To verify that the A004A A* allele is alternatively spliced and produces a putative haploid inducer allele, we examined the mature mRNA sequences of the CENH3α-A gene in A004A juvenile stage E0 leaf. Total RNA of juvenile leaves was extracted using INVITROGEN TRIzol following manufacturer's instructions. cDNA was synthesized from 1 mg of total RNA via Superscript III first-strand synthesis system (Invitrogen) with oligo-dT primer. KOD-Plus-Neo (TOYOBO) was used to amplify TaCenH3α-A transcripts with primers F1 (SEQ ID NO:54) and R1 (SEQ ID NO:55). PCR performed according to manufacturers instructions and as follows: 95° C. 5 min; 35 cycles of 95° C. 30 sec, 62° C. 20 sec, 68° C. 20 sec, 35 cycles; 68° C. 10 min. PCR reaction mixture comprises 11.5 μl distilled water, 2.5 μl 10×PCR buffer for KOD-Plus-Neo, 1 μl 2 mM dNTPs, 1 μl 25 mM MgSO₄, 1 μl KOD-Plus-Neo, 1 μl F1 primer (10 μM), 1 μl R1 primer (10 μM), and 1 μl cDNA. PCR product was purified by GeneJET PCR Purification Kit (Thermo Scientific) and cloned into pEASY-Blunt Zero cloning vector (Transgen Biotech). Primers M13R and M13F were used for colony sequencing. Several clones per PCR product were sequenced and analyzed by Vector NTI software (Invitrogen). Relative expression of splicing variants were calculated by number of clones. Analysis of the PCR sequencing of the colonies indicated the TaCENH3α-A mRNA in A004A has two transcripts, indicative of alternative splicing. One of the transcripts (SEQ ID NO:58), found in 8 out of 18 (44%) of colonies, was spliced using the canonical 5' splice site. For these transcripts, normal splicing of Intron 2 means that the gRNA1 edit did not impact the amino acid translation of the mature mRNA; however, the gRNA2 edit caused a frame-shift. So, in this instance the constitutively spliced mature mRNAs are actually knockout transcripts. On the other hand, 10 out of 18 (56%) of the colonies had mature mRNA transcripts with intron 2 retained (SEQ ID NO:57), leading to an N terminal RFS allele which contains 47 new amino acids, thus 32 amino acids were inserted from intron 2 along with 15 amino acids that are altered by the frame-shift in exon 3. This 32aa insertion and 47aa overall change severely alters the N terminal domain of the proteins produced by translation of the RFS mRNA. Importantly, the mature mRNA sequence that we obtained in our AS allele A004A—TaCENH3α-A* is the exact mature mRNA sequence outcome that we predicted would happen. A004A E0 plant was maintained through flowering. We did not observe any abnormal phenotypes, and the E1 seeds (after self-pollination) were harvested from the spikes produced by this plant.

The ploidy level of E1 progeny seeds, produced by self-pollination of the A004A plant, was checked. The seeds were planted and the seedlings that germinated were sampled and analyzed for DNA content by flow cytometry. Haploids were obtained in the first batch of progeny plants sowed: the haploid induction rate ("HIR") was 3.8%. In the second batch of seedlings, haploids were observed again, and the HIR was 4.2%. Wheat haploids are smaller than their diploid counterparts, similar to haploids in rice and corn. Importantly, these plants either did not have both copies of the "B" allele knocked out, or did not have a restored frameshift induced by a mutation at gRNA2 target site. This suggests that only the right combination of edits at both the target sites at gRNA1 and gRNA2 in the CENH3α-A gene, when paired with a knockout of both copies of the "B" allele, is sufficient to trigger haploid induction.

In the first batch, we observed two twin-seedling plants; both seedlings were haploids based on flow cytometry check. This indicates there are two haploid embryos in one seed. Twin embryos may be caused by a disruption of ovule development, which may be triggered in part by the edits in CENH3α, although more experimental work is needed to confirm this.

While we were slightly surprised that we observed haploids after self-pollination (because normally haploids are only induced in CENH3 modifications during outcross), the continuous capacity for editing the E0 plants mean that the male and female sex cells may inherit different sequences (edits) and thus have different centromere binding and kinetochore construction than each other, leading to haploidy after selfing.

Example 6: Wheat Event C003A

Plant C003A is edited such that the TaCenH3α genotype is A*abbdd at E0 plant stage. A* is introduced by deleting a guanine in gRNA1 and inserting an adenine in gRNA2. At the protein level, there is an eleven amino acid difference in N-terminal domain compared to the wildtype sequence. SEQ ID NOs: 63-65 show the A* genomic CenH3 sequence, the A* CDS sequence, and the A* protein sequence, respectively, for C003A.

E1 seeds were produced by selfing C003A E0 plant. E1 plants with A*A*bbdd genotype were grown in the greenhouse to determine its ability to induce haploids upon outcross. A wildtype plant (Tester 03S0352-22) was selected as pollen donor. E1 C003A was manually emasculated, and pollinated with the wildtype pollen. Haploids were detected by SNP markers (SEQ ID #29-43), which can tell difference between Fielder and 03S0352-22, then confirmed by flow cytometry check. In 208 F1 plants, we obtained one haploid. This showed paternal-only genotypes for four markers but maternal genotype for one marker (KW 11091).

Example 7: Wheat Event A073A

Plant A073A had the genotype AA*B*bdd for TaCENH3α at the E0 seedling stage. The A073A A* allele has an adenine insertion, caused by gRNA 3, and a guanine deletion, caused by gRNA4 in the genomic DNA. This triggers a restored frameshift at the protein level, with a thirty-one amino acid difference between the wild type and edited versions in the N-terminal domain. This plant was highlighted as a potential progenitor of haploid inducer lines because of its capacity to generate offspring that were A*A*bbdd—an ideal genetic combination for triggering haploid induction. SEQ ID NOs: 69-71 show the A* genomic CenH3 sequence, the A* CDS sequence, and the A* protein sequence, respectively, for A073A.

E1 seeds were produced by allowing self-pollination of the A073A E0 plant. E1 plants were sequenced and those with the genotypic combination AA*bbdd were selected to be grown further in the greenhouse for determining haploid induction potential upon outcrossing. Using the tester line 03S0352-22 selected as the pollen donor, E1 edited plants were manually emasculated and hand pollinated. Haploids were detected by SNP markers that can distinguish Fielder and 03S0352-22 genotypically. The putative haploids, as identified by homozygousity for these markers, were then confirmed by flow cytometry check of total DNA content. Among 57 F1 plants, 53 were predominantly heterozygous for the SNP markers and were diploid by ploidy check, indicating that they were hybrids. In contrast, four had only paternal genomic SNP markers and were haploids by flow cytometry, amounting to a 7% outcross haploid induction rate.

E1 plants with AA*bbdd also led to E2 haploids during selfing (Table 3). We observed one haploid from 13 E2 plants (a 7.7% haploid induction rate). Meanwhile we observed several plants with partially chromosome elimination.

TABLE 3

| Ploidy level of selfed E2 plants derived from A073A. | |
| --- | --- |
| F1 plant ID | Ploidy |
| 001-11 | 1n + X (Aneuploidy) |
| 001-13 | 1n + X (Aneuploidy) |
| 001-14 | 1n + X (Aneuploidy) |
| 001-17 | 1n + X (Aneuploidy) |
| 001-18 | 1n + X (Aneuploidy) |
| 001-19 | 2n (Diploid) |
| 001-22 | 1n + X (Aneuploidy) |
| 001-23 | 1n + X (Aneuploidy) |
| 001-24 | 2n (Diploid) |
| 001-26 | 1n + X (Aneuploidy) |
| 001-27 | 2n (Diploid) |
| 001-28 | 1n (Haploid) |
| 001-30 | 2n (Diploid) |

What is claimed is:

1. A method of generating a haploid-inducing wheat plant, the method comprising: a. obtaining at least a wheat plant cell comprising an A genome, a B genome, and a D genome; b. mutating the B genome to obtain a homozygous knock-out mutation in a CENH3α gene; c. mutating the D genome to obtain a homozygous knock-out mutation in a CENH3α gene; d. mutating the A genome to obtain a knock-down mutation at a 5' splice site of an intron in a CENH3α gene; and e. generating a wheat plant therefrom; whereby the wheat plant generated from step e. produces haploid progeny when crossed with a wildtype wheat plant.

2. The method of claim 1, wherein the knock-down mutation in the CENH3α gene is a restored frame shift mutation.

3. The method of claim 2, wherein the restored frame shift mutation is selected from the group consisting of SEQ ID NO: 56, a nucleic acid sequence 98% identical to SEQ ID NO: 56, SEQ ID NO: 63, a nucleic acid sequence 98% identical to SEQ ID NO: 63, or a combination thereof.

* * * * *

SEQUENCE LISTING

Sequence total quantity: 167
SEQ ID NO: 1            moltype =   length =
SEQUENCE: 1
000

SEQ ID NO: 2            moltype = RNA  length = 20
FEATURE                 Location/Qualifiers
source                  1..20
                        mol_type = other RNA
                        organism = synthetic construct -continued

```
misc_feature           1..20
                       note = primer or gRNA
SEQUENCE: 2
acgtcggcga caccggtgcg                                                   20

SEQ ID NO: 3           moltype = RNA   length = 20
FEATURE                Location/Qualifiers
source                 1..20
                       mol_type = other RNA
                       organism = synthetic construct
misc_feature           1..20
                       note = primer or gRNA
SEQUENCE: 3
cttgtgggag caggggcaac                                                   20

SEQ ID NO: 4           moltype = RNA   length = 20
FEATURE                Location/Qualifiers
source                 1..20
                       mol_type = other RNA
                       organism = synthetic construct
misc_feature           1..20
                       note = primer or gRNA
SEQUENCE: 4
acgtcggcga caccggtgcg                                                   20

SEQ ID NO: 5           moltype = RNA   length = 20
FEATURE                Location/Qualifiers
source                 1..20
                       mol_type = other RNA
                       organism = synthetic construct
misc_feature           1..20
                       note = primer or gRNA
SEQUENCE: 5
cttgtgggag caggggcaac                                                   20

SEQ ID NO: 6           moltype = RNA   length = 20
FEATURE                Location/Qualifiers
misc_feature           1..20
                       note = primer or gRNA
source                 1..20
                       mol_type = other RNA
                       organism = synthetic construct
SEQUENCE: 6
acgtcggcga caccggtgcg                                                   20

SEQ ID NO: 7           moltype = RNA   length = 20
FEATURE                Location/Qualifiers
misc_feature           1..20
                       note = primer or gRNA
source                 1..20
                       mol_type = other RNA
                       organism = synthetic construct
SEQUENCE: 7
cttgtgggag caggggcaac                                                   20

SEQ ID NO: 8           moltype = DNA   length = 15
FEATURE                Location/Qualifiers
source                 1..15
                       mol_type = other DNA
                       organism = synthetic construct
misc_feature           1..15
                       note = primer or gRNA
SEQUENCE: 8
tggcccgcac caagc                                                        15

SEQ ID NO: 9           moltype = DNA   length = 23
FEATURE                Location/Qualifiers
misc_feature           1..23
                       note = primer or gRNA
source                 1..23
                       mol_type = other DNA
                       organism = synthetic construct
SEQUENCE: 9
gctgtatgtc cttttgcatg acg                                               23

SEQ ID NO: 10          moltype = DNA   length = 20
FEATURE                Location/Qualifiers
source                 1..20
                       mol_type = other DNA
```

-continued

```
                              organism = synthetic construct
misc_feature                  1..20
                              note = primer or gRNA
SEQUENCE: 10
agcgaatgaa acaacacacg                                              20

SEQ ID NO: 11                 moltype = DNA   length = 20
FEATURE                       Location/Qualifiers
misc_feature                  1..20
                              note = primer or gRNA
source                        1..20
                              mol_type = other DNA
                              organism = synthetic construct
SEQUENCE: 11
gaagtcggtg acctccttga                                              20

SEQ ID NO: 12                 moltype = DNA   length = 20
FEATURE                       Location/Qualifiers
source                        1..20
                              mol_type = other DNA
                              organism = synthetic construct
misc_feature                  1..20
                              note = primer or gRNA
SEQUENCE: 12
caaggaggtc accgacttct                                              20

SEQ ID NO: 13                 moltype = DNA   length = 20
FEATURE                       Location/Qualifiers
source                        1..20
                              mol_type = other DNA
                              organism = synthetic construct
misc_feature                  1..20
                              note = primer or gRNA
SEQUENCE: 13
gccttgcaag ctgtatgtcc                                              20

SEQ ID NO: 14                 moltype = DNA   length = 20
FEATURE                       Location/Qualifiers
source                        1..20
                              mol_type = other DNA
                              organism = synthetic construct
misc_feature                  1..20
                              note = primer or gRNA
SEQUENCE: 14
actagacgag tcgggacgaa                                              20

SEQ ID NO: 15                 moltype = DNA   length = 20
FEATURE                       Location/Qualifiers
misc_feature                  1..20
                              note = primer or gRNA
source                        1..20
                              mol_type = other DNA
                              organism = synthetic construct
SEQUENCE: 15
gaagtcggtg acctccttga                                              20

SEQ ID NO: 16                 moltype = DNA   length = 20
FEATURE                       Location/Qualifiers
misc_feature                  1..20
                              note = primer or gRNA
source                        1..20
                              mol_type = other DNA
                              organism = synthetic construct
SEQUENCE: 16
caaggaggtc accgacttct                                              20

SEQ ID NO: 17                 moltype = DNA   length = 18
FEATURE                       Location/Qualifiers
misc_feature                  1..18
                              note = primer or gRNA
source                        1..18
                              mol_type = other DNA
                              organism = synthetic construct
SEQUENCE: 17
acgcctcgcg agctgtat                                                18

SEQ ID NO: 18                 moltype = DNA   length = 20
FEATURE                       Location/Qualifiers
source                        1..20
```

-continued

```
                              mol_type = other DNA
                              organism = synthetic construct
misc_feature                  1..20
                              note = primer or gRNA
SEQUENCE: 18
gggtccaaga aagacacacg                                                        20

SEQ ID NO: 19                 moltype = DNA   length = 20
FEATURE                       Location/Qualifiers
source                        1..20
                              mol_type = other DNA
                              organism = synthetic construct
misc_feature                  1..20
                              note = primer or gRNA
SEQUENCE: 19
gaagtcggtg acctccttga                                                        20

SEQ ID NO: 20                 moltype = DNA   length = 20
FEATURE                       Location/Qualifiers
source                        1..20
                              mol_type = other DNA
                              organism = synthetic construct
misc_feature                  1..20
                              note = primer or gRNA
SEQUENCE: 20
caaggaggtc accgacttct                                                        20

SEQ ID NO: 21                 moltype = DNA   length = 18
FEATURE                       Location/Qualifiers
source                        1..18
                              mol_type = other DNA
                              organism = synthetic construct
misc_feature                  1..18
                              note = primer or gRNA
SEQUENCE: 21
acgcctcgcg agctgtat                                                          18

SEQ ID NO: 22                 moltype = DNA   length = 31
FEATURE                       Location/Qualifiers
source                        1..31
                              mol_type = other DNA
                              organism = synthetic construct
misc_feature                  1..31
                              note = primer or gRNA
SEQUENCE: 22
caaaacagat aaaacaaaat gtagggaatg t                                           31

SEQ ID NO: 23                 moltype = DNA   length = 23
FEATURE                       Location/Qualifiers
source                        1..23
                              mol_type = other DNA
                              organism = synthetic construct
misc_feature                  1..23
                              note = primer or gRNA
SEQUENCE: 23
ggtgcaaacg ggatgagaaa gtc                                                    23

SEQ ID NO: 24                 moltype = DNA   length = 20
FEATURE                       Location/Qualifiers
misc_feature                  1..20
                              note = primer or gRNA
source                        1..20
                              mol_type = other DNA
                              organism = synthetic construct
SEQUENCE: 24
cgactcgcct cgcgctagta                                                        20

SEQ ID NO: 25                 moltype = DNA   length = 17
FEATURE                       Location/Qualifiers
source                        1..17
                              mol_type = other DNA
                              organism = synthetic construct
misc_feature                  1..17
                              note = primer or gRNA
SEQUENCE: 25
gtaaaacgac ggccagt                                                           17

SEQ ID NO: 26                 moltype = DNA   length = 17
FEATURE                       Location/Qualifiers
```

-continued

```
misc_feature           1..17
                       note = primer or gRNA
source                 1..17
                       mol_type = other DNA
                       organism = synthetic construct
SEQUENCE: 26
caggaaacag ctatgac                                                      17

SEQ ID NO: 27          moltype = DNA  length = 15
FEATURE                Location/Qualifiers
source                 1..15
                       mol_type = other DNA
                       organism = synthetic construct
misc_feature           1..15
                       note = primer or gRNA
SEQUENCE: 27
tggcccgcac caagc                                                        15

SEQ ID NO: 28          moltype = DNA  length = 23
FEATURE                Location/Qualifiers
source                 1..23
                       mol_type = other DNA
                       organism = synthetic construct
misc_feature           1..23
                       note = primer or gRNA
SEQUENCE: 28
gctgtatgtc cttttgcatg acg                                               23

SEQ ID NO: 29          moltype = DNA  length = 17
FEATURE                Location/Qualifiers
source                 1..17
                       mol_type = other DNA
                       organism = synthetic construct
misc_feature           1..17
                       note = primer or gRNA
SEQUENCE: 29
ggttcaggcc aggcacg                                                      17

SEQ ID NO: 30          moltype = DNA  length = 19
FEATURE                Location/Qualifiers
misc_feature           1..19
                       note = primer or gRNA
source                 1..19
                       mol_type = other DNA
                       organism = synthetic construct
SEQUENCE: 30
caaatggtgc aaacgggat                                                    19

SEQ ID NO: 31          moltype = DNA  length = 15
FEATURE                Location/Qualifiers
misc_feature           1..15
                       note = primer or gRNA
source                 1..15
                       mol_type = other DNA
                       organism = synthetic construct
SEQUENCE: 31
aggtatcaga agtcg                                                        15

SEQ ID NO: 32          moltype = DNA  length = 30
FEATURE                Location/Qualifiers
misc_feature           1..30
                       note = primer or gRNA
source                 1..30
                       mol_type = other DNA
                       organism = synthetic construct
SEQUENCE: 32
gtcgttagaa agtattgtag gtgtatcatt                                        30

SEQ ID NO: 33          moltype = DNA  length = 23
FEATURE                Location/Qualifiers
misc_feature           1..23
                       note = primer or gRNA
source                 1..23
                       mol_type = other DNA
                       organism = synthetic construct
SEQUENCE: 33
ctgaatgcaa aagtcgaatg atc                                               23

SEQ ID NO: 34          moltype = DNA  length = 19
```

-continued

```
FEATURE                Location/Qualifiers
source                 1..19
                       mol_type = other DNA
                       organism = synthetic construct
misc_feature           1..19
                       note = primer or gRNA
SEQUENCE: 34
tagatgtgtc ttcaaagtt                                                  19

SEQ ID NO: 35          moltype = DNA  length = 21
FEATURE                Location/Qualifiers
source                 1..21
                       mol_type = other DNA
                       organism = synthetic construct
misc_feature           1..21
                       note = primer or gRNA
SEQUENCE: 35
cgttcgactc gctggagtag t                                               21

SEQ ID NO: 36          moltype = DNA  length = 23
FEATURE                Location/Qualifiers
source                 1..23
                       mol_type = other DNA
                       organism = synthetic construct
misc_feature           1..23
                       note = primer or gRNA
SEQUENCE: 36
cctgccgatt gtttgtttta ctg                                             23

SEQ ID NO: 37          moltype = DNA  length = 24
FEATURE                Location/Qualifiers
source                 1..24
                       mol_type = other DNA
                       organism = synthetic construct
misc_feature           1..24
                       note = primer or gRNA
SEQUENCE: 37
tagtagtaac cgcgcctccc gcac                                            24

SEQ ID NO: 38          moltype = DNA  length = 4396
FEATURE                Location/Qualifiers
source                 1..4396
                       mol_type = other DNA
                       organism = Triticum aestivum
SEQUENCE: 38
atggcccgca ccaagcaccc ggccgtcagg aagaccaagg cgccgcccaa gaagcagctc    60
gggccccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gtgcgcggga ccttcccggg tcgcttcctt ttcgtttcgt cttgttttct   300
gttttttggt ctgacttgct cgtcacctgt tcgacggaat gcagaggcga gccgggcggg   360
cggcggcccc aggggggggct caaggtgcgg ccttctttgc gcttttcggt tttccgccgc   420
gtgtttaggg ccatttccgt cttgtttggg ggtgcgcggg gcgggggctt gttttttttc   480
ctcccccctt cgttgttgcg cacattgctc gggaatgctg ccaggagcgg ttgcggttct   540
tctttgaccc ttcgggaggg ctggatcggc agtttcttcg cttccttgct ccagatttta   600
gttcatcttg taccagtaca gtagcaagat gatggatggg ggcttgtttt ttctttctcc   660
ttccttgttc cggacatttc tctggagcga cttttatgca tttcccagta ttgtcctttg   720
tccttagagg gtagtggatc ggcagttttc ttcgcctcat tggtccagat tttagtttat   780
cttgtacggt accaagatga tggatgtggc acaaagttct cagtttgggg gttgcgctct   840
tccgggcagt tgttattttg gtctgtgatg actaactcgt atctattctt gtgggagcag   900
gggctgggca acccaagcag aggaaaccac accggttcag gccaggcacg gtggcactgc   960
gggagatcag gaggtatcag aagtcggtcg actttctcat cccgtttgca ccatttgtcc  1020
gtctggtggg tacctctgtc tgtcatatcc tctcgctctc tctacaaacg atctgcagtg  1080
cagagtgtaa ttggaatatt ttgttcctga caaatttgca gatcaaggag gtcaccgact  1140
tcttctgtcc tgaaatcagc cgctggactc cccaagcgct cgtcgcgatt caagaggtca  1200
gtgctaaaac ctggcatgta ctattagatc tgatggtttg attagagtac tacaatgcag  1260
atgaattcaa tatccgaaaa ccatgaactg tggggtagat acatgtatcg ccttaattca  1320
tggtttctga atgctctgct attaattcag tttgatatat ttatttagca gcatggtatt  1380
gttttggtgg ctggtaaatc aaaactgaaa tgtgattacg agcaaaacgg tatcgattgt  1440
cgatcctgtg tgtttttgtg cacatctggt tgtttggtca agatgtgttt gtgcacatct  1500
tgcaacatga tcctgcccac acactcaaaa ctgactattg gttaggttcc atttgtctta  1560
tggaatttag ggtgtaactg agaggtgagc aagtggtagt aacgttcaat tttgattcag  1620
gatgaggata ttgtgatcca gaaaattgca tgttatggtt atgtgtccaa acgcaaatg   1680
attatgtcta tatccagtac tttagaacca gtacaacaac aaaaagtact ttagaaccag  1740
tcaagtttat tgtgcattta tacaagagtg ttgtttgcac aatagacttg ctttagtcgt  1800
ctcttgccag aaatgccttc ttctgcacaa cgagcaaaaa taacataaag ttgactatac  1860
tcagtgtggc ctaagaaatg agttgtactt tttagtcact ggcctgtgta tttgctttga  1920
attgacacat aattcccttt tcctttccct ctgcaggctg cagagtatca cctcgtcgac  1980
gtatttgaaa gggcaaatca ctgtgccatc catgcaaagc gtgttaccgt cagtaagttc  2040
```

-continued

```
tcactgaatg aaaactccct ttcttttaca atattgcgca gaaggaaaca tgccagttat    2100
gaaagagttt caattacagg atcacctttg ctttcatttg atgtgatatc tagttttgat    2160
gttgtttcaa ggttcaagaa ttctaatgat aaatgatagg atccacaatt gttatatctc    2220
tgcagctcct cgtatctgtt gtccacgaac aaacatatca aacaattcat taaaaagatg    2280
aagaagtcaa acaaacagta tatgtgcact gcatattaga tatcaaacct ggttactata    2340
cgactgatct ggcctgaccc ccgcgtcgcc tctccctggc ggcacggggg gaaccactcc    2400
ggcgccgcca ccttccctcc tccctccacc ccccacctcg ccgccgcctg aggagttcgc    2460
cggcgaagcc cggtctggct ccagggaggg tggcggcggg gcatctctct gcgaggcgtg    2520
agggcgcatc tcgtgcgcgg gcgcggcgag cttgggcggg atcgcgggcg cggctctggc    2580
tcgggctggt gaggctccgg cggtccgagg ggtgtcgcgg cgcggcgggg gtctcgctcc    2640
ggcgcgggcg gtccgagggc gcgcgggatc tggcgctcca gcaggggcgc cgtcaagggg    2700
agccgggcag ggaagctcgt caggcgggct cgtcaggcag gcgtgacgcg gggcggcggc    2760
cgcgggctgg aagccatggc gttttggcca tggtgtcgtg tgcgctcgct tctcattcgc    2820
agcttgaggt gctgctgctg agggtggtgc gcggtgaagc ttggtggtcg gcgttggaga    2880
gtgcaaggcg caacaggaat ggctccaatg atctccacgc ttctgggtgg atcagatctg    2940
cggccctcca taggggtgtg ttccgggcga aagccttgac ccgactttgt cggtgccgtc    3000
gacggcggcg ctttcgggcg tcgtttccct ccttggaggc gtcgttgtgg aactcatctt    3060
cttctatgtg gggctcgggc tctccgggtg aaaacctaag ctccagattt tccggagcgg    3120
gcgatggcgg cgtcttcgtc gtttccctct tgggggcgtt gcttgggaga gttagcttgt    3180
gcttggtgcg tttggttttc tcctacgtcg ggtttggtgg atgccggggc agcggccccg    3240
gacggctgat gaacgccgag gcggcggcct cggaaagtga tgcgcggtgc ggctccatgg    3300
ggcggggcgg tggctcggcc ttcacttggg tggcaatctt gggccacttg gctggcaggc    3360
ttgtcggtcc ggtcgacgcg ttccagaggg ggcggtctga ctttgcgtcg ggcgggcggc    3420
cccggatgtg gtgcgacgtt cgtggtctgc gagcggttgc cttgagcagc gtgggctgcg    3480
ggcagctggg tcgcgcggcg ttgctgctcg agcggagcgg tggtacgtcg gggcggcggc    3540
cccggaaggt gatgccggtt gattgcgctg ggcgtgacgg gtcgggggcg    3600
cggccccgag aaaatcactg tggcgtccag atttctgtgg caacgatgat ggtgggagcg    3660
atgtcggcga cgcggcaatg gttgcgatag tcggctcttc tccggcgtgt ccacgatatt    3720
gcctcggttt gtttgttgct gtggagtcga agctgcggcg gcgaggccct gtggtatacg    3780
atgactggtt ccaggtgtcc tttcgtcgat cttccgtcgc gcagccgccg cctggtttcg    3840
ttcttccgag ttctccgtca gaatcggagc tgcgttgtct gtccgcaggt cgacatgttg    3900
tcgagaaggg tgggctttgc cctgtgtgtt tcagtctatg cgagtgggct cggcccttgt    3960
tgttctggtt tttgcccggt tttccgtaat taactgggca attctcttct gcttaattaa    4020
tagatgaggc aatctttgcc tccctttcaa aaaaaaacct ggttactata gcaggaaatt    4080
cagggttgat tactttattt cttatctgaa ggataaacat tgtatcaaat cagaatttta    4140
tttgtaagtt acatttttttt ttacttataa aacttggaaa ctgtttttact gtgacaaata    4200
gatgccacta gaatcatgat cacatcgtgg ctgttgctat tctaacaaat aaatgctcct    4260
gaacaaatgg gaactatata tgaagatgta tggaccagca tgttcctgtt aacctgacct    4320
ttttccttttt tttgctgctg cagtgcaaaa ggacatacag cttgcaaggc gtatcggcgg    4380
gaggaggctt tggtga                                                    4396
```

```
SEQ ID NO: 39          moltype = RNA  length = 489
FEATURE                Location/Qualifiers
source                 1..489
                       mol_type = other RNA
                       organism = Triticum aestivum
SEQUENCE: 39
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacaccg    120
aggcgagccg ggcgggcggc ggccccaggg ggggctcaag gggctgggca acccaagcag    180
aggaaaccac accggttcag gccaggcacg gtggcactgc gggagatcag gaggtatcga    240
aagtcggtcg actttctcat cccgtttgca ccatttgtcc gtctgatcaa ggaggtcacc    300
gacttcttct gtcctgaaat cagccgctgg actcccaag cgctcgtcgc gattcaagag    360
gctgcagagt atcacctcgt cgacgtattt gaaagggcaa atcactgtgc catccatgca    420
aagcgtgtta ccgtcatgca aaaggacata cagcttgcaa ggcgtatcgg cgggaggagg    480
ctttggtga                                                            489
```

```
SEQ ID NO: 40          moltype = AA  length = 162
FEATURE                Location/Qualifiers
source                 1..162
                       mol_type = protein
                       organism = Triticum aestivum
SEQUENCE: 40
MARTKHPAVR KTKAPPKKQL GPRPAQRRQE TDGAGTSATP RRAGRAAAPG GAQGAGQPKQ    60
RKPHRFRPGT VALREIRRYQ KSVDFLIPFA PFVRLIKEVT DFFCPEISRW TPQALVAIQE    120
AAEYHLVDVF ERANHCAIHA KRVTVMQKDI QLARRIGGRR LW                       162
```

```
SEQ ID NO: 41          moltype = DNA  length = 4396
FEATURE                Location/Qualifiers
source                 1..4396
                       mol_type = other DNA
                       organism = Triticum aestivum
SEQUENCE: 41
atggcccgca ccaagcaccc ggccgtcagg aagaccaagg cgccgcccaa gaagcagctc    60
gggccccgcc ccgcgcagcg gcggcaggag acaggtcagc ccttccctcc ttcctccccc    120
cgtctccgc ctctcgagcg aacgccgtcg ccatttcgtc gcgagagatg gacggacgga    180
cgccccacgc atgacgctaa tgtgctcttc ctctcccttt gcagatggcg cgggcacgtc    240
ggcgacacgc gcgggacctt cccgggtcgc ttccttttcg tttcgtcttg ttttctgttt    300
tttggtctga cttgctcgtc acctgttcga cggaatgcag aggcgagccg ggcgggcggc    360
```

-continued

```
ggccccaggg ggggctcaag gtgcggcctt ctttgcgctt ttcggttttc cgccgcgtgt   420
ttagggccat ttccgtcttg tttggggggtg cgcggggcgg gggcttgttt tttttcctcc   480
cccctctgtt gttgcgcaca ttgctcggga atgctgccag gagcggttgc ggttcttctt   540
tgacccttcg ggagggctgg atcggcagtt tcttcgcttc cttgctccag attttagttc   600
atcttgtacc agtacagtag caagatgatg gatggggggct tgtttttttct ttctccttcc   660
ttgttccgga catttctctg gagcgacttt tatgcatttc ccagtattgt cctttgtcct   720
tagagggtag tggatcggca gttttcttcg cctcattggt ccagatttta gtttatcttg   780
tacggtacca agatgatgga tgtggcacaa agttctcagt ttggggggttg cgctcttccg   840
ggcagttgtt attttggtct gtgatgacta actcgtatct attcttgtgg gagcaggggc   900
aaactgggca acccaagcag aggaaaccac accggttcag gccaggcacg gtggcactgc   960
gggagatcag gaggtatcag aagtcggtcg actttctcat cccgtttgca ccatttgtcc  1020
gtctggtggg tacctctgtc tgtcatatcc tctcgctctc tctacaaacg atctgcagtg  1080
cagagtgtaa ttggaatatt ttgttcctga caaatttgca gatcaaggag gtcaccgact  1140
tcttctgtcc tgaaatcagc cgctggactc cccaagcgct cgtcgcagtt caagaggtca  1200
gtgctaaaac ctggcatgta ctattagatc tgatggtttg attagagtac tacaatgcag  1260
atgaattcaa tatccgaaaa ccatgaactg tggggtagat acatgtatcg ccttaattca  1320
tggtttctga atgctctgct attaattcag tttgatatat ttatttagca gcatggtatt  1380
gtttggtgg ctggtaaatc aaaactgaaa tgtgattacg agcaaaacgg tatcgattgt  1440
cgatcctgtg tgtttttgtg cacatctggt tgtttggtca agatgtgttt gtgcacatct  1500
tgcaacatga tcctgcccac acactcaaaa ctgactattg gttaggttcc atttgtctta  1560
tggaattttag ggtgtaactg agaggtgagc aagtggtagt aacgttcaat tttgattcag  1620
gatgaggata ttgtgatcca gaaaattgca tgttatggtt atgtgtccaa acgccaaatg  1680
attatgtcta tatccagtac tttagaacca gtacaacaac aaaaagtact ttagaaccag  1740
tcaagtttat tgtgcattta tacaagagtg ttgtttgcac aatagacttg ctttagtcgt  1800
ctcttgccag aaatgccttc ttctgcacaa cgagcaaaaa taacataaag ttgactatac  1860
tcagtgtggc ctaagaaatg agttgtactt tttagtcact ggcctgtgta tttgctttga  1920
attgacacat aattccctt tcctttccct ctgcaggctg cagagtatca cctcgtcgac  1980
gtatttgaaa gggcaaatca ctgtgccatc catgcaaagc gtgttaccgt cagtaagttc  2040
tcactgaatg aaaactccct ttcttttaca atattgcgca gaaggaaaca tgccagttat  2100
gaaagagttt caattacagg atcacctttg ctttcatttg atgtgatatc tagtttttgat  2160
gttgtttcaa ggttcaagaa ttctaatgat aaatgatagg atccacaatt gttatatctc  2220
tgcagctcct cgtatctgtt gtccacgaac aaacatatca aacaattcat taaaaagatg  2280
aagaagtcaa acaaacagta tatgtgcact gcatattaga tatcaaacct ggttactata  2340
cgactgatct ggcctgaccc ccgcgtcgcc tctccctggc ggcacggggg gaaccactcc  2400
ggcgccgcca ccttccctcc tccctccacc ccccacctcg ccgccgcctg aggagttcgc  2460
cggcgaagcc cggtctggct ccaggggaggg tggcggcggg gcatctctct gcgaggcgtg  2520
agggcgcatc tcgtgcgcgg gcgcggcgag cttgggcggg atcgcgggcg cggctctggc  2580
tcgggctggt gaggctccgg cggtccgagg ggtgtcgcgg cgcggcgggg gtctcgctcc  2640
ggcgcggcgg gtccgagggc gcgcgggatc tggcgctcca gcagggcgcg cgtcaagggg  2700
agccgggcag ggaagctcgt caggcgggct cgtcaggcag gcgtgacgcg gggcggcggc  2760
cgcgggctgg aagccatggc gttttggcca tggtgtcgtg tgcgctcgct tctcattcgc  2820
agcttgaggt gctgctgctg agggtggtgc gcggtgaagc ttggtggtcg gcgttggaga  2880
gtgcaaggcg caacaggaat ggctccaatg atctccacgc ttctgggtgg atcagatctg  2940
cggccctcca taggggtgtg ttccgggcga aagccttgac ccgactttgt cggtgccgtc  3000
gacggcggcg ctttcgggcg tcgtttccct ccttggaggc gtcgttgtgg aactcatctt  3060
cttctatgtg gggctcgggc tctccgggtg aaaacctaag ctccagattt tccggagcgg  3120
gcgatggcgg cgtcttcgtc gtttccctct tgggggcgtt gcttgggaga gttagcttgt  3180
gcttggtgcg tttggttttc tcctacgtcg ggtttggtgg atgccggggc agcggccccg  3240
gacggctgat gaacgccgag gcggcggcct cggaaagtga tgcgcggtgc ggctccatgg  3300
ggcgggggcgg tggctcggcc ttcacttggg tggcaatctt gggccacttg ggtggcaggc  3360
ttgtcggtcc ggtcgacgcg ttccagaggg ggcggtctga ctttgcgtcg gggcggcggc  3420
cccggatgtg gtgcgacgtt cgtggtctgc gagcggttgc cttgagcagc gtgggctgcg  3480
ggcagctggg tcgcgcggcg ttgctgctcg agcggagcgg tggtacgtcg gggcggcggc  3540
cccggaaggt gatgccggtt gattgcgctg ggcgtgacgg agcggtggat gtcggggcgg  3600
cggccccgag aaaatcactg tggcgtccag atttctgctg caacgatgat ggtgggagcg  3660
atgtcggcga cgcggcaatg gttgcgatag tcggctcttc tccggcgtgt ccacgatatt  3720
gcctcggttt gtttgttgct gtggagtcga agctgcggcg gcgaggccct gtggtatacg  3780
atgactggtt ccaggtgtcc tttcgtcgat cttccgtggc gccagccgtg cctggtttcg  3840
ttcttccgag ttctccgtca gaatcggagc tgcgttgtct gtccgcaggt cgacatgttg  3900
tcgagaaggg tgggctttgc cctgtgtgtt tcagtctatg cgagtgggct cggcccttgt  3960
tgttctggtt tttgcccggt tttccgtaat taactgggca atttctcttct gcttaattaa  4020
tagatgaggc aatctttgcc tccctttcaa aaaaaaacct ggttactata gcaggaaatt  4080
cagggttgat tactttattt cttatctgaa ggataaacat tgtatcaaat cagaattta  4140
tttgtaagtt acatttttt ttacttataa aacttggaaa ctgttttact gtgacaaata  4200
gatgccacta gaatcatgat cacatctgtg ctgttgctat tctaacaaat aaatgctcct  4260
gaacaaatgg gaactatata tgaagatgta tggaccagca tgttcctgtt aacctgacct  4320
ttttccttttt tttgctgctg cagtgcaaaa ggacatacag cttgcaaggc gtatcggcgg  4380
gaggaggctt tggtga                                                 4396

SEQ ID NO: 42          moltype = RNA   length = 583
FEATURE                Location/Qualifiers
source                 1..583
                       mol_type = other RNA
                       organism = Triticum aestivum
SEQUENCE: 42
atggcccgca ccaagcaccc ggccgtcagg aagaccaagg cgccgcccaa gaagcagctc    60
gggcccgcc ccgcgcagcg gcggcaggag acagatggcg cgggcacgtc ggcgacacgc   120
gcgggacctt cccgggtcgc ttcctttcg tttcgtcttg ttttctgttt tttggtctga   180
cttgctcgtc acctgttcga cggaatgcag aggcgagccg ggcgggcggc ggccccaggg   240
```

```
ggggctcaag gggcaaactg ggcaacccaa gcagaggaaa ccacaccggt tcaggccagg  300
cacggtggca ctgcgggaga tcaggaggta tcagaagtcg gtcgactttc tcatcccgtt  360
tgcaccattt gtccgtctga tcaaggaggt caccgacttc ttctgtcctg aaatcagccg  420
ctggactccc caagcgctcg tcgcgattca agaggctgca gagtatcacc tcgtcgacgt  480
atttgaaagg gcaaatcact gtgccatcca tgcaaagcgt gttaccgtca tgcaaaagga  540
catacagctt gcaaggcgta tcggcgggag gaggctttgg tga                    583

SEQ ID NO: 43              moltype = AA  length = 59
FEATURE                    Location/Qualifiers
source                     1..59
                           mol_type = protein
                           organism = Triticum aestivum
SEQUENCE: 43
MARTKHPAVR KTKAPPKKQL GPRPAQRRQE TDGAGTSATR AGPSRVASFS FRLVFCFLV     59

SEQ ID NO: 44              moltype = DNA  length = 4396
FEATURE                    Location/Qualifiers
source                     1..4396
                           mol_type = other DNA
                           organism = Triticum aestivum
SEQUENCE: 44
atggcccgca ccaagcaccc ggccgtcagg aagaccaagg cgccgcccaa gaagcagctc  60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacactg cgcgggacct tcccgggtcg cttccttttc gtttcgtctt gtttctgtt   300
ttttggtctg acttgctcgt cacctgttcg acggaatgca gaggcgagcc gggcgggcgg  360
cggcccagg ggggctcaa ggtgcggcct tctttgcgct tttcggtttt ccgccgcgtg   420
tttagggcca tttccgtctt gtttgggggt gcgcgggcg ggggcttgtt tttttcctc   480
cccccttcgt tgttgcgcac attgctcggg aatgctgcca ggacgggttg cggttcttct  540
ttgacccttc gggagggctg gatcggcagt ttcttcgctt ccttgctcca gattttagtt  600
catcttgtac cagtacagta gcaagatgat ggatggggc ttgtttttc tttctccttc   660
cttgttccgg acatttctct ggagcgactt ttatgcattt cccagtattg tcctttgtcc  720
ttagagggta gtggatcggc agttttcttc gcctcattg tccagatttt agtttatctt  780
gtacggtacc aagatgatgg atgtggcaca aagttctcag tttggggggtt gcgctcttcc  840
gggcagttgt tattttggtc tgtgatgact aactcgtatc tattcttgtg ggagcagggg  900
caactgggca acccaagcag aggaaaccac accggttcag gccaggcacg gtggcactgc  960
gggagatcag gaggtatcag aagtcggtcg actttctcat cccgtttgca ccatttgtcc  1020
gtctggtggg tacctctgtc tgtcatatcc tctcgctcca tctacaaacg atctgcagtg  1080
cagagtgtaa ttggaatatt ttgttcctga caaatttgca gatcaaggag gtcaccgact  1140
tcttctgtcc tgaaatcagc cgctggactc ccaagcgct cgtcgcgatt caagaggtca   1200
gtgctaaaac ctggcatgta ctattagatc tgatggtttg attagagtac tacaatgcag  1260
atgaattcaa tatccgaaaa ccatgaactg tggggtagat acatgtatcg ccttaattca  1320
tggtttctga atgctctgct attaattcag tttgatatat ttatttagca gcatggtatt  1380
gttttggtgg ctggtaaatc aaaactgaaa tgtgattacg agcaaaacgg tatcgattgt  1440
cgatcctgtg tgtttttgtg cacatctggt tgtttggtca agatgtgttt gtgcacatct  1500
tgcaacatga tcctgcccac acactcaaaa ctgactattg gttaggttcc atttgtctta  1560
tggaatttag ggtgtaactg agaggtgagc aagtggtagt aacgttcaat tttgattcag  1620
gatgaggata ttgtgatcca gaaaattgca tgttatggtt atgtgtccaa acgccaaatg  1680
attatgtcta tatccagtac tttagaacca gtacaacaac aaaaagtact ttagaaccag  1740
tcaagtttat tgtgcattta tacaagagtg ttgtttgcac aatagacttg ctttagtcgt  1800
ctcttgccag aaatgccttc ttctgcacaa cgagcaaaaa taacataaag ttgactatac  1860
tcagtgtggc ctaagaaatg agttgtactt tttagtcact ggcctgtgta tttgctttga  1920
attgacacat aattcccttt ccttttccct ctgcaggctg cagagtatca cctcgtcgac  1980
gtatttgaaa gggcaaatca ctgtgccatc catgcaaagc gtgttaccgt cagtaagttc  2040
tcactgaatg aaaactccct ttctttaca atattgcgca gaaggaaaca tgccagttat   2100
gaaagagttt caattacagg atcacctttg ctttcatttg atgtgatatc tagttttgat  2160
gttgtttcaa ggttcaagaa ttctaatgat aaatgatagg atccacaatt gttatatctc  2220
tgcagctcct cgtatctgtt gtccacgaac aaacatatca aacaattcat taaaaagatg  2280
aagaagtcaa acaaacagta tatgtgcact gcatattaga tatcaaacct ggttactata  2340
cgactgatct ggcctgaccc ccgcgtcgcc tctccctggc ggcacggggg gaaccactcc  2400
ggcgccgcca ccttccctcc tccctccacc cccacctcg ccgccgcctg aggagttcgc   2460
cggcgaagcc cggtctggct ccaggagggg tggcggcggg gcatctctct gcgaggcgtg  2520
agggcgcatc tcgtgcgcgg gcgcggcgag cttgggcggg atcgcgggga cggctctggc  2580
tcgggctggt gaggtccgg cggtccgagg ggtgtcgcgg cgcggcgggg gtctcgctcc   2640
ggcgcgggcg gtccgagggc gcgcgggatc tggcgctcca gcaggggcgc cgtcaagggg  2700
agccgggcag ggaagctcgt caggcgggct cgtcaggcag gcgtgacgcg gggcggcggc  2760
cgcgggctgg aagccatggc gttttggcca tggtgtcgtg tgcgctcgct tctcattcgc  2820
agcttgaggt gctgctgctg agggtggtgc gcggtgaagc tggttggtcg gcgttggaga  2880
gtgcaaggcg caacaggaat ggctccaatg atctccacgc ttctgggtgg atcagatctg  2940
cggccctcca tagggggtgtg ttccgggcga aagccttgac ccgactttgt cggtgccgtc  3000
gacggcggcg ctttcgggcg tcgtttccct ccttggaggc gtcgttgtgg aactcatctt  3060
cttctatgtg gggctcgggc tctccgggtg aaaacctaag ctccagattt tccggagcgg  3120
gcgatgggcg cgtcttcgtc gtttccctct tgggggcgtt gcttgggaga gttagcttgt  3180
gcttggtgcg tttggtttt tcctacgtcg ggtttggtgg atgccggggc agcggccccg   3240
gacggctgat gaacgccgag gcggcggcct cggaaagtga tgcgcggtgc ggctccatgg  3300
ggcgggegcg tggctcggcc ttcacttggg tggcaatctt gggccacttg ggtggcaggc  3360
ttgtcggtcc ggtcgacgcg ttccagaggg ggcggtctga ctttgcgtcg gggcggcggc  3420
cccggatgtg gtgcgacgtt cgtggtctgc gagcggttgc cttgagcagc gtgggctgcg  3480
```

-continued

```
ggcagctggg tcgcgcggcg ttgctgctcg agcggagcgg tggtacgtcg gggcggcggc    3540
cccggaaggt gatgccggtt gattgcgctg ggcgtgacgg agcggtggat gtcggggcgg    3600
cggccccgag aaaatcactg tggcgtccag atttctgtgg caacgatgat ggtgggagcg    3660
atgtcggcga cgcggcaatg gttgcgatag tcggctcttc tccggcgtgt ccacgatatt    3720
gcctcggttt gtttgttgct gtggagtcga agctgcggcg gcgaggccct gtggtatacg    3780
atgactggtt ccaggtgtcc tttcgtcgat cttccgtggc gccagccgtg cctggtttcg    3840
ttcttccgag ttctccgtca gaatcggagc tgcgttgtct gtccgcaggt cgacatgttg    3900
tcgagaaggg tgggctttgc cctgtgtgtt tcagtctatg cgagtgggct cggcccttgt    3960
tgttctggtt tttgcccggt tttccgtaat taactgggca attctcttct gcttaattaa    4020
tagatgagge aatctttgcc tccctttcaa aaaaaacct ggttactata gcaggaaatt    4080
cagggttgat tactttattt cttatctgaa ggataaacat tgtatcaaat cagaatttta    4140
tttgtaagtt acattttttt ttacttataa aacttggaaa ctgttttact gtgacaaata    4200
gatgccacta gaatcatgat cacatcgtgg ctgttgctat tctaacaaat aaatgctcct    4260
gaacaaatgg gaactatata tgaagatgta tggaccagca tgttcctgtt aacctgacct    4320
ttttcctttt tttgctgctg cagtgcaaaa ggacatacag cttgcaaggc gtatcggcgg    4380
gaggaggctt tggtga                                                    4396
```

```
SEQ ID NO: 45          moltype = RNA    length = 583
FEATURE                Location/Qualifiers
source                 1..583
                       mol_type = other RNA
                       organism = Triticum aestivum
SEQUENCE: 45
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacactg    120
cgcgggacct tcccgggtcg cttccttttc gtttcgtctt gtttctgtt ttttggtctg    180
acttgctcgt cacctgttcg acggaatgca gaggcgagcc gggcgggcgg cggccccagg    240
gggggctcaa ggggcaactg ggcaacccaa gcagaggaaa ccacaccggt tcaggccagg    300
cacggtggca ctgcgggaga tcaggaggta tcagaagtcg gtcgactttc tcatcccgtt    360
tgcaccattt gtccgtctga tcaaggaggt caccgacttc ttctgtcctg aaatcagccg    420
ctggactccc caagcgctcg tcgcgattca agaggctgca gagtatcacc tcgtcgacgt    480
atttgaaagg gcaaatcact gtgccatcca tgcaaagcgt gttaccgtca tgcaaaagga    540
catacagctt gcaaggcgta tcggcgggag gaggctttgg tga                       583
```

```
SEQ ID NO: 46          moltype = AA    length = 136
FEATURE                Location/Qualifiers
source                 1..136
                       mol_type = protein
                       organism = Triticum aestivum
SEQUENCE: 46
MARTKHPAVR KTKAPPKKQL GPRPAQRRQE TDGAGTSATL RGTFPGRFLF VSSCFLFFGL    60
TCSSPVRRNA EASRAGGGPR GGSRGNWATQ AEETTPVQAR HGGTAGDQEV SEVGRLSHPV    120
CTICPSDQGG HRLLLS                                                     136
```

```
SEQ ID NO: 47          moltype = DNA    length = 4396
FEATURE                Location/Qualifiers
source                 1..4396
                       mol_type = other DNA
                       organism = Triticum aestivum
SEQUENCE: 47
atggcccgca ccaagcaccc ggccgtcagg aagaccaagg cgccgcccaa gaagcagctc    60
gggccccgcc ccgcgcagcg gcggcaggag acaggtcagc ccttccctcc ttcctccccc    120
cgtctcccgc ctctcgagcg aacgccgtcg ccatttcgtc gcgagagatg gacggacgga    180
cgccccacgc atgacgctaa tgtgctcttc ctctcccttt gcagatggcg cgggcacgtc    240
ggcgacaccg gtgcgcggga ccttcccggg tcgcttcctt ttcgtttcgt cttgttttct    300
gtttttggt ctgacttgct cgtcacctgt tcgacggaat gcagaggcga gccgggcggg    360
cggcggcccc aggggggggct caaggtgcgc ccttctttgc gcttttcggt tttccgccgc    420
gtgtttaggg ccatttccgt cttgtttggg ggtgcgcggg gcggggggctt gttttttttc    480
ctcccccctt cgttgttgcg cacattgctc gggaatgctg ccaggagcgg ttgcggttct    540
tctttgaccc ttcgggaggg ctggatcggc agtttcttcg cttccttgct ccagattta    600
gttcatcttg taccagtaca gtagcaagat gatggatggg ggcttgtttt ttctttctcc    660
ttccttgttc cggacatttc tctggagcga cttttatgca tttcccagta ttgtcctttg    720
tccttagagg gtagtggatc ggcagttttc ttcgcctcat tggtccagat tttagtttat    780
cttgtacggt accaagatga tggatgtggc acaaagttct cagtttgggg gttgcgtct    840
tccgggcagt tgttatttg gtctgtgatg actaactcgt atctattctt gtgggagcag    900
gggctgggca acccaagcag aggaaaccac accggttcag gccaggcacg gtggcactgc    960
gggagatcag gaggtatcag aagtcggtcg actttctcat cccgtttgca ccatttgtcc    1020
gtctggtggg tacctctgtc tgtcatatcc tctcgctctc tctacaaacg atctgcagtg    1080
cagagtgtaa ttggaatatt ttgttcctga caaatttgca gatcaaggag gtcaccgact    1140
tcttctgtcc tgaaatcagc cgctggactc cccaagcgct cgtcgcgatt caagaggtca    1200
gtgctaaaac ctggcatgta ctattagatc tgatggtttg attagagtac tacaatgcag    1260
atgaattcaa tatccgaaaa ccatgaactg tggggtagat acatgtatcg ccttaattca    1320
tggtttctga atgctctgct attaattcag tttgatatat ttatttagca gcatggtatt    1380
gttttggtgg ctggtaaatc aaaactgaaa tgtgattacg agcaaaacgg tatcgattgt    1440
cgatcctgtg tgtttttgtg cacatctggt tgtttggtca agatgtgttt gtgcacatct    1500
tgcaacatga tcctgcccac acactcaaaa ctgactattg gttaggttcc atttgtctta    1560
tggaatttag ggtgtaactg agaggtgagc aagtggtagt aacgttcaat tttgattcag    1620
gatgaggata ttgtgatcca gaaaattgca tgttatggtt atgtgtccaa acgccaaatg    1680
attatgtcta tatccagtac tttagaacca gtacaacaac aaaaagtact ttagaaccag    1740
```

```
tcaagtttat tgtgcattta tacaagagtg ttgtttgcac aatagacttg ctttagtcgt    1800
ctcttgccag aaatgccttc ttctgcacaa cgagcaaaaa taacataaag ttgactatac    1860
tcagtgtggc ctaagaaatg agttgtactt tttagtcact ggcctgtgta tttgctttga    1920
attgacacat aattcccttt tcctttccct ctgcaggctg cagagtatca cctcgtcgac    1980
gtatttgaaa gggcaaatca ctgtgccatc catgcaaagc gtgttaccgt cagtaagttc    2040
tcactgaatg aaaactccct ttcttttaca atattgcgca gaaggaaaca tgccagttat    2100
gaaagagttt caattacagg atcacctttg ctttcatttg atgtgatatc tagttttgat    2160
gttgtttcaa ggttcaagaa ttctaatgat aaatgatagg atccacaatt gttatatctc    2220
tgcagctcct cgtatctgtt gtccacgaac aaacatatca aacaattcat taaaaagatg    2280
aagaagtcaa acaaacagta tatgtgcact gcatattaga tatcaaacct ggttactata    2340
cgactgatct ggcctgaccc ccgcgtcgcc tctccctggc ggcacggggg gaaccactcc    2400
ggcgccgcca ccttccctcc tccctccacc ccccacctcg ccgccgcctg aggagttcgc    2460
cggcgaagcc cggtctggct ccaggagggg tggcggcggg gcatctctct gcgaggcgtg    2520
agggcgcatc tcgtgcgcgg gcgcgggcga g cttgggcggg atcgcgggcg cggctctggc    2580
tcgggctggt gaggctccgg cggtccgagg ggtgtcgcgg cgcggcgggg gtctcgctcc    2640
ggcgcggggcg gtccgagggc gcgcgggatc tggcgctcca gcaggggcgc cgtcaagggg    2700
agccgggcag ggaagctcgt caggcgggct cgtcaggcag gcgtgacgcg gggcggcggc    2760
cgcggcgtgg aagccatggc gttttggcca tggtgtcgtg tgcgctcgct tctcattcgc    2820
agcttgaggt gctgctgctg agggtggtgc gcggtgaagc ttggtggtcg cgcttggaga    2880
gtgcaaggcg caacaggaat ggctccaatg atctccacgc ttctgggtgg atcagatctg    2940
cggccctcca taggggtgtg ttccgggcga aagccttgac ccgactttgt cggtgccgtc    3000
gacggcgggcg ctttcgggcg tcgtttccct ccttggaggc gtcgttgtgg aactcatctt    3060
cttctatgtg gggctcgggc tctccgggtg aaaacctaag ctccagattt tccggagcgg    3120
gcgatggcgcg cgtcttcgtc gtttccctct tggggggcgtt gcttgggaga gttagcttgt    3180
gcttggtgcg tttggtttttc tcctacgtcg ggtttggtgg atgccggggc agcggccccg    3240
gacggctgat gaacgccgag gcggcgggcct cggaaagtga tgcgcggtgc ggctccatgg    3300
ggcgggggcgg tggctcggcc ttcacttggg tggcaatctt gggccacttg ggtggcaggc    3360
ttgtcggtcc ggtcgacgcg ttccagaggg ggcggtctga cttttgcgtcg gggcggcggc    3420
cccgatgtg tgtcgcgacgtt cgtggtctgc gagcggttgc cttgagcagc gtgggctgcg    3480
ggcagctggg tcgcgcgggcg ttgctgctcg agcggagcgg tggtacgtcg gggcggcggc    3540
cccggaaggt gatgccggtt gattgcgctg ggcgtgacgg agcggtggat gtcggggcgg    3600
cggccccgag aaaatcactg tggcgtccag atttctgtgg caacgatgat ggtgggagcg    3660
atgtcggcga cgcggcaatg gttgcgatag tcggctcttc tccggcgtgt ccacgatatt    3720
gcctcggttt gtttgttgct gtggagtcga agctgcggcg gcgaggccct gtggtatacg    3780
atgactggtt ccaggtgtcc tttcgtcgat cttccgtggc gccagccgtg cctggtttcg    3840
ttcttccgag ttctccgtca gaatcggagc tgcgttgtct gtccgcaggt cgacatgttg    3900
tcgagaaggg tgggctttgc cctgtgtgtt tcagtctatg cgagtgggct cggcccttgt    3960
tgttctggtt tttgcccggt tttccgtaat taactgggca attctcttct gcttaattaa    4020
tagatgaggc aatctttgcc tccctttcaa aaaaaaacct ggttactata gcaggaaatt    4080
cagggttgat tactttatTt cttatctgaa ggataaacat tgtatcaaat cagaatttta    4140
tttgtaagtt acatttttttt ttacttataa aacttggaaa ctgttttact gtgacaaata    4200
gatgccacta gaatcatgat cacatcgtgg ctgttgctat tctaacaaat aaatgctcct    4260
gaacaaatgg gaactatata tgaagatgta tggaccagca tgttcctgtt aacctgacct    4320
ttttcctttt tttgctgctg cagtgcaaaa ggacatacag cttgcaaggc gtatcggcgg    4380
gaggaggctt tggtga    4396
```

SEQ ID NO: 48                 moltype = RNA   length = 489
FEATURE                       Location/Qualifiers
source                        1..489
                              mol_type = other RNA
                              organism = Triticum aestivum
SEQUENCE: 48
```
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacaccg    120
aggcgagccg ggcgggcggc ggccccaggg ggggctcaag gggctgggca acccaagcag    180
aggaaaccac accggttcag gccaggcacg gtggcactgc gggagatcag gaggtatcag    240
aagtcggtcg actttctcat cccgtttgca ccatttgtcc gtctgatcaa ggaggtcacc    300
gacttcttct gtcctgaaat cagccgctgg actccccaag cgctcgtcgc gattcaagag    360
gctgcagagt atcacctcgt cgacgtattt gaaaggggcaa atcactgtgc catccatgca    420
aagcgtgtta ccgtcatgca aaaggacata cagcttgcaa ggcgtatcgg cgggaggagg    480
ctttggtga    489
```

SEQ ID NO: 49                 moltype = AA   length = 162
FEATURE                       Location/Qualifiers
source                        1..162
                              mol_type = protein
                              organism = Triticum aestivum
SEQUENCE: 49
```
MARTKHPAVR KTKAPPKKQL GPRPAQRRQE TDGAGTSATP RRAGRAAAPG GAQGAGQPKQ    60
RKPHRFRPGT VALREIRRYQ KSVDFLIPFA PFVRLIKEVT DFFCPEISRW TPQALVAIQE    120
AAEYHLVDVF ERANHCAIHA KRVTVMQKDI QLARRIGGRR LW    162
```

SEQ ID NO: 50                 moltype = DNA   length = 4384
FEATURE                       Location/Qualifiers
source                        1..4384
                              mol_type = other DNA
                              organism = Triticum aestivum
SEQUENCE: 50
```
atggcccgca ccaagcaccc ggccgtcagg aagaccaagg cgccgcccaa gaagcagctc    60
```

```
gggccccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gcgcgggacc ttcccgggtc gcttcctttt cgtttcgtct tgttttctgt   300
tttttggtct gacttgctcg tcacctgttc gacggaatgc agaggcgagc cgggcgggcg   360
gcggccccag ggggggctca aggtgcggcc ttctttgcgc ttttcggttt tccgccgcgt   420
gtttagggcc atttccgtct tgtttggggg tgcgcggggc gggggcttgt ttttttttcct   480
ccccccttcg ttgttgcgca cattgctcgg gaatgctgcc aggagcggtt gcggttcttc   540
tttgaccctt cgggagggct ggatcggcag tttcttcgct tccttgctcc agatttttagt   600
tcatcttgta ccagtacagt agcaagatga tggatggggg cttgtttttt ctttctcctt   660
ccttgttccg gacatttctc tggagcgact tttatgcatt tcccagtatt gtcctttgtc   720
cttagagggt agtggatcgg cagtttttctt cgcctcattg gtccagattt tagtttatct   780
tgtacggtac caagatgatg gatgtggcac aaagttctca gtttggggggt tgcgctcttc   840
cgggcagttg ttattttggt ctgtgatgac taactcgtat ctattcttga actgggcaac   900
ccaagcagag gaaaccacac cggttcaggc caggcacggt ggcactgcgg gagatcagga   960
ggtatcagaa gtcggtcgac tttctcatcc cgtttgcacc atttgtccgt ctggtgggta   1020
cctctgtctg tcatatcctc tcgctctctc tacaaacgat ctgcagtgca gagtgtaatt   1080
ggaatatttt gttcctgaca aatttgcaga tcaaggaggt caccgacttc ttctgtcctg   1140
aaatcagccg ctggactccc caagcgctcg tcgcgattca agaggtcagt gctaaaacct   1200
ggcatgtact attagatctg atggtttgat tagagtacta caatgcagat gaattcaata   1260
tccgaaaacc atgaactgtg gggtagatac atgtatcgcc ttaattcatg gtttctgaat   1320
gctctgctat taattcagtt tgatatattt atttagcagc atggtattgt tttggtggct   1380
ggtaaatcaa aactgaaatg tgattacgag caaaacggta tcgattgtcg atcctgtgtg   1440
tttttgtgca catctggttg tttggtcaag atgtgtttgt gcacatcttg caacatgatc   1500
ctgcccacac actcaaaact gactattggt taggttccat ttgtcttatg gaatttaggg   1560
tgtaactgag aggtgagcaa gtggtagtaa cgttcaattt tgattcagga tgaggatatt   1620
gtgatccaga aaattgcatg ttatggttat gtgtccaaac gccaaatgat tatgtctata   1680
tccagtactt tagaaccagt acaacaacaa aaagtacttt agaaccagtc aagtttattg   1740
tgcatttata caagagtgtt gtttgcacaa tagacttgct ttagtcgtct cttgccagaa   1800
atgccttctt ctgcacaacg agcaaaaata acataaagtt gactatactc agtgtggcct   1860
aagaaatgag ttgtacttttt tagtcactgg cctgtgtatt tgctttgaat tgacacataa   1920
ttcccttttc ctttccctct gcaggctgca gagtatcacc tcgtcgacgt atttgaaagg   1980
gcaaatcact gtgccatcca tgcaaagcgt gttaccgtca gtaagttctc actgaatgaa   2040
aactcccttt ctttttacaat attgcgcaga aggaaacatg ccagttatga aagagtttca   2100
attacaggat cacctttgct ttcatttgat gtgatatcta gttttgatgt tgtttcaagg   2160
ttcaagaatt ctaatgataa atgataggat ccacaattgt tatatctctg cagctcctcg   2220
tatctgttgt ccacgaacaa acatatcaaa caattcatta aaaagatgaa gaagtcaaac   2280
aaacagtata tgtgcactgc atattagata tcaaacctgg ttactatacg actgatctgg   2340
cctgacccc gcgtcgcctc tccctggcgg cacgggggga accatccgg cgccgccacc   2400
ttccctcctc cctccacccc ccacctcgcc gccgcctgag gagttcgccg gcgaagcccg   2460
gtctggctcc agggagggtg gcggcggggc atctctctgc gaggcgtgag ggcgcatctc   2520
gtgcgcgggc gcggcgagct tgggcgggat cgcgggcgcg gctctggctc gggctggtga   2580
ggctccggcg gtccgagggg tgtcgcggcg cggcggggat ctcgctccgg cgcggggcct   2640
ccgagggcgc gcgggatctg gcgctccagc aggggcgccg tcaaggggag ccgggcaggg   2700
aagctcgtca ggcgggctcg tcaggcaggc gtgacgcggg gcggcggccg cgggctggaa   2760
gccatggcgt tttggccatg gtgtcgtgtg cgctcgcttc tcattcgcag cttgaggtgc   2820
tgctgctgag ggtggtgcgc ggtgaagctt ggtggtcggc ggtggagagt gcaaggcgca   2880
acaggaatgg ctccaatgat ctccacgctt ctgggtggat cagatctgcg gccctccata   2940
ggggtgtgtt ccgggcgaaa gccttgaccc gactttgtcg gtgccgtcga cggcggcgct   3000
ttcgggcgtc gtttccctcc ttggaggcgt cgttgtggaa ctcatcttct tctatgtggg   3060
gctcgggctc tccgggtgaa aacctaagct ccagattttc cggagcgggc gatgcgggcg   3120
tcttcgtcgt ttccctcttg ggggcgttgc ttgggagagt tagcttgtgc ttggtgcgtt   3180
tggtttttctc ctacgtcggg tttggtggat gccggggcag cggccccgga cggctgatga   3240
acgccgaggc ggcggcctcg gaaagtgatg cgcggtgcgg ctccatgggg cggggcggtg   3300
gctcggcctt cacttgggtg gcaatcttgg gccacttggg tggcaggctt gtcggtccgg   3360
tcgacgcgtt ccagagggggg cggtctgact ttgcgtcggg gcggcggccc cggatgtggt   3420
gcgacgttcg tggtctgcga gcggttgcct tgagcagcgt gggctgcggg cagctgggtc   3480
gcgcggcgtt gctgctcgag cggagcggtg gtacgtcggg gcggcggccc cggaaggtga   3540
tgccggttga ttgcgctggg cgtgacggag cggtggatgt cgggcgcggcg gccccgagaa   3600
aatcactgtg gcgtccagat ttctgtggca acgatgatgg tgggagcgat gtcggcgacg   3660
cggcaatggt tgcgatagtc ggctcttctc cggcgtgtcc acgatattgc ctcggtttgt   3720
ttgttgctgt ggagtcgaag ctgcggcggc gaggccctgt ggtatacgat gactggttcc   3780
aggtgtcctt tcgtcgatct tccgtggcgc cagccgtgcc tggtttcgtt cttccgagtt   3840
ctccgtcaga atcggagctg cgttgtctgt ccgcaggtcg gagaaggggtg   3900
ggctttgccc tgtgtgtttc agtctatgcg agtgggctcg gcccttgttg ttctggtttt   3960
tgcccggttt tccgtaatta actgggcaat tctcttctgc ttaattaata gatgaggcaa   4020
tctttgcctc ccttttcaaaa aaaaacctgg ttactatagc aggaaattca gggttgatta   4080
ctttatttct tatctgaagg ataaacattg tatcaaatca gaatttttatt tgtaagttac   4140
atttttttttt acttataaaa cttggaaact gtttttactgt gacaaataga tgccactaga   4200
atcatgatca catcgtggct gttgctattc taacaaataa atgctcctga acaaatggga   4260
actatatatg aagatgtatg gaccagcatg ttcctgttaa cctgaccttt ttcctttttt   4320
tgctgctgca gtgcaaaagg acatacagct tgcaaggcgt atcggcggga ggaggctttg   4380
gtga                                                                4384
```

```
SEQ ID NO: 51        moltype = RNA   length = 562
FEATURE              Location/Qualifiers
source               1..562
                     mol_type = other RNA
                     organism = Triticum aestivum
```

```
SEQUENCE: 51
atggcccgca ccaagcaccc ggccgtcagg aagaccaagg cgccgcccaa gaagcagctc  60
gggccccgcc ccgcgcagcg gcggcaggag acagatggcg cgggcacgtc ggcgacaccg  120
gcgcgggacc ttcccgggtc gcttcctttt cgtttcgtct tgttttctgt tttttggtc   180
tgacttgctc gtcacctgtt cgacggaatg cagaggcgag ccggccgggc ggcggcccca  240
gggggggctc aagaggaaac cacaccggtt caggccaggc acggtggcac tgcgggagat  300
caggaggtat cagaagtcgg tcgactttct catcccgttt gcaccatttg tccgtctgat  360
caaggaggtc accgacttct tctgtcctga aatcagccgc tggactcccc aagcgctcgt  420
cgcgattcaa gaggctgcag agtatcacct cgtcgacgta tttgaaaggg caaatcactg  480
tgccatccat gcaaagcgtg ttaccgtcat gcaaaaggac atacagcttg caaggcgtat  540
cggcgggagg aggctttggt ga                                          562

SEQ ID NO: 52          moltype = AA   length = 60
FEATURE                Location/Qualifiers
source                 1..60
                       mol_type = protein
                       organism = Triticum aestivum
SEQUENCE: 52
MARTKHPAVR KTKAPPKKQL GPRPAQRRQE TDGAGTSATP ARDLPGSLPF RFVLFSVFLV  60

SEQ ID NO: 53          moltype = DNA   length = 4401
FEATURE                Location/Qualifiers
source                 1..4401
                       mol_type = other DNA
                       organism = Triticum aestivum
SEQUENCE: 53
atggcccgca ccaagcaccc ggccgtcagg aagaccaagg cgccgcccaa gaagcagctc  60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacaccg gttgcgcggg accttcccgg gtcgcttcct tttcgtttcg tcttgttttc  300
tgttttttgg tctgacttgc tcgtcacctg ttcgacggaa tgcagaggcg agccgggcgg  360
gcggcggccc caggggggggc tcaaggtgcg gccttctttg cgcttttcgg ttttccgccg  420
cgtgtttagg gccatttccg tcttgtttgg gggtgcgcgg ggcgggggct tgttttttt   480
cctcccccct tcgttgttgc gcacattgct cgggaatgct gccaggacg gttgcggttc   540
ttctttgacc cttcgggagg gctggatcgg cagtttcttc gcttccttgc tccagatttt  600
agttcatctt gtaccagtac agtagcaaga tgatggatgg gggcttgttt tttctttctc  660
cttccttgtt ccggacattt ctctggagcg actttttatgc atttcccagt attgtccttt  720
gtccttagag ggtagtggat cggcagtttt cttcgcctca ttggtccaga ttttagttta  780
tcttgtacgg taccaagatg atggatgtgg cacaaagttc tcagtttggg ggttgcgctc  840
ttccgggcag ttgttatttt ggtctgtgat gactaactcg tatctattct tgtgggagca  900
ggggctaact gggcaaccca agcagaggaa accacaccgg ttcaggccag gcacggtggc  960
actgcgggag atcaggaggt atcagaagtc ggtcgacttt ctcatcccgt ttgcaccatt  1020
tgtccgtctg gtgggtacct ctgtctgtca tatcctctcg ctctctctac aaacgatctg  1080
cagtgcagag tgtaattgga atattttgtt cctgacaaat ttgcagatca aggaggtcac  1140
cgacttcttc tgtcctgaaa tcagccgctg gactccccaa gcgctcgtcg cgattcaaga  1200
ggtcagtgct aaaacctggc atgtactatt agatctgatg gtttgattag agtactacaa  1260
tgcagatgaa ttcaatatcc gaaaaccatg aactgtgggg tagatacatg tatcgcctta  1320
attcatggtt tctgaatgct ctgctattaa ttcagtttga tatatttatt tagcagcatg  1380
gtattgtttt ggtggctggt aaatcaaaac tgaaatgtga ttacgagcaa aacggtatcg  1440
attgtcgatc ctgtgtgttt ttgtgcacat ctggttgttt ggtcaagatg tgtttgtgca  1500
catcttgcaa catgatcctg cccacacact caaaactgac tattggttag gttccatttg  1560
tcttatggaa tttagggtgt aactgagagg tgagcaagtg gtagtaacgt tcaattttga  1620
ttcaggatga ggatattgtg atccagaaaa ttgcatgtta tggttatgtg tccaaacgcc  1680
aaatgattat gtctatatcc agtactttag aaccagtaca acaacaaaaa gtactttaga  1740
accagtcaag tttattgtgc atttatacaa gagtgttgtt tgcacaatag acttgcttta  1800
gtcgtctctt gccagaaatg ccttcttctg cacaacgagc aaaaataaca taaagttgac  1860
tatactcagt gtggcctaag aaatgagttg tactttttag tcactggcct gtgtatttgc  1920
tttgaattga cacataattc ccttttcctt tccctctgca ggctgcagag tatcacctg   1980
tcgacgtatt tgaaagggca aatcactgtg ccatccatg aaagcgtgtt accgtcagta  2040
agttctcact gaatgaaaac tcccttttctt ttacaatatt gcgcagaagg aaacatgcca  2100
gttatgaaag agtttcaatt acaggatcac ctttgctttc atttgatgtg atatctagtt  2160
ttgatgttgt ttcaaggttc aagaattcta atgataaatg ataggatcca caattgttat  2220
atctctgcag ctcctcgtat ctgttgtcca cgaacaaaaa tatcaaacaa ttcattaaaa  2280
agatgaagaa gtcaaacaaa cagtatatgt gcactgcata ttagatatca aacctggtta  2340
ctatacgact gatctggcct gaccccgcg tcgcctctcc ctggcggcac ggggggaacc   2400
actccgcgcg cgccaccttc cctcctccct ccaccccca cctcgccgcc gcctgaggag   2460
ttcgccggc aagcccggtc tggctccagg gaggtggc gcggggcatc tctctgcgag    2520
gcgtgaggg gcatctcgtg cgcgggcgcg gcgagcttgg ggcgcggcgt               2580
ctggctcggg ctggtgaggc tccggcggtc cgaggggtgt cgcggcgcgg cggggggtctc  2640
gctccggcgc gggcggtccg aggggcgcgc ggatctggcg ctccagcagg ggcgccgtca  2700
aggggagccg ggcagggaag ctcgtcaggc gggctcgtca ggcaggcgtg acgcggggcg  2760
gcggccgcgc gctggaagcc atggcgtttt ggccatggtg tcgtgtgcgc tcgcttctca  2820
ttcgcaggtt gaggtgctgc tgctgagggt ggtgcgcggt gaagcttggt ggtgcgcgtt  2880
ggagagtgca aggcgcaaca ggaatggctc caatgatctc cacgcttctg ggtggatcag  2940
atctgcggcc ctccatagg gtgtgttccg ggcgaaagcc ttgacccgac tttgtcggtg  3000
ccgtcgacgc cggcgctttc gggcgtcgtt ccctccttg gaggcgtcgt gtggaactc    3060
atcttcttct atgtggggct cgggctctcc gggtgaaaac ctaagctcca gattttccgg  3120
agcgggcgat ggcggcgtct tcgtcgtttc cctcttgggg gcgttgcttg ggagagttag  3180
```

-continued

```
cttgtgcttg gtgcgtttgg ttttctccta cgtcgggttt ggtggatgcc ggggcagcgg   3240
cccccggacgg ctgatgaacg ccgaggcggc ggcctcggaa agtgatgcgc ggtgcggctc   3300
catgggggcgg ggcggtggct cggccttcac ttgggtggca atcttgggcc acttgggtgg   3360
caggcttgtc ggtccggtcg acgcgttcca gaggggggcgg tctgactttg cgtcggggcg   3420
gcggcccgga atgtggtgcg acgttcgtgg tctgcgagcg gttgccttga gcagcgtggg   3480
ctgcgggcag ctgggtcgcg cggcgttgct gctcgagcgg agcggtggta cgtcggggcg   3540
gcggccccgg aaggtgatgc cggttgattg cgctgggcgt gacggagcgg tggatgtcgg   3600
ggcggcggcc ccgagaaaat cactgtggcg tccagatttc tgtggcaacg atgatggtgg   3660
gagcgatgtc ggcgacgcgg caatggttgc gatagtcggc tcttctccgg cgtgtccacg   3720
atattgcctc ggtttgtttg ttgctggtgga gtcgaagctg cggcggcgag gccctgtggt   3780
atacgatgac tggttccagg tgtcctttcg tcgatcttcc gtggcgccag ccgtgcctgg   3840
tttcgttctt ccgagttctc cgtcagaatc ggagctgcgt tgtctgtccg caggtcgaca   3900
tgttgtcgag aaggggtgggc tttgccctgt gtgtttcagt ctatgcgagt gggctcggcc   3960
cttgtgtctc tggttttttgc ccggtttttcc gtaattaact gggcaattct cttctgctta   4020
attaatagat gaggcaatct ttgcctccct ttcaaaaaaa aacctggtta ctatagcagg   4080
aaattcaggg ttgattactt tatttcttat ctgaaggata aacattgtat caaatcagaa   4140
ttttatttgt aagttacatt ttttttttact tataaaactt ggaaactgtt ttactgtgac   4200
aaatagatgc cactagaatc atgatcacat cgtggctgtt gctattctaa caaataaatg   4260
ctcctgaaca aatgggaact atatatgaag atgtatggac cagcatgttc ctgttaacct   4320
gaccttttc cttttttttgc tgctgcagtg caaaaggaca tacagcttgc aaggcgtatc   4380
ggcgggagga ggctttggtg a                                             4401
```

```
SEQ ID NO: 54              moltype = RNA   length = 587
FEATURE                    Location/Qualifiers
source                     1..587
                           mol_type = other RNA
                           organism = Triticum aestivum
SEQUENCE: 54
atggcccgca ccaagcaccc ggccgtcagg aagaccaagg cgccgcccaa gaagcagctc   60
gggcccccgcc ccgcgcagcg gcggcaggag acagatgggcg cgggcacgtc ggcgacaccg   120
gttgcgcggg accttcccgg gtcgcttcct tttcgtttcg tcttgttttc tgttttttgg   180
tctgacttgc tcgtcacctg ttcgacggaa tgcagaggcg agccgggcgg gcggcggccc   240
cagggggggc tcaaggggct aactgggcaa cccaagcaga ggaaaccaca ccggttcagg   300
ccaggcacgg tggcactgcg ggagatcagg aggtatcgaa agtcggtcga ctttctcatc   360
ccgtttgcac catttgtccg tctgatcaag gaggtcaccg acttcttctg tcctgaaatc   420
agccgctgga ctccccaagc gctcgtcgcg attcaagagg ctgcagagta tcacctcgtc   480
gacgtattga aagggcaaat cactgtgcca tccatgcaaa gcgtgttacc gtcatgcaaa   540
aggacataca gcttgcaagg cgtatcggcg ggaggaggct ttggtga              587
```

```
SEQ ID NO: 55              moltype = AA   length = 195
FEATURE                    Location/Qualifiers
source                     1..195
                           mol_type = protein
                           organism = Triticum aestivum
SEQUENCE: 55
MARTKHPAVR KTKAPPKKQL GPRPAQRRQE TDGAGTSATP VARDLPGSLP FRFVLFSVFW   60
SDLLVTCSTE CRGEPGGRRP QGGLKGLTGQ PKQRKPHRFR PGTVALREIR RYQKSVDFLI   120
PFAPFVRLIK EVTDFFCPEI SRWTPQALVA IQEAAEYHLV DVLKGQITVP SMQSVLPSCK   180
RTYSLQGVSA GGGFG                                                     195
```

```
SEQ ID NO: 56              moltype = RNA   length = 512
FEATURE                    Location/Qualifiers
source                     1..512
                           mol_type = other RNA
                           organism = Triticum aestivum
SEQUENCE: 56
atggcccgca ccaagcaccc ggccgtcagg aagaccaagg cgccgcccaa gaagcagctc   60
gggcccccgcc ccgcgcagcg gcggcaggag acagatggcg cgggcacgtc ggcgacaccg   120
gttgcgcggg accttcccgg aggcgagccg ggcgggcggc ggcccccaggg ggggctcaag   180
gggctaactg ggcaacccaa gcagaggaaa ccacaccggt tcaggccagg cacggtggca   240
ctgcgggaga tcaggaggta tcagaagtcg gtcgactttc tcatcccgtt tgcaccattt   300
gtccgtctga tcaaggaggt caccgacttc ttctgtcctg aaatcagccg ctggactccc   360
caagcgctcg tcgcgattca agaggctgca gagtatcacc tcgtcgacgt attgaaaggg   420
caaatcactg tgccatccat gcaaagcgtg ttaccgtcat gcaaaaggac atacagcttg   480
caaggcgtat cggcgggagg aggctttggt ga                                 512
```

```
SEQ ID NO: 57              moltype = AA   length = 170
FEATURE                    Location/Qualifiers
source                     1..170
                           mol_type = protein
                           organism = Triticum aestivum
SEQUENCE: 57
MARTKHPAVR KTKAPPKKQL GPRPAQRRQE TDGAGTSATP VARDLPGGEP GGRRPQGGLK   60
GLTGQPKQRK PHRFRPGTVA LREIRRYQKS VDFLIPFAPF VRLIKEVTDF FCPEISRWTP   120
QALVAIQEAA EYHLVDVLKG QITVPSMQSV LPSCKRTYSL QGVSAGGGFG              170
```

```
SEQ ID NO: 58              moltype = DNA   length = 4401
FEATURE                    Location/Qualifiers
source                     1..4401
```

-continued

```
                          mol_type = other DNA
                          organism = Triticum aestivum
SEQUENCE: 58
atggcccgca ccaagcaccc ggccgtcagg aagaccaagg cgccgcccaa gaagcagctc    60
gggccccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gttgcgcggg accttccggg gtcgcttcct tttcgtttcg tcttgttttc   300
tgtttttttgg tctgacttgc tcgtcacctg ttcgacggaa tgcagaggcg agccgggcgg   360
gcggcggccc caggggggc tcaaggtgcg gccttctttg cgcttttcgg ttttccgccg    420
cgtgtttagg gccatttccg tcttgtttgg gggtgcgcgg ggcgggggct tgttttttt    480
cctcccccct tcgttgttgc gcacattgct cgggaatgct gccaggagcg gttgcggttc    540
ttctttgacc cttcgggagg gctggatcgg cagtttcttc gcttccttgc tccagatttt   600
agttcatctt gtaccagtac agtagcaaga tgatggatgg gggcttgttt tttctttctc    660
cttccttgtt ccggacattt ctctggagcg acttttatgc atttcccagt attgtccttt   720
gtccttagag ggtagtggat cggcagtttt cttcgcctca ttggtccaga ttttagttta   780
tcttgtacgg taccaagatg atggatgtgg cacaaagttc tcagtttggg ggttgcgctc    840
ttccgggcag ttgttatttt ggtctgtgat gactaactcg tatctattct tgtgggagca   900
ggggcaaact gggcaaccca agcagaggaa accacaccgg ttcaggccag gcacggtggc    960
actgcgggag atcaggaggt atcagaagtc ggtcgacttt ctcatcccgt ttgcaccatt   1020
tgtccgtctg gtgggtacct ctgtctgtca tatcctctcg ctctctctac aaacgatctg    1080
cagtgcagag tgtaattgga atattttgtt cctgacaaat ttgcagatca aggaggtcac   1140
cgacttcttc tgtcctgaaa tcagccgctg gactccccaa gcgctcgtcg cgattcaaga   1200
ggtcagtgct aaaacctggc atgtactatt agatctgatg gtttgattag agtactacaa   1260
tgcagatgaa ttcaatatcc gaaaaccatg aactgtgggg tagatacatg tatcgcctta   1320
attcatggtt tctgaatgct ctgctattaa ttcagtttga tatatttatt tagcagcatg   1380
gtattgtttt ggtggctggt aaatcaaaac tgaaatgtga ttacgagcaa aacggtatcg    1440
attgtcgatc ctgtgtgttt ttgtgcacat ctggttgttt ggtcaagatg tgtttgtgca   1500
catcttgcaa catgatcctg cccacacact caaaactgac tattggttag gttccatttg   1560
tcttatggaa tttagggtgt aactgagagg tgagcaagtg gtagtaacgt tcaattttga   1620
ttcaggatga ggatattgtg atccagaaaa ttgcatgtta tggttatgtg tccaaacgcc   1680
aaatgattat gtctatatcc agtactttag aaccagtaca acaacaaaaa gtactttaga   1740
accagtcaag tttattgtgc atttatacaa gagtgttgtt tgcacaatag acttgcttta   1800
gtcgtctctt gccagaaatg ccttcttctg cacaacgagc aaaaataaca taaagttgac   1860
tatactcagt gtggcctaag aaatgagttg tactttttag tcactggcct gtgtatttgc   1920
tttgaattga cacataattc ccttttcctt tccctctgca ggctgcagag tatcacctcg    1980
tcgacgtatt tgaaagggca aatcactgtg ccatccatgc aaagcgtgtt accgtcagta   2040
agttctcact gaatgaaaac tccctttctt ttacaatatt gcgcagaagg aaacatgcca   2100
gttatgaaag agtttcaatt acaggatcac ctttgctttc atttgatgtg atatctagtt   2160
ttgatgttgt ttcaaggttc aagaattcta atgataaatg ataggatcca caattgttat   2220
atctctgcag ctcctcgtat ctgttgtcca cgaacaaaca tatcaaacaa ttcattaaaa   2280
agatgaagaa gtcaaacaaa cagtatatgt gcactgcata ttagatatca aacctggtta   2340
ctatacgact gatctggcct gaccccccgcg tcgcctctcc ctggcggcac gggggggaacc   2400
actccggcgc cgccaccttc cctcctccct ccaccccca cctcgccgcc gcctgaggag   2460
ttcgccggcg aagcccggtc tggctccagg gagggtggcg gcggggcatc tctctgcgag   2520
gcgtgagggc gcatctcgtg cgcgggcgcg gcgagcttgg gcgggatcgc gggcgcggct   2580
ctggctcggg ctggtgaggc tccggcgcgtc cgaggggtgt gggcgcggag cggggggtctc   2640
gctccggcgc gggcggtccg agggcgcgcg ggatctggcg ctccagcagg ggcgccgtca   2700
aggggagccg ggcagggaag ctcgtcaggc gggctcgtca ggcaggcgtg acgcggggcg   2760
gcggccgcgg gctggaagcc atggcgtttt ggccatggtg tcgtgtgcgc tcgcttctca   2820
ttcgcagctt gaggtgctgc tgctgagggt ggtgcgcggt gaagcttggt ggtcggcgtt   2880
ggagagtgca aggcgcaaca ggaatggctc caatgatctc cacgcttctg ggtggatcag    2940
atctgcggcc ctccataggg gtgtgttccg ggcgaaagcc ttgacccgac tttgtcggtg   3000
ccgtcgacgg cggcgctttc gggcgtcgtt tccctccttg gaggcgtcgt tgtggaactc    3060
atcttcttct atgtggggct cgggctctcc gggtgaaaac ctaagctcca gattttccgg   3120
agcgggcgat ggcggcgtct tcgtcgtttc cctcttgggg gcgttgcttg ggagagttag   3180
cttgtgcttg gtgcgtttgg ttttctccta cgtcgggttt ggtggatgcc ggggcagcgg   3240
ccccggacgg ctgatgaacg ccgaggcggc ggcctcggaa agtgatgcgc ggtgcggctc    3300
catggggcgg ggcggtggct cggccttcac ttgggtggca atcttgggcc acttgggtgg   3360
caggcttgtc ggtccggtcg acgcgttcca gagggggcgg tctgactttg cgtcgggggcg   3420
gcggcccgg atgtggtgcg acgttcgtgg tctgcgagcg gttgccttga gcagcgtggg   3480
ctgcgggcag ctgggtcgcg cggcgttgct gctcgagcgg agcggtggta cgtcggggcg   3540
gcggccccgg aaggtgatgc cggttgattg cgctgggcgt gacggagcgg tggatgtcgg   3600
ggcggcggcc ccgagaaaat cactgtggcg tccagatttc tgtggcaacg atgatggtgg   3660
gagcgatgtc ggcgacgcgg caatggttgc gatagtcggc tcttctccgg cgtgtccacg   3720
atattgcctc ggtttgtttg ttgctgtgga gtcgaagctg cggcggcgag gccctgtggt   3780
atacgatgac tggttccagg tgtcctttcg tcgatcttcc gtggcgccag ccgtgcctgg   3840
tttcgttctt ccgagttctc cgtcagaatc ggagctgcgt tgtctgtccg caggtcgaca   3900
tgttgtcgag aagggtgggc tttgccctgt gtgtttcagt ctatgcgagt gggctcggcc   3960
cttgttgttc tggtttttgc ccggtttttcc gtaattaact gggcaattct cttctgctta   4020
attaatagat gaggcaatct ttgcctccct ttcaaaaaaa aacctggtta ctatagcagg   4080
aaattcaggg ttgattactt tatttcttat ctgaaggata aacattgtat caaatcagaa   4140
ttttatttgt aagttacatt ttttttttact tataaaactt ggaaactgtt ttactgtgac    4200
aaatagatgc cactagaatc atgatcacat cgtggctgtt gctattctaa caaataaatg   4260
ctcctgaaca aatgggaact atatatgaag atgtatggac cagcatgttc ctgttaacct   4320
gacctttttc ctttttttgc tgctgcagtg caaaaggaca tacagcttgc aaggcgtatc   4380
ggcgggagga ggctttggtg a                                               4401

SEQ ID NO: 59          moltype = RNA   length = 588
```

```
FEATURE                Location/Qualifiers
source                 1..588
                       mol_type = other RNA
                       organism = Triticum aestivum
SEQUENCE: 59
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacaccg   120
gttgcgcggg accttcccgg gtcgcttcct tttcgtttcg tcttgttttc tgtttttttgg  180
tctgacttgc tcgtcacctg ttcgacgaa tgcagaggcg agccgggcgg cgcggcggccc    240
caggggggc tcaaggggca aactgggcaa cccaagcaga ggaaaccaca ccggttcagg     300
ccaggcacgt tggcactgcg ggagatcagg aggtatcaga agtcggtcga ctttctcatc     360
ccgtttgcac catttgtccg tctgatcaag gaggtcaccg acttcttctg tcctgaaatc    420
agccgctgga ctccccaagc gctcgtcgcg attcaagagg ctgcagagta tcacctcgtc     480
gacgtatttg aaagggcaaa tcactgtgcc atccatgcaa agcgtgttac cgtcatgcaa     540
aaggacatac agcttgcaag gcgtatcggc gggaggaggc tttggtga                 588

SEQ ID NO: 60            moltype = AA   length = 195
FEATURE                Location/Qualifiers
source                 1..195
                       mol_type = protein
                       organism = Triticum aestivum
SEQUENCE: 60
MARTKHPAVR KTKAPPKKQL GPRPAQRRQE TDGAGTSATP VARDLPGSLP FRFVLFSVFW    60
SDLLVTCSTE CRGEPGGRRP QGGLKGQTGQ PKQRKPHRFR PGTVALREIR RYQKSVDFLI   120
PFAPFVRLIK EVTDFFCPEI SRWTPQALVA IQEAAEYHLV DVFERANHCA IHAKRVTVMQ   180
KDIQLARRIG GRRLW                                                   195

SEQ ID NO: 61            moltype = RNA   length = 513
FEATURE                Location/Qualifiers
source                 1..513
                       mol_type = other RNA
                       organism = Triticum aestivum
SEQUENCE: 61
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacaccg   120
gttgcgcggg accttcccgg aggcgagccg ggcgggcggc ggcccagggg ggggctcaag   180
gggcaaactg ggcaacccaa gcagaggaaa ccacaccggt tcaggccagg cacggtggca   240
ctgcgggaga tcaggaggta tcagaagtcg gtcgactttc tcatcccgtt tgcaccattt   300
gtccgtctga tcaaggaggt caccgacttc ttctgtcctg aaatcagccg ctggactccg   360
caagcgctcg tcgcgattca agaggctgca gagtatcacc tcgtcgacgt atttgaaagg   420
gcaaatcact gtgccatcca tgcaaagcgt gttaccgtca tgcaaaagga catacagctt   480
gcaaggcgta tcggcgggag gaggctttgg tga                               513

SEQ ID NO: 62            moltype = AA   length = 170
FEATURE                Location/Qualifiers
source                 1..170
                       mol_type = protein
                       organism = Triticum aestivum
SEQUENCE: 62
MARTKHPAVR KTKAPPKKQL GPRPAQRRQE TDGAGTSATP VARDLPGGEP GGRRPQGGLK    60
GQTGQPKQRK PHRFRPGTVA LREIRRYQKS VDFLIPFAPF VRLIKEVTDF FCPEISRWTP   120
QALVAIQEAA EYHLVDVFER ANHCAIHAKR VTVMQKDIQL ARRIGGRRLW             170

SEQ ID NO: 63            moltype = DNA   length = 4249
FEATURE                Location/Qualifiers
source                 1..4249
                       mol_type = other DNA
                       organism = Triticum aestivum
SEQUENCE: 63
atggcccgca ccaagcaccc ggccgtcagg aagaccaagg cgccgcccaa gaagcagctc    60
gggccccgcc ccgcgcagcg gcggcaggag acaggttcag cccttccctc cttcctcccc   120
ccgtctcccg cctctcgagc gaacgccgtc gccatttcgt cgcgagagat ggacggacgg   180
acgccccacg catgacgcta atgtgctctt cctctccctt tgcagatggc gcgggcacgt   240
cggcgacacc ggtgcgcggg accttcccgg gtcgcttcct tttcgtttcg tcttgtttc    300
tgtttttttgg tctgacttgc tcgtcacctg ttcgacgaa tgcagaggcg agccgggcgg   360
cgcggcggccc caggggggc tcaaggtgcg gccttcttg cgcttttcgg ttttccgccg   420
cgtgtttagg gccatttccg tcttgtttgg gggtgcgcgg ggcggggggct tgttttttt   480
cctcccccct tcgttgttgc gcacattgct cgggaatgct gccaggagcg gttcggttc   540
ttctttgacc cttcgggagg gctggatcgg cagtttcttc gcttccttgc tccagatttt   600
agttcatctt gtaccagtac agtagcaaga tgatggatgg gggcttgttt tttcttctc   660
cttccttgtt ccggacattt ctctggagcg actttatgc atttcccagt attgtccttt   720
gtccttagag ggtagtggat cggcagtttt cttcaactgg gcaacccaag cagaggaaac   780
cacaccggtt caggccaggc acggtggcac tgcgggagat caggaggtat cagaagtcgg   840
tcgactttct catcccgttt gcaccatttg tccgtctgt gtctgtcata                900
tcctctcgct ctctacaa acgatctgca gtgcagagtg taattggaat attttgttcc   960
tgacaaattt gcagatcaag gaggtcaccg acttcttctg tcctgaaatc agccgctgga  1020
ctccccaagc gctcgtcgcg attcaagagg tcagtgctaa aacctggcat gtactattag  1080
atctgatggt ttgattagag tactacaatg cagatgaatt caatatccga aaaccatgaa  1140
ctgtggggta gatacatgta tcgccttaat tcatggtttc tgaatgctct gctattaatt  1200
```

```
cagtttgata tatttattta gcagcatggt attgttttgg tggctggtaa atcaaaactg  1260
aaatgtgatt acgagcaaaa cggtatcgat tgtcgatcct gtgtgttttt gtgcacatct  1320
ggttgtttgg tcaagatgtg tttgtgcaca tcttgcaaca tgatcctgcc cacacactca  1380
aaactgacta ttggttaggt tccatttgtc ttatggaatt tagggtgtaa ctgagaggtg  1440
agcaagtggt agtaacgttc aattttgatt caggatgagg atattgtgat cagaaaatt   1500
gcatgttatg gttatgtgtc caaacgccaa atgattatgt ctatatccag tactttagaa  1560
ccagtacaac aacaaaaagt actttagaac cagtcaagtt tattgtgcat ttatacaaga  1620
gtgttgtttg cacaatagac ttgctttagt cgtctcttgc cagaaatgcc ttcttctgca  1680
caacgagcaa aaataacata aagttgacta tactcagtgt ggcctaagaa atgagttgta  1740
cttttagtc actggcctgt gtatttgctt tgaattgaca cataattccc ttttcctttc   1800
cctctgcagg ctgcagagta tcacctcgtc gacgtatttg aaaggcaaa tcactgtgcc   1860
atccatgcaa agcgtgttac cgtcagtaag ttctcactga atgaaaactc cctttctttt  1920
acaatattgc gcagaaggaa acatgccagt tatgaaaag tttcaattac aggatcacct   1980
ttgctttcat ttgatgtgat atctagtttt gatgttgttt caaggttcaa gaattctaat  2040
gataaatgat aggatccaca attgttatat ctctgcagct cctcgtatct gttgtccacg   2100
aacaaacata tcaaacaatt cattaaaaag atgaagaagt caaacaaaca gtatatgtgc  2160
actgcatatt agatatcaaa cctggttact atacgactga tctggcctga cccccgcgtc   2220
gcctctccct ggcggcacgg ggggaaccac tccggcgcgg ccaccttccc tcctccctcc  2280
accccccacc tcgccgccgc ctgaggagtt cgccggcgaa gcccggtctg gctccaggga  2340
gggtggcggc ggggcatctc tctgcgaggc gtgagggcgc atctcgtgcg cgggcgcggc  2400
gagcttgggc gggatcgcgg gcgcggctct ggctcgggct ggtgaggctc cggcggtccg  2460
aggggtgtcg cggcgcgggcg ggggtctcgc tccggccggg ggcgccgag ggcgcgcggg  2520
atctggcgct ccagcagggg cgccgtcaag gggagccggg cagggaagct cgtcaggcgg  2580
gctcgtcagg caggcgtgac gcggggcggc ggccgcgggc tggaagccat ggcgttttgg  2640
ccatggtgtc gtgtgcgctc gcttctcatt cgcagcttga ggtgctgctg ctgagggtgg  2700
tgcgcggtga agcttggtgg tcggcgttgg agagtgcaag gcgcaacagg aatggctcca  2760
atgatctcca cgcttctggg tggatcagat ctgcggccct ccataggggt gtgttccggg  2820
cgaaagcctt gacccgactt tgtcggtgcc gtcgacggcg gcgctttcgg gcgtcgtttc  2880
cctccttgga ggcgtcgttg tggaactcat cttcttctat gtggggctcg ggctctccgg  2940
gtgaaaacct aagctccaga tttttccggag cgggcgatgg cggcgtcttc gtcgtttccc  3000
tcttgggggc gttgcttggg agagttagct tgtgtcttggt gcgtttggtt ttctcctacg  3060
tcgggtttgg tggatgccgg ggcagcggcc ccggacggct gatgaacgcc gaggcggcgg  3120
cctcggaaag tgatgcgcgg tgcggctcca tggggcgggg cggtggctcg gccttcactt  3180
gggtggcaat cttgggccac ttgggtgcca ggcttgtcgg tccggtcgac gcgttccaga  3240
gggggcggtc tgactttgcg tcggggcggc ggccccggag gtggtgcgac gttcgtggtc  3300
tgcgagcggt tgccttgagc agcgtgggct gcgggcagct gggtcgcgcg gcgttgctgc  3360
tcgagcggag cggtggtacg tcggggcggc ggccccggaa ggtgatgccg gttgattgcg  3420
ctgggcgtga cggagcggtg gatgtcgggg cggcggcccc gagaaaatca ctgtggcgtc  3480
cagatttctg tggcaacgat gatggtggga gcgatgtcgg cgacgcggca atggttgcga  3540
tagtcggctc ttctccggcg tgtccacgat attgcctcgg tttgtttgtt gctgtggagt  3600
cgaagctgcg gcggcgaggc cctgtggtat acgatgactg gttccaggtg tcctttcgtc  3660
gatcttccgt ggcgccagcc gtgcctggtt tcgttcttcc gagttctccg tcagaatcgg  3720
agctgcgttg tctgtccgca ggtcgacatg ttgtcgaaga gggtgggctt tgccctgtcg  3780
gtttcagtct atgcgagtgg gctcggccct tgttgttctg gtttttgccc ggttttccgt  3840
aattaactgg gcaattctct tctgcttaat taatagatga ggcaatcttt gcctcccttt  3900
caaaaaaaaa cctggttact atagcaggaa attcaggggtt gattacttta tttcttatct  3960
gaaggataaa cattgtatca aatacagaatt ttatttgtaa atgacatttt ttttacttta  4020
taaaacttgg aaactgtttt actgtgacaa atagatgcca ctagaatcat gatcacatcg  4080
tggctgttgc tattctaaca aataaatgct cctgaacaaa tgggaactat atatgaagat  4140
gtatggacca gcatgttcct gttaacctga ccttttttcct tttttttgctg ctgcagtgca  4200
aaaggacata cagcttgcaa ggcgtatcgg cgggaggagg ctttggtga            4249
```

```
SEQ ID NO: 64              moltype = RNA   length = 591
FEATURE                    Location/Qualifiers
source                     1..591
                           mol_type = other RNA
                           organism = Triticum aestivum
SEQUENCE: 64
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
gttgcgcggg accttcccgg gtcgcttcct tttcgtttcg tcttgttttc tgtttttttgg  180
tctgacttgc tcgtcacctg ttcgacggaa tgcagaggcg agccgggcgg gcggcggccc   240
cagggggggc tcaagttttc ttcaactggg caacccaagc agaggaaacc acaccggttc   300
aggccaggca cggtggcact gcgggagatc aggaggtca cgaagtcggt cgacttctcc    360
atcccgtttg caccatttgt ccgtctgatc aaggaggtca ccgacttctt ctgtcctgaa   420
atcagccgct ggactcccca agcgctcgtc gcgattcaag aggctgcaga gtatcacctc   480
gtcgacgtat ttgaaagggc aaatcactgt gccatccatg caaagcgtgt taccgtcatg   540
caaaaggaca tacagcttgc aaggcgtatc ggcgggagga ggctttggtg a            591
```

```
SEQ ID NO: 65              moltype = AA   length = 196
FEATURE                    Location/Qualifiers
source                     1..196
                           mol_type = protein
                           organism = Triticum aestivum
SEQUENCE: 65
MARTKHPAVR KTKAPPKKQL GPRPAQRRQE TDGAGTSATP VARDLPGSLP FRFVLFSVFW   60
SDLLVTCSTE CRGEPGGRRP QGGLKFSSTG QPKQRKPHRF RPGTVALREI RRYQKSVDFL   120
IPFAPFVRLI KEVTDFFCPE ISRWTPQALV AIQEAAEYHL VDVFERANHC AIHAKRVTVM   180
QKDIQLARRI GGRRLW                                                   196
```

-continued

```
SEQ ID NO: 66              moltype = RNA   length = 609
FEATURE                    Location/Qualifiers
source                     1..609
                           mol_type = other RNA
                           organism = Triticum aestivum
SEQUENCE: 66
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacaccg   120
gttgcgcggg accttcccgg gtcgcttcct tttcgtttcg tcttgttttc tgttttttgg   180
tctgacttgc tcgtcacctg ttcgacggaa tgcagaggcg agccgggcgg cggcggcccc   240
cagggggggc tcaagagggt agtggatcgg cagtttcctt caactgggca acccaagcag   300
aggaaaccac accggttcag gccaggcacg gtggcactgc gggagatcag gaggtatcag   360
aagtcggtcg actttctcat cccgtttgca ccatttgtcc gtctgatcaa ggaggtcacc   420
gacttcttct gtcctgaaat cagccgctgg actcccaag cgctcgtcgc gattcaagag    480
gctgcagagt atcacctcgt cgacgtattt gaaagggcaa atcactgtgc catccatgca   540
aagcgtgtta ccgtcatgca aaaggacata cagcttgcaa ggcgtatcgg cgggaggagg   600
ctttggtga                                                           609

SEQ ID NO: 67              moltype = AA   length = 202
FEATURE                    Location/Qualifiers
source                     1..202
                           mol_type = protein
                           organism = Triticum aestivum
SEQUENCE: 67
MARTKHPAVR KTKAPPKKQL GPRPAQRRQE TDGAGTSATP VARDLPGSLP FRFVLFSVFW    60
SDLLVTCSTE CRGEPGGRRP QGGLKRVVDR QFSSTGQPKQ RKPHRFRPGT VALREIRRYQ   120
KSVDFLIPFA PFVRLIKEVT DFFCPEISRW TPQALVAIQE AAEYHLVDVF ERANHCAIHA   180
KRVTVMQKDI QLARRIGGRR LW                                            202

SEQ ID NO: 68              moltype = RNA   length = 534
FEATURE                    Location/Qualifiers
source                     1..534
                           mol_type = other RNA
                           organism = Triticum aestivum
SEQUENCE: 68
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacaccg   120
gttgcgcggg accttcccgg aggcgagccg ggcggggcgg ggcccagggg ggggctcaag   180
agggtagtgg atcggcagtt ttcttcaact gggcaaccca agcagaggaa accacaccgg   240
ttcaggccag gcacggtggc actgcgggag atcaggaggt atcagaagtc ggtcgacttt   300
ctcatcccgt ttgcaccatt tgtccgtctg atcaaggagg tcaccgactt cttctgtcct   360
gaaatcagcc gctggactcc ccaagcgctc gtcgcgaatc aagaggctgc agagtatcac   420
ctcgtcgacg tatttgaaag ggcaaatcac tgtgccatcc atgcaaagcg tgttaccgtc   480
atgcaaaagg acatacagct tgcaaggcgc atcggcggga ggaggctttg gtga         534

SEQ ID NO: 69              moltype = AA   length = 177
FEATURE                    Location/Qualifiers
source                     1..177
                           mol_type = protein
                           organism = Triticum aestivum
SEQUENCE: 69
MARTKHPAVR KTKAPPKKQL GPRPAQRRQE TDGAGTSATP VARDLPGGEP GGRRPQGGLK    60
RVVDRQFSST GQPKQRKPHR FRPGTVALRE IRRYQKSVDF LIPFAPFVRL IKEVTDFFCP   120
EISRWTPQAL VAIQEAAEYH LVDVFERANH CAIHAKRVTV MQKDIQLARR IGGRRLW      177

SEQ ID NO: 70              moltype = DNA   length = 4401
FEATURE                    Location/Qualifiers
source                     1..4401
                           mol_type = other DNA
                           organism = Triticum aestivum
SEQUENCE: 70
atggcccgca ccaagcaccc ggccgtcagg aagaccaagg cgccgcccaa gaagcagctc    60
gggccccgcc ccgcgcagcg gcggcaggag acaggtcagc ccttccctcc ttcctcccc    120
cgtctcccgc ctctcgagcg aacgccgtcg ccatttcgtc gcgagagatg acggacggga   180
cgccccacgc atgacgctaa tgtgctcttc ctctcccttt gcagatggc cgggcacgtc    240
ggcgacaccg gttgcgcggg accttcccgg gtcgcttcct tttcgtttcg tcttgttttc   300
tgttttttgg tctgacttgc tcgtcacctg ttcgacggaa tgcagaggcg agccgggcgg   360
cggcggcccc cagggggggc tcaaggtgcg gccttctttg cgttttcgg ttttccgccg    420
cgtgtttagg gccatttccg tcttgtttgg gggtgcgcgg ggcggggggct tgtttttttt   480
cctccccect tcgttgttgc gcacattgct cgggaatgct gccaggagcg gttgcggttc   540
ttctttgacc cttcgggagg gctggatcgg cagtttcttc gcttccttgc tccagatttt   600
agttcatctt gtaccagtac agtagcaaga tgatggatgg gggcttgttt tttctttctc   660
cttccttgtt ccggacattt ctctggagcg actttatgc atttcccagt attgtccttt    720
gtccttagag ggtagtggat cggcagtttt cttcgcctca ttggtccaga tttttagttta   780
tcttgtacgg taccaagatg atggatgtgg cacaaagttc tcagtttggg ggttgcgctc   840
ttccgggcag ttgttatttt ggtctgtgat gactaactcg tatctattct tgtgggagca   900
ggggcaaact gggcaaccca agcagaggaa accacaccgg ttcaggccag gcacggtggc   960
actgcgggag atcaggaggt atcagaagtc ggtcgacttt ctcatcccgt ttgcaccatt  1020
```

-continued

```
tgtccgtctg gtgggtacct ctgtctgtca tatcctctcg ctctctctac aaacgatctg   1080
cagtgcagag tgtaattgga atattttgtt cctgacaaat ttgcagatca aggaggtcac   1140
cgacttcttc tgtcctgaaa tcagccgctg gactcccaa gcgctcgtcg cgattcaaga    1200
ggtcagtgct aaaacctggc atgtactatt agatctgatg gtttgattag agtactacaa   1260
tgcagatgaa ttcaatatcc gaaaaccatg aactgtggga tagatacatg tatcgcctta   1320
attcatggtt tctgaatgct ctgctattaa ttcagtttga tatatttatt tagcagcatg   1380
gtattgtttt ggtggctggt aaatcaaaac tgaaatgtga ttacgagcaa aacggtatcg   1440
attgtcgatc ctgtgtgttt ttgtgcacat ctggttgttt ggtcaagatg tgtttgtgca   1500
catcttgcaa catgatcctg cccacacact caaaactgac tattggttag gttccatttg   1560
tcttatggaa tttagggtgt aactgagagg tgagcaagtg gtagtaacgt tcaattttga   1620
ttcaggatga ggatattgtg atccagaaaa ttgcatgtta tggttatgtg tccaaacgcc   1680
aaatgattat gtctatatcc agtactttag aaccagtaca acaacaaaaa gtactttaga   1740
accagtcaag tttattgtgc atttatacaa gagtgttgtt tgcacaatag acttgcttta   1800
gtcgtctctt gccagaaatg ccttcttctg cacaacgagc aaaaataaca taaagttgac   1860
tatactcagt gtggcctaag aaatgagttg tactttttag tcactggcct gtgtatttgc   1920
tttgaattga cacataattc ccttttcctt tccctctgca ggctgcagag tatcacctcg   1980
tcgacgtatt tgaaagggca aatcactgtg ccatccatgc aaagcgtgtt accgtcagta   2040
agttctcact gaatgaaaac tccctttctt ttacaatatt gcgcagaagg aaacatgcca   2100
gttatgaaag agtttcaatt acaggatcac ctttgctttc atttgatgtg atatctagtt   2160
ttgatgttgt ttcaaggttc aagaattcta atgataaatg ataggatcca caattgttat   2220
atctctgcag ctcctcgtat ctgttgtcca cgaacaaaca tatcaaacaa ttcattaaaa   2280
agatgaagaa gtcaaacaaa cagtatatgt gcactgcata ttagatatca aacctggtta   2340
ctatacgact gatctggcct gacccccgcg tcgcctctcc ctggcggcac ggggggaacc   2400
actccggcgc cgccaccttc cctcctccct ccacccccca cctcgccgcc gcctgaggag   2460
ttcgccggcg aagcccggtc tggctccagg gagggtggcg gcggggcatc tctctgcgag   2520
gcgtgagggc gcatctcgtg cgcggggcgcg gcgagcttgg gcgggatgcg gggcgcggct   2580
ctggctcggg ctggtgaggc tccggcggtc cgagggggtgt cgcggcgcgg cgggggtctc   2640
gctccggcgc gggcggtccg agggcgcgcg ggatctggcg ctccagcagg ggcgccgtca   2700
aggggagccg ggcagggaag ctcgtcaggc gggctcgtca ggcaggcgtg acgcggggcg   2760
gcggccgcgg gctggaagcc atggcgtttt ggccatggtg tcgtgtgcgc tcgcttctca   2820
ttcgcagctt gaggtgctgc tgctgagggt ggtgcgcggt gaagcttggt ggtcggcgtt   2880
ggagagtgca aggcgcaaca ggaatggctc caatgatctc cacgcttctg ggtggatcag   2940
atctgcggcc ctccataggg gtgtgttccg ggcgaaagcc ttgacccgac tttgtcggtg   3000
ccgtcgacgg cggcgctttc gggcgtcgtt tccctccttg gaggcgtcgt tgtggaactc   3060
atcttcttct atgtggggct cgggctctcc gggtgaaaac ctaagctcca gattttccgg   3120
agcgggcgat ggcggcgtct tcgtcgtttc cctcttgggg gcgttgcttg ggagagttag   3180
cttgtgcttg gtgcgtttgg ttttctccta cgtcgggttt ggtggatgcc ggggcagcgg   3240
ccccggacgg ctgatgaacg ccgaggcggc ggcctcggaa agtgatgcgc ggtgcggctc   3300
catggggcgg ggcggtggct cggccttcac ttgggtggca atcttgggcc acttgggtgg   3360
caggcttgtc ggtccggtcg acgcgttcca gagggggcgg tctgactttg cgtcggggcg   3420
gcggccccgg atgtggtgcg acgttcgtgg tctgcgagcg gttgccttga gcagcgtggg   3480
ctgcgggcag ctgggtcgcg cggcgttgct gctcgagcg agcggtggta cgtcggggcg   3540
gcggccccgg aaggtgatgc cggttgattg cgctgggcgt gacggagcgg tggatgtcgg   3600
ggcggcggcc ccgagaaaat cactgtggcg tccagatttc tgtggcaacg atgatggtgg   3660
gagcgatgtc ggcgacgcgg caatggttgc gatagtcggc tcttctccgg cgtgtccacg   3720
atattgcctc ggtttgtttg ttgctgtgga gtcgaagctg cggcggcgag gccctgtggt   3780
atacgatgac tggttccagg tgtcctttcg tcgatcttcc gtggcgccag ccgtgcctgg   3840
tttcgttctt ccgagttctc cgtcagaatc ggagctgcgt tgtctgtccg caggtcgaca   3900
tgttgtcgag aagggtgggc tttgccctgt gtgtttcagt ctatgcgagt gggctcggcc   3960
cttgttgttc tggttttttgc ccggttttcc gtaattaact gggcaattct cttctgctta   4020
attaatagat gaggcaatct ttgcctccct ttcaaaaaaa aacctggtta ctatagcagg   4080
aaattcaggg ttgattactt tatttcttat ctgaaggata aacattgtat caaatcagaa   4140
ttttatttgt aagttacatt ttttttttact tataaaactt ggaaactgtt ttactgtgac   4200
aaatagatgc cactagaatc atgatcacat cgtggctgtt gctattctaa caaataaatg   4260
ctcctgaaca aatgggaact atatatgaag atgtatggac cagcatgttc ctgttaacct   4320
gaccttttc cttttttgc tgctgcagtg caaaaggaca tacagcttgc aaggcgtatc    4380
ggcgggagga ggctttggtg a                                            4401
```

```
SEQ ID NO: 71          moltype = RNA  length = 588
FEATURE                Location/Qualifiers
source                 1..588
                       mol_type = other RNA
                       organism = Triticum aestivum
SEQUENCE: 71
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
gttgcgcggg accttccggg gtcgcttcct tttcgtttcg tcttgttttc tgttttttgg   180
tctgacttgc tcgtcacctg ttcgacgaaa tgcagaggcg agccgggcgg gcggcggccc   240
caggggggca tcaaggggca aactgggcaa cccaagcaga ggaaaccaca ccggttcagg   300
ccaggcacgc tggcactgcg ggagatcagg aggtatcaga agtcggtcga ctttctcatc   360
ccgtttgcac catttgtccg tctgatcaag gaggtcaccg acttcttctg tcctgaaatc   420
agccgctgga ctccccaagc gctcgtcgcg attcaagagg ctgcagagta tcacctcgtc   480
gacgtatttg aaagggcaaa tcactgtgcc atccatgcaa agcgtgttac cgtcatgcaa   540
aaggacatac agcttgcaag gcgtatcggc gggaggaggc tttggtga               588
```

```
SEQ ID NO: 72          moltype = AA  length = 195
FEATURE                Location/Qualifiers
source                 1..195
                       mol_type = protein
```

-continued

```
                   organism = Triticum aestivum
SEQUENCE: 72
MARTKHPAVR KTKAPPKKQL GPRPAQRRQE TDGAGTSATP VARDLPGSLP FRFVLFSVFW   60
SDLLVTCSTE CRGEPGGRRP QGGLKGQTGQ PKQRKPHRFR PGTVALREIR RYQKSVDFLI  120
PFAPFVRLIK EVTDFFCPEI SRWTPQALVA IQEAAEYHLV DVFERANHCA IHAKRVTVMQ  180
KDIQLARRIG GRRLW                                                  195

SEQ ID NO: 73           moltype = RNA  length = 513
FEATURE                 Location/Qualifiers
source                  1..513
                        mol_type = other RNA
                        organism = Triticum aestivum
SEQUENCE: 73
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
gttgcgcggg accttcccgg aggcgagccg ggcgggcggc ggccccaggg ggggctcaag  180
gggcaaactg ggcaacccaa gcagaggaaa ccacaccggt tcaggccagg cacggtggca  240
ctgcggggaga tcaggaggta tcagaagtcg gtcgactttc tcatcccgct tgcaccattt  300
gtccgtctga tcaaggaggt caccgacttc ttctgtcctg aaatcagccg ctggactccc  360
caagcgctcg tcgcgattca agaggctgca gagtatcacc tcgtcgacgt atttgaaagg  420
gcaaatcact gtgccatcca tgcaaagcgt gttaccgtca tgcaaaagga catacagctt  480
gcaaggcgta tcggcgggag gaggctttgg tga                              513

SEQ ID NO: 74           moltype = AA  length = 170
FEATURE                 Location/Qualifiers
source                  1..170
                        mol_type = protein
                        organism = Triticum aestivum
SEQUENCE: 74
MARTKHPAVR KTKAPPKKQL GPRPAQRRQE TDGAGTSATP VARDLPGGEP GGRRPQGGLK   60
GQTGQPKQRK PHRFRPGTVA LREIRRYQKS VDFLIPFAPF VRLIKEVTDF FCPEISRWTP  120
QALVAIQEAA EYHLVDVFER ANHCAIHAKR VTVMQKDIQL ARRIGGRRLW             170

SEQ ID NO: 75           moltype = DNA  length = 4397
FEATURE                 Location/Qualifiers
source                  1..4397
                        mol_type = other DNA
                        organism = Triticum aestivum
SEQUENCE: 75
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc  120
cgtctcccgc ctctcgagcg aacgccgtcc ccatttcgtc gcgagagatg gacggacgga  180
cgcccacgc atgacgctaa tgtgctcttc ctctcccttt gcagatggcg cgggcacgtc  240
ggcgacactg cgcgggacct tcccgggtcg cttccttttc gtttcgtctt gttttctgtt  300
ttttggtctg acttgctcgt cacctgttcg acggaatgca gaggcgagcc gggcgggcgg  360
cggccccagg gggggctcaa ggtgcggcct tctttgcgct tttcggtttt ccgccgcgtg  420
tttagggcca tttccgtctt gtttgggggt gcgcgggggcg gggcttgtt tttttccctc  480
cccccttcgt tgttgcgcac attgctcggg aatgctgcca ggagcggttg cggttcttct  540
ttgacccttc gggagggctg gatcggcagt ttcttcgctt ccttgctcca gatttttagtt  600
catcttgtac cagtacagta gcaagatgat ggatgggggc ttgtttttc tttctccttc  660
cttgttccgg acatttctct ggagcgactt ttatgcattt cccagtattg tcctttgtcc  720
ttagagggta gtggatcggc agttttcttc gcctcattgg tccagatttt agtttatctt  780
gtacggtacc aagatgatgg atgtggcaca aagttctcag tttgggggtt gcgctcttcc  840
gggcagttgt tattttggtc tgtgatgact aactcgtatc tattcttgtg ggagcagggg  900
caaactgggc aacccaagca gaggaaacca caccggtca ggccaggcac ggtggcactg  960
cgggagatca ggaggtatca gaagtcggtc gactttctca tcccgtttgc accatttgtc 1020
cgtctggtgg gtacctctgt ctgtcatatc ctctcgctct ctctacaaac gatctgcagt 1080
gcagagtgta attggaatat tttgttcctg acaaatttgc agatcaagga ggtcaccgac 1140
ttcttctgtc ctgaaatcag ccgctggact ccccaagcgc tcgtcgcgat tcaagaggtc 1200
agtgctaaaa cctggcatgt actattagat ctgatggtt gattagagta ctacaatgca 1260
gatgaattca atatccgaaa accatgaact gtggggtaga tacatgtatc gccttaattc 1320
atggtttctg aatgctctgc tattaattca gtttgatata tttatttagc agcatgggtat 1380
tgttttggtg gctggtaaat caaaactgaa atgtgattac gagcaaaacg gtatcgattg 1440
tcgatcctgt gtgtttttgt gcacatctgg ttgtttgatc aagatgtgtt tgtgcacatc 1500
ttgcaacatg atcctgccca cacactcaaa actgactatt ggttaggttc catttgtctt 1560
atggaattta gggtgtaact gagaggtgag caagtggtag taacgttcaa ttttgattca 1620
ggatgaggat attgtgatcc agaaaattgc atgttatggt tatgtgtcca aacgccaaat 1680
gattatgtct atatccagta cttttagaacc agtacaacaa caaaaagtac tttagaacca 1740
gtcaagttta ttgtgcattt atacaagagt gttgtttgca caatagactt gcttttagtcg 1800
tctcttgcca gaaatgcctt cttctgcaca acgagcaaaa ataacataaa gttgactata 1860
ctcagtgtgg cctaagaaat gagttgtact ttttagtcac tggcctgtgt atttgctttg 1920
aattgacaca taattccctt ttcctttccc tctgcaggct gcagagtatc acctcgtcga 1980
cgtatttgaa agggcaaatc actgtgccat ccatgcaaag cgtgttaccg tcagtaagtt 2040
ctcactgaat gaaaactccc tttcttttac aatattgcgc agaaggaaac gtgccagtta 2100
tgaaagagtt tcaattacag gatcaccttt gctttcattt gatgtgatat ctagtttga 2160
tgttgtttca aggttcaaga attctaatga taaatgatag gatccacaat gttatatct 2220
ctgcagctcc tcgtatctgt tgtccacgaa caaacatatc aaacaattca ttaaaaagat 2280
gaagaagtca aacaaacagt atatgtgcac tgcatattag atatcaaacc tggttactat 2340
acgactgatc tggcctgacc cccgcgtcgc ctctcccctgg cggcacgggg ggaaccactc 2400
```

-continued

```
cggcgccgcc accttccctc ctccctccac cccccacctc gccgccgcct gaggagttcg    2460
ccggcgaagc ccggtctggc tccaggagg  gtgcggcgg  ggcatctctc tgcgaggcgt    2520
gagggcgcat ctcgtgcgcg ggcgcggcga gcttgggcgg gatcgcgggc gcggctctgg    2580
ctcgggctgg tgaggctccg gcggtccgag gggtgtcgcg gcgcggcggg ggtctcgctc    2640
cggcgcgggc ggtccgaggg cgcgcgggat ctggcgctcc agcaggggcg ccgtcaaggg    2700
gagccgggca gggaagctcg tcaggcgggc tcgtcaggca ggcgtgacgc ggggcggcgg    2760
ccgcgggctg gaagccatgg cgttttggcc atggtgtcgt gtgcgctcgc ttctcattcg    2820
cagcttgagg tgctgctgct gagggtggtg cgcggtgaag cttggtggtc ggcgttggag    2880
agtgcaaggc gcaacaggaa tggctccaat gatctccacg cttctgggtg gatcagatct    2940
gcggccctcc ataggggtgt gttccgggcg aaagccttga cccgactttg tcggtgccgt    3000
cgacggcggc gctttcgggc gtcgtttccc tccttggagg cgtcgttgtg gaactcatct    3060
tcttctatgt ggggctcggg ctctccgggt gaaaacctaa gctccagatt ttccggagcg    3120
ggcgatggcg gcgtcttcgt cgtttccctc ttggggggcgt tgcttgggag agttagcttg    3180
tgcttggtgc gtttggtttt ctcctacgtc gggtttggtg gatgccgggg cagcggcccc    3240
ggacggctga tgaacgccga ggcggcggcc tcggaaagtg atgcgcggtg cggctccatg    3300
gggcggggcg gtggctcggc cttcacttgg gtggcaatct tgggccactt gggtggcagg    3360
cttgtcggtc cggtcgacgc gttccagagg gggcggtctg actttgcgtc ggggcggcgg    3420
ccccgatgt  ggtgcgacgt tcgtggtctg cgagcggttg cctgagcag  cgtgggctgc    3480
gggcagctgg gtcgcgcggc gttgctgctc gagcggagcg gtggtacgtc ggggcggcgg    3540
ccccggaagg tgatgccggt tgattgcgct gggcgtgacg gagcggtgga tgtcggggcg    3600
gcggccccga gaaaatcact gtggcgtcca gatttctgtg gcaacgatga tggtgggagc    3660
gatgtcggcg acgcggcaat ggttgcgata gtcggctctt ctccggcgtg tccacgatat    3720
tgcctcggtt tgtttgttgc tgtggagtcg aagctgcggc ggcgaggccc tgtggtatac    3780
gatgactggt tccaggtgtc ctttcgtcga tcttccgtgg cgccagccgt gcctggtttc    3840
gttcttccga gttctccgtc agaatcggag ctgcgttgtc tgtccgcagg tcgacatgtt    3900
gtcgagaagg gtgggctttg ccctgtgtgt ttcagtctat gcgagtgggc tcggcccttg    3960
ttgttctggt ttttgcccgg ttttccgtaa ttaactgggc aattctcttc tgcttaatta    4020
atagatgagg caatctttgc ctcccttca  aaaaaaaacc tggttactat agcaggaaat    4080
tcagggttga ttactttatt tcttatctga aggataaaca ttgtatcaaa tcagaatttt    4140
atttgtaagt tacatttttt tttacttata aaacttggaa actgttttac tgtgacaaat    4200
agatgccact agaatcatga tcacatcgtg gctgttgcta ttctaacaaa taaatgctcc    4260
tgaacaaatg ggaactatat atgaagatgt atggaccagc atgttcctgt taacctgacc    4320
tttttccttt ttttgctgct gcagtgcaaa aggacataca gcttgcaagg cgtatcggcg    4380
ggaggaggct ttggtga                                                   4397
```

SEQ ID NO: 76             moltype = RNA   length = 584
FEATURE                   Location/Qualifiers
source                    1..584
                          mol_type = other RNA
                          organism = Triticum aestivum
SEQUENCE: 76
```
atggcccgca ccaagcaccc ggccgtcagg aagaccaagg cgccgcccaa gaagcagctc    60
gggccccgcc ccgcgcagcg gcggcaggag acagatgggc gggcgcacgtc ggcgacactg    120
cgcgggacct tccgggtcg  cttccttttc gtttcgtctt gtttttctgtt ttttggtctg    180
acttgctcgt cacctgttcg acggaatgca gaggcgagcc gggcggggcgg cggccccagg    240
gggggctcaa ggggcaaact gggcaaccca agcagaggaa accacaccgg ttcaggccag    300
gcacggtggc actgcgggag atcaggaggt atcagaagtc ggtcgacttt ctcatcccgt    360
ttgcaccatt tgtccgtctg atcaaggagg tcaccgactt cttctgtcct gaaatcagcc    420
gctggactcc ccaagcgctc gtcgcgattc aagaggctgc agagtatcac ctcgtcgacg    480
tatttgaaag ggcaaatcac tgtgccatcc atgcaaagcg tgttaccgtc atgcaaaagg    540
acatacagct tgcaaggcgt atcggcggga ggaggctttg gtga                     584
```

SEQ ID NO: 77             moltype = AA   length = 126
FEATURE                   Location/Qualifiers
source                    1..126
                          mol_type = protein
                          organism = Triticum aestivum
SEQUENCE: 77
```
MARTKHPAVR KTKAPPKKQL GPRPAQRRQE TDGAGTSATL RGTFPGRFLF VSSCFLFFGL    60
TCSSPVRRNA EASRAGGGPR GGSRGKLGNP SRGNHTGSGQ ARWHCGRSGG IRSRSTFSSR    120
LHHLSV                                                                126
```

SEQ ID NO: 78             moltype = DNA   length = 4396
FEATURE                   Location/Qualifiers
source                    1..4396
                          mol_type = other DNA
                          organism = Triticum aestivum
SEQUENCE: 78
```
atggcccgca ccaagcaccc ggccgtcagg aagaccaagg cgccgcccaa gaagcagctc    60
gggccccgcc ccgcgcagcg gcggcaggag acaggtcagc ccttccctcc ttcctccccc    120
cgtctcccgc ctctcgagcg aacgccgtcg ccatttcgtc gcgagagatg gacggacgga    180
cgccccacgc atgacgctaa tgtgctcttc ctctcccttt gcagatggcg cgggcacgtc    240
ggcgacactg cgcgggacct tccgggtcg  cttccttttc gtttcgtctt gtttttctgtt    300
ttttggtctg acttgctcgt cacctgttcg acggaatgca gaggcgagcc gggcggggcgg    360
cggccccagg gggggctcaa ggtgcggcct tctttgcgct tttcggtttt ccgccgcgtg    420
tttaggccba tttccgtctt gtttgggggt gcgcgggggcg ggggcttgtt ttttttcctc    480
ccccccttcg tgttgcgcac attgctcggg aatgctgcca ggagcggttg cggttcttct    540
ttgacccttc gggagggctg gatcggcagt ttcttcgctt ccttgctcca gattttagtt    600
catcttgtac cagtacagta gcaagatgat ggatggggggc ttgtttttttc tttctccttc    660
```

```
cttgttccgg acatttctct ggagcgactt ttatgcattt cccagtattg tcctttgtcc    720
ttagagggta gtggatcggc agttttcttc gcctcattgg tccagatttt agtttatctt    780
gtacggtacc aagatgatgg atgtggcaca aagttctcag tttgggggtt gcgctcttcc    840
gggcagttgt tattttggtc tgtgatgact aactcgtatc tattcttgtg ggagcagggg    900
caactgggca acccaagcag aggaaaccac accggttcag gccaggccag gtggcactgc    960
gggagatcag gaggtatcag aagtcggtcg actttctcat cccgtttgca ccatttgtcc   1020
gtctggtggg tacctctgtc tgtcatatcc tctcgctctc tctacaaacg atctgcagtg   1080
cagagtgtaa ttggaatatt ttgttcctga caaatttgca gatcaaggag gtcaccgact   1140
tcttctgtcc tgaaatcagc cgctggactc cccaagcgct cgtcgcgatt caagaggtca   1200
gtgctaaaac ctggcatgta ctattagatc tgatggtttg attagagtac tacaatgcag   1260
atgaattcaa tatccgaaaa ccatgaactg tggggtagat acatgtatcg ccttaattca   1320
tggtttctga atgctctgct attaattcag tttgatatat ttatttagca gcatggtatt   1380
gttttggtgg ctggtaaatc aaaactgaaa tgtgattacg agcaaaacgg tatcgattgt   1440
cgatcctgtg tgtttttgtg cacatctggt tgtttggtcg agatgtgttt gtgcacatct   1500
tgcaacatga tcctgcccac acactcaaaa ctgactattg gttaggttcc atttgtctta   1560
tggaatttag ggtgtaactg agaggtgagc aagtggtagt aacgttcaat tttgattcag   1620
gatgaggata ttgtgatcca gaaaattgca tgttatggtt atgtgtccaa acgccaaatg   1680
attatgtcta tatccagtac tttagaacca gtacaacaac aaaaagtact ttagaaccag   1740
tcaagtttat tgtgcattta tacaagagtg ttgtttgcac aatagacttg ctttagtcgt   1800
ctcttgccag aaatgccttc ttctgcacaa cgagcaaaaa taacataaag ttgactatac   1860
tcagtgtggc ctaagaaatg agttgtactt tttagtcact ggcctgtgta tttgctttga   1920
attgacacat aattcccttt tcctttccct ctgcaggctg agatgatca cctcgtcgac   1980
gtatttgaaa gggcaaatca ctgtgccatc catgcaaagc gtgttaccgt cagtaagttc   2040
tcactgaatg aaaactccct ttctttttaca atattgcgca gaaggaaaca tgccagttat   2100
gaaagagttt caattacagg atcacctttg ctttcatttg atgtgatatc tagttttgat   2160
gttgtttcaa ggttcaagaa ttctaatgat aaatgataag atccacaatt gttatatctc   2220
tgcagctcct cgtatctgtt gtccacgaac aaacatatca aacaattcat taaaaagatg   2280
aagaagtcaa acaaacagta tatgtgcact gcatattaga tatcaaacct ggttactata   2340
cgactgatct ggcctgaccc ccgcgtcgcc tctccctggc ggcacggggg gaaccactcc   2400
ggcgccgcca ccttccctcc tccctccacc ccccacctcg ccgccgcctg aggagttcgc   2460
cggcgaagcc cggtctggct ccagggaggg tggcggcggg gcatctctct gcgaggcgtg   2520
agggcgcatc tcgtgcgcgg gcgcggcgag cttgggcggg atcgcgggcg cggctctggc   2580
tcgggctggt gaggctccgg cggtccgagg ggtgtcgcgg cgcggcgggg gtctcgctcc   2640
ggcgcggggcg gtccgagggc gcgcgggatc tggcgctcca gcaggggcgc cgtcaagggg   2700
agccgggcag ggaagctcgt caggcgggct cgtcaggcag gcgtgacgcg gggcggcggc   2760
cgcgggctgg aagccatggc gttttggcca tggtgtcgtg tgcgctcgct tctcattcgc   2820
agcttgaggt gctgctgctg agggtggtgc gcggtgaagc ttggtggtcg gcgttggaga   2880
gtgcaaggcg caacaggaat ggctccaatg atctccacgc ttctgggtgg atcagatctg   2940
cggccctcca taggggtgtg ttccgggcga aagccttgac ccgactttgt cggtgccgtc   3000
gacggcggcg ctttcgggcg tcgtttccct ccttggaggc gtcgttgtgg aactcatctt   3060
cttctatgtg gggctcgggc tctccgggtg aaaacctaag ctccagattt tccggagcgg   3120
gcgatggcgg cgtcttcgtc gtttccctct tgggggcgtt gcttgggaga gttagcttgt   3180
gcttggtcgg tttggttttc tcctacgtcg ggtttggtgg atgccggggc agcggccccg   3240
gacggctgat gaacgccgag gcggcggcct cggaaagtga tgcgcggtgc ggctccatgg   3300
ggcgggggcgg tggctcggcc ttcacttggg tggcaatctt gggccacttg ggtggcaggc   3360
ttgtcggtcc ggtcgacgcg ttccagaggg ggcggtctga ctttgcgtcg gggcggcggc   3420
cccggatggg gtgcgacgtt cgtggtctgc gagcggttgc cttgagcagc gggcggctgcg   3480
ggcagctggg tcgcgcggcg ttgctgctcg agcggagcgg tggtacgtcg gggcggcggc   3540
cccggaaggt gatgccggtt gattgcgctg ggcgtgacgg agcggtggat gtcggggcgg   3600
cggccccgag aaaatcactg tggcgtccag atttctgtgg caacgatgat ggtgggagcg   3660
atgtcggcga cgcggcaatg gttgcgatag tcggctcttc tccggccgtgt ccacgatatt   3720
gcctcggttt gtttgttgct gtggagtcga agctcgcggcg gcgaggccct gtggtatacg   3780
atgactggtt ccaggtgtcc tttcgtcgat cttccgtggc gccagccgtg cctgtttcg   3840
ttcttccgag ttctccgtca gaatcggagc tgcgttgtct gtccgcaggt cgacatgttg   3900
tcgagaaggg tgggcttgc cctgtgtgtt tcagtctatg cgagtgggct cggccccttgt   3960
tgttctggtt tttgcccggt tttccgtaat taactgggca attctcttct gcttaattaa   4020
tagatgaggc aatctttgcc tcccctttcaa aaaaaaacct ggttactata gcaggaaatt   4080
cagggttgat tactttatttt cttatctgaa ggataaacat tgtatcaaat cagaatttta   4140
tttgtaagtt acatttttttt ttacttataa aacttggaaa ctgttttact gtgacaaata   4200
gatgccacta gaatcatgat cacatcgtgg ctgttgctat tctaacaaat aaatgctcct   4260
gaacaaatgg gaactatata tgaagatgta tggaccagca tgttcctgtt aacctgacct   4320
ttttcctttt tttgctgctg cagtgcaaaa ggacatacag cttgcaaggc gtatcggcgg   4380
gaggaggctt tggtga                                                    4396
```

```
SEQ ID NO: 79      moltype = RNA  length = 583
FEATURE            Location/Qualifiers
source             1..583
                   mol_type = other RNA
                   organism = Triticum aestivum
SEQUENCE: 79
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacactg   120
cgcgggacct tcccgggtcg cttccttttc gtttcgtctt gtttttctgtt ttttggtctg   180
acttgctcgt cacctgttcg acggaatgca gaggcggcgc ggcggggcgg cggccccagg   240
gggggctcaa ggggcaactg ggcaacccaa gcagaggaaa ccacaccggt tcaggccagg   300
cacggtggca ctgcgggaga tcaggaggta tcagaagtcg tcgactttc tcatcccgtt   360
tgcaccattt gtccgtctga tcaaggaggt caccgacttc ttctgtcctg aaatcagccg   420
ctggactccc aagcgctcg tcgcgattca agaggctgca gagtatcacc tcgtcgacgt   480
atttgaaagg gcaaatcact gtgccatcca tgcaaagcgt gttaccgtca tgcaaaagga   540
```

```
catacagctt gcaaggcgta tcggcgggag gaggctttgg tga                      583

SEQ ID NO: 80              moltype = AA   length = 136
FEATURE                    Location/Qualifiers
source                     1..136
                           mol_type = protein
                           organism = Triticum aestivum
SEQUENCE: 80
MARTKHPAVR KTKAPPKKQL GPRPAQRRQE TDGAGTSATL RGTFPGRFLF VSSCFLFFGL     60
TCSSPVRRNA EASRAGGGPR GGSRGNWATQ AEETTPVQAR HGGTAGDQEV SEVGRLSHPV    120
CTICPSDQGG HRLLLS                                                    136

SEQ ID NO: 81              moltype = DNA   length = 4401
FEATURE                    Location/Qualifiers
source                     1..4401
                           mol_type = other DNA
                           organism = Triticum aestivum
SEQUENCE: 81
atggcccgca ccaagcaccc ggccgtcagg aagaccaagg cgccgcccaa gaagcagctc     60
gggccccgcc ccgcgcagcg gcggcaggag acaggtcagc ccttccctcc ttcctccccc    120
cgtctcccgc ctctcgagcg aacgccgtcg ccatttcgtc gcgagagatg gacggacgga    180
cgcccacgc atgacgctaa tgtgctcttc ctctcccttt gcagatggcg cgggcacgtc     240
ggcgacaccg gtagcgcggg accttcccgg gtcgcttcct tttcgtttcg tcttgttttc    300
tgtttttttgg tctgacttgc tcgtcacctg ttcgacggaa tgcagaggcg agccgggcgg    360
gcggcggccc caggggggggc tcaaggtgcg gccttctttg cgcttttcgg ttttccgccg    420
cgtgtttagg gccatttccg tcttgtttgg gggtgcgcgg gggggggct tgttttttt     480
cctcccccct tcgttgttgc gcacattgct cgggaatgct gccaggagcg gttgcggttc    540
ttctttgacc cttcgggagg gctggatcgg cagtttcttc gcttccttgc tccagatttt    600
agttcatctt gtaccagtac agtagcaaga tgatggatgg gggcttgttt tttctttctc    660
cttccttgtt ccggacattt ctctggagcg acttttatgc atttcccagt attgtccttt    720
gtccttagag ggtagtggat cggcagtttt cttcgcctca ttggtccaga tttttagttta    780
tcttgtacgg taccaagatg atggatgtgg cacaaagttc tcagtttggg ggttgcgctc    840
ttccgggcag ttgttatttt ggtctgtgat gactaactcg tatctattct tgtgggagca    900
ggggcaaact gggcaaccca agcagaggaa accacaccgg ttcaggccag gcacggtggc    960
actgcgggag atcaggaggt atcagaagtc ggtcgacttt ctcatcccgt ttgcaccatt   1020
tgtccgtctg gtgggtacct ctgtctgtca tatcctctcg ctctctctac aaacgatctg   1080
cagtgcagag tgtaattgga atattttgtt cctgacaaat ttgcagatca aggaggtcac   1140
cgacttcttc tgtcctgaaa tcagccgctg gactccccaa gcgctcgtcg cgattccaaga   1200
ggtcagtgct aaaacctggc atgtactatt agatctgatg gtttgattag agtactacaa   1260
tgcagatgaa ttcaatatcc gaaaaccatg aactgtgggg tagatacatg tatcgcctta   1320
attcatggtt tctgaatgct ctgctattaa ttcagtttga tatatttatt tagcagcatg   1380
gtattgtttt ggtggctggt aaatcaaaac tgaaatgtga ttacgagcaa aacggtatcg   1440
attgtcgatc ctgtgtgttt ttgtgcacat ctggttgttt ggtcaagatg tgtttgtgca   1500
catcttgcaa catgatcctg cccacacact caaaactgac tattggttag gttccatttg   1560
tcttatggaa tttagggtgt aactgagagg tgagcaagtg gtagtaacgt tcaattttga   1620
ttcaggatga ggatattgtg atccagaaaa ttgcatgtta tggttatgtg tccaaacgcc   1680
aaatgattat gtctatatcc agtactttag aaccagtaca acaacaaaaa gtacttttaga   1740
accagtcaag tttattgtgc atttatacaa gagtgttgtt tgcacaatag acttgcttta   1800
gtcgtctctt gccagaaatg ccttcttctg cacaacgagc aaaaataaca taaagttgac   1860
tatactcagt gtggcctaag aaatgagttg tacttttag tcactggcct gtgtatttgc   1920
tttgaattga cacataattc ccttttcctt tccctctgca ggctgcagag tatcacctcg   1980
tcgacgtatt tgaaagggca aatcactgtg ccatccatgc aaagcgtgtt accgtcagta   2040
agttctcact gaatgaaaac tcccttctt ttacaatatt gcgcagaagg aaacatgcca   2100
gttatgaaag agtttcaatt acaggatcac ctttgctttc atttgatgtg atatctagtt   2160
ttgatgttgt ttcaaggttc aagaattcta atgataaatg ataggatcca caattgttat   2220
atctctgcag ctcctcgtat ctgttgtcca cgaacaaaca tatcaaacaa ttcattaaaa   2280
agatgaagaa gtcaaacaaa cagtatatgt gcactgcata ttagatatca aacctggtta   2340
ctatacgact gatctggcct gacccccgcg tcgcctctcc ctggcggcac gggggggaacc   2400
actccggcgc cgccaccttc cctcctccct ccacccccca cctcgccgcc gcctgaggag   2460
ttcgccgggcg aagcccggtc tggctccagg gagggtggcg gcggggcatc tctctgcgag   2520
gcgtgagggc gcatctcgtg cgcgggcgcg gcgagcttgg gcgggatcgc gggcgcggct   2580
ctggctcggg ctggtgaggc tccggcggtc gaggggtgt cgcggcgcgg cggggggtctc   2640
gctccggcgc gggcggtccg agggcgcgcg ggatctggcg ctccagcagg ggcgccgtca   2700
aggggagccg ggcagggaag ctcgtcaggc gggctcgtca gcaggcgtg acgcggggcg   2760
gcggccgcgg gctggaagcc atggcgtttt ggccatggtg tcgtgtgcgc tcgcttctca   2820
ttcgcagctt gaggtgctgc tgctgagggt ggtgcgcgt gaagcttggt ggtcggcgtt   2880
ggagagtgca aggcgcaaca ggaatggctc caatgatctc cacgcttctg ggtggatcag   2940
atctgcggcc ctccataggg gtgtgttccg ggcgaaagcc ttgacccgac tttgtcggtg   3000
ccgtcgacgg cggcgcttca cggcctcttt gggcgtcgtt ccctcctggg gaggcgtcgt tgtggaactc   3060
atcttcttct atgtggggct cgggctctcc gggtgaaaac ctaagctcca gattttccgg   3120
agcgggcgat ggcggcgtct tcgtcgtttc cctcttgggg gcgttgcttg ggagagttag   3180
cttgtgcttg gtgcgtttgg ttttctccta cgtcgggttt ggtggatgcc ggggcagcgg   3240
ccccggacgg ctgatgaacg ccgaggcggc ggcctcggaa agtgatgcgc ggtcggcgtc   3300
catggggcgg ggcgtggct gccgcttcac ttgggtggca atcttgggcc acttgggttg   3360
caggcttgtc ggtccggtcg acgcgttcca gaggggggcgg tctgactttg cgtcggggcg   3420
gcggccccgg atgtggtgcg acgttcgtgg tctgcgagcg gttgccttga gcagcgtggg   3480
ctgcgggcag ctgggtcgcg cggcgttgct gctcagcgg agcggtggta cgtcgggggcg   3540
gcggccccgg aaggtgatgc cggttgattg cgctgggcgt gacggagcgg tggatgtcgg   3600
ggcggcggcc ccgagaaaat cactgtggcg tccagatttc tgtggcaacg atgatggtgg   3660
```

-continued

```
gagcgatgtc ggcgacgcgg caatggttgc gatagtcggc tcttctccgg cgtgtccacg   3720
atattgcctc ggtttgtttg ttgctgtgga gtcgaagctg cggcggcgag gccctgtggt   3780
atacgatgac tggttccagg tgtcctttcg tcgatcttcc gtggcgccag ccgtgcctgg   3840
tttcgttctt ccgagttctc cgtcagaatc ggagctgcgt tgtctgtccg caggtcgaca   3900
tgttgtcgag aagggtgggc tttgccctgt gtgtttcagt ctatgcgagt gggctcggcc   3960
cttgttgttc tggttttttgc ccggtttttc gtaattaact gggcaattct cttctgctta   4020
attaatagat gaggcaatct ttgcctccct ttcaaaaaaa aacctggtta ctatagcagg   4080
aaattcaggg ttgattactt tatttcttat ctgaaggata aacattgtat caaatcagaa   4140
ttttatttgt aagttacatt ttttttttact tataaaactt ggaaactgtt ttactgtgac   4200
aaatagatgc cactagaatc atgatcacat cgtggctgtt gctattctaa caaataaatg   4260
ctcctgaaca aatgggaact atatatgaag atgtatggac cagcatgttc ctgttaacct   4320
gacctttttc ctttttttgc tgctgcagtg caaaaggaca tacagcttgc aaggcgtatc   4380
ggcgggagga ggctttggtg a                                              4401
```

SEQ ID NO: 82          moltype = RNA   length = 588
FEATURE                Location/Qualifiers
source                 1..588
                       mol_type = other RNA
                       organism = Triticum aestivum
SEQUENCE: 82

```
atggcccgca ccaagcaccc ggccgtcagg aagaccaagg cgccgcccaa gaagcagctc   60
gggccccgcc ccgcgcagcg gcggcaggag acagatgtcagc ccttccctcc ttcctcccccc   120
cgtctcccgc ctctcgagcg aacgccgtcg ccatttcgtc gcgagagatg gacggacgga   180
tctgacttgc tcgtcacctg ttcgacggaa tgcagaggcg agccgggcgg gcggcggccc   240
caggggggc tcaaggggca aactgggcaa cccaagcaga ggaaaccaca ccggttcagg   300
ccaggcacgg tggcactgcg ggagatcagg aggtatcaga agtcggtca ctttctcatc   360
ccgtttgcac catttgtccg tctgatcaag gaggtcaccg acttcttctg tcctgaaatc   420
agccgctgga ctccccaagc gctcgtcgcg attcaagagg ctgcagagta tcacctcgtc   480
gacgtatttg aaagggcaaa tcactgtgcc atccatgcaa agcgtgttac cgtcatgcaa   540
aaggacatac agcttgcaag gcgtatcggc gggaggaggc tttggtga                 588
```

SEQ ID NO: 83          moltype = AA   length = 195
FEATURE                Location/Qualifiers
source                 1..195
                       mol_type = protein
                       organism = Triticum aestivum
SEQUENCE: 83

```
MARTKHPAVR KTKAPPKKQL GPRPAQRRQE TDGAGTSATP VARDLPGSLP FRFVLFSVFW   60
SDLLVTCSTE CRGEPGGRRP QGGLKGQTGQ PKQRKPHRFR PGTVALREIR RYQKSVDFLI   120
PFAPFVRLIK EVTDFFCPEI SRWTPQALVA IQEAAEYHLV DVFERANHCA IHAKRVTVMQ   180
KDIQLARRIG GRRLW                                                      195
```

SEQ ID NO: 84          moltype = DNA   length = 4400
FEATURE                Location/Qualifiers
source                 1..4400
                       mol_type = other DNA
                       organism = Triticum aestivum
SEQUENCE: 84

```
atggcccgca ccaagcaccc ggccgtcagg aagaccaagg cgccgcccaa gaagcagctc   60
gggccccgcc ccgcgcagcg gcggcaggag acaggtcagc ccttccctcc ttcctcccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gtgcgcggga ccttcccggg tcgcttcctt ttcgtttcgt cttgttttct   300
gtttttttggt ctgacttgct cgtcacctgt tcgacggaat gcagaggcga gccgggcggg   360
cggcggcccc aggggggggct caaggtgcgg ccttctttgc gcttttcggt ttccgccgc   420
gtgtttaggg ccatttccgt cttgtttggg ggtgcgcggg gcgggggctt gttttttttc   480
ctccccccctt cgttgttgcg cacattgctc gggaatgctg ccaggagcgg ttgcggttct   540
tctttgaccc ttcgggaggg ctggatcggc agtttcttcg cttccttgct ccagattttta   600
gttcatcttg taccagtaca gtagcaagat gatggatggg ggcttgtttt ttctttctcc   660
ttccttgttc cggacatttc tctggagcga cttttatgca tttcccagta ttgtcctttg   720
tcctagagg gtagtggatc ggcagttttc ttcgcctcat tggtccagat tttagtttat   780
cttgtacggt accaagatga tggatgtggc acaaagttct cagtttgggg gttgcgctct   840
tccgggcagt tgttattttg gtctgtgatg actaactcgt atctattctt gtgggagcag   900
gggcaaactg ggcaacccaa gcagaggaaa ccacaccggt tcaggccagg cacggtggca   960
ctgcgggaga tcaggaggta tcagaagtcg gtcgactttc tcatcccgtt tgcaccattt   1020
gtccgtctgg tgggtacctc tgtctgtcat atcctctcgc tctctctaca aacgatctgc   1080
agtgcagagt gtaattggaa tattttgttc ctgacaaatt tgcagatcaa ggaggtcacc   1140
gacttcttct gtcctgaaat cagccgctgg actccccaag cgctcgtcgc gattcaagag   1200
gtcagtgcta aaacctggca ttgtactatta gatctgatgg tttgattaga gtactacaat   1260
gcagatgaat tcaatatccg aaaaccatga actgtggggt agatacatgt atcgccttaa   1320
ttcatggttt ctgaatgctc tgctattaat tcagtttgat atatttattt agcagcatgg   1380
tattgttttg gtggctggta aatcaaaact gaaatgtgat tacgagcaaa acggtatcga   1440
ttgtcgatcc tgtgtgtttt tgtgcacatc tggttgtttg gtcaagatgt gtttgtgcac   1500
atcttgcaac atgtcctgc ccacacactc aaaactgact attggttagg ttccatttgt   1560
cttatggaat ttagggtgta actgagaggt gagcaagtgg tagtaacgtt caattttgat   1620
tcaggatgag gatattgtga tccagaaaat tgcatgttat ggttatgtgt ccaaacgcca   1680
aatgattatg tctatatcca gtactttaga accagtacaa caacaaaaag tactttgaaa   1740
ccagtcaagt ttattgtgca tttatacaag agtgttgttt gcacaataga cttgctttag   1800
tcgtctcttg ccagaaatgc cttcttctgc acaacgagca aaaataacat aaagttgact   1860
```

```
atactcagtg tggcctaaga aatgagttgt acttttttagt cactggcctg tgtatttgct    1920
ttgaattgac acataattcc ctttttcctt ccctctgcag gctgcagagt atcacctcgt    1980
cgacgtattt gaaagggcaa atcactgtgc catccatgca aagcgtgtta ccgtcagtaa    2040
gttctcactg aatgaaaact cccttttctt tacaatattg cgcagaagga aacatgccag    2100
ttatgaaaga gtttcaatta caggatcacc tttgctttca tttgatgtga tatctagttt    2160
tgatgttgtt tcaaggttca agaattctaa tgataaatga taggatccac aattgttata    2220
tctctgcagc tcctcgtatc tgttgtccac gaacaaacat atcaaacaat tcattaaaaa    2280
gatgaagaag tcaaacaaac agtatatgtg cactgcatat tagatatcaa acctggttac    2340
tatacgactg atctggcctg accccgcgt cgcctctccc tggcggcacg gggggaacca    2400
ctccggcgcc gccaccttcc ctcctccctc caccccccac ctcgccgccg cctgaggagt    2460
tcgccggcga agcccggtct ggctccaggg agggtggcgg cggggcatct ctctgcgagg    2520
cgtgagggcg catctcgtgc gcgggcgcgg cgagcttggg cgggatcgcg ggcgcggctc    2580
tggctcgggc tggtgaggct ccggcggtcc gagggtgtc gcgcgcggc gggggtctcg    2640
ctccggcgcg ggcggtccga gggcgcgcgg gatctggcgc tccagcaggg gcgccgtcaa    2700
ggggagccgg gcagggaagc tcgtcaggcg ggctcgtcag gcaggcgtga cgcggggcgg    2760
cggccgcggg ctggaagcca tggcgttttg gccatggtgt cgtgtgcgct cgcttctcat    2820
tcgcagcttg aggtgctgct gctgagggtg gtgcgcggtg aagcttggtg gtcggcgttg    2880
gagagtgcaa ggcgcaacag gaatggctcc aatgatctcc acgcttctgg gtggatcaga    2940
tctgcggccc tccataggggg tgtgttccgg gcgaaagcct tgacccgact ttgtcggtgc    3000
cgtcgacggc ggcgctttcg ggcgtcgttt ccctccttgg aggcgtcgtt gtggaactca    3060
tcttcttcta tgtggggctc gggctctccg ggtgaaaacc taagctccag attttccgga    3120
gcgggcgatg gcggcgtctt cgtcgtttcc ctcttggcgg cgttgcttgg gagagttagc    3180
ttgtgcttgg tgcgtttggt tttctcctac gtcgggtttg gtggatgccg gggcagcggc    3240
cccgacggc tgatgaacgc cgaggcggcg gcctcggaaa gtgatgcgcg gtgcggctcc    3300
atggggcggg gcggtggctc ggccttcact tgggtggcaa tcttgggcca cttgggtggc    3360
aggcttgtcg gtccggtcga cgcgttccag agggggcggt ctgactttgc gtcggggcgg    3420
cggccccgga tgtggtgcga cgttcgtggt ctgcgagcgg ttgccttgag cagcgtgggc    3480
tgcgggcagc tgggtcgcgc ggcgttgctg ctcgagcgga gcggtggtac gtcggggcgg    3540
cggccccgga aggtgatgcc ggttgattgc gctgggcgtg acggagcggt ggatgtcggg    3600
gcggcggccc cgagaaaatc actgtggcgt ccagatttct gtggcaacga tgatggtggg    3660
agcgatgtcg gcgacgcggc aatggttgcg atagtcggct cttctccggc gtgtccacga    3720
tattgcctcg gtttgtttgt tgctgtggag tcgaagctgc ggcggcgagg ccctgtggta    3780
tacgatgact ggttccaggt gtcctttcgt cgatcttccg tggcgccagc cgtgcctggt    3840
ttcgttcttc cgagttctcc gtcagaatcg gagctgcgtt gtctgtccgc aggtcgacat    3900
gttgtcgaga agggtgggct ttgccctgtg tgtttcagtc tatgcgagtg ggctcggccc    3960
ttgttgttct ggtttttgcc cggttttccg taattaactg ggcaattctc ttctgcttaa    4020
ttaatagatg aggcaatctt tgcctccctt tcaaaaaaaa acctggttac tatagcagga    4080
aattcagggt tgattacttt atttcttatc tgaaggataa acattgtatc aaatcagaat    4140
tttatttgta agttacattt tttttttactt ataaaacttg gaaactgttt tactgtgaca    4200
aatagatgcc actagaatca tgatcacatc gtggctgttg ctattctaac aaataaatgc    4260
tcctgaacaa atgggaacta tatatgaaga tgtatggacc agcatgttcc tgttaacctg    4320
acctttttcc ttttttttgct gctgcagtgc aaaaggacac acagcttgca aggcgtatcg    4380
gcgggaggag gctttggtga                                                4400

SEQ ID NO: 85           moltype = RNA   length = 493
FEATURE                 Location/Qualifiers
source                  1..493
                        mol_type = other RNA
                        organism = Triticum aestivum
SEQUENCE: 85
atggcccgca ccaagcaccc ggccgtcagg aagaccaagg cgccgcccaa gaagcagctc    60
gggccccgcc ccgcgcagcg gcggcaggag acagatggcg cggcacgtc ggcgacaccg    120
aggcgagccg ggcgggcggc ggccccaggg ggggctcaag gggcaaactg ggcaacccaa    180
gcagaggaaa ccacaccggt tcaggccagg cacggtggca ctgcgggaga tcaggaggta    240
tcagaagtcg gtcgactttc tcatcccgtt tgcaccattt gtccgtctga tcaaggaggt    300
caccgacttc ttctgtcctg aaatcagccg ctggactccc caagcgctcg tcgcgattca    360
agaggctgca gagtatcacc tcgtcgacgt atttgaaagg gcaaatcact gtgccatcca    420
tgcaaagcgt gttaccgtca tgcaaaagga catacagctt gcaaggcgta tcggcgggag    480
gaggctttgg tga                                                       493

SEQ ID NO: 86           moltype = AA   length = 106
FEATURE                 Location/Qualifiers
source                  1..106
                        mol_type = protein
                        organism = Triticum aestivum
SEQUENCE: 86
MARTKHPAVR KTKAPPKKQL GPRPAQRRQE TDGAGTSATP RRAGRAAAPG GAQGANWATQ    60
AEETTPVQAR HGGTAGDQEV SEVGRLSHPV CTICPSDQGG HRLLLS                   106

SEQ ID NO: 87           moltype = DNA   length = 4399
FEATURE                 Location/Qualifiers
source                  1..4399
                        mol_type = other DNA
                        organism = Triticum aestivum
SEQUENCE: 87
atggcccgca ccaagcaccc ggccgtcagg aagaccaagg cgccgcccaa gaagcagctc    60
gggccccgcc ccgcgcagcg gcggcaggag acaggtcagc ccttccctcc ttcctccccc    120
cgtctcccgc ctctcgagcg aacgccgtcg ccatttcgtc gcgagagatg gacggacgga    180
cgccccacgc atgacgctaa tgtgctcttc ctctcccttt gcagatggcg cgggcacgtc    240
```

```
ggcgacaccg gtgcgcggga ccttcccggg tcgcttcctt ttcgtttcgt cttgtttttct  300
gttttttggt ctgacttgct cgtcacctgt tcgacggaat gcagaggcga gccgggcggg  360
cggcggcccc aggggggggct caaggtgcgg ccttctttgc gcttttcggt tttccgccgc  420
gtgtttaggg ccatttccgt cttgtttggg ggtgcgcggg gcggggggctt gtttttttttc  480
ctcccccctt cgttgttgcg cacattgctc gggaatgctc gcaggagcgg ttgcggttct  540
tctttgaccc ttcgggaggg ctggatcggc agtttcttcg cttccttgct ccagatttta  600
gttcatcttg taccagtaca gtagcaagat gatggatggg ggcttgtttt ttcttttctcc  660
ttccttgttc cggacatttc tctggagcga cttttatgca tttcccagta ttgtcctttg  720
tccttagagg gtagtggatc ggcagttttc ttcgcctcat tggtccagat tttagtttat  780
cttgtacggt accaagatga tggatgtggc acaaagttct cagtttgggg gttgcgctct  840
tccgggcagt tgttattttg gtctgtgatg actaactcgt atctattctt gtgggagcag  900
gggcaactgg gcaacccaag cagaggaaac cacaccggtt caggccaggc acggtggcac  960
tgcgggagat caggaggtat cagaagtcgg tcgacttctt catcccgttt gcaccatttg  1020
tccgtctggt gggtacctct gtctgtcata tcctctcgct ctctctacaa acgatctgca  1080
gtgcagagtg taattggaat attttgttcc tgacaaattt gcagatcaag gaggtcaccg  1140
acttcttctg tcctgaaatc agccgctgga ctccccaagc gctcgtcgcg attcaagagg  1200
tcagtgctaa aacctggcat gtactattag atctgatggt ttgattagag tactacaatg  1260
cagatgaatt caatatccga aaaccatgaa ctgtggggta gatacatgta tcgccttaat  1320
tcatggtttc tgaatgctct gctattaatt cagtttgata tatttattta gcagcatggt  1380
attgtttttgg tggctggtaa atcaaaactg aaatgtgatt acgagcaaaa cggtatcgat  1440
tgtcgatcct gtgtgttttt gtgcacatct ggttgtttgg tcaagatgtg tttgtgcaca  1500
tcttgcaaca tgatcctgcc cacacactca aaactgacta ttggttaggt tccatttgtc  1560
ttatggaatt tagggtgtaa ctgagaggtg agcaagtggt agtaacgttc aattttgatt  1620
caggatgagg atattgtgat ccagaaaatt gcatgttatg gttatgtgtc caaacgccaa  1680
atgattatgt ctatatccag tactttagaa ccagtacaac aacaaaaagt actttagaac  1740
cagtcaagtt tattgtgcat ttatacaaga gtgttgtttg cacaatagac ttgctttagt  1800
cgtctcttgc cagaaatgcc ttcttctgca caacgagcaa aaataacata aagttgacta  1860
tactcagtgt ggcctaagaa atgagttgta ctttttagtc actggcctgt gtatttgctt  1920
tgaattgaca cataattccc ttttccttttc cctctgcagg ctgcagagta tcacctcgtc  1980
gacgtatttg aaagggcaaa tcactgtgcc atccatgcaa agcgtgttac cgtcagtaag  2040
ttctcactga atgaaaactc cctttctttt acaatattgc gcagaaggaa acatgccagt  2100
tatgaaaagag tttcaattac aggatcacct ttgctttcat ttgatgtgat atctagtttt  2160
gatgttgttt caaggttcaa gaattctaat gataaatgat aggatccaca attgttatat  2220
ctctgcagct cctcgtatct gttgtccacg aacaaacata tcaaacaatt cattaaaaag  2280
atgaagagt caaacaaaca gtatatgtgc actgcatatt agatatcaaa cctggttact  2340
atacgactga tctggcctga ccccccgcgtc gcctctccct ggcggcacgg ggggaaccac  2400
tccgcgccg ccaccttccc tcctccctcc acccccacc tcgccgccgc ctgaggagtt  2460
cgccggcgaa gcccggtctg gctccaggga gggtggcggc ggggcatctc tctgcgaggc  2520
gtgagggcgc atctcgtgcg cgggcgcggc gagcttgggc gggatcgcgg gcgcggctct  2580
ggctcgggct ggtgaggctc cggcggtccg aggggtgtcg cggcgcggcg ggggtctcgc  2640
tccggcgcgg gcggtccgag ggcgcgcggg atctggcgct ccagcagggg cgccgtcaag  2700
gggagccggg caggggaagct cgtcaggcgg gctcgtcagg caggcgtgac gcggggcggc  2760
ggccgcgggc tggaagccat ggcgtttttg ccatggtgtc gtgtgcgctc gcttctcatt  2820
cgcagcttga ggtgctgctg ctgagggtgg tgcgcggtga agcttggtgg tcggcgttgg  2880
agagtgcaag gcgcaacagg aatggctcca atgatctcca cgcttctggg tggatcagat  2940
ctgcggccct ccataggggt gtgttccggg cgaaagcctt gacccgactt tgtcggtgcc  3000
gtcgacggcg gcgctttcgg gcgtcgtttc cctccttgga ggcggtcgttg tggaactcat  3060
cttcttctat gtggggctcg ggctctccgg gtgaaaacct aagctccaga tttttccggag  3120
cgggcgatgg cggcgtcttc gtcgtttccc tcttgggggc gttgcttggg agagttagct  3180
tgtgcttggt gcgtttggtt ttctcctacg tcgggtttgg tggatgccgg ggcagcggcc  3240
ccggacggct gatgaacgcc gaggcggcgg cctcggaaag tgatgcgcgg tgcggctcca  3300
tggggcgggg cggtggctcg gccttcactt gggtggcaat cttgggccac ttgggtggca  3360
ggcttgtcgg tccggtcgac gcgttccaga gggggcggtc tgactttgcg tcggggcggc  3420
ggccccggat gtggtgcgac gttcgtggtc tgcgagcggt tgccttgagc agcgtgggct  3480
gcgggcagct gggtcgcgcg gcgttgctgc tcgagcggag cggtggtacg tcggggcggc  3540
ggccccggaa ggtgatgccg gttgattgcg ctgggcgtga cggagcggtg gatgtcgggg  3600
cggcggcccc gagaaaatca ctgtggcgtc cagattctg tggcaacgat gatggtggga  3660
gcgatgtcgg cgacgcggca atggttgcga tagtcggctc ttctccggcg tgtccacgat  3720
attgcctcgg tttgtttgtt gctgtggagt cgaagctgcg gcggcgaggc cctgtggtat  3780
acgatgactg gttccaggtg tcctttcgtc gatcttccgt ggcgccagcc gtgcctggtt  3840
tcgttcttcc gagttctccg tcagaatcgg agctgcgttg tctgtccgca ggtcgacatg  3900
ttgtcgagaa gggtgggctt tgccctgtgt gtttcagtct atgcgagtgg gctcggccct  3960
tgttgttctg gtttttgccc ggtttttccgt aattaactgg gcaattctct tctgcttaat  4020
taatagatga ggcaatcttt gcctccctttt caaaaaaaa cctggttact atagcaggaa  4080
attcaggggtt gattacttta tttcttatct gaaggataaa cattgtatca aatcagaatt  4140
ttatttgtaa gttacatttt ttttttactta taaaacttgg aaactgtttt actgtgacaa  4200
atagatgcca ctagaatcat gatcacatcg tggctgttgc tattctaaca aataaatgct  4260
cctgaacaaa tgggaactat atatgaagat gtatggacca gcatgttcct gttaacctga  4320
ccttttttcct ttttttgctg ctgcagtgca aaaggacata cagcttgcaa ggcgtatcgg  4380
cgggaggagg ctttggtga                                                 4399
```

SEQ ID NO: 88          moltype = RNA   length = 492
FEATURE                Location/Qualifiers
source                 1..492
                       mol_type = other RNA
                       organism = Triticum aestivum
SEQUENCE: 88
```
atggcccgca ccaagcaccc ggccgtcagg aagaccaagg cgccgcccaa gaagcagctc  60
gggccccgcc ccgcgcagcg gcggcaggag acagatggcc cgggcacgtc ggcgacaccg  120
```

-continued

```
aggcgagccg ggcgggcggc ggccccaggg ggggctcaag gggcaactgg gcaacccaag   180
cagaggaaac cacaccggtt caggccaggc acggtggcac tgcgggagat caggaggtat   240
cagaagtcgg tcgactttct catcccgttt gcaccatttg tccgtctgat caaggaggtc   300
accgacttct tctgtcctga aatcagccgc tggactcccc aagcgctcgt cgcgattcaa   360
gaggctgcag agtatcacct cgtcgacgta tttgaaaggg caaatcactg tgccatccat   420
gcaaagcgtg ttaccgtcat gcaaaaggac atacagcttg caaggcgtat cggcgggagg   480
aggctttggt ga                                                       492

SEQ ID NO: 89              moltype = AA  length = 163
FEATURE                    Location/Qualifiers
source                     1..163
                           mol_type = protein
                           organism = Triticum aestivum
SEQUENCE: 89
MARTKHPAVR KTKAPPKKQL GPRPAQRRQE TDGAGTSATP RRAGRAAAPG GAQGATGQPK    60
QRKPHRFRPG TVALREIRRY QKSVDFLIPF APFVRLIKEV TDFFCPEISR WTPQALVAIQ   120
EAAEYHLVDV FERANHCAIH AKRVTVMQKD IQLARRIGGR RLW                     163

SEQ ID NO: 90              moltype = DNA  length = 4400
FEATURE                    Location/Qualifiers
source                     1..4400
                           mol_type = other DNA
                           organism = Triticum aestivum
SEQUENCE: 90
atggcccgca ccaagcaccc ggccgtcagg aagaccaagg cgccgcccaa gaagcagctc    60
gggcccgccc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gttgcgcggg accttcccgg gtcgcttcct tttcgtttcg tcttgttttc   300
tgtttttgg tctgacttgc tcgtcacctg ttcgacggaa gtcagaggcg agccggggcgg   360
gcggcggccc caggggggc tcaaggtgcg gccttcttg cgcttttcgg ttttccgccg   420
cgtgtttagg gccatttccg tcttgtttgg gggtgcgcgg ggcgggggct tgtttttttt   480
cctcccccct tcgttgttgc gcacattgct cgggaatgct gccaggagcg gttgcggttc   540
ttctttgacc cttcgggagg gctggatcgg cagtttcttc gcttccttgc tccagatttt   600
agttcatctt gtaccagtac agtagcaaga tgatggatgg gggcttgttt tttctttctc   660
cttccttgtt ccggacattt ctctggagcg acttttatgc atttcccagt attgtccttt   720
gtccttagag ggtagtggat cggcagtttt cttcgcctca ttggtccaga ttttagttta   780
tcttgtacgg taccaagatg atggatgtgg cacaaagttc tcagtttggg ggttgcgctc   840
ttccgggcag ttgttatttt ggtctgtgat gactaactcg tatctattct tgtgggagca   900
ggggcaactg ggcaacccaa gcagaggaaa ccacaccggt tcaggccagg cacggtggca   960
ctgcgggaga tcaggaggta tcagaagtcg gtcgactttc tcatcccgtt tgcaccattt   1020
gtccgtctgt tgggtacctc tgtctgtcat atcctctcgc tctctctaca aacgatctgc   1080
agtgcagagt gtaattggaa tattttgttc ctgacaaatt tgcagatcaa ggaggtcacc   1140
gacttcttct gtcctgaaat cagccgctgg actccccaag cgctcgtcgc gattcaagag   1200
gtcagtgcta aaacctggca tgtactatta gatctgatgg tttgattaga gtactacaat   1260
gcagatgaat tcaatatccg aaaaccatga actgtggggt agatacatgt atcgccttaa   1320
ttcatggttt ctgaatgctc tgctattaat tcagtttgat atatttattt agcagcatgg   1380
tattgttttg gtggctggta aatcaaaact gaaatgtgat tacgagcaaa acggtatcga   1440
ttgtcgatcc tgtgtgtttt tgtgcacatc tggttgtttg gtcaagatgt gtttgtgcac   1500
atcttgcaac atgatcctgc ccacacactc aaaactgact attggttagg ttccatttgt   1560
cttatggaat ttagggtgta actgagaggt gagcaagtgg tagtaacgtt caattttgt   1620
tcaggatgag gatattgtga tccagaaaat tgcatgttat ggttatgtgt ccaaacgcca   1680
aatgattatg tctatatcca gtactttaga accagtacaa caacaaaaag tactttagaa   1740
ccagtcaagt ttattgtgca tttatacaag agtgttgttt gcacaataga cttgctttag   1800
tcgtctcttg ccagaaatgc cttcttctgc acaacgagca aaaataacat aaagttgact   1860
atactcagtg tggcctaaga aatgagttgc acttttttagt cactggcctg tgtatttgct   1920
ttgaattgac acataattcc cttttccttt ccctctgcag gctgcagagt atcacctcgt   1980
cgacgtattt gaaagggcaa atcactgtgc catccatgca aagcgtgtta ccgtcagtaa   2040
gttctcactg aatgaaaact cccttctttt tacaatattg cgcagaagga aacatgccag   2100
ttatgaaaga gtttcaatta caggatcacc tttgctttca tttgatgtga tatctagttt   2160
tgatgttgtt tcaaggttca agaattctaa tgataaatga taggatccac aattgttata   2220
tctctgcagc tcctcgtatc tgttgtccac gaacaaacat atcaaacaat tcattaaaaa   2280
gatgaagaag tcaaacaaac agtatatgtg cactgcatat tagatatcaa acctggttac   2340
tatacgactg atctggcctg accccgcgt cgcctctccc tggcggcacg ggggaacca   2400
ctccggcgcc gccaccttcc ctcctccctc cacccccac ctcgccgccg cctgaggagt   2460
tcgccggcga agcccggtct ggctccaggg agggtggcgg cggggcatct ctctgcgagg   2520
cgtgagggc catctcgtgc gcgggcgcgg cgagcttggg cgggatcgcg ggcgcggctc   2580
tggctcgggc tggtgaggct ccggcggtcc gaggggtgtc gcggcgcggc gggggtctcg   2640
ctccggcgcg ggcggtccga gggcggcgcg gatctggcgc tccagcaggg gccgccgtcaa   2700
ggggagccgg gcaggggaagc tcgtcaggcg ggctcgtcag gcaggcgtga cgcggggcgg   2760
cggccgcggg ctgaagccga tggcgtttt gccatggtgt cgtgtgcgct cgcttctcat   2820
tcgcagcttg aggtgctgct gctgagggtg gtgcgcggtg aagcttggtg gtcggcgttg   2880
gagagtgcaa ggcgcaacag gaatggctcc aatgatctcc acgcttctgg gtggatcaga   2940
tctgcgggcc tccataggg tgtgttccgg gcgaaagcct gacccgact ttgtcgggtc   3000
cgtcgacggc ggcgctttcg ggcgtcgttt ccctccttgg aggcgtcgtt gtggaactca   3060
tcttcttcta tgtggggctc gggctctccg ggtgaaaacc taagtccag attttccgga   3120
gcgggcgatg gcggcgtctt cgtcgtttcc ctcttggggg cgttgcttgg gagagttagc   3180
ttgtgcttgg tgcgtttggt tttctcctac gtcgggtttg gtggatgccg gggcagcggc   3240
cccggacggc tgatgaacgc cgaggcggcg gcctcggaaa gtgatgcgcg gtgcggctcc   3300
```

-continued

```
atggggcggg gcggtggctc ggccttcact tgggtggcaa tcttgggcca cttgggtggc  3360
aggcttgtcg gtccggtcga cgcgttccag aggggcggt ctgactttgc gtcggggcgg  3420
cggccccgga tgtggtgcga cgttcgtggt ctgcgagcgg ttgccttgag cagcgtgggc  3480
tgcgggcagc tgggtcgcgc ggcgttgctg ctcgagcgga gcggtggtac gtcggggcgg  3540
cggcccggaa aggtgatgcc ggttgattgc gctgggcgtg acggagcggt ggatgtcggg  3600
gcggcggccc cgagaaaatc actgtggcgt ccagatttct gtggcaacga tgatggtggg  3660
agcgatgtcg gcgacgcggc aatggttgcg atagtcggct cttctccggc gtgtccacga  3720
tattgcctcg gtttgtttgt tgctgtggag tcgaagctgc ggcggcgagg ccctgtggta  3780
tacgatgact ggttccaggt gtcctttcgt cgatcttccg tggcgccagc cgtgcctggt  3840
ttcgttcttc cgagttctcc gtcagaatcg gagctgcgtt gtctgtccgc aggtcgacat  3900
gttgtcgaga agggtgggct ttgccctgtg tgtttcagtc tatgcgagtg ggctcggccc  3960
ttgttgttct ggtttttgcc cggttttccg taattaactg ggcaattctc ttctgcttaa  4020
ttaatagatg aggcaatctt tgcctccctt tcaaaaaaaa acctggttac tatagcagga  4080
aattcagggt tgattacttt atttcttatc tgaaggataa acattgtatc aaatcagaat  4140
tttatttgta agttacattt tttttttactt ataaaacttg gaaactgttt tactgtgaca  4200
aatagatgcc actagaatca tgatcacatc gtggctgttg ctattctaac aaataaatgc  4260
tcctgaacaa atgggaacta tatatgaaga tgtatggacc agcatgttcc tgttaacctg  4320
accttttttcc tttttttgct gctgcagtgc aaaaggacat acagcttgca aggcgtatcg  4380
gcgggaggag gctttggtga                                                4400

SEQ ID NO: 91            moltype = RNA   length = 587
FEATURE                  Location/Qualifiers
source                   1..587
                         mol_type = other RNA
                         organism = Triticum aestivum
SEQUENCE: 91
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
gttgcgcggg accttcccgg gtcgcttcct tttcgtttcg tcttgttttc tgtttttttgg  180
tctgacttgc tcgtcacctg ttcgacggaa tgcagagcg agccgggcgg gcggcggccc  240
caggggggc tcaaggggca actgggcaac ccaagcagag gaaaccacac cggttcaggc  300
caggcacggt ggcactgcgg gagatcagga ggtatcagaa gtcggtcgac tttctcatcc  360
cgtttgcacc atttgtccgt ctgatcaagg aggtcaccga cttcttctgt cctgaaatca  420
gccgctggac tccccaagcg ctcgtcgcga ttcaagaggc tgcagagtat cacctcgtcg  480
acgtatttga aagggcaaat cactgtgcca tccatgcaaa gcgtgttacc gtcatgcaaa  540
aggacataca gcttgcaagg cgtatcggcg ggaggaggct ttggtga             587

SEQ ID NO: 92            moltype = AA   length = 127
FEATURE                  Location/Qualifiers
source                   1..127
                         mol_type = protein
                         organism = Triticum aestivum
SEQUENCE: 92
MARTKHPAVR KTKAPPKKQL GPRPAQRRQE TDGAGTSATP VARDLPGSLP FRFVLFSVFW    60
SDLLVTCSTE CRGEPGGRRP QGGLKGQLGN PSRGNHTGSG QARWHCGRSG GIRSRSTFSS   120
RLHHLSV                                                             127

SEQ ID NO: 93            moltype = DNA   length = 4391
FEATURE                  Location/Qualifiers
source                   1..4391
                         mol_type = other DNA
                         organism = Triticum aestivum
SEQUENCE: 93
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacaccg gtgcgcggga ccttcccggg tcgcttcctt ttcgtttcgt cttgttttct  300
gtttttttggt ctgacttgct cgtcacctgt tcgacggaat gcagaggcga gccgggcggg  360
cggcggcccc aggggggct caaggtgcgg ccttcttgc gcttttcggt tttccgccgc  420
gtgtttaggg ccatttccgt cttgtttggg ggtgcgcggg gcggggcctt gtttttttttc  480
ctccccccctt cgttgttgcg cacattgctc gggaatgctg ccaggagcgg ttgcggttct  540
tctttgaccc ttcgggaggg ctggatcggc agttcttcg cttccttgct ccagatttta  600
gttcatcttg taccagtaca gtagcaagat gatggatggg ggcttgtttt ttcttttctc  660
ttccttgttc cggacatttc tctggagcga ctttttatgca tttcccagta ttgtcctttg  720
tcctttagagg gtagtggatc ggcagttttc ttcgcctcat tggtccagat tttagtttat  780
cttgtacggt accaagatga tggatgtggc acaaagttct cagtttgggg gttgcgctct  840
tccgggcagt tgttattttg gtctgtgatg actaactcgt atctattcgt gtgggagcag  900
gggcaaccca agcagaggaa accacaccgg ttcaggccag gcacggtggc actgcgggag  960
atcaggaggt atcagaagtc ggtcgacttt ctcatcccgt ttgcaccatt tgtccgtctg  1020
gtgggtacct ctgtctgtca tatcctctcg ctctctctac aaacgatctg cagtgcagag  1080
tgtaattgga atattttgtt cctgacaaat ttgcagatca aggaggtcac cgacttcttc  1140
tgtcctgaaa tcagccgctg gactccccaa gcgctcgtcg cgattcaaga ggtcagtgct  1200
aaaacctggc atgtactatt agatctgatg gtttgattag agtactacaa tgcagatgaa  1260
ttcaatatcc gaaaaccatg aactgtgggg tagatacatg tatcgcctta attcatggtt  1320
tctgaatgct ctgctattaa ttcagtttga tatatttatt tagcagcatg gtattgtttt  1380
ggtggctggt aaatcaaaac tgaaatgtga ttacgagcaa aacggtatcg attgtcgatc  1440
ctgtgtgtt ttgtgcacat ctggttgttt ggtcaagatg tgtttgtgca catcttgcaa  1500
catgatcctg cccacacact caaaactgac tattggttag gttccatttg tcttatggaa  1560
```

-continued

```
tttagggtgt aactgagagg tgagcaagtg gtagtaacgt tcaatttttga ttcaggatga   1620
ggatattgtg atccagaaaa ttgcatgtta tggttatgtg tccaaacgcc aaatgattat   1680
gtctatatcc agtactttag aaccagtaca acaacaaaaa gtactttaga accagtcaag   1740
tttattgtgc atttatacaa gagtgttgtt tgcacaatag acttgcttta gtcgtctctt   1800
gccagaaatg ccttcttctg cacaacgagc aaaaataaca taaagttgac tatactcagt   1860
gtggcctaag aaatgagttg tacttttttag tcactggcct gtgtatttgc tttgaattga   1920
cacataattc ccttttcctt tccctctgca ggctgcagag tatcacctcg tcgacgtatt   1980
tgaaagggca aatcactgtg ccatccatgc aaagcgtgtt accgtcagta agttctcact   2040
gaatgaaaac tcccttttctt ttacaatatt gcgcagaagg aaacatgcca gttatgaaag   2100
agtttcaatt acaggatcac ctttgctttc atttgatgtg atatctagtt ttgatgttgt   2160
ttcaaggttc aagaattcta atgataaatg ataggatcca caattgttat atctctgcag   2220
ctcctcgtat ctgttgtcca cgaacaaaca tatcaaacaa ttcattaaaa agatgaagaa   2280
gtcaaacaaa cagtatatgt gcactgcata ttagatatca aacctggtta ctatacgact   2340
gatctggcct gacccccgcg tcgcctctcc ctggcggcac ggggggaacc actccggcgc   2400
cgccaccttc cctcctccct ccaccccca cctcgccgcc gcctgaggag ttcgccggcg   2460
aagcccggtc tggctccagg gagggtggcg gcggggcatc tctctgcgag gcgtgagggc   2520
gcatctcgtg cgcgggcgcg gcgagcttgg gcgggatcgc gggcgcggct ctggctcggg   2580
ctggtgaggc tccggcggtc cgagggtgt cgcggccggg cgggggtctc gctccggcgc   2640
gggcggtccg agggcgcgcg ggatctggcg ctccagcagg ggcgccgtca aggggagccg   2700
ggcaggggaag ctcgtcaggc gggctcgtca ggcaggcgtg acgcggggcg gcgggccgcg   2760
gctggaagcc atggcgtttt ggccatggtg tcgtgtgcgc tcgcttctca ttcgcagctt   2820
gaggtgctgc tgctgagggt ggtgcgcggt gaagcttggt ggtcggcgtt ggagagtgca   2880
aggcgcaaca ggaatggctc caatgatctc cacgcttctg ggtggatcag atctgcggcc   2940
ctccataggg gtgtgttccg ggcgaaagcc ttgacccgac tttgtcggtg ccgtcgacgg   3000
cggcgctttc gggcgtcgtt tccctccttg gaggcgtcgt tgtggaactc atcttcttct   3060
atgtggggct cgggctctcc gggtgaaaac ctaagctcca gattttccgg agcgggcgat   3120
ggcggccgtct tcgtcgtttc cctcttgggg gcgttgcttg ggagagttag cttgtgcttg   3180
gtgcgtttgg ttttctccta cgtcgggttt ggtggatgcc ggggcagcgg ccccggacgg   3240
ctgatgaacg ccgaggcggc ggcctcggaa agtgatgcgc ggtgcggctc catgggogcgg   3300
ggcggtggct cggccttcac ttgggtggca atcttgggac acttgggtgg caggcttgtc   3360
ggtccggtcg acgcgttcca gagggggcgg tctgactttg cgtcggggcg gcggcccgg   3420
atgtggtgcg acgttcgtgg tctgcgagcg gttgccttga gcagcgtggg ctgcgggcag   3480
ctgggtcgcg cggcgttgct gctcgagcgg agcggtggta cgtcggggcg gcggcccgg   3540
aaggtgatgc cggttgattg cgctgggcgt gacggagcgg tggatgtcgg ggcggcggc   3600
ccgagaaaat cactgtggcg tccagatttc tgtggcaacg atgatggtgg gagcgatgtc   3660
ggcgacgcgg caatggttgc gatagtcggc tcttctccgg cgtgtccacg atattgcctc   3720
ggtttgtttg ttgctgtgga gtcgaagctg cggcggcgag gccctgtggt atacgatgac   3780
tggttccagg tgtcctttcg tcgatcttcc gtggcgccag ccgtgcctgg tttcgttctt   3840
ccgagttctc cgtcagaatc ggagctgcgt tgtctgtcga cagttgtcgag   3900
aagggtgggc tttgccctgt gtgtttcagt ctatgcgagt gggctcggcc cttgttgttc   3960
tggttttgc ccggtttcc gtaattaact gggcaattct cttctgctta attaatagat   4020
gaggcaatct ttgcctccct ttcaaaaaaa aacctggtta ctatagcagg aaattcaggg   4080
ttgattactt tatttcttat ctgaaggata aacattgtat caaatcagaa ttttatttgt   4140
aagttacatt tttttttact tataaaactt ggaaactgtt ttactgtgac aaatagatgc   4200
cactagaatc atgatcacat cgtggctgtt gctattctaa caaataaatg ctcctgaaca   4260
aatgggaact atatatgaag atgtatggac cagcatgttc ctgttaacct gacctttttc   4320
ctttttttgc tgctgcagtg caaaaggaca tacagcttgc aaggcgtatc ggcgggagga   4380
ggctttggtg a                                                         4391
```

```
SEQ ID NO: 94         moltype = RNA  length = 484
FEATURE               Location/Qualifiers
source                1..484
                      mol_type = other RNA
                      organism = Triticum aestivum
SEQUENCE: 94
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
aggcgagccg ggcgggcggc ggccccaggg ggggctcaag gggcaaccca gcagaggaa    180
accacaccgg ttcaggccag gcacgctggc actgcgggag atcaggaggt atcagaagtc   240
ggtcgacttt ctcatcccgt ttgcaccatt tgtccgtctg atcaaggagg tcaccgactt   300
cttctgtcct gaaatcagcc gctggactcc ccaagcgctc gtcgcgattc aagaggctgc   360
agagtatcac ctcgtcgacg tatttgaaag ggcaaatcac tgtgccatcc atgcaaagcg   420
tgttaccgtc atgcaaaagg acatacagct tgcaaggcgt atcggcggga ggaggctttg   480
gtga                                                                 484
```

```
SEQ ID NO: 95         moltype = AA  length = 103
FEATURE               Location/Qualifiers
source                1..103
                      mol_type = protein
                      organism = Triticum aestivum
SEQUENCE: 95
MARTKHPAVR KTKAPPKKQL GPRPAQRRQE TDGAGTSATP RRAGRAAAPG GAQGATQAEE    60
TTPVQARHGG TAGDQEVSEV GRLSHPVCTI CPSDQGGHRL LLS                      103
```

```
SEQ ID NO: 96         moltype = DNA  length = 4399
FEATURE               Location/Qualifiers
source                1..4399
                      mol_type = other DNA
                      organism = Triticum aestivum
```

```
SEQUENCE: 96
atggcccgca ccaagcaccc ggccgtcagg aagaccaagg cgccgcccaa gaagcagctc    60
gggccccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gtgcgcggga ccttcccggg tcgcttcctt ttcgtttcgt cttgtttttct  300
gtttttttggt ctgacttgct cgtcacctgt tcgacggaat gcagaggcga gccgggcggg   360
cggcggcccc agggggggct caaggtgcgg ccttctttgc gcttttcggt tttccgccgc   420
gtgtttaggg ccatttccgt cttgtttggg ggtgcgcggg gcgggggctt gtttttttc   480
ctcccccctt cgttgttgcg cacattgctc gggaatgctg ccaggagcgg ttgcggttcc   540
tctttgaccc ttcgggaggg ctggatcggc agtttcttcg cttccttgct ccagatttta   600
gttcatcttg taccagtaca gtagcaagat gatggatggg ggcttgtttt ttctttctcc   660
ttccttgttc cggacatttc tctggagcga cttttatgca tttcccagta ttgtcctttg   720
tccttagagg gtagtggatc ggcagttttc ttcgcctcat tggtccagat tttagtttat   780
cttgtacggt accaagatga tggatgtggc acaaagttct cagtttgggg gttgcgctct   840
tccgggcagt tgttattttg gtctgtgatg actaactcgt atctattctt gtgggagcag   900
gggcaactgg gcaacccaag cagaggaaac cacaccggtt caggccaggc acggtggcac   960
tgcgggagat caggaggtat cagaagtcgg tcgactttct catcccgttt cgcaccatttg  1020
tccgtctggt gggtacctct gtctgtcata tcctctcgct ctctctacaa acgatctgca  1080
gtgcagagtg taattggaat attttgttcc tgacaaattt gcagatcaag gaggtcaccg   1140
acttcttctg tcctgaaatc agccgctgga ctccccaagc gctcgtcgcg attcaagagg   1200
tcagtgctaa aacctggcat gtactattag atctgatggt ttgattagag tactacaatg   1260
cagatgaatt caatatccga aaaccatgaa ctgtggggta gatacatgta tcgccttaat   1320
tcatggtttc tgaatgctct gctattaatt cagtttgata tatttattta gcagcatggt   1380
attgtttttgt tggctggtaa atcaaaactg aaatgtgatt acgagcaaaa cggtatcgat   1440
tgtcgatcct gtgtgtttttt gtgcacatct ggttgtttgg tcaagatgtg tttgtgcaca   1500
tcttgcaaca tgatcctgcc cacacactca aaactgacta ttggttaggt tccatttgtc   1560
ttatggaatt tagggtgtaa ctgagaggtg agcaagtggt agtaacgttc aattttgatt   1620
caggatgagg atattgtgat ccagaaaatt gcatgttatg gttatgtgtc caaacgccaa   1680
atgattatgt ctatatccag tactttagaa ccagtacaac aacaaaaagt actttagaac   1740
cagtcaagtt tattgtgcat ttatacaaga gtgttgtttg cacaatagac ttgctttagt   1800
cgtctcttgc cagaaatgcc ttcttctgca caacgagcaa aaataacata aagttgacta   1860
tactcagtgt ggcctaagaa atgagttgta cttttttagtc actggcctgt gtatttgctt   1920
tgaattgaca cataattccc tttttccttttc cctctgcagg ctgcagagta tcacctcgtc   1980
gacgtatttg aaaggggcaaa tcactgtgcc atccatgcaa agcgtgttac cgtcagtaag   2040
ttctcactga atgaaaactc cctttctttt acaatattgc gcagaaggaa acatgccagt   2100
tatgaaaagg tttcaattac aggatcacct ttgctttcat ttgatgtgat atctagtttt   2160
gatgttgttt caaggttcaa gaattctaat gataaatgat aggatccaca attgttatat   2220
ctctgcagct cctcgtatct gttgtccacg aacaaacata tcaaacaatt cattaaaaag   2280
atgaagaagt caaacaaaca gtatatgtgc actgcatatt agatatcaaa cctggttact   2340
atacgactga tctggcctga cccccgcgtc gcctctccct ggcggcacgg ggggaaccac   2400
tccggcgccg ccaccttccc tcctccctcc accccccacc tcgccgccgc ctgaggagtt   2460
cgccggcgaa gcccggtctg gctccaggga gggtggcggc gggcatctc tctgcgaggc   2520
gtgagggcgc atctcgtgcg cgggcgcggc gagcttgggc gggatcgcgg gcgcggctct   2580
ggctcgggct ggtgaggctc cggcggtccg aggggtgtcg cggcgcggcg ggggtctcgc   2640
tccggcgcgg gcggtccgag ggcgcgcggg atctggcgct ccagcagggg cgccgtcaag   2700
gggagccggg cagggaagct cgtcagcgcg gctcgtcagg caggcgtgac gcggggcggc   2760
ggccgcgggc tggaagccat ggcgtttttgg ccatggtgtc gtgtgcgctc gcttctcatt   2820
cgcagcttga ggtgctgctg ctgagggtgg tgcgcggtga agcttggtgg tcggcgttgg   2880
agagtgcaag gcgcaacagg aatggctcca atgatctcca cgcttctggg tggatcagat   2940
ctgcggccct ccatagggt gtgttccggg cgaaagcctt gacccgactt tgtcggtgcc   3000
gtcgacggcg gcgctttcgg gcgtcgtttc cctccttgga ggcgtcgttg tggaactcat   3060
cttcttctat gtggggctcg ggctctccgg gtgaaaacct aagctccaga ttttccggag   3120
cgggcgatgg cggcgtcttc gtcgtttccc tcttgggggc gttgcttggg agagttagct   3180
tgtgcttggt gcgtttggtt ttctcctacg tcgggtttgg tggatgccgg ggcagcggcc   3240
ccggacggct gatgaacgcc gaggcggcgg cctcggaaag tgatgcgcgg tgcggctcca   3300
tggggcgggg cggtggctcg gccttcactt gggtggcaat cttgggccac ttgggtggca   3360
ggcttgtcgg tccggtcgac gcgttccaga gggggcggtc tgactttgcg tcggggcggc   3420
ggccccggat gtggtcgcgac gttcgtggtc tgcgagcggt tgccttgagc agcgtgggct   3480
gcgggcagct gggtcgcgcg gcgttgctgc tcgagcggag cggtggtacg tcggggcggc   3540
ggccccggaa ggtgatgccg gttgattgcg ctgggcgtga cggagcggtg gatgtcgggg   3600
cggcggcccc gagaaaatca ctgtggcgtc cagatttctg tggcaacgat gatggtggga   3660
gcgatgtcgg cgacgcggca atggttgcga tagtcggctc ttctccggcg tgtccacgat   3720
attgcctcgg tttgtttgtt gctgtggagt cgaagctgcg gaggcc cctgtgtat     3780
acgatgactg gttccaggtg tcctttcgtc gatcttccgt ggcgccagcc gtgcctggtt   3840
tcgttcttcc gagttctccg tcagaatcgg agctgcgttg tctgtccgca ggtcgacatg   3900
ttgtcgagaa gggtgggctt tgccctgtgt gtttcagtct atgcgagtgg gctcggccct   3960
tgttgttctg gttttttgccc ggttttccgt aattaactgg gcaattctct tctgcttaat   4020
taatagatga ggcaatcttt gcctcccttt caaaaaaaaa cctggttact atagcaggaa   4080
attcagggtt gattacttta tttcttatct gaaggataaa cattgtatca aatcagaatt   4140
ttatttgtaa gttacatttt tttttactta taaaacttgg aaactgtttt actgtgacaa   4200
atagatgcca ctagaatcat gatcacatcg tggctgttgc tattctaaca aataaatgct   4260
cctgaacaaa tgggaactat atatgaagat gtatggacca gcatgttcct gttaacctga   4320
cctttttcct tttttttgctg ctgcagtgca aaaggacata cagcttgcaa ggcgtatcgg   4380
cgggaggagg ctttggtga                                                4399
```

```
SEQ ID NO: 97        moltype = RNA   length = 492
FEATURE              Location/Qualifiers
source               1..492
```

-continued

```
                        mol_type = other RNA
                        organism = Triticum aestivum
SEQUENCE: 97
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
aggcgagccg ggcggcggc ggccccaggg ggggctcaag gggcaactgg gcaacccaag  180
cagaggaaac cacaccggtt caggccaggc acggtggcac tgcgggagat caggaggtat  240
cagaagtcgg tcgactttct catcccgttt gcaccatttg tccgtctgat caaggaggtc  300
accgacttct tctgtcctga aatcagccgc tggactcccc aagcgctcgt cgcgattcaa  360
gaggctgcag agtatcacct cgtcgacgta tttgaaaggg caaatcactg tgccatccat  420
gcaaagcgtg ttaccgtcat gcaaaaggac atacagcttg caaggcgtat cggcgggagg  480
aggctttggt ga                                                      492

SEQ ID NO: 98          moltype = AA   length = 163
FEATURE                Location/Qualifiers
source                 1..163
                        mol_type = protein
                        organism = Triticum aestivum
SEQUENCE: 98
MARTKHPAVR KTKAPPKKQL GPRPAQRRQE TDGAGTSATP RRAGRAAAPG GAQGATGQPK   60
QRKPHRFRPG TVALREIRRY QKSVDFLIPF APFVRLIKEV TDFFCPEISR WTPQALVAIQ  120
EAAEYHLVDV FERANHCAIH AKRVTVMQKD IQLARRIGGR RLW                    163

SEQ ID NO: 99          moltype = DNA   length = 4401
FEATURE                Location/Qualifiers
source                 1..4401
                        mol_type = other DNA
                        organism = Triticum aestivum
SEQUENCE: 99
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacaccg gtagcgcggg accttcccgg gtcgcttcct tttcgtttcg tcttgttttc  300
tgtttttttgg tctgacttgc tcgtcacctg ttcgacggaa tgcagaggcg agccgggcgg  360
gcggcggccc caggggggggc tcaaggtgcg gccttcttg cgctttttcgg ttttccgccg  420
cgtgtttagg gccatttccg tcttgtttgg gggtgcgcgg ggcgggggct tgtttttttt  480
cctcccccct tcgttgttgc gcacattgct cgggaatgct gccaggagcg gttgcggttc  540
ttctttgacc cttcgggagg gctggatcgg cagtttcttc gcttccttgc tccagatttt  600
agttcatctt gtaccagtac agtagcaaga tgatggatgg gggcttgttt tttctttctc  660
cttccttgtt ccggacattt ctctggagcg acttttatgc atttcccagt attgtccttt  720
gtccttagag ggtagtggat cggcagtttt cttcgcctca ttggtccaga ttttagttta  780
tcttgtacgg taccaagatg atggatgtgg cacaaagttc tcagtttggg ggttgcgctc  840
ttccgggcag ttgttatttt ggtctgtgat gactaactcg tatctattct tgtgggagca  900
ggggcaaact gggcaaccca agcagaggaa accacaccgg ttcaggccag gcacggtggc  960
actgcgggag atcaggaggt atcagaagtc ggtcgacttt ctcatcccgt tgcaccatt  1020
tgtccgtctg gtgggtacct ctgtctgtca tatcctctcg ctctctctac aaacgatctg 1080
cagtgcagag tgtaattgga atattttgtt cctgacaaat ttgcagatca aggaggtcac 1140
cgacttcttc tgtcctgaaa tcagccgctg gactccccaa gcgctcgtcg cgattcaaga 1200
ggtcagtgct aaaacctggc atgtactatt agatctgatg gtttgattag agtactacaa 1260
tgcagatgaa ttcaatatcc gaaaaccatg aactgtgggg tagatacatg taatccatgg 1320
attcatggtt tctgaatgct ctgctattaa ttcagtttga tatatttatt tagcagcatg 1380
gtattgtttt ggtggctggt aaatcaaaac tgaaatgtga ttacgagcaa aacggtatcg 1440
attgtcgatc ctgtgtgttt ttgtgcacat ctggttgttt ggtcaagatg tgtttgtgca 1500
catcttgcaa catgatcctg cccacacact caaaactgac tattggttag gttccattg  1560
tcttatggaa tttagggtgt aactgagagg tgagcaagtg gtagtaacgt tcaatttga  1620
ttcaggatga ggatattgtg atccagaaaa ttgcatgtta tggttatgtg tccaaacgcc 1680
aaatgattat gtctatatcc agtactttag aaccagtaca acaacaaaaa gtactttaga 1740
accagtcaag tttattgtgc atttatacaa gagtgttgtt tgcacaatag acttgcttta 1800
gtcgtctctt gccagaaatg ccttcttctg cacaacgagc aaaaataaca taaagttgac 1860
tatactcagt gtggcctaag aaatgagttg tactttttag tcactggcct gtgtatttgc 1920
tttgaattga cacataattc cctttccctt tccctctgca ggctgcagag tatcacctcg 1980
tcgacgtatt tgaaagggca aatcactgtg ccatccatgc aaagcgtgtt accgtcagta 2040
agttctcact gaatgaaaac tcccttcttt ttacaatatt aaaacatggg aaacatgcca 2100
gttatgaaag agtttcaatt acaggatcac ctttgctttc atttgatgtg atatctagtt 2160
ttgatgttgt ttcaaggttc aagaattcta atgataaatg ataggatcca caattgttat 2220
atctctgcag ctcctcgtat ctgttgtcca cgaacaaaca tatcaaacaa ttcattaaaa 2280
agatgaagaa gtcaaacaaa cagtatatgt gcactgcata ttagatatca aacctggtta 2340
ctatacgact gatctggcct gacccccgcg tcgcctctcc ctggcggcac gggggggaacc 2400
actccggcgc cgccaccttc cctcctcct ccaccccca cctcgccgcc gcctgaggag 2460
ttcgccggcg aagcccggtc tggctccagg gaggtggcg gcgggcatc tctctgcgag 2520
gcgtgagggc gcatctcgtg cgcgggcgcg gcgagcttgg gcgggatcgc gggcgcggct 2580
ctggctcggg ctggtgaggc tccggcggtc cgaggggtgt cgcggcgcgg cggggggtctc 2640
gctccggccg gggcggtccg agggcgccg ggatctggcg ctccagcagg gcgccccgtca 2700
aggggagccg ggcagggaag ctcgtcaggc gggctcgtca ggcaggcgtg acgcgggggc 2760
gcggccgcgg gctggaagcc atggccgtttt ggccatggtg tcgtgtgcgc tcgcttctca 2820
ttcgcagctt gaggtgctgc tgctgagggt ggtgcgcggt gaagcttggt ggtcggcgtt 2880
ggagagtgca aggcgcaaca ggaatggctc caatgatctc cacgcttctg ggtggatcag 2940
atctgcggcc ctccataggg gtgtgttccg ggcgaaagcc ttgacccgac tttgtcggtg 3000
```

```
ccgtcgacgg cggcgctttc gggcgtcgtt tccctccttg gaggcgtcgt tgtggaactc   3060
atcttcttct atgtggggct cgggctctcc gggtgaaaac ctaagctcca gattttccgg   3120
agcgggcgat ggcggcgtct tcgtcgtttc cctcttgggg gcgttgcttg ggagagttag   3180
cttgtgcttg gtgcgtttgg ttttctccta cgtcgggttt ggtggatgcc ggggcagcgg   3240
ccccgagcgg ctgatgaacg ccgaggcggc ggcctgcaca agtgatgcgc ggtgcggctc   3300
catggggcgg ggcggtggct cggccttcac ttgggtggca atcttgggcc acttgggtgg   3360
caggcttgtc ggtccggtcg acgcgttcca gagggggcgg tctgactttg cgtcggggcg   3420
gcggccccgg atgtggtgcg acgttcgtgg tctgcgagcg gttgccttga gcagcgtggg   3480
ctgcgggcag ctgggtcgcg cggcgttgct gctcgagcgg agcggtggta cgtcggggcg   3540
gcggccccgg aaggtgatgc cggttgattg cgctggggcgt gacggagcgg tggatgtcgg   3600
ggcggcggcc ccgagaaaat cactgtggcg tccagatttc tgtggcaacg atgatggtgg   3660
gagcgatgtc ggcgacgcgg caatggttgc gatagtcggc tcttctccgg cgtgtccacg   3720
atattgcctc ggtttgtttg ttgctgtgga gtcgaagctg cggcggcgag gccctgtggt   3780
atacgatgac tggttccagg tgtcctttcg tcgatcttcc gtgggcgccag ccgtgcctgg   3840
tttcgttctt ccgagttctc cgtcagaatc ggagctgcgt tgtctgtccg caggtcgaca   3900
tgttgtcgag aagggtgggc tttgccctgt gtgtttcagt ctatgcgagt gggctcggcc   3960
cttgttgttc tggtttttgc ccggtttttcc gtaattaact gggcaattct cttctgctta   4020
attaatagat gaggcaatct ttgcctccct ttcaaaaaaa aacctggtta ctatagcagg   4080
aaattcaggg ttgattactt tatttcttat ctgaaggata aacattgtat caaatcagaa   4140
ttttatttgt aagttacatt tttttttact tataaaactt ggaaactgtt ttactgtgac   4200
aaatagatgc cactagaatc atgatcacat cgtggctgtt gctattctaa caaataaatg   4260
ctcctgaaca aatgggaact atatatgaag atgtatggac cagcatgttc ctgttaacct   4320
gaccttttc ctttttttgc tgctgcagtg caaaaggaca tacagcttgc aaggcgtatc   4380
ggcgggagga ggctttggtg a                                             4401
```

```
SEQ ID NO: 100        moltype = RNA   length = 588
FEATURE               Location/Qualifiers
source                1..588
                      mol_type = other RNA
                      organism = Triticum aestivum
SEQUENCE: 100
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
gtagcgcggg accttcccgg gtcgcttcct tttcgtttcg tcttgttttc tgtttttttgg   180
tctgacttgc tcgtcacctg ttcgacggaa tgcagaggcg agccgggcgg gcggcggccc   240
caggggggc tcaaggggca aactgggcaa cccaagcaga ggaaaccaca ccggttcagg    300
ccaggcacgg tggcactgcg ggagatcagg aggtatcaga agtcggtcga ctttctcatc   360
ccgtttgcac catttgtccg tctgatcaag gaggtcaccg acttcttctg tcctgaaatc   420
agccgctgga ctcccaagc gctcgtcgcg attcaagagg ctgcagagta tcacctcgtc    480
gacgtatttg aaagggcaaa tcactgtgcc atccatgcaa agcgtgttac cgtcatgcaa   540
aaggacatac agcttgcaag gcgtatcggc gggaggaggc tttggtga               588
```

```
SEQ ID NO: 101        moltype = AA   length = 195
FEATURE               Location/Qualifiers
source                1..195
                      mol_type = protein
                      organism = Triticum aestivum
SEQUENCE: 101
MARTKHPAVR KTKAPPKKQL GPRPAQRRQE TDGAGTSATP VARDLPGSLP FRFVLFSVFW   60
SDLLVTCSTE CRGEPGGRRP QGGLKGQTGQ PKQRKPHRFR PGTVALREIR RYQKSVDFLI   120
PFAPFVRLIK EVTDFFCPEI SRWTPQALVA IQEAAEYHLV DVFERANHCA IHAKRVTVMQ   180
KDIQLARRIG GRRLW                                                     195
```

```
SEQ ID NO: 102        moltype = RNA   length = 493
FEATURE               Location/Qualifiers
source                1..493
                      mol_type = other RNA
                      organism = Triticum aestivum
SEQUENCE: 102
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
aggcgagccg ggcgggcggc ggccccaggg ggggctcaag gggcaaactg gcaacccaa    180
gcagaggaaa ccacaccggt tcaggccagg cacggtggca ctgcgggaga tcaggaggta   240
tcagaagtcg gtcgactttc tcatcccgtt tgcaccattt gtccgtctga tcaaggaggta  300
caccgacttc ttctgtcctg aaatcagccg ctgactccc caagcgctcg tcgcgattca   360
agaggctgca gagtatcacc tcgtcgacgt atttgaaagg gcaaatcact gtgccatcca   420
tgcaaagcgt gttaccgtca tgcaaaagga catacagctt gcaaggcgta tcggcgggag   480
gaggctttgg tga                                                       493
```

```
SEQ ID NO: 103        moltype = AA   length = 106
FEATURE               Location/Qualifiers
source                1..106
                      mol_type = protein
                      organism = Triticum aestivum
SEQUENCE: 103
MARTKHPAVR KTKAPPKKQL GPRPAQRRQE TDGAGTSATP RRAGRAAAPG GAQGANWATQ   60
AEETTPVQAR HGGTAGDQEV SEVGRLSHPV CTICPSDQGG HRLLLS                   106
```

```
SEQ ID NO: 104        moltype = DNA   length = 4399
```

-continued

```
FEATURE            Location/Qualifiers
source             1..4399
                   mol_type = other DNA
                   organism = Triticum aestivum
SEQUENCE: 104
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg tgcgcgggac cttcccgggt cgcttccttt tcgtttcgtc ttgtttttctg   300
ttttttggtc tgacttgctc gtcacctgtt cgacggaatg cagaggcgag ccgggcgggc   360
ggcggcccca ggggggggctc aaggtgcggc cttctttgcg cttttcggtt ttccgccgcg   420
tgtttagggc catttccgtc ttgtttgggg gtgcgcgggg cgggggcttg tttttttttcc   480
tcccccccttc gttgttgcgc acattgctcg ggaatgctgc caggagcggt tgcggttctt   540
ctttgaccct tcggggagggc tggatcggca gtttcttcgc ttccttgctc cagattttag   600
ttcatcttgt accagtacag tagcaagatg atggatgggg gcttgtttttt tctttctcct   660
tccttgttcc ggacatttct ctggagcgac ttttatgcat ttcccagtat tgtccttttgt   720
cctagaggg tagtggatcg gcagtttttct tcgcctcatt ggtccagatt ttagtttatc   780
ttgtacggta ccaagatgat ggatgtggca caaagttctc agtttggggg ttgcgctctt   840
ccgggcagtt gttattttgg tctgtgatga ctaactcgta tctattcttg tgggagcagg   900
ggcaaactgg gcaacccaag cagaggaaac cacaccggtt caggccaggc acggtggcac   960
tgcgggagat caggaggtat cagaagtcgg tcgactttct catcccgttt gcaccatttg   1020
tccgtctggt gggtacctct gtctgtcata tcctctcgct ctctctacaa acgatctgca   1080
gtgcagagtg taattggaat attttgttcc tgacaaattt gcagatcaag gaggtcaccg   1140
acttcttctg tcctgaaatc agccgctgga ctccccaagc gctcgtcgcg attcaagagg   1200
tcagtgctaa aacctggcat gtactattag atctgatggt ttgattagag tactacaatg   1260
cagatgaatt caatatccga aaaccatgaa ctgtggggta gatacatgta tcgcccttaat   1320
tcatggtttc tgaatgctct gctattaatt cagtttgata tatttattta gcagcatggt   1380
attgtttttgg tggctggtaa atcaaaactg aaatgtgatt acgagcaaaa cggtatcgat   1440
tgtcgatcct gtgtgttttt gtgcacatct ggttgtttgg tcaagatgtg tttgtgcaca   1500
tcttgcaaca tgatcctgcc cacacactca aaactgacta ttggttaggt tccatttgtc   1560
ttatggaatt tagggtgtaa ctgagaggtg agcaagtggt agtaacgttc aattttgatt   1620
caggatgagg atattgtgat ccagaaaatt gcatgttatg gttatgtgtc caaacgccaa   1680
atgattatgt ctatatccag tactttagaa ccagtacaac aacaaaaagt actttagaac   1740
cagtcaagtt tattgtgcat ttatacaaga gtgttgtttg cacaatagac ttgctttagt   1800
cgtctcttgc cagaaatgcc ttcttctgca caacgagcaa aaataacata aagttgacta   1860
tactcagtgt ggcctaagaa atgagttgta ctttttagtc actggcctgt gtatttgctt   1920
tgaattgaca cataattccc ttttcctttc cctctgcagg ctgcagagta tcacctcgtc   1980
gacgtatttg aaaagggcaaa tcactgtgcc atccatgcaa agcgtgttac cgtcagtaag   2040
ttctcactga atgaaaactc cctttctttt acaatattgc gcagaaggaa acatgccagt   2100
tatgaaaagg tttcaattac aggatcacct ttgctttcat ttgatgtgat atctagtttt   2160
gatgttgttt caaggttcaa gaattctaat gataaatgat aggatccaca attgttatat   2220
ctctgcagct cctcgtatct gttgtccacg aacaaacata tcaaacaatt cattaaaaag   2280
atgaagaagt caaacaaaca gtatatgtgc actgcatatt agatatcaaa cctggttact   2340
atacgactga tctggcctga cccccgcgtc gcctctccct ggcggcacgg ggggaaccac   2400
tccggcgccg ccaccttccc tcctccctcc acccccccacc tcgccgccgc ctgaggagtt   2460
cgccgggcgaa gcccggtctg gctccaggga gggtggcggc gggcatctc tctgcgaggc   2520
gtgagggcgc atctcgtgcg cgggcgcggc gagcttgggc gggatcgcgg gcgcggcctct   2580
ggctcgggct ggtgaggctc cggcggtccg aggggtgtcg cggcgcggcg ggggtctcgc   2640
tccggcgcgg gcggtccgag ggcgcgcggg atctggcgct ccagcagggg cgccgtcaag   2700
gggacgaggc cagggaagct cgtcgagcgg gctcgtcagg caggcgtgac gggacgcggt   2760
ggccgcgggc tggaagccat ggcgttttgg ccatggtgtc gtgtgcgctc gcttctcatt   2820
cgcagcttga ggtgctgctg ctgagggtgg tgcgcggtga agcttggtgg tcggcgttgg   2880
agagtgcaag gcgcaacagg aatggctcca atgatctcca cgcttctggg tggatcagat   2940
ctgcggccct ccatagggggt gtgttccggg cgaaagcctt gacccgactt tgtcggtgcc   3000
gtcgacggcg gcgctttcgg gcgtcgtttc cctccttgga ggcgtcgttg tggaactcat   3060
cttcttctat gtggggctcg ggctctccgg gtgaaaacct aagctccaga ttttccggag   3120
cgggcgatgg cggcgtcttc gtcgtttccc tcttgggggc gttgcttggg agagttagct   3180
tgtgcttggt gcgtttggtt ttctcctacg tcgggtttgg tggatgccgg ggcagcggcc   3240
ccggacggct gatgaacgcc gaggcggcgg cctcggaaga tgatgcgcgg tgcggctcca   3300
tggggcgggg cggtggctcg gccttcactt gggtggcaat cttgggccac ttgggtggca   3360
ggcttgtcgg tccggtcgac gcgttccaga ggggcggtc tgactttgcg tcggggcggc   3420
ggccccggat gtggtgcgac gttcgtggtc tgcgagcggt tgccttgagc agcgtgggct   3480
gcgggcagct gggtcgcgcg gcgttgctgc tcgagcggag cggtggtacg tcggggcggc   3540
ggccccggaa ggtgatgccg gttgattgcg ctgggcgtga cggagcggtg gatgtcgggg   3600
cggcggcccc gagaaaatca ctgtggcgtc cagatttctg tggcaacgat gatggtggga   3660
gcgatgtcgc cgacgcggca atggttgcga tagtcggctc ttctccggcg tgtccacgat   3720
attgcctcgg tttgtttgtt gctgtggagt cgaagctgcg gcggcgaggc cctgtggtat   3780
acgatgactg gttccaggtg tcctttcgtc gatcttccgt ggcgccagcc gtgcctggtt   3840
tcgttcttcc gagttctccg tcagaatcgg agctgcgttg tctgtccgca ggtcgacatg   3900
ttgtcgagaa gggtggggctt tgccctgtgt gtttcagtct atgcgagtgg gctcggccct   3960
tgttgttctg gtttttgccc ggtttttccgt aattaactgg gcaattctct tctgcttaat   4020
taatagatga ggcaatcttt gcctcccttt caaaaaaaaa cctggttact atagcaggaa   4080
attcaggtt gattacttta tttcttatct gaaggataaa cattgtatca aatcagaatt   4140
ttatttgtaa gttacatttt tttttactta taaaacttgg aaactgtttt actgtgacaa   4200
atagatgcca ctagaatcat gatcacatcg tggctgttgc tattctaaca aataaatgct   4260
cctgaacaaa tgggaactat atatgaagat gtatggacca gcatgttcct gttaacctga   4320
cctttttcct tttttgctg ctgcagtgca aaaggacata cagcttgcaa ggcgtatcgg   4380
cgggaggagg ctttggtga                                               4399
```

```
SEQ ID NO: 105           moltype = RNA  length = 492
FEATURE                  Location/Qualifiers
source                   1..492
                         mol_type = other RNA
                         organism = Triticum aestivum
SEQUENCE: 105
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacacca  120
ggcgagccgg gcgggcggcg gccccagggg gggctcaagg ggcaaactgg gcaacccaag  180
cagaggaaac cacaccggtt caggccaggc acggtggcac tgcgggagat caggaggtat  240
cagaagtcgg tcgactttct catcccgttt gcaccatttg tccgtctgat caaggaggtc  300
accgacttct tctgtcctga aatcagccgc tggactcccc aagcgctcgt cgcgattcaa  360
gaggctgcag agtatcacct cgtcgacgta tttgaaaggg caaatcactg tgccatccat  420
gcaaagcgtg ttaccgtcat gcaaaaggac atacagcttg caaggcgtat cggcgggagg  480
aggctttggt ga                                                       492

SEQ ID NO: 106           moltype = AA  length = 163
FEATURE                  Location/Qualifiers
source                   1..163
                         mol_type = protein
                         organism = Triticum aestivum
SEQUENCE: 106
MARTKHPAVR KTKAPPKKQL GPRPAQRRQE TDGAGTSATP GEPGGRRPQG GLKGQTGQPK   60
QRKPHRFRPG TVALREIRRY QKSVDFLIPF APFVRLIKEV TDFFCPEISR WTPQALVAIQ  120
EAAEYHLVDV FERANHCAIH AKRVTVMQKD IQLARRIGGR RLW                     163

SEQ ID NO: 107           moltype = RNA  length = 586
FEATURE                  Location/Qualifiers
source                   1..586
                         mol_type = other RNA
                         organism = Triticum aestivum
SEQUENCE: 107
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
tgcgcgggac cttcccgggt cgcttccttt tcgtttcgtc ttgttttctg tttttttggtc  180
tgacttgctc gtcacctgtt cgacggaatg cagaggcgag ccgggcgggc ggcggcccca  240
gggggggctc aagggggcaaa ctgggcaacc caagcagagg aaaccacacc ggttcaggcc  300
aggcacggtg gcactgcggg agatcaggag gtatcagaag tcggtcgact ttctcatccc  360
gtttgcacca tttgtccgtc tgatcaagga ggtcaccgac ttcttctgtc ctgaaatcag  420
ccgctggact ccccaagcgc tcgtcgcgat tcaagaggct gcagagtatc acctcgtcga  480
cgtatttgaa agggcaaatc actgtgccat ccatgcaaag cgtgttaccg tcatgcaaaa  540
ggacatacag cttgcaaggc gtatcggcgg gaggaggctt tggtga                 586

SEQ ID NO: 108           moltype = AA  length = 60
FEATURE                  Location/Qualifiers
source                   1..60
                         mol_type = protein
                         organism = Triticum aestivum
SEQUENCE: 108
MARTKHPAVR KTKAPPKKQL GPRPAQRRQE TDGAGTSATP CAGPSRVASF SFRLVFCFLV   60

SEQ ID NO: 109           moltype = RNA  length = 511
FEATURE                  Location/Qualifiers
source                   1..511
                         mol_type = other RNA
                         organism = Triticum aestivum
SEQUENCE: 109
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
tgcgcgggac cttcccggag gcgagccggg cggcgcggcgg ccccaggggg ggctcaaggg  180
gcaaactggg caacccaagc agaggaaacc acaccggttc aggccaggca cggtggcact  240
gcgggagatc aggaggtatc agaagtcggt cgactttctc atcccgtttg caccatttgt  300
ccgtctgatc aaggaggtca ccgacttctt ctgtcctgaa atcagccgct ggactccccc  360
agcgctcgtc gcgattcaag aggctgcaga gtatcacctc gtcgacgtat ttgaaagggc  420
aaatcactgt gccatccatg caaagcgtgt taccgtcatg caaaaggaca tacagcttgc  480
aaggcgtatc ggcgggagga ggctttggtg a                                  511

SEQ ID NO: 110           moltype = AA  length = 112
FEATURE                  Location/Qualifiers
source                   1..112
                         mol_type = protein
                         organism = Triticum aestivum
SEQUENCE: 110
MARTKHPAVR KTKAPPKKQL GPRPAQRRQE TDGAGTSATP CAGPSRRRAG RAAAPGGAQG   60
ANWATQAEET TPVQARHGGT AGDQEVSEVG RLSHPVCTIC PSDQGGHRLL LS           112

SEQ ID NO: 111           moltype = DNA  length = 4401
FEATURE                  Location/Qualifiers
```

-continued

```
source                  1..4401
                        mol_type = other DNA
                        organism = Triticum aestivum SEQUENCE: 111
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacaccg gttgcgcggg accttcccgg gtcgcttcct tttcgtttcg tcttgttttc  300
tgttttttgg tctgacttgc tcgtcacctg ttcgacggaa tgcagaggcg agccgggcgg  360
gcggcggccc caggggggggc tcaaggtgcg gccttctttg cgcttttcgg ttttccgccg  420
cgtgtttagg gccatttccg tcttgtttgg gggtgcgcgg ggcgggggct tgtttttttt  480
cctcccccct tcgttgttgc gcacattgct cgggaatgct gccaggagcg gttgcggttc  540
ttctttgacc cttcgggagg gctggatcgg cagtttcttc gcttccttgc tccagatttt  600
agttcatctt gtaccagtac agtagcaaga tgatggatgg gggcttgttt tttctttctc  660
cttccttgtt ccggacattt ctctggagcg acttttatgc atttcccagt attgtccttt  720
gtccttagag ggtagtggat cggcagtttt cttcgcctca ttggtccaga tttagttta   780
tcttgtacgg taccaagatg atggatgtgg cacaaagttc tcagtttggg ggttgcgctc  840
ttccgggcag ttgttatttt ggtctgtgat gactaactcg tatctattct tgtgggagca  900
ggggcaaact gggcaaccca agcagaggaa accacaccgg ttcaggccag gcacggtggc  960
actgcgggag atcaggaggt atcagaagtc ggtcgacttt ctcatcccgt ttgcaccatt 1020
tgtccgtctg gtgggtacct ctgtctgtca tatcctcctg ctctctctac aaacgatctg 1080
cagtgcagag tgtaattgga atattttgtt cctgacaaat ttgcagatca aggaggtcac 1140
cgacttcttc tgtcctgaaa tcagccgctg gactccccaa gcgctcgtcg cgattcaaga 1200
ggtcagtgct aaaacctggc atgtactatt agatctgatg gtttgattag agtactacaa 1260
tgcagatgaa ttcaatatcc gaaaaccatg aactgtgggg tagatacatg tatcgccttta 1320
attcatggtt tctgaatgct ctgctattaa ttcagtttga tatatttatt tagcagcatg 1380
gtattgtttt ggtggctggt aaatcaaaac tgaaatgtga ttacgagcaa aacggtatcg 1440
attgtcgatc ctgtgtgttt ttgtgcacat ctggttgttt ggtcaagatg tgtttgtgca 1500
catcttgcaa catgatcctg cccacacact caaaactgac tattggttag gttccatttg 1560
tcttatggaa tttaggggtgt aactgagagg tgagcaagtg gtagtaacgt tcaatttgta 1620
ttcaggatga ggatattgtg atccagaaaa ttgcatgtta tggttatgtg tccaaacgcc 1680
aaatgattat gtctatatcc agtactttag aaccagtaca acaacaaaaa gtactttaga 1740
accagtcaag tttattgtgc atttatacaa gagtgttgtt tgcacaatag acttgcttta 1800
gtcgtctctt gccagaaatg ccttcttctg cacaacgagc aaaaataaca taaagttgac 1860
tatactcagt gtggcctaag aaatgagttg tacttttag tcactggcct gtgtatttgc 1920
tttgaattga cacataattc ccttttcctt tccctctgca ggctgcagag tatcacctcg 1980
tcgacgtatt tgaaagggca aatcactgtg ccatccatgc aaagcgtgtt accgtcagta 2040
agttctcact gaatgaaaac tccctttctt ttacaatatt gcgcagaagg aaacatgcca 2100
gttatgaaag agtttcaatt acaggatcac ctttgctttc atttgatgtg atatctagtt 2160
ttgatgttgt ttcaaggttc aagaattcta atgataaatg ataggatcca caattgttat 2220
atctctgcag ctcctcgtat ctgttgtcca cgaacaaaca tatcaaacaa ttcattaaaa 2280
agatgaagaa gtcaaacaaa cagtatatgt gcactgcata ttagatatca aacctggtta 2340
ctatacgact gatctggcct gacccccgcg tcgcctctcc ctggcggcac gggggggaacc 2400
actccggcgc cgccaccttc cctcctccct ccacccccca cctcgccgcc gcctgaggag 2460
ttcgccggcg aagcccggtc tggctccagg gagggtggcg gcggggcatc tctctgcgag 2520
gcgtgagggc gcatctcgtg cgcggggcgcg gcgagcttgg gcggggatcgc gggcggcggct 2580
ctggctcggg ctggtgaggc tccggcggtc cgagggtgt cgcggcgcgg cgggggtctc 2640
gctccggcgc gggcggtccg agggcgcgcg ggatctggcg ctccagcagg ggcgccgtca 2700
aggggagccg ggcagggaag ctcgtcaggc gggctcgtca ggcaggcgtg acgcggggcg 2760
gcgggcggcg gctggaagcc atggcgtttt ggccatggtg tcgtgtgcgc tcgcttctca 2820
ttcgcagctt gaggtgctgc tgctgagggt ggtgcgcggt gaagcttggt ggtcggcgtt 2880
ggagagtgca aggcgcaaca ggaatggctc caatgatctc cacgcttctg ggtggatcag 2940
atctgcggcc ctccataggg gtgtgttccg ggcgaaagcc ttgacccgac tttgtcggtg 3000
ccgtcgacgg cggcgctttc gggcgtcgtt tccctccttg gacggcgtcgt tgtggaactc 3060
atcttcttct atgtggggct cgggctctcc gggtgaaaac ctaagctcca gattttccgg 3120
agcgggcgat ggcggcgtct tcgtcgtttc cctcttgggg gcgttgcttg ggagagttag 3180
cttgtgcttg gtgcgtttgg ttttctccta cgtcgggttt ggtggatgcc ggggcagcgg 3240
ccccggacgg ctgatgaacg ccgaggcggc ggcctcggaa agtgatgcgc ggtgcggctc 3300
catggggcgg ggcggtggct cggccttcac ttgggtggca atcttgggcc acttgggtgg 3360
caggcttgtc ggtccggtcg acgcgttcca gaggggggcgg tctgactttg cgtcgggggcg 3420
gcggccccgg atgtggtgcg acgttcgtgg tctgcgagcg gttgccttga gcagcgtggg 3480
ctgcgggcag ctgggtcgcg cggcgttgct gctcgagcgg agcggtggta cgtcgggggcg 3540
gcggccccgg aaggtgatgc cggttgattg cgctgggcgt gacggaggcg tggatgtcgg 3600
ggcggcggcc ccgagaaaat cactgtggcg tccagatttc tgtggcaacg atgatggtgg 3660
gagcgatgtc ggcgacgcgg caatggttgc gatagtcggc tcttctccgg cgtgtccacg 3720
atattgcctc ggtttgtttg ttgctgtgga gtcgaagctg cggcggcgag gccctgtggt 3780
atacgatgac tggttccagg tgtccttttcg tcgatcttcc gtggcgccag ccgtgcctgc 3840
tttcgttctt ccgagttctc cgtcagaatc ggagctgcgt tgtctgtccg caggtcgaca 3900
tgttgtcgag aagggtgggc tttgcccgt gtgtttcagt ctatgcgagt gggctcggcc 3960
cttgttgttc tggttttttgc ccggtttttcc gtaattaact gggcaattct cttctgctta 4020
attaatagat gaggcaatct ttgcctccct ttcaaaaaaa aacctggtta ctatagcagg 4080
aaattcaggg ttgattactt tatttcttat ctgaaggata aacattgtat caaatcagaa 4140
ttttatttgt aagttacatt tttttttact tataaaacct ggaaactgtt ttactgtgac 4200
aaatagatgc cactagaatc atgatcacat cgtggctgtt gctattctaa caaataaatg 4260
ctcctgaaca aatgggaact atatatgaag atgtatggac cagcatgttc ctgttaacct 4320
gacctttttc cttttttttgc tgctgcagtg caaaaggaca tacagcttgc aaggcgtatc 4380
ggcgggagga ggctttggtg a                                           4401
```

```
SEQ ID NO: 112          moltype = RNA   length = 588
FEATURE                 Location/Qualifiers
source                  1..588
                        mol_type = other RNA
                        organism = Triticum aestivum
SEQUENCE: 112
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
gttgcgcggg accttcccgg gtcgcttcct tttcgtttcg tcttgttttc tgtttttggg  180
tctgacttgc tcgtcacctg ttcgacggaa tgcagaggcg agccgggcgg cgggcggccc  240
caggggggc tcaagggca aactgggcaa cccaagcaga ggaaaccaca ccggttcagg     300
ccaggcacgtg tggcactgcg ggagatcagg aggtatcaga agtcggtcga ctttctcatc  360
ccgtttgcac catttgtccg tctgatcaag gaggtcaccg acttcttctg tcctgaaatc  420
agccgctgga ctccccaagc gctcgtcgcg attcaagagg ctgcagagta tcacctcgtc  480
gacgtatttg aaagggcaaa tcactgtgcc atccatgcaa agcgtgttac cgtcatgcaa  540
aaggacatac agcttgcaag gcgtatcggc gggaggaggc tttggtga              588

SEQ ID NO: 113          moltype = AA   length = 195
FEATURE                 Location/Qualifiers
source                  1..195
                        mol_type = protein
                        organism = Triticum aestivum
SEQUENCE: 113
MARTKHPAVR KTKAPPKKQL GPRPAQRRQE TDGAGTSATP VARDLPGSLP FRFVLFSVFW   60
SDLLVTCSTE CRGEPGGRRP QGGLKGQTGQ PKQRKPHRFR PGTVALREIR RYQKSVDFLI  120
PFAPFVRLIK EVTDFFCPEI SRWTPQALVA IQEAAEYHLV DVFERANHCA IHAKRVTVMQ  180
KDIQLARRIG GRRLW                                                   195

SEQ ID NO: 114          moltype = RNA   length = 513
FEATURE                 Location/Qualifiers
source                  1..513
                        mol_type = other RNA
                        organism = Triticum aestivum
SEQUENCE: 114
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
gttgcgcggg accttcccgg aggcgagccg ggcgggcggc ggccccaggg ggggctcaag  180
gggcaaactg ggcaacccaa gcagaggaaa ccacaccggt tcaggccagg cacggtggca  240
ctgcgggaga tcaggaggta tcagaagtcg gtcgactttc tcatcccgtt tgcaccattt  300
gtccgtctga tcaaggaggt caccgacttc ttctgtcctg aaatcagccg ctggactccc  360
caagcgctcg tcgcgattca agaggctgca gagtatcacc tcgtcgacgt atttgaaagg  420
gcaaatcact gtgccatcca tgcaaagcgt gttaccgtca tgcaaaagga catacagctt  480
gcaaggcgta tcggcgggag gaggctttgg tga                              513

SEQ ID NO: 115          moltype = AA   length = 170
FEATURE                 Location/Qualifiers
source                  1..170
                        mol_type = protein
                        organism = Triticum aestivum
SEQUENCE: 115
MARTKHPAVR KTKAPPKKQL GPRPAQRRQE TDGAGTSATP VARDLPGGEP GGRRPQGGLK   60
GQTGQPKQRK PHRFRPGTVA LREIRRYQKS VDFLIPFAPF VRLIKEVTDF FCPEISRWTP  120
QALVAIQEAA EYHLVDVFER ANHCAIHAKR VTVMQKDIQL ARRIGGRRLW             170

SEQ ID NO: 116          moltype = RNA   length = 493
FEATURE                 Location/Qualifiers
source                  1..493
                        mol_type = other RNA
                        organism = Triticum aestivum
SEQUENCE: 116
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
aggcgagccg ggcgggcggc ggccccaggg ggggctcaag gggcaaactg ggcaacccaa  180
gcagaggaaa ccacaccggt tcaggccagg cacggtggca ctgcgggaga tcaggaggta  240
tcagaagtcg gtcgactttc tcatcccgtt tgcaccattt gtccgtctga tcaaggaggt  300
caccgacttc ttctgtcctg aaatcagccg ctggactccc caagcgctcg tcgcgattca  360
agaggctgca gagtatcacc tcgtcgacgt atttgaaagg gcaaatcact gtgccatcca  420
tgcaaagcgt gttaccgtca tgcaaaagga catacagctt gcaaggcgta tcggcgggag  480
gaggctttgg tga                                                    493

SEQ ID NO: 117          moltype = AA   length = 106
FEATURE                 Location/Qualifiers
source                  1..106
                        mol_type = protein
                        organism = Triticum aestivum
SEQUENCE: 117
MARTKHPAVR KTKAPPKKQL GPRPAQRRQE TDGAGTSATP RRAGRAAAPG GAQGANWATQ   60
AEETTPVQAR HGGTAGDQEV SEVGRLSHPV CTICPSDQGG HRLLLS                 106
```

| SEQ ID NO: 118 | moltype = DNA length = 4400 |
| FEATURE | Location/Qualifiers |
| source | 1..4400 |
| | mol_type = other DNA |
| | organism = Triticum aestivum |

SEQUENCE: 118

```
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacaccg gttgcgcggg accttccggg gtcgcttcct tttcgtttcg tcttgttttc  300
tgtttttttgg tctgacttgc tcgtcacctg ttcgacggaa tgcagaggcg agccgggcgg  360
gcggcggccc caggggggggc tcaaggtgcg gccttctttg cgcttttcgg ttttccgccg  420
cgtgtttagg gccatttccg tcttgtttgg gggtgcgcgg ggcggggggct tgttttttttt  480
cctcccccct tcgttgttgc gcacattgct cgggaatgct gccaggagcg gttgcggttc  540
ttctttgacc cttcgggagg gctggatcgg cagtttcttc gcttccttgc tccagatttt  600
agttcatctt gtaccagtac agtagcaaga tgatggatgg gggcttgttt tttctttctc  660
cttccttgtt ccggacattt ctctggagcg acttttatgc atttcccagt attgtccttt  720
gtccttagag ggtagtggat cggcagtttt cttcgcctca ttggtccaga ttttagttta  780
tcttgtacgg taccaagatg atggatgtgg cacaaagttc tcagtttggg ggttgcgctc  840
ttccgggcag ttgttatttt ggtctgtgat gactaactcg tatctattct tgtgggagca  900
ggggcaactg ggcaacccaa gcagaggaaa ccacaccggt tcaggccagg cacggtggca  960
ctgcgggaga tcaggaggta tcagaagtcg gtcgactttc tcatcccgtt tgcaccattt 1020
gtccgtctgg tgggtacctc tgtctgtcat atcctctcgc tctctctaca aacgatctgc 1080
agtgcagagt gtaattggaa tattttgttc ctgacaaatt tgcagatcaa ggaggtcacc 1140
gacttcttct gtcctgaaat cagccgctgg actccccaag cgctcgtcgc gattcaagag 1200
gtcagtgcta aaacctggca tgtactatta gatctgatgg tttgattaga gtactacaat 1260
gcagatgaat tcaatatccg aaaaccatga actgtggggt agatacatgt atcgccttaa 1320
ttcatggttt ctgaatgctc tgctattaat tcagtttgat atatttattt agcagcatgg 1380
tattgttttg gtggctggta aatcaaaact gaaatgtgat tacgagcaaa acggtatcga 1440
ttgtcgatcc tgtgtgtttt tgtgcacatc tggttgtttg gtcaagatgt gtttgtgcac 1500
atcttgcaac atgatcctgc ccacacactc aaaactgact attggttagg ttccatttgt 1560
cttatggaat ttagggtgta actgagaggt gagcaagtgg tagtaacgtt caattttgat 1620
tcaggatgag gatattgtga tccagaaaat tgcatgttat ggttatgtgt ccaaacgcca 1680
aatgattatg tctatatcca gtactttaga accagtacaa caacaaaaag tactttagaa 1740
ccagtcaagt ttattgtgca tttatacaag agtgttgttt gcacaataga cttgctttag 1800
tcgtctcttg ccagaaatgc cttcttctgc acaacgagca aaaataacat aaagttgact 1860
atactcagtg tggcctaaga aatgagttgt actttttagt cactggcctg tgtatttgct 1920
ttgaattgac acataattcc cttttccttt ccctctgcag gctgcagagt atcacctcgt 1980
cgacgtattt gaaagggcaa atcactgtgc catccatgca aagcgtgtta ccgtcagtaa 2040
gttctcactg aatgaaaact cccttttcttt tacaatattg cgcagaagga aacatgccag 2100
ttatgaaaga gtttcaatta caggatcacc tttgctttca tttgatgtga tatctagttt 2160
tgatgttgtt tcaaggttca agaattctaa tgataaatga taggatccac aattgttata 2220
tctctgcagc tcctcgtatc tgttgtccac gaacaaacat atcaaacaat tcattaaaaa 2280
gatgaagaag tcaaacaaac agtatatgtg cactgcatat tagatatcaa acctggttac 2340
tatacgactg atctggcctg accccgcgct cgcctctccc tggcggcacg gggggaacca 2400
ctccggcgcc gccaccttcc ctcctccctc cacccccaac ctcgccgccg cctgaggagt 2460
tcgccggcga agcccggtct ggctccaggg agggtggcgg cggggcatct ctctgcgagg 2520
cgtgagggcg catctcgtgc gcgggcgcgg cgagcttggg cgggatcgcg ggcgcggctc 2580
tggctcgggc tggtgaggct ccggcggtcc gagggggtgtc gcggcgcggc gggggtctcg 2640
ctccggcgcg ggcggtccga gggcgcgcgg gatctggcgc tccagcaggg gcgccgtcaa 2700
ggggagccgg gcagggaagc tcgtcaggcg ggctcgtcag gcaggcgtga cgcggggcgg 2760
cggccgcggg ctggaagcca tggcgttttg gccatggtgt cgtgtgcgct cgcttctcat 2820
tcgcagcttg aggtgctgct gctgagggtg gtgcgcggtg aagcttggtg gtcggcgttg 2880
gagagtgcaa ggcgcaacag gaatggctcc aatgatctcc acgcttctgg gtggatcaga 2940
tctgcggccc tccataggg g tgtgttccgg gcgaaagcct tgacccgact ttgtcggtgc 3000
cgtcgacggc ggcgctttcg ggcgtcgttt ccctccttgg aggcgtcgtt gtggaactca 3060
tcttcttcta tgtggggctc gggctctccg ggtgaaaacc taagctccag attttccgga 3120
gcgggcgatg gcggcgtctt cgtcgtttcc ctcttggggg cgttgcttgg gagagttagc 3180
ttgtgcttgg tgcgtttggt tttctcctac gtcgggtttg gtggatgccg ggcgcagcggc 3240
cccggacggc tgatgaacgc cgaggcggcg gcctcggaaa gtgatgcgcg gtgcggctcc 3300
atggggcggg gcggtggctc ggccttcact tgggtggcaa tcttgggcca cttgggtggc 3360
aggcttgtcg gtccggtcga cgcgttccag agggggcggt ctgactttgc gtcggggcgg 3420
cggccccgga tgtggtgcga cgttcgtggt ctgcgagcgg ttgccttgag cagcgtgggc 3480
tgcgggcagc tgggtcgcgc ggcgttgctc ctcgagcgga gcggtggtac gtcggggcgg 3540
cggccccgga aggtgatgcc ggttgattgc gctgggcgtg acggagcggt ggatgtcggg 3600
gcggcggccc cgagaaaatc actgtggcgt ccagatttct gtggcaacga tgatggtggg 3660
agcgatgtcg gcgacgcggc aatggttgcg atagtcggct cttctccggc gtgtccacga 3720
tattgcctcg gtttgtttgt tgctgtggag tcgaagctgc ggcggcaagg ccctgtggta 3780
tacgatgact ggttccaggt gtcctttcgt cgatcttccg tggcgccagc cgtgcctggt 3840
ttcgttcttc cgagttctcc gtcagaatcg gagctgcgtt gtctgtccgc aggtcgacat 3900
gttgtcgaga agggtgggct ttgccctgtg tgtttcagtc tatgcgagtg ggctcggccc 3960
ttgttgttct ggttttttgcc cggttttccg taattaactg ggcaattctc ttctgcttaa 4020
ttaatagatg aggcaatctt tgcctccctt tcaaaaaaaa acctggttac tatagcagga 4080
aattcagggt tgattacttt atttcttatc tgaaggataa acattgtatc aaatcagaat 4140
tttatttgta agttacattt ttttttactt ataaaacttg gaaactgttt tactgtgaca 4200
aatagatgcc actagaatca tgatcacatc gtggctgttg ctattctaac aaataaaatgc 4260
tcctgaacaa atgggaacta tatatgaaga tgtatggacc agcatgttcc tgttaacctg 4320
acctttttcc ttttttgct gctgcagtgc aaaaggacat acagcttgca aggcgtatcg 4380
```

-continued

```
gcgggaggag gctttggtga                                                      4400

SEQ ID NO: 119          moltype = RNA   length = 587
FEATURE                 Location/Qualifiers
source                  1..587
                        mol_type = other RNA
                        organism = Triticum aestivum
SEQUENCE: 119
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
gttgcgcggg accttcccgg gtcgcttcct tttcgtttcg tcttgttttc tgttttttgg   180
tctgacttgc tcgtcacctg ttcgacggaa tgcagaggcg agccgggcgg gcggcggccc   240
cagggggggc tcaaggggca actgggcaac ccaagcagag gaaaccacac cggttcaggc   300
caggcacggt ggcactgcgg gagatcagga ggtatcagaa gtcggtcgac tttctcatcc   360
cgtttgcacc atttgtccgt ctgatcaagg aggtcaccga cttcttctgt cctgaaatca   420
gccgctggac tccccaagcg ctcgtcgcga ttcaagaggc tgcagagtat cacctcgtcg   480
acgtatttga aagggcaaat cactgtgcca tccatgcaaa gcgtgttacc gtcatgcaaa   540
aggacataca gcttgcaagg cgtatcggcg ggaggaggct ttggtga               587

SEQ ID NO: 120          moltype = AA   length = 127
FEATURE                 Location/Qualifiers
source                  1..127
                        mol_type = protein
                        organism = Triticum aestivum
SEQUENCE: 120
MARTKHPAVR KTKAPPKKQL GPRPAQRRQE TDGAGTSATP VARDLPGSLP FRFVLFSVFW   60
SDLLVTCSTE CRGEPGGRRP QGGLKGQLGN PSRGNHTGSG QARWHCGRSG GIRSRSTFSS   120
RLHHLSV                                                             127

SEQ ID NO: 121          moltype = DNA   length = 4394
FEATURE                 Location/Qualifiers
source                  1..4394
                        mol_type = other DNA
                        organism = Triticum aestivum
SEQUENCE: 121
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgcccacgc atgacgctaa tgtgctcttc ctctcccttt gcagatggcg cgggcacgtc   240
ggcgacaccg gtagcgcggg accttcccgg gtcgcttcct tttcgtttcg tcttgttttc   300
tgttttttgg tctgacttgc tcgtcacctg ttcgacggaa tgcagaggcg agccgggcgg   360
gcggcggccc caggggggc tcaaggtgcg gccttctttg cgcttttcgg ttttccgccg   420
cgtgtttagg gccatttccg tcttgtttgg gggtgcgcgg ggcgggggct tgttttttt   480
cctcccccct tcgttgttgc gcacattgct cgggaatgct gccaggagcg gttgcggttc   540
ttctttgacc cttcgggagg gctggatcgg cagtttcttc gcttccttgc tccagatttt   600
agttcatctt gtaccagtac agtagcaaga tgatggatgg gggcttgttt tttctttctc   660
cttccttgtt ccggacattt ctctggagcg acttttatgc atttcccagt attgtccttt   720
gtccttagag ggtagtggat cggcagtttt cttcgcctca ttggtccaga tttttagttta   780
tcttgtacgg taccaagatg atggatgtgg cacaaagttc tcagtttggg ggttgcgctc   840
ttccgggcag ttgttatttt ggtctgtgat gactaactcg tatctattct tgtgggagca   900
ggtggggcaac ccaagcagag gaaaccacac cggttcaggc caggcacggt ggcactgcgg   960
gagatcagga ggtatcagaa gtcggtcgac tttctcatcc cgtttgcacc atttgtccgt   1020
ctggtgggta cctctgtctg tcatatcctc tcgctctctc tacaaacgat ctgcagtgca   1080
gagtgtaatt ggaatatttt gttcctgaca aatttgcaga tcaaggaggt caccgacttc   1140
ttctgtcctg aaatcagccg ctggactccc caagcgctcg tcgcgattca agaggtcagt   1200
gctaaaacct ggcatgtact attagatctg atggtttgat tagagtacta caatgcagat   1260
gaattcaata tccgaaaacc atgaactgtg gggtagatac atgtatcgcc ttaattcatg   1320
gtttctgaat gctctgctat taattcagtt tgatatattt atttagcagc atggtattgt   1380
tttggtggct ggtaaatcaa aactgaaatg tgattacgaa caaaacggta tcgattgtcg   1440
atcctgtgtg tttttgtgca catctggttg tttggtcaag atgtgttttgt gcacatcttg   1500
caacatgatc ctgcccacac actcaaaact gactattggt taggttccat ttgtcttatg   1560
gaatttaggg tgtaactgag aggtgagcaa gtggtagtaa cgttcaattt tgattcagga   1620
tgaggatatt gtgatccaga aaattgcatg ttatggttat gtgtccaaac gccaaatgat   1680
tatgtctata tccagtactt tagaaccagt acaacaacaa aaagtacttt agaaccagtc   1740
aagtttattg tgcatttata caagagtgtt gtttgcacaa tagacttgct ttagtcgtct   1800
cttgccagaa atgccttctt ctgcacaacg agcaaaaata acataaagtt gactatactc   1860
agtgtggcct aagaaatgag ttgtactttt tagtcactgg cctgtgtatt tgctttgaat   1920
tgacacataa ttccctttc ctttccctct gcaggctgca gagtatcacc tcgtcgacgt   1980
atttgaaagg gcaaatcact gtgccatcca tgcaaagcgt gttaccgtca gtaagttctc   2040
actgaatgaa aactccctt cttttacaat attgcgcaga aggaaacatg ccagttatga   2100
aagagtttca attacaggat caccttgct ttcatttgat gtgatatcta gttttgatgt   2160
tgtttcaagg ttcaagaatt ctaatgataa atgataggat ccacaattgt tatatctctg   2220
cagctcctcg tatctgttgt ccacgaacaa acatatcaaa caattcatta aaaagatgaa   2280
gaagtcaaac aaacagtata tgtgcactgc atattagata tcaaacctgg ttactatacg   2340
actgatctgg cctgacccc gcgtcgcctc tccctggcgg cacggggga accactccgg   2400
cgccgccacc ttccctcctc cctccacccc ccacctcgcc gccgcctgag gagttcgccg   2460
gcgaagcccg gtctggctcc agggaggtg cggcgcgggc atctctctgc gaggcgtgag   2520
ggcgcatctc gtgcgcgggc gcggcggagct tgggcggat cgcgggcgcg gctctggctc   2580
gggctggtga ggctccggcg gtccgagggg tgtcgcggcg cggcgggggt ctcgctccgg   2640
```

-continued

```
cgcgggcggt ccgagggcgc gcgggatctg gcgctccagc aggggcgccg tcaaggggag   2700
ccgggcaggg aagctcgtca ggcgggctcg tcaggcaggc gtgacgcggg gcggcggccg   2760
cgggctggaa gccatggcgt tttggccatg gtgtcgtgtg cgctcgcttc tcattcgcag   2820
cttgaggtgc tgctgctgag ggtggtgcgc ggtgaagctt ggtggtcggc gttggagagt   2880
gcaaggcgca acaggaatgg ctccaatgat ctccacgctt ctgggtggat cagatctgcg   2940
gccctccata ggggtgtgtt ccgggcgaaa gccttgaccc gactttgtcg gtgccgtcga   3000
cggcggcgct ttcgggcgtc gtttccctcc ttggaggcgt cgttgtggaa ctcatcttct   3060
tctatgtggg gctcgggctc tccgggtgaa aacctaagct ccagattttc cggagcgggc   3120
gatggcggcg tcttcgtcgt ttccctcttg ggggcgttgc ttgggagagt tagcttgtgc   3180
ttggtgcgtt tggttttctc ctacgtcggg tttggtggat gccggggcag cggccccgga   3240
cggctgatga acgccgaggc ggcggcctcg gaaagtgatg cgcggtgcgg ctccatgggg   3300
cggggcggtg gctcggcctt cacttgggtg gcaatcttgg gccacttggg tggcaggctt   3360
gtcggtccgg tcgacgcgtt ccagagggg cggtctgact ttgcgtcggg gcggcggccc   3420
cggatgtggt gcgacgttcg tggtctgcga gcggttgcct tgagcagcgt gggctgcgga   3480
cagctgggtc gcgcggcgtt gctgctcgag cggagcggtg gtacgtcggg gcggcggccc   3540
cggaaggtga tgccggttga ttgcgctggg cgtgacggag cggtggatgt cggggcggcg   3600
gccccgagaa aatcactgtg gcgtccagat ttctgtggca acgatgatgg tgggagcgat   3660
gtcggcgacg cggcaatggt tgcgatagtc ggctcttctc cggcgtgtcc acgatattgc   3720
ctcggtttgt ttgttgctgt gggagtcgaag ctgcggcggc gaggccctgt ggtatacgat   3780
gactggttcc aggtgtcctt tcgtcgatct tccgtggcgc cagccgtgcc tggtttcgtt   3840
cttccgagtt ctccgtcaga atcggagctg cgttgtctgt ccgcaggtcg acatgttgtc   3900
gagaaggGtg ggctttgccc tgtgtgtttc agtctatgcg agtgggctcg gcccttgttg   3960
ttctggtttt tgcccggttt tccgtaatta actgggcaat tctcttctgc ttaattaata   4020
gatgaggcaa tctttgcctc cctttcaaaa aaaaacctgg ttactatagc aggaaattca   4080
gggttgatta ctttatttct tatctgaagg ataaacattg tatcaaatca gaattttatt   4140
tgtaagttac attttttttt acttataaaa cttggaaact gtttactgt gacaaataga   4200
tgccactaga atcatgatca catcgtggct gttgctattc taacaaataa atgctcctga   4260
acaaatggga actatatatg aagatgtatg gaccagcatg ttcctgttaa cctgacctt   4320
ttccttttt tgctgctgca gtgcaaaagg acatacagct tgcaaggcgt atcggcggga   4380
ggaggctttg gtga                                                     4394
```

SEQ ID NO: 122          moltype = RNA   length = 486
FEATURE                 Location/Qualifiers
source                  1..486
                        mol_type = other RNA
                        organism = Triticum aestivum
SEQUENCE: 122
```
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
aggcgagccg ggcgggcggc ggccccaggg ggggctcaag gtgggcaacc caagcagagg   180
aaaccacacc ggttcaggcc aggcacggtg gcactgcggg agatcaggag gtatcagaag   240
tcggtcgact ttctcatccc gtttgcacca tttgtccgtc tgatcaagga ggtcaccgac   300
ttcttctgtc ctgaaatcag ccgctggact ccccaagcgc tcgtcgcgat tcaagaggct   360
gcagagtatc acctcgtcga cgtatttgaa agggcaaatc actgtgccat ccatgcaaag   420
cgtgttaccg tcatgcaaaa ggacatacag cttgcaaggc gtatcggcgg gaggaggctt   480
tggtga                                                               486
```

SEQ ID NO: 123          moltype = AA   length = 161
FEATURE                 Location/Qualifiers
source                  1..161
                        mol_type = protein
                        organism = Triticum aestivum
SEQUENCE: 123
```
MARTKHPAVR KTKAPPKKQL GPRPAQRRQE TDGAGTSATP RRAGRAAAPG GAQGGQPKQR   60
KPHRFRPGTV ALREIRRYQK SVDFLIPFAP FVRLIKEVTD FFCPEISRWT PQALVAIQEA   120
AEYHLVDVFE RANHCAIHAK RVTVMQKDIQ LARRIGGRRL W                        161
```

SEQ ID NO: 124          moltype = RNA   length = 581
FEATURE                 Location/Qualifiers
source                  1..581
                        mol_type = other RNA
                        organism = Triticum aestivum
SEQUENCE: 124
```
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
gtagcgcggg accttcccgg gtcgcttcct tttcgtttcg tcttgttttc tgttttttgg   180
tctgacttgc tcgtcacctg ttcgacgaaa tgcagaggcg agccgggcgg cgcggcggccc 240
cagggggggc tcaaggtggg caacccaagc agaggaaacc acaccggttc aggcaggca   300
cggtggcact gcgggagatc aggaggtatc agaagtcggt cgactttctc atcccgtttg   360
caccatttgt ccgtctgatc aaggaggtca ccgacttctt ctgtcctgaa atcagccgct   420
ggactcccca agcgctcgtc gcgattcaag aggctgcaga gtatcacctc gtcgactat   480
ttgaaagggc aaatcactgt gccatccatg caaagcgtgt taccgtcatg caaaaggaca   540
tacagcttgc aaggcgtatc ggcggagga ggctttggtg a                        581
```

SEQ ID NO: 125          moltype = AA   length = 125
FEATURE                 Location/Qualifiers
source                  1..125
                        mol_type = protein
                        organism = Triticum aestivum

```
SEQUENCE: 125
MARTKHPAVR KTKAPPKKQL GPRPAQRRQE TDGAGTSATP VARDLPGSLP FRFVLFSVFW   60
SDLLVTCSTE CRGEPGGRRP QGGLKVGNPS RGNHTGSGQA RWHCGRSGGI RSRSTFSSRL  120
HHLSV                                                              125

SEQ ID NO: 126           moltype = RNA   length = 506
FEATURE                  Location/Qualifiers
source                   1..506
                         mol_type = other RNA
                         organism = Triticum aestivum
SEQUENCE: 126
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
gtagcgcggg accttcccgg aggcgagccg ggcgggcggc ggcccaggg ggggctcaag  180
gtgggcaacc caagcagagg aaaccacacc ggttcaggcc aggcacggtg cgactgcggg  240
agatcaggag gtatcagaag tcggtcgact ttctcatccc gtttgcacca tttgtccgtc  300
tgatcaagga ggtcaccgac ttcttctgtc ctgaaatcag ccgctggact ccccaagcgc  360
tcgtcgcgat tcaagaggct gcagagtatc acctcgtcga cgtatttgaa agggcaaatc  420
actgtgccat ccatgcaaag cgtgttaccg tcatgcaaaa ggacatacag cttgcaaggc  480
gtatcggcgg gaggaggctt tggtga                                      506

SEQ ID NO: 127           moltype = AA   length = 144
FEATURE                  Location/Qualifiers
source                   1..144
                         mol_type = protein
                         organism = Triticum aestivum
SEQUENCE: 127
MDGTVICPFK YVDEVILCSL LNRDERLGSP AADFRTEEVG DLLDQTDKWC KRDEKVDRLL   60
IPPDLPQCHR AWPEPVWFPL LGLPTLSPPW GRRPPGSPPG RSRATGVADV PAPSVSCRRC  120
AGRGPSCFLG GALVFLTAGC LVRA                                         144

SEQ ID NO: 128           moltype = DNA   length = 4401
FEATURE                  Location/Qualifiers
source                   1..4401
                         mol_type = other DNA
                         organism = Triticum aestivum
SEQUENCE: 128
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacaccg gttgcgcggg accttccggg tcgcttcct tttcgtttcg tcttgttttc  300
tgtttttgg tctgacttgc tcgtcacctg ttcgacggaa tgcagaggcg agccgggcgg  360
gcggcggccc caggggggc tcaaggtgcg gccttcttg cgcttttcgg ttttccgccg  420
cgtgtttagg gccatttccg tcttgtttgg gggtgcgcgg ggcggggct tgttttttt  480
cctcccccct tcgttgttgc gcacattgct cgggaatgct gccaggagcg gttgcggttc  540
ttctttgacc cttcgggagg gctggatcgg cagtttcttc gcttccttgc tccagatttt  600
agttcatctt gtaccagtac agtagcaaga tgatggatgg gggcttgttt tttctttctc  660
cttccttgtt ccggacattt ctctggagcg acttttatgc atttcccagt attgtccttt  720
gtccttagag ggtagtggat cggcagtttt cttcgcctca ttggtccaga tttttagttta  780
tcttgtacgg taccaagatg atggatgtgg cacaaagttc tcagtttggg ggttgcgctc  840
ttccgggcag ttgttatttt ggtctgtgat gactaactcg tatctattct tgtgggagca  900
ggggcaaact gggcaaccca agcagaggaa accacaccgg ttcaggccag gcacggtggc  960
actgcgggag atcaggaggt atcagaagtc ggtcgacttt ctcatcccgt ttgcaccatt 1020
tgtccgtctg gtgggtacct ctgtctgtca tatcctctcg ctctctctac aaacgatctg 1080
cagtgcagag tgtaattgga atattttgtt cctgacaaat ttgcagatca aggaggtcac 1140
cgacttcttc tgtcctgaaa tcagccgctg gactccccaa gcgctcgtcg cgattcaaga 1200
ggtcagtgct aaaacctggc atgtactatt agatctgatg gtttgattag agtactacaa 1260
tgcagatgaa ttcaatatcc gaaaaccatg aactgtgggg tagatacatg tatcgcctta 1320
attcatggtt tctgaatgct ctgctattaa ttcagtttga tatatttatt tagcagcatg 1380
gtattgtttt ggtggctggt aaatcaaaac tgaaatgtga ttacgagcaa aacggtatcg 1440
attgtcgatc ctgtgtgttt ttgtgcacat ctggttgttt ggtcaagatg tgtttgtgca 1500
catcttgcaa catgatcctg cccacacact caaaactgac tattggttag gttccatttg 1560
tcttatggaa tttagggtgt aactgagagg tgagcaagtg gtagtaacgt tcaattttga 1620
ttcaggatga ggatattgtg atccagaaaa ttgcatgtta tggttatgtg tccaaacgcc 1680
aaatgattat gtctatatcc agtactttag aaccagtaca acaacaaaaa gtactttaga 1740
accagtcaag tttattgtgc atttatacaa gagtgttgtt tgcacaatag acttgcttta 1800
gtcgtctctt gccagaaatg ccttcttctg cacaacgagc aaaaataaca taaagttgac 1860
tatactcagt gtggcctaag aaatggattg tacttttag tcactggcct gtgtatttgc 1920
tttgaattga cacataattc cctttttctt tccctctgca ggctgcagag tatcacctcg 1980
tcgacgtatt tgaaagggca aatcactgtg ccatccatgc aaagcgtgtt accgtcagta 2040
agttctcact gaatgaaaac tcccttttctt ttacaatatt gcgcagaagg aaacatgcca 2100
gttatgaaag agtttcaatt acaggatcac ctttgctttc atttgatgtg atatctagtt 2160
ttgatgttgt ttcaaggttc aagaattcta atgataaatg ataggatcca caattgttat 2220
atctctgcag ctcctcgtat ctgttgtcca cgaacaaaca tatcaaacaa ttcattaaaa 2280
agatgaagaa gtcaaacaaa cagtatatgt gcactgcata ttagatatca aacctggtta 2340
ctatacgact gatctggcct gaccccgcg tcgcctctcc ctggcggcac gggggggaacc 2400
actccggcgc cgcacccttc cctcctccct ccacccccca cctcgccgcc gcctgaggag 2460
ttcgccggcg aagcccggtc tggctccagg gagggtggcg cgggggcatc tctctgcgag 2520
```

```
gcgtgagggc gcatctcgtg cgcgggcgcg gcgagcttgg gcgggatcgc gggcgcggct    2580
ctggctcggg ctggtgaggc tccggcggtc cgagggtgt cgcggcgcgg cggggggtctc    2640
gctccggcgc gggcggtccg agggcgcgcg ggatctggcg ctccagcagg ggcgccgtca    2700
aggggagccg ggcagggaag ctcgtcaggc gggctcgtca ggcaggcgtg acgcggggcg    2760
gcggccgcgg gctggaagcc atggcgtttt ggccatggtg tcgtgtgcgc tcgcttctca    2820
ttcgcagctt gaggtgctgc tgctgagggt ggtgcgcggt gaagcttggt ggtcggcgtt    2880
ggagagtgca aggcgcaaca ggaatggctc caatgatctc cacgcttctg ggtggatcag    2940
atctgcggcc ctccataggg gtgtgttccg ggcgaaagcc ttgacccgac tttgtcggtg    3000
ccgtcgacgg cggcgctttc gggcgtcgtt tccctccttg gaggcgtcgt tgtggaactc    3060
atcttcttct atgtggggct cgggctctcc gggtgaaaac ctaagctcca gattttccgg    3120
agcgggcgat ggcggcgtct tcgtcgtttc cctcttgggg gcgttgcttg ggagagttag    3180
cttgtgcttg gtgcgtttgg ttttctccta cgtcgggttt ggtggatgcc ggggcagcgg    3240
ccccggacgg ctgatgaacg ccgaggcggc ggcctcggaa agtgatgcgc ggtgcggctc    3300
catggggcgg ggcggtggct cggccttcac ttgggtggca atcttgggcc acttgggtgg    3360
caggcttgtc ggtccggtcg acgcgttcca gaggggggcgg tctgactttg cgtcggggcg    3420
gcggcccggg atgtggtgcg acgttcgtgg tctgcgagcg gttgccttga gcagcgtggg    3480
ctgcgggcag ctgggtcgcg cggcgttgct gctcgagcgg agcggtggta cgtcggggcg    3540
gcggccccgg aaggtgatgc cggttgattg cgctgggcgt gacggagcgg tggatgtcgg    3600
ggcggcggcc ccgagaaaat cactgtggcg tccagatttc tgtggcaacg atgatggtgg    3660
gagcgatgtc ggcgacgcgg caatggttgc gatagtcggc tcttctccgg cgtgtccacg    3720
atattgcctc ggtttgtttg ttgctgtgga gtcgaagctg cggcggcgag gccctgtggt    3780
atacgatgac tggttccagg tgtcctttcg tcgatcttcc gtggcgccag ccgtgcctgg    3840
tttcgttctt ccgagttctc cgtcagaatc ggagctgcgt tgtctgtccg caggtcgaca    3900
tgttgtcgag aaggggtgggc tttgccctgt gtgtttcagt ctatgcgagt gggctcggcc    3960
cttgttgttc tggttttttgc ccggtttttcc gtaattaact gggcaattct cttctgctta    4020
attaatagat gaggcaatct ttgcctccct ttcaaaaaaa aacctggtta ctatagcagg    4080
aaattcaggg ttgattactt tatttcttat ctgaaggata aacattgtat caaatcagaa    4140
ttttatttgt aagttacatt ttttttttact tataaaactt ggaaactgtt ttactgtgac    4200
aaatagatgc cactagaatc atgatcacat cgtggctgtt gctattctaa caaataaatg    4260
ctcctgaaca aatgggaact atatatgaag atgtatggac cagcatgttc ctgttaacct    4320
gacctttttc ctttttttgc tgctgcagtg caaaaggaca tacagcttgc aaggcgtatc    4380
ggcgggagga ggctttggtg a                                                4401
```

```
SEQ ID NO: 129           moltype = RNA   length = 513
FEATURE                  Location/Qualifiers
source                   1..513
                         mol_type = other RNA
                         organism = Triticum aestivum
SEQUENCE: 129
atggcccgca ccaagcaccc ggccgtcagg aagaccaagg cgccgcccaa gaagcagctc     60
gggccccgcc ccgcgcagcg gcggcaggag acagatggcg cgggcacgtc ggcgacaccg    120
gttgcgcggg accttcccgg aggcgagccg ggcgggcggc ggcccagggg ggggctcaag    180
gggcaaactg ggcaacccaa gcagaggaaa ccacaccggt tcaggccagg cacggtggca    240
ctgcgggaga tcaggaggta tcagaagtcg gtcgactttc tcatcccgtt tgcaccattt    300
gtccgtctga tcaaggaggt caccgacttc ttctgtcctg aaatcagccg ctggactccc    360
caagcgctcg tcgcgattca agaggctgca gagtatcacc tcgtcgacgt atttgaaagg    420
gcaaatcact gtgccatcca tgcaaagcgt gttaccgtca tgcaaaagga catacagctt    480
gcaaggcgta tcggcgggag gaggctttgg tga                                   513
```

```
SEQ ID NO: 130           moltype = AA   length = 170
FEATURE                  Location/Qualifiers
source                   1..170
                         mol_type = protein
                         organism = Triticum aestivum
SEQUENCE: 130
MARTKHPAVR KTKAPPKKQL GPRPAQRRQE TDGAGTSATP VARDLPGGEP GGRRPQGGLK     60
GQTGQPKQRK PHRFRPGTVA LREIRRYQKS VDFLIPFAPF VRLIKEVTDF FCPEISRWTP    120
QALVAIQEAA EYHLVDVFER ANHCAIHAKR VTVMQKDIQL ARRIGGRRLW               170
```

```
SEQ ID NO: 131           moltype = DNA   length = 4392
FEATURE                  Location/Qualifiers
source                   1..4392
                         mol_type = other DNA
                         organism = Triticum aestivum
SEQUENCE: 131
atggcccgca ccaagcaccc ggccgtcagg aagaccaagg cgccgcccaa gaagcagctc     60
gggccccgcc ccgcgcagcg gcggcaggag acaggtcagc ccttccctcc ttcctcccccc    120
cgtctcccgc ctctcgagcg aacgccgtcg ccatttcgtc gcgagagatg gacggacgga    180
cgccccacgc atgacgctaa tgtgctcttc ctctcccttt gcagatgcg cgggcacgtc    240
ggcgacaccg gttgcgcggg accttcccgg gtcgcttcct tttcgtttcg tcttgttttc    300
tgttttttgg tctgacttgc tcgtcacctg ttcgacggaa tgcagaggcg agccgggcgg    360
gcggcggccc caggggggggc tcaaggtgcg gccttctttg cgcttttcgg ttttccgccg    420
cgtgtttagg gccatttccg tcttgtttgg gggtgcgcgg ggcgggggct tgtttttttt    480
cctccccccct tcgttgttgc gcacattgct cgggaatgct gccaggagcg gttgcggttc    540
ttctttgacc cttcgggagg gctggatcgg cagtttcttc gcttccttgc tccagatttt    600
agttcatctt gtaccagtac agtagcaaga tgatggatgg gggcttgttt tttctttctc    660
cttccttgtt ccggacattt ctctggagcg actttttatgc atttcccagt attgtccttt    720
gtccttagag ggtagtggat cggcagtttt cttcgcctca ttggtccaga ttttagttta    780
tcttgtacgg taccaagatg atggatgtgg cacaaagttc tcagtttggg ggttgcgctc    840
```

```
ttccgggcag ttgttatttt ggtctgtgat gactaactcg tatctattct tgtgggagca    900
ggggcaaccc aagcagagga aaccacaccg gttcaggcca ggcacggtgg cactgcggga    960
gatcaggagg tatcagaagt cggtcgactt tctcatcccg tttgcaccat ttgtccgtct   1020
ggtgggtacc tctgtctgtc atatcctctc gctctctcta caaacgatct gcagtgcaga   1080
gtgtaattgg aatattttgt tcctgacaaa tttgcagatc aaggaggtca ccgacttctt   1140
ctgtcctgaa atcagccgct ggactcccca agcgctcgtc gcgattcaag aggtcagtgc   1200
taaaacctgg catgtactat tagatctgat ggtttgatta gagtactaca atgcagatga   1260
attcaatatc cgaaaaccat gaactgtggg gtagatacat gtatcgcctt aattcatggt   1320
ttctgaatgc tctgctatta attcagtttg atatatttat ttagcagcat ggtattgttt   1380
tggtggctgg taaatcaaaa ctgaaatgtg attacgagca aaacggtatc gattgtcgat   1440
cctgtgtgtt tttgtgcaca tctggttgtt tggtcaagat gtgtttgtgc acatcttgca   1500
acatgatcct gcccacacac tcaaaactga ctattggtta ggttccattt gtcttatgga   1560
atttaggvtg taactgagag gtgagcaagt ggtagtaacg ttcaattttg attcaggatg   1620
aggatattgt gatccagaaa attgcatgtt atggttatgt gtccaaacgc caaatgatta   1680
tgtctatatc cagtacttta gaaccagtac aacaacaaaa agtactttag aaccagtcaa   1740
gtttattgtg catttataca agagtgttgt ttgcacaata gacttgcttt agtcgtctct   1800
tgccagaaat gccttcttct gcacaacgag caaaaataac ataaagttga ctatactcag   1860
tgtggcctaa gaaatgagtt gtacttttta gtcactggcc tgtgtatttg ctttgaattg   1920
acacataatt cccttttcct ttccctctgc aggctgcaga gtatcacctc gtcgacgtat   1980
ttgaaagggc aaatcactgt gccatccatg caaagcgtgt taccgtcagt aagttctcac   2040
tgaatgaaaa ctcccttttct tttacaatat tgcgcagaag gaaacatgcc agttatgaaa   2100
gagtttcaat tacaggatca cctttgcttt catttgatgt gatatctagt tttgatgttg   2160
tttcaaggtt caagaattct aatgataaat gataggatcc acaattgtta tatctctgca   2220
gctcctcgta tctgttgtcc acgaacaaac atatcaaaca attcattaaa aagatgaaga   2280
agtcaaacaa acagtatatg tgcactgcat attagatatc aaacctggtt actatacgac   2340
tgatctggcc tgaccccgc gtcgcctctc cctggcggca cggggggaac cactccgggca   2400
ccgccacctt ccctcctccc tccacccccc acctcgccgc cgcctgagga gttcgccggc   2460
gaagcccggt ctggctccag ggagggtggc ggcggggcat ctctctgcga ggcgtgaggg   2520
cgcatctcgt gcgcgggcgc ggcgagcttg ggcgggatcg cgggcgcggc tctggctcgg   2580
gctggtgagg ctccggcggt ccgagggtg tcgcggccgcg gcggggtct cgctccggcg   2640
cgggcggtcc gagggcgcgc gggatctggc gctccagcag gggcgccgtc aaggggagcc   2700
gggcagggaa gctcgtcagg cgggctcgtc aggcaggcgt gacgcgggc ggcggccgcg   2760
ggctggaagc catggcgttt tggccatggt gtcgtgtgcg ctcgcttctc attcgcagct   2820
tgaggtgctg ctgctgaggg tggtgcgcgg tgaagcttgg tggtcggcgt tggagagtgc   2880
aaggcgcaac aggaatggct ccaatgatct ccacgcttct gggtggatca gatctgccgc   2940
cctccatagg ggtgtgttcc gggcgaaagc cttgacccga ctttgtcggt gccgtcgacg   3000
gcgggcgcttt cgggcgtcgt ttccctcctt ggaggcgtcg ttgtggaact catcttcttc   3060
tatgtggggc tcgggctctc cgggtgaaaa cctaagctcc agattttccg gagcgggcga   3120
tggcggcgtc ttcgtcgttt ccctcttggg ggcgttgctt gggagagtta gcttgtgctt   3180
ggtgcgtttg gttttctcct acgtcgggtt tggtggatgc cggggcagcg gccccggacg   3240
gctgatgaac gccgaggcgg cggcctcgga aagtgatgcg cggtgcggct ccatgggggc   3300
gggcggtggc tcggccttca cttgggtggc aatcttgggc cacttgggtg gcaggcttgt   3360
cggtccggtc gacgcgttcc agaggggggcg gtctgacttt gcgtcggggc gcgggcggtc   3420
gatgtggtgc gacgttcgtg gtctgcgagc ggttgccttg agcagcgtgg gctgcgggca   3480
gctgggtcgc gcggcgttgc tgctcgagcg gagcggtggt acgtcgggc ggcggccccg   3540
gaaggtgatg ccgttgatt gcgctgggcg tgacggagcg gtggatgtcg gggcggcggc   3600
cccgagaaaa tcactgtggc gtccagattt ctgtggcaac gatgatggtg ggagcgatgt   3660
cggcgacgcg gcaatggttg cgatagtcgg ctcttctccg gcgtgtccac gatattgcct   3720
cggtttgttt gttgctgtgg agtcgaagct gcggcggcga ggccctgtgg tatacgatga   3780
ctggttccag gtgtcctttc gtcgatcttc cgtggcgcca gccgtgcctg gtttcgttct   3840
tccgagttct ccgtcagaat cggagctgcg ttgtctgtcc gcaggtcgac atgttgctga   3900
gaagggtggg ctttgccctg tgtgtttcag tctatgcgag tgggctcggc ccttgttgtt   3960
ctggtttttg cccggttttc cgtaattaac tgggcaattc tcttctgctt aattaataga   4020
tgaggcaatc tttgcctccc tttcaaaaaa aaacctggtt actatagcag gaaattcagg   4080
gttgattact ttatttctta tctgaaggat aaacattgta tcaaatcaga attttatttg   4140
taagttacat tttttttttac ttataaaact tggaaactgt tttactgtga caaatagatg   4200
ccactagaat catgatcaca tcgtggctgt tgctattcta acaaataaat gctcctgaac   4260
aaatgggaac tatatatgaa gatgtatgga ccagcatgtt cctgttaacc tgacctttt   4320
ccttttttg ctgctgcagt gcaaaaggac atacagcttg caaggcgtat cggcgggagg   4380
aggctttggt ga                                                       4392
```

SEQ ID NO: 132          moltype = RNA  length = 579
FEATURE                 Location/Qualifiers
source                  1..579
                        mol_type = other RNA
                        organism = Triticum aestivum

```
SEQUENCE: 132
atggcccgca ccaagcaccc ggccgtcagg aagaccaagg cgccgcccaa gaagcagctc     60
gggcccgcc ccgcgcagcg gcggcaggag acagatggcg cgggcacgtc ggcgacaccg    120
gttgcgcggg accttcccgg gtcgcttcct tttcgtttcg tcttgttttc tgttttttgg    180
tctgacttgc tcgtcacctg ttcgacggaa tgcagaggcg agccgggcgg gcggcggccc    240
cagggggggc tcaaggggca acccaagcag aggaaaccac accggttcag gccaggcacg    300
gtggcactgc gggagatcag gaggtatcag aagtcggtcg actttctcat cccgtttgca    360
ccatttgtcc gtctgatcaa ggaggtcacc gacttcttct gtcctgaaat cagccgctgg    420
actccccaag cgctcgtcgc gattcaagag gctgcagagt atcacctcgt cgacgtattt    480
gaaagggcaa atcactgtgc catccatgca aagcgtgtta ccgtcatgca aaaggacata    540
cagcttgcaa ggcgtatcgg cgggaggagg ctttggtga                          579
```

SEQ ID NO: 133          moltype = AA  length = 192

-continued

```
FEATURE                  Location/Qualifiers
source                   1..192
                         mol_type = protein
                         organism = Triticum aestivum
SEQUENCE: 133
MARTKHPAVR KTKAPPKKQL GPRPAQRRQE TDGAGTSATP VARDLPGSLP FRFVLFSVFW   60
SDLLVTCSTE CRGEPGGRRP QGGLKGQPKQ RKPHRFRPGT VALREIRRYQ KSVDFLIPFA  120
PFVRLIKEVT DFFCPEISRW TPQALVAIQE AAEYHLVDVF ERANHCAIHA KRVTVMQKDI  180
QLARRIGGRR LW                                                     192

SEQ ID NO: 134           moltype = DNA   length = 4394
FEATURE                  Location/Qualifiers
source                   1..4394
                         mol_type = other DNA
                         organism = Triticum aestivum
SEQUENCE: 134
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacaccg gtagcgcggg accttccggg gtcgcttcct tttcgtttcg tcttgttttc  300
tgttttttgg tctgacttgc tcgtcacctg ttcgacggaa tgcagaggcg agccgggcgg  360
gcggcggccc caggggggc tcaaggtgcg gccttctttg cgcttttcgg ttttccgccg  420
cgtgtttagg gccatttccg tcttgtttgg gggtgcgcgg ggcgggggct tgttttttt  480
cctccccct tcgttgttgc gcacattgct cgggaatgct gccaggagcg gttgcggttc  540
ttctttgacc cttcgggagg gctggatcgg cagtttcttc gcttccttgc tccagatttt  600
agttcatctt gtaccagtac agtagcaaga tgatggatgg gggcttgttt tttctttctc  660
cttccttgtt ccggacattt ctctggagcg actttatgc atttcccagt attgtccttt  720
gtccttagag ggtagtggat cggcagtttt cttcgcctca ttggtccaga ttttagttta  780
tcttgtacgg taccaagatg atggatgtgg cacaaagtc tcagtttggg ggttgcgctc  840
ttccgggcag ttgttatttt ggtctgtgat gactaactcg tatctattct tgtgggagca  900
ggtgggcaac ccaagcagag gaaaccacac cggttcaggc caggcacggt ggcactgcgg  960
gagatcagga ggtatcagaa gtcggtcgac tttctcatcc cgtttgcacc atttgtccgt 1020
ctggtgggta cctctgtctg tcatatcctc tcgctctctc tacaaacgat ctgcagtgca 1080
gagtgtaatt ggaatatttt gttcctgaca aatttgcaga tcaaggaggt caccgacttc 1140
ttctgtcctg aaatcagccg ctggactccc aagcgctcg tcgcgattca agaggtcagt 1200
gctaaaacct ggcatgtact attagatctg atggtttgat tagagtacta caatgcagat 1260
gaattcaata tccgaaaacc atgaactgtg gggtagatac atgtatcgcc ttaattcatg 1320
gtttctgaat gctctgctat taattcagtt tgatatattt atttagcagc atggtattgt 1380
tttggtggct ggtaaatcaa aactgaaatg tgattacgac caaaacggta tcgattgtcg 1440
atcctgtgtg tttttgtgca catctggttg tttggtcaag atgtgtttgt gcacatcttg 1500
caacatgatc ctgcccacac actcaaaact gactattggt taggttccat ttgtcttatg 1560
gaatttaggg tgtaactgag aggtgagcaa gtggtagtaa cgttcaattt tgattcagga 1620
tgaggatatt gtgatccaga aaattgcatg ttatggttat gtgtccaaac gccaaatgat 1680
tatgtctata tccagtactt tagaaccagt acaacaacaa aaagtacttt agaaccagtc 1740
aagtttattg tgcatttata caagagtgtt gtttgcacaa tagacttgct ttagtcgtct 1800
cttgccagaa atgccttctt ctgcacaacg agcaaaaata acataaagtt gactatactc 1860
agtgtggcct aagaaatgag ttgtacttt tagtcactgg cctgtgtatt tgctttgaat 1920
tgacacataa ttcccttttc cttttccctct gcaggctgca gagtatcacc tcgtcgacgt 1980
atttgaaagg gcaaatcact gtgccatcca tgcaaagcgt gttaccgtca gtaagttctc 2040
actgaatgaa aactcccttt cttttacaat attgcgcaga aggaaacatg ccagttatga 2100
aagagtttca attacaggat cacctttgct ttcatttgat gtgatatcta gttttgatgt 2160
tgtttcaagg ttcaagaatt ctaatgataa atgataggat ccacaattgt tatatctctg 2220
cagctcctcg tatctgttgt ccacgaacaa acatatcaaa caattcatta aaaagatgaa 2280
gaagtcaaac aaacagtata tgtgcactgc atattagata tcaaacctgg ttactatacg 2340
actgatctgg cctgaccccc gcgtcgcctc tccctggcgg cacgggggga accactccgg 2400
cgccgccacc ttccctcctc cctccacccc ccacctcgcc gccgcctgag gagttcgccg 2460
gcgaagcccg gtctggctcc agggagggtg cggcggggc atctctctgc gaggcgtgag 2520
ggcgcatctc gtgcgcgggc gcggcgagct tgggcgggat cgcgggcgcg gctctggctc 2580
gggctggtga ggctccggcg gtccgagggg tgtcgcggcg cggcggggat ctcgctccga 2640
cgcgggcggt ccgagggcgc gcgggatctg gcgctccagc aggggcgccg tcaaggggag 2700
ccgggcaggg aagctcgtca ggcgggctcg tcaggcaggc gtgacgcggg gcggcggccg 2760
cgggctggaa gccatggcgt tttggccatg gtgtcgtgtg cgctcgcttc tcattcgcag 2820
cttgaggtgc tgctgctgag ggtggtgcgc ggtgaagctt ggtggtcagc gttggagagt 2880
gcaaggcgca acaggaatgg ctccaatgat ctccacgctt ctgggtggat cagatctgcg 2940
gccctccata ggggtgtgtt ccgggcgaaa gcctcaccc gacttgtcg gtgccgtcga 3000
cggcggcgct tcgggcgtc gtttccctcc ttggaggcgt cgttgtggaa ctcatcttct 3060
tctatgtggg gctcgggctc tccgggtgaa aacctaagct ccagattttc cggagcgggc 3120
gatggcggcg tcttcgtcgt ttccctcttg ggggcgttgc ttgggagagt tagcttgtgc 3180
ttggtgcgtt tggttttctc ctacgtcggg tttggtggat gccaggagcag cggccccgga 3240
cggctgatga acgccgaggc ggcggcctcg gaaagtgatg cgcgggtcgg ctccatgggg 3300
cggggcggtg gctcggcctt cacttgggtg gcaatcttgg gccacttggg tggcaggctt 3360
gtcggtccgg tcgacgcgtt ccagaggggg cggtctgact ttgcgtcggg gcggcggccc 3420
cggatgtggt gcgacgttcg tggtctgcga gcggttgcgt ggtgagcggc gggctgcggg 3480
cagctgggtc gcgcggcgtt gctgctcgag cggagcggtg tacgtcgggc gggcggcccc 3540
cggaaggtga tgccggttga ttcgctgggc cgtgacggag cggtggatgt cggggcggcg 3600
gccccgagaa aatcactgtg gcgtccgat ttctgtggca acgatgatgg tgggagcgat 3660
gtcggcgacg cggcaatggt tgcgatagtc ggctcttctc cggcgtgtcc acgatattgc 3720
ctcggtttgt ttgttgctgt ggagtcgaag ctgcggcggc gaggccctgt ggtatacgat 3780
```

```
gactggttcc aggtgtcctt tcgtcgatct tccgtggcgc cagccgtgcc tggtttcgtt   3840
cttccgagtt ctccgtcaga atcggagctg cgttgtctgt ccgcaggtcg acatgttgtc   3900
gagaagggtg ggctttgccc tgtgtgtttc agtctatgcg agtgggctcg gcccttgttg   3960
ttctggtttt tgcccggttt tccgtaatta actgggcaat tctcttctgc ttaattaata   4020
gatgaggcaa tctttgcctc cctttcaaaa aaaaacctgg ttactatagc aggaaattca   4080
gggttgatta ctttatttct tatctgaagg ataaacattg tatcaaatca gaatttatt    4140
tgtaagttac attttttttt acttataaaa cttggaaact gttttactgt gacaaatagac  4200
tgccactaga atcatgatca catcgtggct gttgctattc taacaaataa atgctcctga   4260
acaaatggga actatatatg aagatgtatg gaccagcatg ttcctgttaa cctgaccttt   4320
ttcctttttt tgctgctgca gtgcaaaagg acatacagct tgcaaggcgt atcggcggga   4380
ggaggctttg gtga                                                     4394

SEQ ID NO: 135          moltype = RNA   length = 581
FEATURE                 Location/Qualifiers
source                  1..581
                        mol_type = other RNA
                        organism = Triticum aestivum
SEQUENCE: 135
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
gtagcgcggg accttccggg gtcgcttcct tttcgtttcg tcttgttttc tgttttttgg   180
tctgacttgc tcgtcacctg ttcgacggaa tgcagaggcg agccgggcgg gcggcggccc   240
caggggggggc tcaaggtggg caacccaagc agaggaaacc acaccggttc aggccaggca   300
cggtggcact gcgggagatc aggaggtatc agaagtcggt cgactttctc atcccgtttg   360
caccattgt ccgtctgatc aaggaggtca ccgacttctt ctgtcctgaa atcagccgct    420
ggactcccca agcgctcgtc gcgattcaag aggctgcaga gtatcacctc gtcgacgtat   480
ttgaaagggc aaatcactgt gccatccatg caaagcgtgt taccgtcatg caaaaggaca   540
tacagcttgc aaggcgtatc ggcgggagga ggctttggtg a                       581

SEQ ID NO: 136          moltype = AA   length = 125
FEATURE                 Location/Qualifiers
source                  1..125
                        mol_type = protein
                        organism = Triticum aestivum
SEQUENCE: 136
MARTKHPAVR KTKAPPKKQL GPRPAQRRQE TDGAGTSATP VARDLPGSLP FRFVLFSVFW   60
SDLLVTCSTE CRGEPGGRRP QGGLKVGNPS RGNHTGSGQA RWHCGRSGGI RSRSTFSSRL   120
HHLSV                                                               125

SEQ ID NO: 137          moltype = RNA   length = 486
FEATURE                 Location/Qualifiers
source                  1..486
                        mol_type = other RNA
                        organism = Triticum aestivum
SEQUENCE: 137
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
aggcgagccg ggcggcggc ggccccaggg ggggctcaag gtgggcaacc caagcagagg    180
aaaccacacc ggttcaggcc aggcacggtg gcactgcggg agatcaggag gtatcagaag   240
tcggtcgact ttctcatccc gtttgcacca tttgtccgtc tgatcaagga ggtcaccgac   300
ttcttctgtc ctgaaatcag ccgctggact ccccaagcgc tcgtcgcgat tcaagaggct   360
gcagagtatc acctcgtcga cgtatttgaa agggcaaatc actgtgccat ccatgcaaag   420
cgtgttaccg tcatgcaaaa ggacatacag cttgcaaggc gtatcggcgg gaggaggctt   480
tggtga                                                              486

SEQ ID NO: 138          moltype = AA   length = 138
FEATURE                 Location/Qualifiers
source                  1..138
                        mol_type = protein
                        organism = Triticum aestivum
SEQUENCE: 138
MDGTVICPFK YVDEVILCSL LNRDERLGSP AADFRTEEVG DLLDQTDKWC KRDEKVDRLL   60
IPPDLPQCHR AWPEPVWFPL LGLPTLSPPW GRRPPGSPRC RRRARAICLL PPLRGAGPEL   120
LLGRRLGLPD GRVLGAGH                                                 138

SEQ ID NO: 139          moltype = DNA   length = 4400
FEATURE                 Location/Qualifiers
source                  1..4400
                        mol_type = other DNA
                        organism = Triticum aestivum
SEQUENCE: 139
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc   120
cgtctcccgc tctctgagcg aacgccgtcc ccatttcgtc gcgagagatg gacggacgga   180
cgccccacgc atgacgctaa tgtgctcttc ctctcccttt gcagatggcg cgggcacgtc   240
ggcgacaccg gttgcgcggg accttccggg gtcgcttcct tttcgtttcg tcttgttttc   300
tgttttttgg tctgacttgc tcgtcacctg ttcgacggaa tgcagaggcg agccgggcgg   360
gcggcggccc caggggggggc tcaaggtgcg gccttctttg cgcttttcgg ttttccgccg   420
cgtgtttagg gccattccg tcttgtttgg gggtgcgcgg ggcggggggct tgtttttttt   480
```

-continued

```
cctcccccct tcgttgttgc gcacattgct cgggaatgct gccaggagcg gttgcggttc  540
ttctttgacc cttcgggagg gctggatcgg cagtttcttc gcttccttgc tccagatttt  600
agttcatctt gtaccagtac agtagcaaga tgatggatgg gggcttgttt tttctttctc  660
cttccttgtt ccggacattt ctctggagcg acttttatgc atttcccagt attgtccttt  720
gtccttagag ggtagtggat cggcagtttt cttcgcctca ttggtccaga tttagttta  780
tcttgtacgg taccaagatg atggatgtgg cacaaagttc tcagtttggg ggttgcgctc  840
ttccgggcag ttgttatttt ggtctgtgat gactaactcg tatctattct tgtgggagca  900
ggggcaactg ggcaacccaa gcagaggaaa ccacaccggt tcaggccagg cacggtggca  960
ctgcgggaga tcaggaggta tcagaagtcg gtcgactttc tcatcccgtt tgcaccattt  1020
gtccgtctgg tgggtacctc tgtctgtcat atcctctcgc tctctctaca aacgatctgc  1080
agtgcagagt gtaattggaa tattttgttc ctgacaaatt tgcagatcaa ggaggtcacc  1140
gacttcttct gtcctgaaat cagccgctgg actcccaag cgctcgtcgc gattcaagag  1200
gtcagtgcta aaacctggca tgtactatta gatctgatgg tttgattaga gtactacaat  1260
gcagatgaat tcaatatccg aaaaccatga actgtggggt agatacatgt atcgccttaa  1320
ttcatggttt ctgaatgctc tgctattaat tcagtttgat atatttattt agcagcatgg  1380
tattgttttg gtggctggta aatcaaaact gaaatgtgat tacgagcaaa acggtatcga  1440
ttgtcgatcc tgtgtgtttt tgtgcacatc tggttgtttg gtcaagatgt gtttgtgcac  1500
atcttgcaac atgatcctgc ccacacactc aaaactgact attggttagg ttccatttgt  1560
cttatggaat ttagggtgta actgagaggt gagcaagtgg tagtaacgtt caattttgat  1620
tcaggatgag gatattgtga tccagaaaat tgcatgttat ggttatgtgt ccaaacgcca  1680
aatgattatg tctatatcca gtactttaga accagtacaa caacaaaaag tactttagaa  1740
ccagtcaagt ttattgtgca tttatacaag agtgttgttt gcacaataga cttgctttag  1800
tcgtctcttg ccagaaatgc cttcttctgc acaacgagca aaaataacat aaagttgact  1860
atactcagtg tggcctaaga aatgagttgt acttttttagt cactggcctg tgtatttgct  1920
ttgaattgac acataattcc cttttccttt ccctctgcag gctgcagagt atcacctcgt  1980
cgacgtattt gaaagggcaa atcactgtgc catccatgca aagcgtgtta ccgtcagtaa  2040
gttctcactg aatgaaaact ccctttcttt tacaatattg cgcagaagga aacatgccag  2100
ttatgaaaga gtttcaatta caggatcacc tttgctttca tttgatgtga tatctagttt  2160
tgatgttgtt tcaaggttca agaattctaa tgataaatga taggatccac aattgttata  2220
tctctgcagc tcctcgtatc tgttgtccac gaacaaacat atcaaacaat tcattaaaaa  2280
gatgaagaag tcaaacaaac agtatatgtg cactgcatat tagatatcaa acctggttac  2340
tatacgactg atctggcctg acccccgcgt cgcctctccc tggcggcacg gggggaacca  2400
ctccggcgcc gccaccttcc ctcctccctc caccccccac ctcgccgccg cctgaggagt  2460
tcgccggcga agcccggtct ggctccaggg agggtggcgg cggggcatct ctctgcgagg  2520
cgtgagggcg catctcgtgc gcgggcgcgg cgagcttggg cgggatcgcg ggcgcggctc  2580
tggctcgggc tggtgaggct ccggcggtcc gagggggtgtc gcggcgcggc gggggtctcg  2640
ctccggcgcg ggcggtccga gggcgcgcgg gatctggcgc tccagcaggg gcgccgtcaa  2700
ggggagccgg gcagggaagc tcgtcaggcg ggctcgtcag gcaggcgtga cgcggggcgg  2760
cggccgacgg ctggaagcca tcggcgtttg gccatggtgt cgtgtgcgct cgcttctcat  2820
tcgcagcttg aggtgctgct gctgagggtg gtgcgcggtg aagcttggtg gtcggcgttg  2880
gagagtgcaa ggcgcaacag gaatggctcc aatgatctcc acgcttctgg gtggatcaga  2940
tctgcggccc tccatagggg tgtgttccgg gcgaaagcct tgacccgact ttgtcggtgc  3000
cgtcgacggc ggcgctttcg ggcgtcgttt ccctccttag aggcgtcgtt gtggaactca  3060
tcttcttcta tgtggggctc gggctctccg ggtgaaaacc taagctccag attttccgga  3120
gcgggcgatg gcggcgtctt cgtcgtttcc ctcttggggg cgttgcttgg gagagttagc  3180
ttgtgcttgg tgcgtttggt tttctcctac gtcgggtttg gtggatgccg gggcagcggc  3240
cccggacggc tgatgaacgc cgaggcggcg gcctcggaaa gtgatgcgcg gtgcggctcc  3300
atggggcggg gcggtggctc ggccttcact tgggtggcaa tcttgggcca cttgggtggc  3360
aggcttgtcg gtccggtcga cgcgttccag aggggcggt ctgactttgc gtcggggcgg  3420
cggccccgga tgtggtgcga cgttcgtggt ctgcgagcgg ttgccttgag cagcgtgggc  3480
tgcgggcagc tgggtcgcgc ggcgttgctg ctcgagcgga gcggtggtac gtcggggcgg  3540
cggccccgga aggtgatgcc ggttgattgc gctgggcgtg acggagcggt ggatgtcggg  3600
gcggcggccc cgagaaaatc actgtggcgt ccagatttct gtggcaacga tgatggtggg  3660
agcgatgtcg gcgacgcggc aatggttgcg atagtcggct cttctccggc gtgtccacga  3720
tattgcctcg gtttgtttgt tgctgtggag tcgaagctgc ggcggcgagg ccctgtggta  3780
tacgatgact ggttccaggt gtcctttcgt cgatcttccg tggcgccagc cgtgcctggt  3840
ttcgttcttc cgagttctcc gtcagaatcg gagctgcgtt gtctgtccgc aggtcgacat  3900
gttgtcgaga agggtgggct ttgccctgtg tgtttcagtc tatgcgagtg ggctcggccc  3960
ttgttgttct ggtttttgcc cggttttccg taattaactg ggcaattctc ttctgcttaa  4020
ttaatagatg aggcaatctt tgcctccctt tcaaaaaaaa acctggttac tatagcagga  4080
aattcagggt tgattacttt atttcttatc tgaaggataa acattgtatc aaatcagaat  4140
tttatttgta agttacattt ttttttactt ataaaacttg gaaactgttt tactgtgaca  4200
aatagatgcc actagaatca tgatcacatc gtggctgttg ctattctaac aaataaaatgc  4260
tcctgaacaa atgggaacta tatatgaaga tgtatgaacc agcatgttcc tgttaacctg  4320
accttttttcc tttttttgct gctgcagtgc aaaaggacat acagcttgca aggcgtatcg  4380
gcgggaggag gctttggtga                                               4400
```

```
SEQ ID NO: 140          moltype = RNA   length = 512
FEATURE                 Location/Qualifiers
source                  1..512
                        mol_type = other RNA
                        organism = Triticum aestivum
SEQUENCE: 140
atggcccgca ccaagcaccc ggccgtcagg aagaccaagg cgccgcccaa gaagcagctc  60
gggccccgcc ccgcgcagcg gcggcaggag acagatggcg cgggcacgtc ggcgacaccg  120
gttgcgcggg accttccogg aggcgagccg ggcgggcggc ggcccagggg ggggctcaag  180
gggcaactgg gcaacccaag cagaggaaac cacaccggtt caggccaggc acggtggcac  240
tgcgggagat caggaggtat cagaagtcgg tcgactttct catcccgttt gcaccatttg  300
tccgtctgat caaggaggtc accgacttct tctgtcctga aatcagccgc tggactcccc  360
```

-continued

```
aagcgctcgt cgcgattcaa gaggctgcag agtatcacct cgtcgacgta tttgaaaggg   420
caaatcactg tgccatccat gcaaagcgtt ttaccgtcat gcaaaaggac atacagcttg   480
caaggcgtat cggcgggagg aggctttggt ga                                 512

SEQ ID NO: 141          moltype = AA   length = 102
FEATURE                 Location/Qualifiers
source                  1..102
                        mol_type = protein
                        organism = Triticum aestivum
SEQUENCE: 141
MARTKHPAVR KTKAPPKKQL GPRPAQRRQE TDGAGTSATP VARDLPGGEP GGRRPQGGLK   60
GQLGNPSRGN HTGSGQARWH CGRSGGIRSR STFSSRLHHL SV                      102

SEQ ID NO: 142          moltype = RNA   length = 587
FEATURE                 Location/Qualifiers
source                  1..587
                        mol_type = other RNA
                        organism = Triticum aestivum
SEQUENCE: 142
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
gttgcgcggg accttcccgg gtcgcttcct tttcgtttcg tcttgttttc tgttttttgg   180
tctgacttgc tcgtcacctg ttcgacggaa tgcagaggcg agccgggcgg cgggcggccc   240
cagggggggc tcaaggggca actgggcaac ccaagcagag gaaaccacac cggttcaggc   300
caggcacggt ggcactgcgg gagatcagga ggtatcagaa gtcggtcgac tttctcatcc   360
cgtttgcacc atttgtccgt ctgatcaagg aggtcaccga cttcttctgt cctgaaatca   420
gccgctggac tccccaagcg ctcgtcgcga ttcaagagge tgcagagtat cacctcgtcg   480
acgtatttga aagggcaaat cactgtgcca tccatgcaaa gcgtgttacc gtcatgcaaa   540
aggacataca gcttgcaagg cgtatcggcg ggaggaggct ttggtga                587

SEQ ID NO: 143          moltype = AA   length = 127
FEATURE                 Location/Qualifiers
source                  1..127
                        mol_type = protein
                        organism = Triticum aestivum
SEQUENCE: 143
MARTKHPAVR KTKAPPKKQL GPRPAQRRQE TDGAGTSATP VARDLPGSLP FRFVLFSVFW   60
SDLLVTCSTE CRGEPGGRRP QGGLKGQLGN PSRGNHTGSG QARWHCGRSG GIRSRSTFSS   120
RLHHLSV                                                            127

SEQ ID NO: 144          moltype = DNA   length = 4392
FEATURE                 Location/Qualifiers
source                  1..4392
                        mol_type = other DNA
                        organism = Triticum aestivum
SEQUENCE: 144
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gttgcgcggg accttcccgg gtcgcttcct tttcgtttcg tcttgttttc   300
tgttttttgg tctgacttgc tcgtcacctg ttcgacggaa tgcagaggcg agccgggcgg   360
gcggcggccc cagggggggc tcaaggtgcg gccttctttg cgcttttcgg ttttccgccg   420
cgtgtttagg gccatttccg tcttgtttgg gggtgcgcgg ggcgggggct tgtttttttt   480
cctccccct tcgttgttgc gcacattgct cgggaatgct gccaggagcg gttgcggttc   540
ttctttgacc cttcgggagg gctggatcgg cagtttcttc gcttccttgc tccagatttt   600
agttcatctt gtaccagtac agtagcaaga tgatggatgg gggcttgttt tttctttctc   660
cttccttgtt ccggacattt ctctggagcg acttttatgc atttcccagt attgtccttt   720
gtccttagag ggtagtggat cggcagtttt cttcgcctca ttggtccaga tttttagttta   780
tcttgtacgg taccaagatg atggatgtgg cacaaagttc tcagtttggg ggttgcgctc   840
ttccgggcag ttgttatttt ggtctgtgat gactaactcg tatctattct tgtgggagca   900
ggggcaaccc aagcagagga aaccacaccg gttcaggcca ggcacggtgg cactgcggga   960
gatcaggagg tatcagaagt cggtcgactt ctctcatcccg tttgcaccat ttgtccgtct   1020
ggtgggtacc tctgtctgtc atatcctctc gctctctcta caaacgatct gcagtgcaga   1080
gtgtaattgg aatattttgt tcctgacaaa tttgcagatc aaggaggtca ccgacttctt   1140
ctgtcctgaa atcagccgct ggactcccca agcgctcgtc gcgattcaag aggtcagtgc   1200
taaaacctgg catgtactat tagatctgat ggtttgatta gagtactaca atgcagatga   1260
attcaatatc cgaaaaccat gaactgtggg gtagatacat gtatcgcctt aattcatggt   1320
ttctgaatgc tctgctatta attcagtttg atatatttat ttagcagcat ggtattgttt   1380
tggtggctgg taaatcaaaa ctgaaatgtg attacgagca aaacggtatc gattgtcgat   1440
cctgtgtgtt tttgtgcaca tctggttgtt tggtcaagat gtgtttgtgc acatcttgca   1500
acatgatcct gcccacacac tcaaaactga ctattggtta ggttccattt gtcttatgga   1560
atttagggtg taactgagag gtgagcaagt ggtagtaacg ttcaattttg attcaggatg   1620
aggatattgt gatccagaaa attgcatgtt atggttatgt gtccaaacgc caaatgatta   1680
tgtctatatc cagtacttta gaaccagtac aacaacaaaa agtactttag aaccagtcaa   1740
gtttattgtg catttataca agagtgttgt ttgcacaata gacttgcttt agtcgtctct   1800
tgccagaaat gccttcttct gcacaacgag caaaaataac ataaagttga ctatactcag   1860
tgtggcctaa gaaatgagtt gtactttta gtcactggcc tgtgtatttg ctttgaattg   1920
acacataatt cccttttcct ttccctctgc aggctgcaga gtatcacctc gtcgacgtat   1980
```

```
ttgaaagggc aaatcactgt gccatccatg caaagcgtgt taccgtcagt aagttctcac   2040
tgaatgaaaa ctccctttct tttacaatat tgcgcagaag gaaacatgcc agttatgaaa   2100
gagtttcaat tacaggatca cctttgcttt catttgatgt gatatctagt tttgatgttg   2160
tttcaaggtt caagaattct aatgataaat gataggatcc acaattgtta tatctctgca   2220
gctcctcgta tctgttgtcc acgaacaaac atatcaaaca attcattaaa aagatgaaga   2280
agtcaaacaa acagtatatg tgcactgcat attagatatc aaacctggtt actatacgac   2340
tgatctggcc tgaccccgc gtcgcctctc cctggcggca cggggggaac cactccggcg   2400
ccgccacctt ccctcctccc tccacccccc acctcgccgc cgcctgagga gttcgccggc   2460
gaagcccggt ctggctccag ggagggtggc ggcggggcat ctctctgcga ggcgtgaggg   2520
cgcatctcgt gcgcgggcgc ggcgagcttg ggcggggatcg cgggcgcggc tctggctcgg   2580
gctggtgagg ctccggcggt ccgaggggtg tcgcggcgcg gcgggggtct cgctccggcg   2640
cgggcggtcc gagggcgcgc gggatctggc gctccagcag gggcgccgtc aaggggagcc   2700
gggcagggaa gctcgtcagg cgggctcgtc aggcaggcgt gacgcggggc ggcggccgcg   2760
ggctggaagc catggcgttt tggccatggt gtcgtgcggc ctcgcttctc attcgcagct   2820
tgaggtgctg ctgctgaggg tggtgcgcgg tgaagcttgg tggtcggcgt tggagagtgc   2880
aaggcgcaac aggaatggct ccaatgatct ccacgcttct gggtggatca gatctgcggc   2940
cctccatagg ggtgtgttcc gggcgaaagc cttgacccga ctttgtcggt gccgtcgacg   3000
gcggcgcttt cgggcgtcgt ttccctcctt ggaggcgtcg ttgtgaact catcttcttc   3060
tatgtggggc tcgggctctc cgggtgaaaa cctaagctcc agattttccg gagcggggcga   3120
tggcggcgtc ttcgtcgttt ccctcttggg ggcgttgctt gggagagtta gcttgtgctt   3180
ggtgcgtttg gtttctcct acgtcgggtt tggtggatgc cggggcagcg gccccggacg   3240
gctgatgaac gccgaggcgg cggcctcgga aagtgatgcg ggctcggct ccatgggggcg   3300
gggcggtggc tcggccttca cttgggtggc aatcttgggc cacttgggtg gcaggcttgt   3360
cggtccgtc gacgcgttcc agaggggggcg gtctgacttt gcgtcgggc ggcggccccg   3420
gatgtggtgc gacgttcgtg gtctgcgagc ggttgccttg agcagcgtgg gctgcgggca   3480
gctgggtcgc gcggcgttgc tgctcgagcg gagcggtggt acgtcggggc ggcggccccg   3540
gaaggtgatg ccggttgatt gcgctgggcg tgacggagcg gtggatgtcg gggcggcggc   3600
cccgagaaaa tcactgtggc gtccagattt ctgtggcaac gatgatggtg ggagcgatgt   3660
cggcgacgcg gcaatggttg cgatagtcgg ctcttctccg gcgtgtccac gatattgcct   3720
cggtttgttt gttgctgtgg agtcgaagct gcggcggcga ggccctgtgg tatacgatga   3780
ctggttccag gtgtccttc gtcgatcttc cgtggcgcca gccgtgcctg gtttcgttct   3840
tccgagttct ccgtcagaat cggagctgcg ttgtctgtcc gcaggtcgac atgttgtcga   3900
gaagggtggg ctttgccctg tgtgtttcag tctatgcgag tgggctcggc ccttgttgtt   3960
ctggtttttg cccggttttc cgtaattaac tgggcaattc tcttctgctt aattaataga   4020
tgaggcaatc tttgcctccc tttcaaaaaa aaacctggtt actatagcag gaaattcagg   4080
gttgattact ttatttctta tctgaaggat aaacattgta tcaaatcaga attttatttg   4140
taagttacat ttttttttac ttataaaact tggaaactgt tttactgtga caaatagatg   4200
ccactagaat catgatcaca tcgtggctgt tgctattcta acaaataaat gctcctgaac   4260
aaatgggaac tatatgtgaa gatgtatgga ccagcatgtt cctgttaacc tgacctttt   4320
cctttttttg ctgctgcagt gcaaaaggac atacagcttg caaggcgtat cggcgggagg   4380
aggctttggt ga                                                        4392
```

```
SEQ ID NO: 145            moltype = RNA   length = 504
FEATURE                   Location/Qualifiers
source                    1..504
                          mol_type = other RNA
                          organism = Triticum aestivum
SEQUENCE: 145
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
gttgcgcggg accttcccgg aggcgagccg ggcgggcggc ggccccaggg ggggctcaag   180
gggcaaccca agcagaggaa accacaccgg ttcaggccag gcacggtggc actgcgggag   240
atcaggaggt atcagaagtc ggtcgacttt ctcatcccgt ttgcaccatt tgtccgtctg   300
atcaaggagg tcaccgactt cttctgtcct gaaatcagcc gctggactcc ccaagcgctc   360
gtcgcgattc aagaggctgc agagtatcac ctcgtcgacg tatttgaaag ggcaaatcac   420
tgtgccatcc atgcaaaagcg tgttaccgtc atgcaaaagg acatacagct tgcaaggcgt   480
atcggcggga ggaggctttg gtga                                           504
```

```
SEQ ID NO: 146            moltype = AA   length = 167
FEATURE                   Location/Qualifiers
source                    1..167
                          mol_type = protein
                          organism = Triticum aestivum
SEQUENCE: 146
MARTKHPAVR KTKAPPKKQL GPRPAQRRQE TDGAGTSATP VARDLPGGEP GGRRPQGGLK   60
GQPKQRKPHR FRPGTVALRE IRRYQKSVDF LIPFAPFVRL IKEVTDFFCP EISRWTPQAL   120
VAIQEAAEYH LVDVFERANH CAIHAKRVTV MQKDIQLARR IGGRRLW                  167
```

```
SEQ ID NO: 147            moltype = DNA   length = 4399
FEATURE                   Location/Qualifiers
source                    1..4399
                          mol_type = other DNA
                          organism = Triticum aestivum
SEQUENCE: 147
atggcccgca ccaagcaccc ggccgtcagg aagaccaagg cgccgcccaa gaagcagctc   60
gggccccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagtggcg cgggcacgtc   240
ggcgacaccg gtgcgcggga ccttcccggg tcgcttcctt ttcgtttcgt cttgtttttct   300
```

```
gttttttggt ctgacttgct cgtcacctgt tcgacggaat gcagaggcga gccgggcggg   360
cggcggcccc aggggggct caaggtgcgg ccttctttgc gcttttcggt tttccgccgc     420
gtgtttaggg ccatttccgt cttgtttggg ggtgcgcggg gcgggggctt gtttttttc     480
ctcccccctt cgttgttgcg cacattgctc gggaatgctg ccaggagcgg ttgcggttct     540
tctttgaccc ttcgggaggg ctggatcggc agtttcttcg cttccttgct ccagattta     600
gttcatcttg taccagtaca gtagcaagat gatggatggg ggcttgtttt ttctttctcc     660
ttccttgttc cggacatttc tctggagcga cttttatgca tttcccagta ttgtcctttg     720
tccttagagg gtagtggatc ggcagttttc ttcgcctcat tggtccagat tttagtttat     780
cttgtacggt accaagatga tggatgtggc acaaagttct cagtttgggg gttgcgctct     840
tccgggcagt tgttattttg gtctgtgatg actaactcgt atctattctt gtgggagcag     900
gggcaactgg gcaacccaag cagaggaaac cacaccggtt caggccaggc acggtggcac     960
tgcgggagat caggaggtat cagaagtcgg tcgactttct catcccgttt gcaccatttg    1020
tccgtctggt gggtacctct gtctgtcata tcctctcgct ctctctacaa acgatctgca    1080
gtgcagagtg taattggaat attttgttcc tgacaaattt gcagatcaag gaggtcaccg    1140
acttcttctg tcctgaaatc agccgctgga ctccccaagc gctcgtcgcg attcaagagg    1200
tcagtgctaa aacctggcat gtactattag atctgatggt ttgattagag tactacaatg    1260
cagatgaatt caatatccga aaaccatgaa ctgtggggta gatacatgta tcgccttaat    1320
tcatggtttc tgaatgctct gctattaatt cagtttgata tatttattta gcagcatggt    1380
attgttttgg tggctggtaa atcaaaactg aaatgtgatt acgagcaaaa cggtatcgat    1440
tgtcgatcct gtgtgttttt gtgcacatct ggttgtttgg tcaagatgtg tttgtgcaca    1500
tcttgcaaca tgatcctgcc cacacactca aaactgacta ttggttaggt tccatttgtc    1560
ttatggaatt tagggtgtaa ctgagaggtg agcaagtggt agtaacgttc aattttgatt    1620
caggatgagg atattgtgat ccagaaaatt gcatgttatg gttatgtgtc caaacgccaa    1680
atgattatgt ctatatccag tactttagaa ccagtacaac aacaaaaagt actttagaac    1740
cagtcaagtt tattgtgcat ttatacaaga gtgttgtttg cacaatagac ttgctttagt    1800
cgtctcttgc cagaaatgcc ttcttctgca caacgagcaa aaataacata aagttgacta    1860
tactcagtgt ggcctaagaa atgagttgta cttttttagtc actggcctgt gtatttgctt    1920
tgaattgaca cataattccc tttctccttttc cctctgcagg ctgcagagta tcacctcgtc    1980
gacgtatttg aaagggcaaa tcactgtgcc atccatgcaa agcgtgttac cgtcagtaag    2040
ttctcactga atgaaaactc cctttctttt acaatattgc cagaaggaa acatgccagt    2100
tatgaaagag tttcaattac aggatcacct ttgctttcat ttgatgtgat atctagtttt    2160
gatgttgttt caaggttcaa gaattctaat gataaatgat aggatccaca attgttatat    2220
ctctgcagct cctcgtatct gttgtccacg aacaaacata tcaaacaatt cattaaaaag    2280
atgaagaagt caaacaaaca gtatatgtgc actgcatatt agatatcaaa cctggttact    2340
atacgactga tctggcctga cccccgcgtc gcctctccct ggcggcacgg ggggaaccac    2400
tccggcgccg ccaccttccc tcctccctcc acccccccacc tcgccgccgc ctgaggagtt    2460
cgccggcgaa gcccggtctg gctccaggga gggtggcggc ggggcatctc tctgcgaggc    2520
gtgagggcgc atctcgtgcg cgggcgcggc gagcttgggc gggatcgcgg gcgcggctct    2580
ggctcgggct ggtgaggctc cggtcgtccg aggggtgtcg cggcgcggcg gggtctcgc     2640
tccggcgcgg gcggtccgag ggcgcgcggg atctggcgct ccagcagggg cgccgtcaag    2700
gggagccggg cagggaagct cgtcaggcgg gctcgtcagg caggcgtgac gcggggcggc    2760
ggccgcgggc tggaagccat ggcgtttgg ccatggtgtc gtgtgcgctc gcttctcatt    2820
cgcagcttga ggtgctgctg ctgagggtgg tgcgcggtga agcttggtgg tcggcgttgg    2880
agagtgcaag gcgcaacagg aatggctcca atgatctcca cgcttctggg tggatcagat    2940
ctgcggccct ccatagggct gtgttccggg cgaaagcctt gacccgactt tgtcggtgcc    3000
gtcgacggcg gcgctttcgg gcgtcgtttc cctccttgga ggcgtcgttg tggaactcat    3060
cttcttctat gtggggctcg ggctctccgg gtgaaaacct aagctccaga ttttccggag    3120
cgggcgatgg cggcgtcttc gtcgtttccc tcttgggggc gttgcttggg agagttagct    3180
tgtgcttggt gcgtttggtt ttctcctacg tcgggtttgg tggatgccgg ggcagcggcc    3240
ccggacggct gatgaacgcc gaggcggcgg cctcggaaag tgatgcgcgg tgcggctcca    3300
tggggcgggg cggtggctcg gccttcactt gggtggcaat cttgggccac ttgggtggca    3360
ggcttgtcgg tccggtcgac gcgttccaga gggggcggtc tgactttgcg tcggggcggc    3420
ggccccggat gtggtgcgac gttcgtggtc tgcgagcggt tgccttgagc agcgtgggct    3480
gcgggcagct gggtcgcgcg gcgttgctgc tcgagcggag cggtggtacg tcggggcggc    3540
ggccccggaa ggtgatgccg gttgattgcg ctgggcgtga cgggagcggtg gatgtcgggg    3600
cggcggcccc gagaaaatca ctgtggcgtc cagatttctg tggcaacgat gatggtggga    3660
gcgatgtcgg cgacgcggca atggttgcga tagtcggctc ttctccggcg tgtccacgat    3720
attgcctcgg tttgtttgtt gctgtggagt cgaagctgcg gcggcgaggc cctgtggtat    3780
acgatgactg gttccaggtg tcctttcgtc gatcttccgt ggcgccagcc gtgcctggtt    3840
tcgttcttcc gagttctccg tcagaatcgg agctgcgttg tctgtccgca ggtcgacatg    3900
ttgtcgagaa gggtgggctt tgccctgtgt gtttcagtct atgcgagtgg gctcggccct    3960
tgttgttctg gttttttgccc ggttttccgt aattaactgg gcaattctct tctgcttaat    4020
taatagatga ggcaatcttt gcctccttt caaaaaaaaa cctggttact atagcaggaa    4080
attcagggtt gattacttta tttcttatct gaaggataaa cattgtatca aatcagaatt    4140
ttatttgtaa gttacatttt ttttttactta taaaacttgg aaactgtttt actgtgacaa    4200
atagatgcca ctagaatcat gatcacatcg tggctgttgc tattctaaca aataaatgct    4260
cctgaacaaa tgggaactat atatgaagat gtatggacca gcatgttcct gttaacctga    4320
cctttttcct ttttttgctg ctgcagtgca aaaggacata cagcttgcaa ggcgtatcgg    4380
cgggaggagg ctttggtga                                                  4399
```

SEQ ID NO: 148          moltype = RNA   length = 492
FEATURE                 Location/Qualifiers
source                  1..492
                        mol_type = other RNA
                        organism = Triticum aestivum
SEQUENCE: 148
```
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg    120
aggcgagccg ggcgggcggc ggccccaggg ggggctcaag gggcaactgg gcaacccaag    180
```

```
cagaggaaac cacaccggtt caggccaggc acggtggcac tgcgggagat caggaggtat   240
cagaagtcgg tcgactttct catcccgttt gcaccatttg tccgtctgat caaggaggtc   300
accgacttct tctgtcctga aatcagccgc tggactcccc aagcgctcgt cgcgattcaa   360
gaggctgcag agtatcacct cgtcgacgta tttgaaaggg caaatcactg tgccatccat   420
gcaaagcgtg ttaccgtcat gcaaaaggac atacagcttg caaggcgtat cggcgggagg   480
aggctttggt ga                                                      492

SEQ ID NO: 149          moltype = AA  length = 163
FEATURE                 Location/Qualifiers
source                  1..163
                        mol_type = protein
                        organism = Triticum aestivum
SEQUENCE: 149
MARTKHPAVR KTKAPPKKQL GPRPAQRRQE TDGAGTSATP RRAGRAAAPG GAQGATGQPK   60
QRKPHRFRPG TVALREIRRY QKSVDFLIPF APFVRLIKEV TDFFCPEISR WTPQALVAIQ   120
EAAEYHLVDV FERANHCAIH AKRVTVMQKD IQLARRIGGR RLW                     163

SEQ ID NO: 150          moltype = DNA  length = 4399
FEATURE                 Location/Qualifiers
source                  1..4399
                        mol_type = other DNA
                        organism = Triticum aestivum
SEQUENCE: 150
atggcccgca ccaagcaccc ggccgtcagg aagaccaagg cgccgcccaa gaagcagctc   60
gggccccgcc ccgcgcagcg gcggcaggag acaggtcagc ccttccctcc ttcctcccccc   120
cgtctcacgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gtgcgcggga ccttcccggg tcgcttcctt ttcgtttcgt cttgtttttct   300
gttttttggt ctgacttgct cgtcacctgt tcgacggaat gcagaggcga gccgggcggg   360
cggcggcacc aggggggct caaggtgcgg ccttctttgc gcttttcggt tttccgccgc   420
gtgtttaggg ccatttccgt cttgtttggg ggtgcgcggg gcggggggctt gtttttttttc   480
ctccccccctt cgttgttgcg cacattgctc gggaatgctg ccaggagcgg ttgcggttct   540
tctttgaccc ttcgggaggg ctggatcggc agtttcttcg cttccttgct ccagattta   600
gttcatcttg taccagtaca gtagcaagat gatggatggg ggcttgtttt ttctttctcc   660
ttccttgttc cggacatttc tctggagcga cttttatgca tttcccagta ttgtcctttg   720
tccttagagg gtagtggatc ggcagttttc ttcgcctcat tggtccagat tttagtttat   780
cttgtacggt accaagatga tggatgtggc acaaagttct cagtttgggg gttgcgctct   840
tccgggcagt tgttattttg gtctgtgatg actaactcgt atcattctt gtgggagcag   900
gggcaactgg gcaacccaag cagaggaaac cacaccggtt caggccaggc acggtggcac   960
tgcgggagat caggaggtat cagaagtcgg tcgactttct catcccgttt gcaccatttg   1020
tccgtctggt gggtacctct gtctgtcata tcctctcgct ctctctacaa acgatctgca   1080
gtgcagagtg taattggaat attttgttcc tgacaaattt gcagatcaag gaggtcaccg   1140
acttcttctg tcctgaaatc agccgctgga ctccccaagc gctcgtcgcg attcaagagg   1200
tcagtgctaa aacctggcat gtactattag atctgatggt ttgattagag tactacaatg   1260
cagatgaatt caatatccga aaaccatgaa ctgtggggta gatacatgta tcgccttaat   1320
tcatggtttc tgaatgctct gctattaatt cagtttgata tatttattta gcagcatggt   1380
attgttttgg tggctggtaa atcaaaactg aaatgtaatt acgagcaaaa cggtatcgat   1440
tgtcgatcct gtgtgttttt gtgcacatct ggttgtttgg tcaagatgtg tttgtgcaca   1500
tcttgcaaca tgatcctgcc cacacactca aaactgacta ttggttaggt tccatttgtc   1560
ttatggaatt tagggtgtaa ctgagaggtg agcaagtggt agtaacgttc aattttgatt   1620
caggatgagg atattgtgat ccagaaaatt gcatgttgtg gttatgtgtc caaacgccaa   1680
atgattatgt ctatatccag tactttagaa ccagtacaac aacaaaaagt actttagaac   1740
cagtcaagtt tattgtgcat ttatacaaga gtgttgtttg cacaatagac ttgctttagt   1800
cgtctcttgc cagaaatgcc ttcttctgca caacgagcaa aaataacata aagttgacta   1860
tactcagtgt ggcctaagaa atgagttgta ctttttagtc actggcctgt gtatttgctt   1920
tgaattgaca cataattccc ttttccttttc cctctgcagg ctgcagagta tcacctcgtc   1980
gacgtatttg aaagggcaaa tcactgtgcc atccatgcaa agcgtgttac cgtcagtaag   2040
ttctcactga atgaaaactc cctttctttt acaatattgc gcagaaggaa acatgccagt   2100
tatgaaagag tttcaattac aggatcacct ttgctttcat ttgatgtgat atctagtttt   2160
gatgttgttt caaggttcaa gaattctaat gataaatgat aggatccaca attgttatat   2220
ctctgcagct cctcgtatct gttgtccacg aacaaacata tcaaacaatt cattaaaaag   2280
atgaagaagt caaacaaaca gtatatgtgc actgcatatt agatatcaaa cctggttact   2340
atacgactga tctggcctga ccccccgcgtc gcctctcctt ggcggcacgg gggaaccac   2400
tccggcgccg ccaccttccc tcctccctcc accccccacc tcgccgccgc ctgaggagtt   2460
cgccggcgaa gcccggtctg ctccagggac gggtggcggc ggggcatctc tctgcgaggc   2520
gtgagggcgc atccgtgcg cgggcgcggc gagcttgggc gggatcgcgg gcgcggctct   2580
ggctcgggct ggtgaggctc cggcggtccg aggggtgtcg cggcgcggcg ggggtctcgc   2640
tccggcgcgc gcggtccgag ggcgcgcggg atctggcgct ccagcagggg cgccgtcaag   2700
gggagccggg cagggaagct cgtcaggcgg gctcgtcagg cgccggcgtgac gcgggggcgac   2760
ggccgcgggc tggaagccat ggcgtttttg ccatggtgtc gtgtgcgctc gcttctcatt   2820
cgcagcttga ggtgctgctg ctgagggtgg tgcgcggtga agcttggtgg tcggcgttgg   2880
agagtgcaag gcgcaacagg aatggctcca atgatctcca cgcttctggg tggatcagat   2940
ctgcggcccct ccatagggggt gtgttccggg cgaaagcctt gacccgactt tgtcggtgcc   3000
gtcgacggcg cgcgctttcg gcgtcgtttc cctccttgga gcgtcgtttg tggaactcat   3060
cttcttctat gtggggctcg ggctctccgg gtgaaaacct aagctccaga ttttccggag   3120
cgggcgatgg cggcgtcttc gtcgtttccc tcttgggggc gttgcttggg agagttagct   3180
tgtgcttggt gcgtttggtt ttctcctacg tcgggtttgg tggatccggg gcagcggcc   3240
ccggacggct gatgaacgcc gaggcggcgg cctcggaaag tgatgcgcgg tgcggctcca   3300
tggggcgggg cggtggctcg gccttcactt gggtggcaat cttgggccac ttgggtggca   3360
```

-continued

```
ggcttgtcgg tccggtcgac gcgttccaga ggggggcggtc tgactttgcg tcggggcggc   3420
ggccccggat gtggtgcgac gttcgtggtc tgcgagcggt tgccttgagc agcgtgggct   3480
gcgggcagct gggtcgcgcg gcgttgctgc tcgagcggag cggtggtacg tcggggcggc   3540
ggccccggaa ggtgatgccg gttgattgcg ctgggcgtga cggagcggtg gatgtcgggg   3600
cggcggcccc gagaaaatca ctgtggcgtc cagatttctg tggcaacgat gatggtggga   3660
gcgatgtcgg cgacgcggca atggttgcga tagtcggctc ttctccggcg tgtccacgat   3720
attgcctcgg tttgtttgtt gctgtggagt cgaagctgcg gcggcgaggc cctgtggtat   3780
acgatgactg gttccaggtg tcctttcgtc gatcttccgt ggcgccagcc gtgcctggtt   3840
tcgttcttcc gagttctccg tcagaatcgg agctgcgttg tctgtccgca ggtcgacatg   3900
ttgtcgagaa gggtgggctt tgccctgtgt gtttcagtct atgcgagtgg gctcggcccct  3960
tgttggttctg gtttttgccc ggtttttccgt aattaactgg gcaattctct tctgcttaat  4020
taatagatga ggcaatcttt gcctcccttt caaaaaaaaa cctggttact atagcaggaa   4080
attcaggggtt gattactta tttcttatct gaaggataaa cattgtatca aatcagaatt    4140
ttatttgtaa gttacatttt tttttactta taaaactgtt aaactgtttt actgtgacaa    4200
atagatgcca ctagaatcat gatcacatcg tggctgttgc tattctaaca aataaatgct    4260
cctgaacaaa tgggaactat atatgaagat gtatggacca gcatgttcct gttaacctga   4320
ccttttttcct tttttttgctg ctgcagtgca aaaggacata cagcttgcaa ggcgtatcgg  4380
cgggaggagg ctttggtga                                                 4399
```

SEQ ID NO: 151          moltype = RNA   length = 492
FEATURE                 Location/Qualifiers
source                  1..492
                        mol_type = other RNA
                        organism = Triticum aestivum
SEQUENCE: 151
```
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg   120
aggcgagccg ggcgggcggc ggccccaggg ggggctcaag gggcaactgg gcaacccaag   180
cagaggaaac cacaccggtt caggccaggc acggtggcac tgcgggagat caggaggtat   240
cagaagtcgg tcgactttct catcccgttt gcaccatttg tccgtctgat caaggaggtc   300
accgacttct tctgtcctga aatcagccgc tggactcccc aagcgctcgt cgcgattcaa   360
gaggctgcag agtatcacct cgtcgacgta tttgaaaggg caaatcactg tgccatccat   420
gcaaagcgtg ttaccgtcat gcaaaaggac atacagcttg caaggcgtat cggcgggagg   480
aggctttggt ga                                                       492
```

SEQ ID NO: 152          moltype = AA   length = 163
FEATURE                 Location/Qualifiers
source                  1..163
                        mol_type = protein
                        organism = Triticum aestivum
SEQUENCE: 152
```
MARTKHPAVR KTKAPPKKQL GPRPAQRRQE TDGAGTSATP RRAGRAAAPG GAQGATGQPK   60
QRKPHRFRPG TVALREIRRY QKSVDFLIPF APFVRLIKEV TDFFCPEISR WTPQALVAIQ   120
EAAEYHLVDV FERANHCAIH AKRVTVMQKD IQLARRIGGR RLW                      163
```

SEQ ID NO: 153          moltype = DNA   length = 4395
FEATURE                 Location/Qualifiers
source                  1..4395
                        mol_type = other DNA
                        organism = Triticum aestivum
SEQUENCE: 153
```
atggcccgca ccaagcaccc ggccgtcagg aagaccaagg cgccgcccaa gaagcagctc   60
gggccccgcc ccgcgcagcg gcggcaggag acaggtcagc ccttccctcc ttcctcccccc  120
cgtctcccgc ctctcgagcg aacgccgtcg ccatttcgtc gcgagagatg gacggacgga    180
cgcccacgc atgacgctaa tgtgctcttc ctctcccttt gcagatgggc cgggcacgtc    240
ggcgacacgc gcgggacctt cccgggtcgc ttccttttcg tttgtcttg ttttctgttt     300
tttggtctga cttgctcgtc acctgttcga cggaatgcag aggcgagccg ggcgggcggc    360
ggccccaggg ggggctcaag gtgcggcctt ctttgcgctt ttcggtttc cgccgcgtgt     420
ttagggccat ttccgtcttg tttggggggtg cgcggggcgg gggcttgttt ttttcctcc    480
ccccttcgtt gttgcgcaca ttgctcggga atgctgccag gagcggttgc ggttcttctt   540
tgacccttcg ggagggctgg atcggcagtt tcttcgcttc cttgctccag attttagttc   600
atcttgtacc agtacagtag caagatgatg gatggggggct tgtttttttt ttctccttcc   660
ttgttccgga catttctctg gagcgacttt tatgcatttc ccagtattgt cctttgtcct   720
tagagggtag tggatcggca gttttcttcg cctcattggt ccagatttta gtttatcttg   780
tacggtacca agatgatgga tgtggcacaa agttctcagt ttgggggttg cgctcttccg   840
ggcagttgtt attttggtct gtgatgacta actcgtatct attcttgtgg gagcagggggc   900
aactgggcaa cccaagcaga ggaaaccaca ccggttcagg ccaggcacgg tggcactgcg   960
ggagatcagg aggtatcaga agtcggtcga ctttctcatc ccgtttgcac catttgtccg   1020
tctggtgggt acctctgtct gtcatatcct ctcgctctct ctacaaacga tctgcagtgc  1080
agagtgtaat tggaatattt tgttcctgac aaatttgcag atcaaggagg tcaccgactt   1140
cttctgtcct gaaatcagcc gctggactcc ccaagcgctc gtcgcgattc aagaggtcag   1200
tgctaaaacc tggcatgtac tattagatct gatggtttga ttagagtact acaatgcaga   1260
tgaattcaat atccgaaaac catgaactgt ggggtagata catgtatcgc cttaattcat   1320
ggttctgaa tgctctgcta ttaattcagt ttgatatatt tattttagcag catggtattg   1380
ttttggtggc tggtaaatca aaactgaaat gtgattacga gcaaaacggt atcgattgtc   1440
gatcctgtgt gttttttgtgc acatctggtt gtttggtcaa gatgtgtttg tgcacatctt   1500
gcaacatgat cctgcccaca cactcaaaac tgactattgg ttaggttcca tttgtcttat   1560
ggaattttagg gtgtaactga gaggtgagca agtggtagta acgttcaatt ttgattcagg   1620
atgaggatat tgtgatccag aaaattgcat gttatggtta tgtgtccaaa cgccaaatga    1680
```

```
ttatgtctat atccagtact ttagaaccag tacaacaaca aaaagtactt tagaaccagt  1740
caagtttatt gtgcatttat acaagagtgt tgtttgcaca atagacttgc tttagtcgtc  1800
tcttgccaga aatgccttct tctgcacaac gagcaaaaat aacataaagt tgactatact  1860
cagtgtggcc taagaaatga gttgtacttt ttagtcactg gcctgtgtat ttgctttgaa  1920
ttgacacata attccctttt cctttccctc tgcaggctgc agagtatcac ctcgtcgacg  1980
tatttgaaag ggcaaatcac tgtgccatcc atgcaaagcg tgttaccgtc agtaagttct  2040
cactgaatga aaactccctt tctttttacaa tattgcgcag aaggaaacat gccagttatg  2100
aaagagtttc aattacagga tcacctttgc tttcatttga tgtgatatct agttttgatg  2160
ttgtttcaag gttcaagaat tctaatgata aatgatagga tccacaattg ttatatctct  2220
gcagctcctc gtatctgttg tccacgaaca aacatatcaa acaattcatt aaaaagatga  2280
agaagtcaaa caaacagtat atgtgcactg catattagat atcaaacctg gttactatac  2340
gactgatctg gcctgacccc cgcgtcgcct ctccctggcg gcacggggggg aaccactccg  2400
gcgccgccac cttccctcct ccctccaccc cccacctcgc cgccgcctga ggagttcgcc  2460
ggcgaagccc ggtctggctc cagggagggt ggcggcgggg catctctctg cgaggcgtga  2520
gggcgcatct cgtgcgcggg cgcggcgagc ttgggcggga tcgcgggcgc ggctctggct  2580
cgggctggtg aggctccggc ggtccgaggg gtgtcgcggc gcggcggggg tctcgctccg  2640
gcgcgggcgg tccgagggcg cgcgggatct ggcgctccag caggggcgcc gtcaagggga  2700
gccgggcagg gaagctcgtc aggcgggctc gtcaggcagg cgtgacgcgg ggcggcggcc  2760
gcgggctgga agccatggcg ttttggccat ggtgtcgtgt gcgctcgctt ctcattcgca  2820
gcttgaggtg ctgctgctga gggtggtgcg cggtgaagct tggtggtcgg cgttggagag  2880
tgcaaggcgc aacaggaatg gctccaatga tctccacgct tctgggtgga tcagatctgc  2940
ggccctccat aggggtgtgt tccgggcgaa agccttgcct cgactttgtc ggtgccgtcg  3000
acggcggcgc tttcgggcgt cgtttccctc cttggaggcg tcgttgtgga actcatcttc  3060
ttctatgtgg ggctcgggct ctccgggtga aaacctaagc tccagatttt ccggagcggg  3120
cgatggcggc gtcttcgtcg tttccctctt ggggggcgttg cttgggagag ttagcttgtg  3180
cttggtgcgt ttggtttct cctacgtcgg gtttggtgga tgccgggca gcgggccccg  3240
acggctgatg aacgccgagg cggcggcctc ggaaagtgat gcgcggtgcg gctccatggg  3300
gcgggggcggg ggctcggcct tcacttgggt ggcaatcttg ggccacttgg gtggcaggct  3360
tgtcggtccg gtcgacgcgt tccagagggg gcggctgac tttgcgtcgg ggcggcggcc  3420
ccggatgtgg tgcgacgttc gtggtctgcg agcggttgcc ttgagcagcg tgggctgcgg  3480
gcagctgggt cgcgcggcgt tgctgctcga gcggagcggt ggtacgtcgg gcgggcggcc  3540
ccggaaggtg atgccggttg attgcgctgg gcgtgacgga gcggtggatg tcggggcggc  3600
ggccccgaga aaatcactgt ggcgtccaga tttctgtggc aacgatgatg gtgggagcga  3660
tgtcggcgac gcggcaatgg ttgcgatagt cggctcttct ccggcgtgtc cacgatattg  3720
cctcggtttg tttgttgctg tggagtcgaa gctgcggcgg cgaggccctg tggtatacga  3780
tgactggttc caggtgtcct ttcgtcgatc ttccgtggcg ccagccgtgc ctggtttcgt  3840
tcttccgagt tctccgtcag aatcggagct gcgttgtctg tccgcaggtc gacatgttgt  3900
cgagaagggt gggctttgcc ctgtgtgttt cagtctatgc gagtgggctc ggcccttgtt  3960
gttctggttt ttgcccggtt ttccgtaatt aactgggcaa ttctcttctg cttaattaat  4020
agatgaggca atctttgcct ccctttcaaa aaaaaacctg gttactatag caggaaattc  4080
agggttgatt actttatttc ttatctgaag gataaacatt gtatcaaatc agaattttat  4140
ttgtaagtta catttttttt tacttataaa acttggaaac tgtttactg tgacaaatag  4200
atgccactag aatcatgatc aatcgtggc tgttgctatt ctaacaaata aatgctcctg  4260
aacaaatggg aactatatat gaagatgtat ggaccagcat gttcctgtta acctgacctt  4320
tttccttttt ttgctgctgc agtgcaaaag gacatacagc ttgcaaggcg tatcggcggg  4380
aggaggcttt ggtga                                                    4395
```

```
SEQ ID NO: 154        moltype = RNA   length = 582
FEATURE               Location/Qualifiers
source                1..582
                      mol_type = other RNA
                      organism = Triticum aestivum
SEQUENCE: 154
atggcccgca ccaagcaccc ggccgtcagg aagaccaagg cgccgcccaa gaagcagctc  60
gggccccgcc ccgcgcagcg gcggcaggag acagatggcg cgggcacgtc ggcgacacgc  120
gcgggacctt cccgggtcgc ttcctttcg tttcgtcttg ttttctgttt tttggtctga  180
cttgctcgtc acctgttcga cggaatgcag aggcgagccg ggcgggcggc ggccccaggg  240
ggggctcaag gggcaactgg gcaacccaag cagaggaaac cacaccggtt caggccaggc  300
acggtggcac tgcgggagat caggaggtat cagaagtcgg tcgactttct catcccgttt  360
gcaccatttg tccgtctgat caaggaggtc accgacttct tctgtcctga aatcagccgc  420
tggactcccc aagcgctcgt cgcgattcaa gaggctgcag agtatcacct cgtcgacgta  480
tttgaaaggg caaatcactg tgccatccat gcaaagcgtg ttaccgtcat gcaaaaggac  540
atacagcttg caaggcgtat cggcgggagg aggctttggt ga                     582
```

```
SEQ ID NO: 155        moltype = AA   length = 59
FEATURE               Location/Qualifiers
source                1..59
                      mol_type = protein
                      organism = Triticum aestivum
SEQUENCE: 155
MARTKHPAVR KTKAPPKKQL GPRPAQRRQE TDGAGTSATR AGPSRVASFS FRLVFCFLV   59
```

```
SEQ ID NO: 156        moltype = DNA   length = 4390
FEATURE               Location/Qualifiers
source                1..4390
                      mol_type = other DNA
                      organism = Triticum aestivum
SEQUENCE: 156
atggcccgca ccaagcaccc ggccgtcagg aagaccaagg cgccgcccaa gaagcagctc  60
```

```
gggccccgcc ccgcgcagcg gcggcaggag acaggtcagc ccttccctcc ttcctccccc    120
cgtctcccgc ctctcgagcg aacgccgtcg ccatttcgtc gcgagagatg gacggacgga    180
cgccccacgc atgacgctaa tgtgctcttc ctctcccttt gcagatggcg cgggcacgtc    240
ggcgacacgc gcgggacctt cccgggtcgc ttccttttcg tttcgtcttg ttttctgttt    300
tttggtctga cttgctcgtc acctgttcga cggaatgcag aggcgagccg ggcgggcggc    360
ggccccaggg ggggctcaag gtgcggcctt ctttgcgctt ttcggttttc cgccgcgtgt    420
ttagggccat ttccgtcttg tttgggggtg cgcggggcgg gggcttgttt tttttcctcc    480
cccttcgtt gttgcgcaca ttgctcggga atgctgccag gagcggttgc ggttcttctt    540
tgacccttcg ggagggctgg atcggcagtt tcttcgcttc cttgctccag attttagttc    600
atcttgtacc agtacagtag caagatgatg gatggggggct tgttttttct ttctccttcc    660
ttgttccgga catttctctg gagcgacttt tatgcatttc ccagtattgt cctttgtcct    720
tagagggtag tggatcggca gttttcttcg cctcattggt ccagatttta gtttatcttg    780
tacggtacca agatgatgga tgtggcacaa agttctcagt ttgggggttg cgctcttccg    840
ggcagttgtt attttggtct gtgatgacta actcgtatct attcttgtgg tgactaactg    900
ggcaacccaa gcagaggaaa ccacaccggt tcaggccagg cacggtggca ctgcgggaga    960
tcaggaggta tcagaagtcg gtcgactttc tcatcccgtt tgcaccattt gtccgtctgg   1020
tgggtacctc tgtctgtcat atcctctcgc tctctctaca aacgatctgc agtgcagagt   1080
gtaattggaa tattttgttc ctgacaaatt tgcagatcaa ggaggtcacc gacttcttct   1140
gtcctgaaat cagccgctgg actccccaag cgctcgtcgc gattcaagag gtcagtgcta   1200
aaacctggca tgtactatta gatctgatgg tttgattaga gtactacaat gcagatgaat   1260
tcaatatccg aaaaccatga actgtggggt agatacatgt atcgccttaa ttcatggttt   1320
ctgaatgctc tgctattaat tcagtttgat atatttattt agcagcatgg tattgttttg   1380
gtggctggta aatcaaaact gaaatgtgat tacgagcaaa acggtatcga ttgtcgatcc   1440
tgtgtgtttt tgtgcacatc tggttgtttg gtcaagatgt gtttgtgcac atcttgcaac   1500
atgatcctgc ccacacactc aaaactgact attggttagg ttccatttgt cttatggaat   1560
ttagggtgta actgagaggt gagcaagtgg tagtaacgtt caattttgat tcaggatgag   1620
gatattgtga tccagaaaat tgcatgttat ggttatgtgt ccaaacgcca aatgattatg   1680
tctatatcca gtactttaga accagtacaa caacaaaaag tactttagaa ccagtcaagt   1740
ttattgtgca tttatacaag agtgttgttt gcacaataga cttgctttag tcgtctcttg   1800
ccagaaatgc cttcttctgc acaacgagca aaaataacat aaagttgact atactcagtg   1860
tggcctaaga aatgagttgt acttttttagt cactggcctg tgtatttgct ttgaattgac   1920
acataattcc cttttccttt ccctctgcag gctgcagagt atcacctcgt cgacgtattt   1980
gaaagggcaa atcactgtgc catccatgca aagcgtgtta ccgtcagtaa gttctcactg   2040
aatgaaaact cccttttctt tacaatattg cgcagaagga aacatgccag ttatgaaaga   2100
gtttcaatta caggatcacc tttgctttca tttgatgtga tatctagttt tgatgttgtt   2160
tcaaggttca agaattctaa tgataaatga taggatccac aattgttata tctctgcagc   2220
tcctcgtatc tgttgtccac gaacaaacat atcaaacaat tcattaaaaa gatgaagaag   2280
tcaaacaaac agtatatgtg cactgcatat tagatatcaa acctggttac tatacgactg   2340
atctggcctg accccgcgct cgcctctccc tggcggcacg gggggaacca ctccggccgc   2400
gccaccttcc ctcctccctc cacccccccac ctcgccgccg cctgaggagt tcgccggcga   2460
agcccggtct ggctccaggg agggtggcgg cggggcatct ctctgcgagg cgtgagggcg   2520
catctcgtgc gcgggcgcgg cgagcttggg cgggatcgcg ggcgcggctc tggctcgggc   2580
tggtgaggct ccggcggtcc gaggggtgtc gcggcgcggc ggggtctcg ctccggccgg   2640
ggcggtccga gggcgcgcgg gatctggcgc tccagcaggg gcgccgtcaa ggggagccgg   2700
gcagggaagc tcgtcaggcg ggctcgtcag gcaggcgtga cgcggggcgg cggccgcggg   2760
ctggaagcca tggcgttttg gccatggtgt cgtgtgcgct cgcttctcat tcgcagcttg   2820
aggtgctgct gctgagggtg gtgcgcggtg aagcttggtg gtcggcgttg gagagtgcaa   2880
ggcgcaacag gaatggctcc aatgatctcc acgcttctgg gtggatcaga tctgcggccc   2940
tccatagggg tgtgttccgg gcgaaagcct tgacccgact ttgtcggtgc cgtcgacggc   3000
ggcgctttcg ggcgtcgttt ccctccttgg aggcgtcgtt gtggaactca tcttcttcta   3060
tgtggggcgtc gggctctccg ggtgaaaacc taagctccag attttccgga cggcgtcgaga   3120
gcggcgtctt cgtcgtttcc ctcttggggg cgttgcttgg gagagttagc ttgtgcttgg   3180
tgcgtttggt tttctcctac gtcgggtttg gtggatgccg gggcagcggc cccggacggc   3240
tgatgaacgc cgaggcggcg gcctcggaaa gtgatgcgcg gtgcggctcc atggggcggg   3300
gcggtggctc ggccttcact tgggtggcaa tcttgggtgg cttgggtggc aggcttgtcg   3360
gtccggtcga cgcgttccag aggggcgggt ctgactttgc gtcggggcgg cggccccgga   3420
tgtggtgcga cgttcgtggt ctgcgagcgg ttgccttgag cagcgtgggc tgcgggcagc   3480
tgggtcgcgc ggcgttgctg ctcgagcgga gcggtggtac gtcggggcgg cggccccgga   3540
aggtgatgcc ggttgattgc gctgggcgtg acggagcggt ggatggtggg gcggcggccc   3600
cgagaaaatc actgtggcgt ccagatttct gtggcaacga tgatggtggg agcgatgtcg   3660
gcgacgcggc aatggttgcg atagtcggct cttctccggc gtgtccacga tattgcctcg   3720
gtttgtttgt tgctgtggag tcgaagctgc ggcggcgagg ccctgtggta tacgatgact   3780
ggttccaggt gtcctttcgt cgatcttccg tggcgccagc cgtgcctggt ttcgttcttc   3840
cgagttctcc gtcagaatcg gagctgcgtt gtctgtccga aggtcgacat gttgtcgaga   3900
agggtggggct ttgccctgtg tgtttcagtc tatgcgagtg ggctcggccc ttgttgttct   3960
ggtttttgcc cggtttttccg taattaactg ggcaattctc ttctgcttaa ttaatagatg   4020
aggcaatctt tgcctccctt tcaaaaaaaa acctggttac tatagcagga aattcagggt   4080
tgattacttt atttcttatc tgaaggataa acattgtatc aaatcagaat tttatttgta   4140
agttacattt ttttttactt ataaaacttg gaaactgttt tactgtgaca aatagatgct   4200
actagaatca tgatcacatc gtggctgttg ctattctaac aaataaatgc tcctgaacaa   4260
atgggaacta tatatgaaga tgtatggacc agcatgttcc tgttaacctg accttttttcc   4320
ttttttttgct gctgcagtgc aaaaggacat acagcttgca aggcgtatcg gcgggaggag   4380
gctttggtga                                                          4390
```

```
SEQ ID NO: 157        moltype = RNA   length = 559
FEATURE               Location/Qualifiers
source                1..559
                      mol_type = other RNA
                      organism = Triticum aestivum
```

```
SEQUENCE: 157
atggcccgca ccaagcaccc ggccgtcagg aagaccaagg cgccgcccaa gaagcagctc  60
gggccccgcc ccgcgcagcg gcggcaggag acagatggcg cgggcacgtc ggcgacacgc  120
gcgggacctt cccgggtcgc ttccttttcg tttcgtcttg ttttctgttt tttggtctga  180
cttgctcgtc acctgttcga cggaatgcag aggcgagccg ggcgggcggc ggccccaggg  240
ggggctcaag aggaaaccac accggttcag gccaggcacg gtggcactgc gggagatcag  300
gaggtatcag aagtcggtcg actttctcat cccgtttgca ccatttgtcc gtctgatcaa  360
ggaggtcacc gacttcttct gtcctgaaat cagccgctgg actccccaag cgctcgtcgc  420
gattcaaagag gctgcagagt atcacctcgt cgacgtattt gaaagggcaa atcactgtgc  480
catccatgca aagcgtgtta ccgtcatgca aaaggacata cagcttgcaa ggcgtatcgg  540
cgggaggagg ctttggtga                                               559

SEQ ID NO: 158         moltype = AA  length = 59
FEATURE                Location/Qualifiers
source                 1..59
                       mol_type = protein
                       organism = Triticum aestivum
SEQUENCE: 158
MARTKHPAVR KTKAPPKKQL GPRPAQRRQE TDGAGTSATR AGPSRVASFS FRLVFCFLV   59

SEQ ID NO: 159         moltype = DNA  length = 4397
FEATURE                Location/Qualifiers
source                 1..4397
                       mol_type = other DNA
                       organism = Triticum aestivum
SEQUENCE: 159
atggcccgca ccaagcaccc ggccgtcagg aagaccaagg cgccgcccaa gaagcagctc  60
gggccccgcc ccgcgcagcg gcggcaggag acaggtcagc ccttccctcc ttcctccccc  120
cgtctcccgc ctctcgagcg aacgccgtcg ccatttcgtc gcgagagatg gacggacgga  180
cgccccacgc atgacgctaa tgtgctcttc ctctcccttt gcagatggcg cgggcacgtc  240
ggcgacactg cgcgggacct tcccgggtcg cttccttttc gtttcgtctt gttttctgtt  300
ttttggtctg acttgctcgt cacctgttcg acggaatgca gaggcgagcc gggcgggcgg  360
cggccccagg ggggggctcaa ggtgcggcct tctttgcgct tttcggtttt ccgccgcgtg  420
tttagggcca tttccgtctt gtttgggggt gcgcggggcg ggggcttgtt ttttttcctc  480
cccccttcgt tgttgcgcac attgctcggg aatgctgccc ggagcggttg cggttcttct  540
ttgaccccttc gggagggctg gatcggcagt ttcttcgctt ccttgctcca gattttagtt  600
catcttgtac cagtacagta gcaagatgat ggatggggggc ttgttttttc tttctccttc  660
cttgttccgg acatttctct ggagcgactt ttatgcattt cccagtattg tcctttgtcc  720
ttagagggta gtggatcggc agttttcttc gcctcattgg tccagatttt agtttatctt  780
gtacggtacc aagatgatgg atgtggcaca aagttctcag tttggggggtt gcgctcttcc  840
gggcagttgt tattttggtc tgtgatgact aactcgtatc tattcttgtg ggagcagggg  900
caaactgggc aacccaagca gaggaaacca caccggttca ggccaggcac ggtggcactg  960
cgggagatca ggaggtatca gaagtcggtc gactttctca tcccgtttgc accatttgtc  1020
cgtctggtgg gtacctctgt ctgtcatatc ctctcgctct ctctacaaac gatctgcagt  1080
gcagagtgta attggaatat tttgttcctg acaaatttgc agatcaagga ggtcaccgac  1140
ttcttctgtc ctgaaatcag ccgctggact ccccaagcgc tcgtcgcgat tcaagaggtc  1200
agtgctaaaa cctggcatgt actattagat ctgatgatgt gattagagta ctacaatgca  1260
gatgaattca atatccgaaa accatgaact gtggggtaga tacatgtatc gccttaattc  1320
atggtttctg aatgctctgc tattaattca gtttgatata tttatttagc agcatggtat  1380
tgtttttggtg gctggtaaat caaaactgaa atgtgattac gagcaaaacg gtatcgattg  1440
tcgatcctgt gtgtttttgt gcacatctgg ttgtttggat aagatgtgtt tgtgcacatc  1500
ttgcaacatg atcctgccca cacactcaaa actgactatt ggttaggttc catttgtctt  1560
atggaattta gggtgtaact gagaggtgag caagtggtag taacgttcaa ttttgattca  1620
ggatgaggat attgtgatcc agaaaattgc atgttatggt tatgtgtcca aacgccaaat  1680
gattatgtct atatccagta ctttagaacc agtacaacaa caaaaagtac tttagaacca  1740
gtcaagtttta ttgtgcattt atacaagagt gttgtttgca caatagactt gctttagtcg  1800
tctcttgcca gaaatgcctt cttctgcaca acgagcaaaa ataacataaa gttgactata  1860
ctcagtgtgg cctaagaaat gagttgtact ttttagtcac tggcctgtgt atttgctttg  1920
aattgacaca taattcccctt ttcctttccc tctgcaggct gcagagtatc acctcgtcga  1980
cgtatttgaa agggcaaatc actgtgccat ccatgcaaag cgtgttaccg tcagtaagtt  2040
ctcactgaat gaaaactccc tttctttttac aatattgcgc agaaggaaac atgccagtta  2100
tgaaagagtt tcaattacag gatcaccttt gctttcattt gatgtgatat ctagttttga  2160
tgttgtttca aggttcaaga attctaatga taaatgatag gatccacaat tgttatatct  2220
ctgcagctcc tcgtatctgt tgtccacgaa caaacattca aaacaattca ttaaaaagat  2280
gaagaagtca aacaaacagt atatgtgcac tgcatattag atatcaaacc tggttactat  2340
acgactgatc tggcctgacc cccgcgtcgc ctctccctgg cggcacgggg ggaaccactc  2400
cggcgccgcc accttccctc ctccctccac ccccaccctc gccgccgcct gaggagttcg  2460
ccggcgaagc ccggtctggc tccagggagg gtggcggcgg ggcatctctc tgcgaggcgt  2520
gagggcgcat ctcgtcgcgcg ggcgcgggcga gcttgggag gatcgcggc gcggctctgg  2580
ctcgggctgg tgaggctccg gcggtccgag gggtgtcgcg gcggcggcgg ggtctcgctc  2640
cggcgcgggc ggtccgaggg cgcgcgggat ctggcgctcc agcaggggcg ccgtcaaggg  2700
gagccgggca gggaagctcg tcaggcgggc tcgtcaggca ggcgtgacgc ggggcggcgg  2760
ccgcgggctg gaagccatgg cgttttggcc atggtgtcgt gtgcgctcgc ttctcattcg  2820
cagcttgagg tgctgctgct gagggtggtg cgcggtgaag cttggtggtc cgcgttggag  2880
agtgcaaggc gcaacaggaa tggctccaat gatctccacg cttctgggtg gatcagatct  2940
gcggccctcc ataggggtgt gttccgggcg aaagccttga cccgactttg tcggtgccgt  3000
cgacggcggc gctttcgggc gtcgtttccc tccttggagg cgtcgttgtg gaactcatct  3060
tcttctatgt ggggctcggg ctctccgggt gaaaacctaa gctccagatt ttccggagcg  3120
ggcgatggcg gcgtcttcgt cgtttccctc ttggggggcgt tgcttgggag agttagcttg  3180
```

-continued

```
tgcttggtgc gtttggtttt ctcctacgtc gggtttggtg gatgccgggg cagcggcccc  3240
ggacggctga tgaacgccga ggcggcggcc tcggaaagtg atgcgcggtg cggctccatg  3300
gggcggggcg gtggctcggc cttcacttgg gtggcaatct tgggccactt gggtggcagg  3360
cttgtcggtc cggtcgacgc gttccagagg gggcggtctg actttgcgtc ggggcggcgg  3420
ccccggatgt ggtgcgacgt tcgtggtctg cgagcggttg ccttgagcag cgtgggctgc  3480
gggcagctgg gtcgcgcggc gttgctgctc gagcggagcg gtggtacgtc ggggcggcgg  3540
ccccggaagg tgatgccggt tgattgcgct gggcgtgacg gagcggtgga tgtcggggcg  3600
gcggccccga gaaaatcact gtggcgtcca gatttctgtg gcaacgatga tggtgggagc  3660
gatgtcggcg acgcggcaat ggttgcgata gtcggctctt ctccggcgtg tccacgatat  3720
tgcctcggtt tgtttgttgc tgtggagtcg aagctgcggc ggcgaggccc tgtggtatac  3780
gatgactggt tccaggtgtc ctttcgtcga tcttccgtgg cgccagccgt gcctggtttc  3840
gttcttccga gttctccgtc agaatcggag ctgcgttgtc tgtccgcagg tcgacatgtt  3900
gtcgagaagg gtgggctttg ccctgtgtgt ttcagtctat gcgagtgggc tcggcccttg  3960
ttgttctggt ttttgcccgg tttttccgtaa ttaactgggc aattctcttc tgcttaatta  4020
atagatgagg caatctttgc ctcccttttca aaaaaaaacc tggttactat agcaggaaat  4080
tcagggttga ttactttatt tcttatctga aggataaaca ttgtatcaaa tcagaatttt  4140
atttgtaagt tacattttttt tttacttata aaacttggaa actgttttac tgtgacaaat  4200
agatgccact agaatcatga tcacatcgtg gctgttgcta ttctaacaaa taaatgctcc  4260
tgaacaaatg ggaactatat atgaagatgt atggaccagc atgttcctgt taacctgacc  4320
tttttcctttt tttttgctgct gcagtgcaaa aggacataca gcttgcaagg cgtatcggcg  4380
ggaggaggct ttggtga                                                  4397
```

```
SEQ ID NO: 160              moltype = RNA   length = 584
FEATURE                     Location/Qualifiers
source                      1..584
                            mol_type = other RNA
                            organism = Triticum aestivum
SEQUENCE: 160
atggcccgca ccaagcaccc ggccgtcagg aagaccaagg cgccgcccaa gaagcagctc  60
gggccccgcc ccgcgcagcg gcggcaggag acagatgqcg cgggcacgtc ggcgacactg  120
cgcgggacct tcccgggtcg cttccttttc gtttcgtctt gttttctgtt ttttggtctg  180
acttgctcgt cacctgttcg acggaatgca gaggcgagcc gggcgggcgg cggccccagg  240
gggggctcaa ggggcaaact gggcaaccca agcagaggaa accacaccgg ttcaggccag  300
gcacggtggc actgcgggag atcaggaggt atcagaagtc ggtcgacttt ctcatcccgt  360
ttgcaccatt tgtccgtctg atcaaggagg tcaccgactt cttcgtcct gaaatcagcc  420
gctggactcc ccaagcgctc gtcgcgattc aagaggctgc agagtatcac ctcgtcgacg  480
tatttgaaag ggcaaatcac tgtgccatcc atgcaaagcg tgttaccgtc atgcaaaagg  540
acatacagct tgcaaggcgt atcggcggga ggaggctttg gtga                   584
```

```
SEQ ID NO: 161              moltype = AA   length = 126
FEATURE                     Location/Qualifiers
source                      1..126
                            mol_type = protein
                            organism = Triticum aestivum
SEQUENCE: 161
MARTKHPAVR KTKAPPKKQL GPRPAQRRQE TDGAGTSATL RGTFPGRFLF VSSCFLFFGL  60
TCSSPVRRNA EASRAGGGPR GGSRGKLGNP SRGNHTGSGQ ARWHCGRSGG IRSRSTFSSR  120
LHHLSV                                                              126
```

```
SEQ ID NO: 162              moltype = DNA   length = 4399
FEATURE                     Location/Qualifiers
source                      1..4399
                            mol_type = other DNA
                            organism = Triticum aestivum
SEQUENCE: 162
atggcccgca ccaagcaccc ggccgtcagg aagaccaagg cgccgcccaa gaagcagctc  60
gggccccgcc ccgcgcagcg gcggcaggag acaggtcagc ccttccctcc ttcctcccc  120
cgtctcccgc ctctcgagcg aacgccgtcg ccatttcgtc gcgagagatg gacggacgga  180
cgcccacgc atgacgctaa tgtgctcttc ctctcccttt gcagatggcg cgggcacgtc  240
ggcgacaccg tgcgcgggac cttcccgggt cgcttccttt tcgtttcgtc ttgttttctg  300
ttttttggtc tgacttgctc gtcacctgtt cgacggaatg cagaggcgag ccgggcgggc  360
ggcggcccca gggggggctc aaggtgcggc cttctttgcg cttttcggtt ttccgccgcg  420
tgtttagggc catttccgtc ttgtttgggg gtgcgcgggg cgggggcttg ttttttttcc  480
tcccccttc gttgttgcgc acattgctcg ggaatgctcg caggagcggt tgcggttctt  540
ctttgaccct tcgggagggc tggatcggca gtttcttcgc ttccttgctc cagatttag  600
ttcatcttgt accagtacag tagcaagatg atggatgggg gcttgttttt tctttctcct  660
tccttgttcc ggacatttct ctggagcgac ttttatgcat ttcccagtat tgtcctttgt  720
ccttagaggg tagtggatcg gcagtttttct tcgcctcatt ggtccagatt ttagtttatc  780
ttgtacggta ccaagatgat ggatgtggca caagttctc agtttggggg ttgcgctctt  840
ccgggcagtt gttattttgg tctgtgatga ctaactcgta tctattcttg tgggagcagg  900
ggctaactgg gcaacccaag cagaggaaac cacaccggtt caggccaggc acggtggcac  960
tgcgggagat caggaggtat cagaagtcgg tcgactttct catcccgttt gcaccatttg  1020
tccgtctggt gggtacctct gtctgtcata tcctctcgct ctctacaa acgatctgca  1080
gtgcagagtg taattggaat attttgttcc tgacaaattt gcagatcaag gaggtcaccg  1140
acttcttctg tcctgaaatc agccgctgga ctcccaagc gctcgtcgcg attcaagagg  1200
tcagtgctaa aacctggcat gtactattag atctgatggt ttgattagag tactacaatg  1260
cagatgaatt caatatccga aaaccatgaa ctgtggggta gatacatgta tcgccttaat  1320
tcatggtttc tgaatgctct gctattaatt cagtttgata tatttattta gcagcatggt  1380
attgtttttgg tggctggtaa atcaaaactg aaatgtgatt acgagcaaaa cggtatcgat  1440
```

-continued

```
tgtcgatcct gtgtgttttt gtgcacatct ggttgtttgg tcaagatgtg tttgtgcaca   1500
tcttgcaaca tgatcctgcc cacacactca aaactgacta ttggttaggt tccatttgtc   1560
ttatggaatt tagggtgtaa ctgagaggtg agcaagtggt agtaacgttc aattttgatt   1620
caggatgagg atattgtgat ccagaaaatt gcatgttatg gttatgtgtc caaacgccaa   1680
atgattatgt ctatatccag tactttagaa ccagtacaac aacaaaaagt actttagaac   1740
cagtcaagtt tattgtgcat ttatacaaga gtgttgtttg cacaatagac ttgctttagt   1800
cgtctcttgc cagaaatgcc ttcttctgca caacgagcaa aaataacata aagttgacta   1860
tactcagtgt ggcctaagaa atgagttgta cttttttagtc actggcctgt gtatttgctt   1920
tgaattgaca cataattccc ttttcctttc cctctgcagg ctgcagagta tcacctcgtc   1980
gacgtatttg aaagggcaaa tcactgtgcc atccatgcaa agcgtgttac cgtcagtaag   2040
ttctcactga atgaaaactc cctttctttt acaatattgc gcagaaggaa acatgccagt   2100
tatgaaaagag tttcaattac aggatcacct ttgctttcat ttgatgtgat atctagtttt   2160
gatgttgttt caaggttcaa gaattctaat gataaatgat aggatccaca attgttatat   2220
ctctgcagct cctcgtatct gttgtccacg aacaaacata tcaaacaatt cattaaaaag   2280
atgaagaagt caaacaaaca gtatatgtgc actgcatatt agatatcaaa cctggttact   2340
atacgactga tctggcctga cccccgcgtc gcctctccct ggcggcacgg ggggaaccac   2400
tccggcgccg ccaccttccc tcctccctcc accccccacc tcgccgccgc ctgaggagtt   2460
cgccggcgaa gcccggtctg gctccaggga gggtggcggc ggggcatctc tctgcgaggc   2520
gtgagggcgc atctcgtgcg cgggcgcggc gagcttgggc gggatcgcgg gcgcggctct   2580
ggctcgggct ggtgaggctc cggcggtccg aggggtgtcg cggcgcggcg ggggtctcgc   2640
tccggcgcgg gcggtccgag ggcgcgcggg atctggcgct ccagcagggg cgccgtcaag   2700
gggagccggg cagggaagct cgtcagacgg gctcgtcagg caggcgtgac gcggggcggc   2760
ggccgcgggc tggaagccat ggcgtttttg ccatggtgtc gtgtgcgctc gcttctcatt   2820
cgcagcttga ggtgctgctg ctgagggtgg tgcgcggtga agcttggtgg tcggcgttgg   2880
agagtgcaag gcgcaacagg aatggctcca atgatctcca cgcttctggg tggatcagat   2940
ctgcggccct ccatagggt gtgttccggg cgaaagcctt gacccgactt tgtcggtgcc   3000
gtcgacggcg gcgctttcgg cgtcgtttc cctccttgga ggcgtcgttg tggaactcat   3060
cttcttctat gtggggctcg ggctctccgg gtgaaaacct aagctccaga ttttccggag   3120
cgggcgatgg cggcgtcttc gtcgtttccc tcttgggggc gttgcttggg agagttagct   3180
tgtgcttggt gcgtttggtt ttctcctacg tcgggtttgg tggatgccgg ggcagcggcc   3240
ccggacggct gatgaacgcc gaggcggcg cctcggaaag tgatgcgcgg tgcggctcca   3300
tggggcgggg cggtggctcg gccttcactt gggtggcaat cttgggccac ttgggtggca   3360
ggcttgtcgg tccggtcgac gcgttccaga gggggcggtc tgactttgcg tcggggcggc   3420
ggccccggat gtggtgcgac gttcgtggtc tgcgagcggt tgccttgagc agcgtgggct   3480
gcgggcagct gggtcgcgcg gcgttgctgc tcgagcggag cggtggtacg tcggggcggc   3540
ggccccggaa ggtgatgccg gttgattgcg ctgggcgtga cggagcggtg gatgtcgggg   3600
cggcggcccc gagaaaatca ctgtggcgtc cagatttctg tggcaacgat gatggtggga   3660
gcgatgtcgg cgacgcggca atggttgcga tagtcggctc ttctccggcg tgtccacgat   3720
attgcctcgg tttgtttgtt gctgtggagt cgaagctgcg gcggcgaggc cctgtggtat   3780
acgatgactg gttccaggtg tcctttcgtc gatcttccgt ggcgccagcc gtgcctggtt   3840
tcgttcttcc gagttctccg tcagaatcgg agctgcgttg tctgtccgca ggtcgacatg   3900
ttgtcgagaa gggtgggctt tgccctgtgt gtttcagtct atgcgagtgg gctcggccct   3960
tgttgttctg gtttttgccc ggttttccgt aattaactgg gcaattctct tctgcttaat   4020
taatagatga ggcaatcttt gcctcccttt caaaaaaaaa cctggttact atagcaggaa   4080
attcagggtt gattactttta tttcttatct gaaggataaa cattgtatca aatcagaatt   4140
ttatttgtaa gttacatttt tttttactta taaaacttgg aaactgtttt actgtgacaa   4200
atagatgcca ctagaatcat gatcacatcg tggctgttgc tattctaaca aataaatgct   4260
cctgaacaaa tgggaactat atatgaagat gtatggacca gcatgttcct gttaacctga   4320
ccttttttcct tttttttgctg ctgcagtgca aaaggacata cagcttgcaa ggcgtatcgg   4380
cgggaggagg ctttggtga                                                4399
```

```
SEQ ID NO: 163          moltype = RNA   length = 586
FEATURE                 Location/Qualifiers
source                  1..586
                        mol_type = other RNA
                        organism = Triticum aestivum
SEQUENCE: 163
atggcccgca ccaagcaccc ggccgtcagg aagaccaagg cgccgcccaa gaagcagctc    60
gggccccgcc ccgcgcagcg gcggcaggag acagatggcg cgggcacgtc ggcgacaccg   120
tgcgcgggac cttcccgggt cgcttccttt tcgtttcgtc ttgtttttctg ttttttggtc   180
tgacttgctc gtcacctgtt cgacggaatg cagaggcgag ccgggcgggc ggcggccca    240
ggggggggctc aagggctaa ctgggcaacc caagcagagg aaaccacacc ggttcaggcc   300
aggcacggtg gcactgcggg agatcaggag gtatcagaag tcggtcgact ttctcatccc   360
gtttgtcacca tttgtccgtc tgatcaagga ggtcaccgac ttcttctgtc ctgaaatcag   420
ccgctggact ccccaagcgc tcgtcgcgat tcaagaggct gcagagtatc acctcgtcga   480
cgtatttgaa agggcaaatc actgtgccat ccatgcaaag cgtgttaccg tcatgcaaaa   540
ggacatacag cttgcaaggc gtatcggcgg gaggaggctt tggtga                  586
```

```
SEQ ID NO: 164          moltype = AA   length = 60
FEATURE                 Location/Qualifiers
source                  1..60
                        mol_type = protein
                        organism = Triticum aestivum
SEQUENCE: 164
MARTKHPAVR KTKAPPKKQL GPRPAQRRQE TDGAGTSATP CAGPSRVASF SFRLVFCFLV    60
```

```
SEQ ID NO: 165          moltype = DNA   length = 4399
FEATURE                 Location/Qualifiers
source                  1..4399
```

```
                    mol_type = genomic DNA
                    organism = Triticum aestivum
SEQUENCE: 165
atggcccgca ccaagcaccc ggccgtcagg aagaccaagg cgccgcccaa gaagcagctc    60
gggcccgcc ccgcgcagcg gcggcaggag acaggtcagc ccttccctcc ttcctccccc   120
cgtctcccgc ctctcgagcg aacgccgtcg ccatttcgtc gcgagagatg gacggacgga   180
cgccccacgc atgacgctaa tgtgctcttc ctctcccttt gcagatggcg cgggcacgtc   240
ggcgacaccg gtgcgcggga ccttcccggg tcgcttcctt ttcgtttcgt cttgttttct   300
gtttttggt ctgacttgct cgtcacctgt tcgacggaat gcagaggcga gccgggcggg   360
cggcggcccc agggggggct caaggtgcgg ccttcctttgc gcttttcggt tttccgccgc   420
gtgtttaggg ccatttccgt cttgtttggg ggtgcgcggg gcggggggctt gtttttttc   480
ctcccccctt cgttgttgcg cacattgctc gggaatgctg ccaggagcgg ttgcggttct   540
tctttgaccc ttcgggaggg ctggatcggc agtttcttcg cttccttgct ccagatttta   600
gttcatcttg taccagtaca gtagcaagat gatggatggg ggcttgtttt ttctttctcc   660
ttccttgttc cggacatttc tctggagcga ctttttatgca tttcccagta ttgtcctttg   720
tccttagagg gtagtggatc ggcagttttc ttcgcctcat tggtccagat tttagtttat   780
cttgtacggt accaagatga tggatgtggc acaaagttct cagtttgggg gttgcgctct   840
tccgggcagt tgttattttg gtctgtgatg actaactcgt atctattctt gtgggagcag   900
gggcaactgg gcaacccaag cagaggaaac cacaccggtt caggccaggc acggtggcac   960
tgcgggagat caggaggtat cagaagtcgg tcgactttct catcccgttt gcaccatttg  1020
tccgtctggt gggtacctct gtctgtcata tcctctcgct ctctctacaa acgatctgca  1080
gtgcagagtg taattggaat attttgttcc tgacaaattt cagagatcaag gaggtcaccg  1140
acttcttctg tcctgaaatc agccgctgga ctccccaagc gctcgtcgcg attcaagagg  1200
tcagtgctaa aacctggcat gtactattag atctgatggt ttgattagag tactacaatg  1260
cagatgaatt caatatccga aaaccatgaa ctgtggggta gatacatgta tcgccttaat  1320
tcatggtttc tgaatgctct gctattaatt cagtttgata tatttattta gcagcatggt  1380
attgtttttgg tggctggtaa atcaaaactg aaatgtgatt acgagcaaaa cggtatcgat  1440
tgtcgatcct gtgtgttttt gtgcacatct ggttgtttgg tcaagatgtg tttgtgcaca  1500
tcttgcaaca tgatcctgcc cacacactca aaactgacta ttggttaggt tccatttgtc  1560
ttatggaatt tagggtgtaa ctgagaggtg agcaagtggt agtaacgttc aattttgatt  1620
caggatgagg atattgtgat ccagaaaatt gcatgttatg gttatgtgtc caaacgccaa  1680
atgattatgt ctatatccag tactttagaa ccagtacaac aacaaaaagt actttagaac  1740
cagtcaagtt tattgtgcat ttatacaaga gtgttgtttg cacaatagac ttgctttagt  1800
cgtctcttgc cagaaatgcc ttcttctgca caacgagcaa aaataacata aagttgacta  1860
tactcagtgt ggcctaagaa atgagttgta ctttttagtc actggcctgt gtatttgctt  1920
tgaattgaca cataattccc ttttcctttc cctctgcagg ctgcagagta tcacctcgtc  1980
gacgtatttg aaagggcaaa tcactgtgcc atccatgcaa agcgtgttac cgtcagtaag  2040
ttctcactga atgaaaactc cctttctttt acaatattgc gcagaaggaa acatgccagt  2100
tatgaaagag tttcaattac aggatcacct ttgctttcat ttgatgtgat atctagtttt  2160
gatgttgttt caaggttcaa gaattctaat gataaatgat aggatccaca attgttatat  2220
ctctgcagct cctcgtatct gttgtccacg aacaaacata tcaaacaatt cattaaaaag  2280
atgaagaagt caaacaaaca gtatatgtgc actgcatatt agatatcaaa cctgttact  2340
atacgactga tctggcctga cccccgcgtc gcctctccct ggcggcacgg gggaaccac  2400
tccggcgccg ccaccttccc tcctcccctcc accccccacc tcgccgccgc ctgaggagtt  2460
cgccggcgaa gcccggtctg gctccaggga gggtggcggc ggggcatctc tctgcgaggc  2520
gtgagggcgc atctcgtgcg cgggcgcggc gagcttgggc gggatcgcgg gcgcggctct  2580
ggctcgggct ggtgaggctc cgcggcggtccg aggggtgtcg cggcgcgggc ggggtccgcg  2640
tccggcgcgg gcggtccgag ggcgcgcggg atctggcgct ccagcagggg cgccgtcaag  2700
gggagccggg cagggaagct cgtcaggcgg gctcgtcagg caggcgtgac gcggggcggc  2760
ggccgcgggc tggaagccat ggcgttttgg ccatggtgtc gtgtgcgctc gcttctcatt  2820
cgcagcttga ggtgctgctg ctgagggtgg tgcgcggtga agcttggtgg tcggcgttgg  2880
agagtgcaag gcgcaacagg aatggctcca atgatctcca cgcttctggg tggatcagat  2940
ctgcggccct ccataggggt gtgttccggg cgaaagcctt gacccgactt tgtcggtgcc  3000
gtcgacggcg gcgctttcgg gcgtcgtttc cctccttgga ggcgtcgttg tggaactcat  3060
cttcttctat gtgggggctcg ggctctccgg gtgaaaacct aagctccaga ttttccggag  3120
cgggcgatgg cggcgtcttc gtcgtttccc tcttgggggc gttgcttggg agagttagct  3180
tgtgcttggt gcgtttggtt ttctcctacg tcgggtttgg tggatgccgg ggcagcggcc  3240
ccggacggct gatgaacgcc gaggcggcgg cctcggaaag tgatgcgcgg tgcggctcca  3300
tggggcgggg cggtggctcg gccttcactt gggtggcaat cttgggccac ttgggtggca  3360
ggcttgtcgg tccggtcgac gcgttccaga gggggcggtc tgacttgcg tcgggggcggc  3420
ggccccggat gtggtgcgac gttcgtggtc tgcgagcggt tgccttgagc agcgtgggct  3480
gcgggcagct gggtcgcgcg gcgttgctgc tcgagcggag cggtggtacg tcggggcggc  3540
ggccccggaa ggtgatgccg gttgattgcg ctgggcgtga cggagcggtg gatgtcgggg  3600
cggcggcccc gagaaaatca ctgtggcgtc cagatttcgtg tggcaacgat gatggtggga  3660
gcgatgtcgg cgacgcggca atggttgcga gagtcggctc ttctccggcg tgtccacgat  3720
attgcctcgg tttgtttgtt gctgtggagt cgaagctgcg gcggcgaggc cctgtggtat  3780
acgatgactg gttccaggtg tcctttcgtc gatcttccgt ggcgccagcc gtgcctggtt  3840
tcgttcttcc gagttctccg tcagaatcgg agctgcgttg tctgtccgca ggtcgacatg  3900
ttgtcgagaa gggtggggct tgccctgtgt gtttcagtct atgcgagtgg gctcggccct  3960
tgttgttctg gtttttgccc ggttttccgt aattaactgg gcaattctct tctgcttaat  4020
taatagatga ggcaatcttt gcctcccttt caaaaaaaaa cctggttact atagcaggaa  4080
attcaggggtt gattacttta tttcttatct gaaggataaa cattgtatca aatcagaatt  4140
ttatttgtaa gttacatttt tttttactta taaaacttgg aaactgtttt actgtgacaa  4200
atagatgcca ctagaatcat gatcacatcg tggctgttgc tattctaaca aataaatgct  4260
cctgaacaaa tgggaactat atatgaagat gtatgggacca gcatgttcct gttaacctga  4320
cctttttcct ttttttgctg ctgcagtgca aaggacata cagcttgcaa ggcgtatcgg  4380
cgggaggagg ctttggtga                                               4399

SEQ ID NO: 166    moltype = RNA   length = 492
```

-continued

```
FEATURE              Location/Qualifiers
source               1..492
                     mol_type = genomic RNA
                     organism = Triticum aestivum
SEQUENCE: 166
atggcccgca ccaagcaccc ggccgtcagg aagaccaagg cgccgcccaa gaagcagctc   60
gggccccgcc ccgcgcagcg gcggcaggag acagatggcg cgggcacgtc ggcgacaccg  120
aggcgagccg ggcgggcggc ggccccaggg ggggctcaag gggcaactgg gcaacccaag  180
cagaggaaac cacaccggtt caggccaggc acggtggcac tgcgggagat caggaggtat  240
cagaagtcgg tcgactttct catcccgttt gcaccatttg tccgtctgat caaggaggtc  300
accgacttct tctgtcctga aatcagccgc tggactcccc aagcgctcgt cgcgattcaa  360
gaggctgcag agtatcacct cgtcgacgta tttgaaaggg caaatcactg tgccatccat  420
gcaaagcgtg ttaccgtcat gcaaaaggac atacagcttg caaggcgtat cggcgggagg  480
aggctttggt ga                                                      492

SEQ ID NO: 167         moltype = AA  length = 163
FEATURE                Location/Qualifiers
source                 1..163
                       mol_type = protein
                       organism = Triticum aestivum
SEQUENCE: 167
MARTKHPAVR KTKAPPKKQL GPRPAQRRQE TDGAGTSATP RRAGRAAAPG GAQGATGQPK   60
QRKPHRFRPG TVALREIRRY QKSVDFLIPF APFVRLIKEV TDFFCPEISR WTPQALVAIQ  120
EAAEYHLVDV FERANHCAIH AKRVTVMQKD IQLARRIGGR RLW                    163
```